US012767989B2

(12) United States Patent
Stark

(10) Patent No.: US 12,767,989 B2
(45) Date of Patent: Oct. 20, 2026

(54) METHOD OF TREATING, DIAGNOSING AND MONITORING MELANOMA UTILIZING MICRO-RNAS

(71) Applicant: The Council of the Queensland Institute of Medical Research, Herston (AU)

(72) Inventor: Mitchell Stark, Riverhills (AU)

( * ) Notice: Subject to any disclaimer, the term of this patent is extended or adjusted under 35 U.S.C. 154(b) by 774 days.

(21) Appl. No.: 17/368,449

(22) Filed: Jul. 6, 2021

(65) Prior Publication Data

US 2022/0136061 A1 May 5, 2022

Related U.S. Application Data

(63) Continuation of application No. 15/506,545, filed as application No. PCT/AU2015/050487 on Aug. 24, 2015, now abandoned.

(30) Foreign Application Priority Data

Aug. 25, 2014 (AU) ................................ 2014903347

(51) Int. Cl.

| | |
|---|---|
| ***C12Q 1/6886*** | (2018.01) |
| ***C07K 16/30*** | (2006.01) |
| ***C12Q 1/6813*** | (2018.01) |
| ***C12Q 1/6883*** | (2018.01) |

(52) U.S. Cl.

CPC ............ *C12Q 1/6886* (2013.01); *C07K 16/30* (2013.01); *C12Q 1/6813* (2013.01); *C12Q 1/6883* (2013.01); *C12Q 2600/106* (2013.01); *C12Q 2600/112* (2013.01); *C12Q 2600/118* (2013.01); *C12Q 2600/158* (2013.01); *C12Q 2600/178* (2013.01)

(58) Field of Classification Search

CPC .. C12Q 1/6886; C12Q 1/6813; C12Q 1/6883; C12Q 2600/106; C12Q 2600/112; C12Q 2600/118; C12Q 2600/158; C12Q 2600/178; C07K 16/30

See application file for complete search history.

(56) References Cited

U.S. PATENT DOCUMENTS

| | | | | |
|---|---|---|---|---|
| 9,597,380 | B2 * | 3/2017 | Chakraborty .......... | A61K 39/00 |
| 2011/0107440 | A1 | 5/2011 | Pivarcsi et al. | |
| 2013/0196869 | A1 | 8/2013 | Qu et al. | |
| 2013/0197060 | A1 | 8/2013 | Markel et al. | |
| 2014/0235488 | A1 | 8/2014 | Markel et al. | |
| 2017/0275703 | A1 | 9/2017 | Stark | |

FOREIGN PATENT DOCUMENTS

| | | | |
|---|---|---|---|
| CN | 103642914 | | 3/2014 |
| CN | 103642914 | A | 3/2014 |
| WO | WO 2012/017430 | A2 | 2/2012 |
| WO | WO 2014/043159 | A1 | 3/2014 |

OTHER PUBLICATIONS

Hisashi Kanemaru et al. The circulating microRNA-221 level in patients with malignant melanoma as a new tumor marker.*

Lim et al., Circulating MicroRNAs: functional biomarkers for melanoma prognosis and treatment. Molecular Cancer 24:99, 1-17, published online Mar. 28, 2025.*

Stark et al. A panel of circulating MicroRNAs detects uveal melanoma with high precision. Trans. Vis. Sci. Tech. 8(6): Article 12, 1-9, published Nov. 14, 2019.*

Bonazzi et al., "MicroRNA regulation of melanoma progression," *Melanoma Research*, vol. 22, No. 2, pp. 101-113, 2011.

Chen et al., "Identification of microRNA profiles in salivary adenoid cystic carcinoma cells during metastatic progression," *Oncology Letters*, vol. 7, pp. 2029-2034, 2014.

Estal et al., "MicroRNA signatures in hereditary breast cancer," *Breast Cancer Res Treat*, vol. 142, pp. 19-30, 2013.

Inamdar et al., "Targeting the MAPK pathway in melanoma: Why some approaches succeed and other fail," *Biotechnical Pharmacology*, vol. 80, pp. 624-637, 2010.

Kanemaru et al., "The circulating microRNA-221 level in patients with malignant melanoma as a new tumor marker," *Journal of Dermatological Science*, vol. 61, pp. 187-193, 2011.

Li et al., "Characterization of microRNA expression in serous ovarian carcinoma," *International Journal of Molecular Medicine*, vol. 34, pp. 491-498, 2014.

Prakash et al., "Gut microbiota: next frontier in understanding human health and development of biotherapeutics," *Biologics*, vol. 5, pp. 71-86, 2011.

Stark et al., "Characterization of the Melanoma miRNAome by Deep Sequencing," *PLoS One*, 5(3):e9685, 2010 (9 pages).

Stark et al., "miR-514a regulates the tumour suppressor NF1 and modulates BRAFi sensitivity in melanoma," *Oncotarget*, vol. 6, No. 19, pp. 17753-17763, 2015.

Stark et al., "The Prognostic and Predictive Value of Melanoma-related MicroRNAs Using Tissue and Serum: A MicroRNA Expression Analysis," *EBioMedicine*, vol. 2, No. 7, pp. 671-680, 2015.

Taveira Da Cruz et al., "miRNAs and Melanoma: How Are They Connected?," *Dermatology Research and Practice*, vol. 2012, No. 11, pp. 1-12, 2012.

Trinh et al., "Ipilimumab in the treatment of melanoma," *Expert Opin Bio Ther*, vol. 12, No. 6, pp. 773-782, 2012 (Abstract).

Zhang et al., "5-Fluorouracil in combination with cisplatin alters the microRNA expression profile in the CNE nasopharyngeal carcinoma cell line," *Molecular Medicine Reports*, vol. 6, pp. 303-308, 2012.

(Continued)

*Primary Examiner* — Alana Harris Dent

(74) *Attorney, Agent, or Firm* — Wolf, Greenfield & Sacks, P.C.

(57) ABSTRACT

Provided are methods for determining or predicting the diagnosis, prognosis, treatment and therapeutic efficacy of melanoma in a subject, which include evaluating the expression level of one or more miRNA biomarkers including miRNA-4487, miRNA-4706, miRNA-4731 and fragments or variants thereof as an indication of whether the subject may have, or be predisposed to, melanoma.

8 Claims, 60 Drawing Sheets

Specification includes a Sequence Listing.

(56) References Cited

OTHER PUBLICATIONS

International Search Report and Written Opinion for Application No. PCT/AU2015/050487, mailed Oct. 20, 2015.
International Preliminary Report on Patentability (Chapter I) for Application No. PCT/AU2015/050487, mailed Mar. 9, 2017.
Extended European Search Report for Application No. EP 15835092.6, mailed Jan. 25, 2018.
Bonazzi et al., MicroRNA regulation of melanoma progression. Melanoma Res. Apr. 2012;22(2):101-13. doi: 10.1097/CMR.0b013e32834f6fbb.
Chen et al., Identification of microRNA profiles in salivary adenoid cystic carcinoma cells during metastatic progression. Oncol Lett. Jun. 2014;7(6):2029-2034. doi: 10.3892/ol.2014.1975. Epub Mar. 14, 2014.
Da Cruz et al., miRNAs and Melanoma: How Are They Connected? Dermatol Res Pract. 2012;2012:528345. doi: 10.1155/2012/528345. Epub Aug. 10, 2011.
Estal et al., MicroRNA signatures in hereditary breast cancer. Breast Cancer Res Treat. Nov. 2013; 142(1):19-30. doi: 10.1007/s10549-013-2723-7. Epub Oct. 16, 2013.
Inamdar et al., Targeting the MAPK pathway in melanoma: why some approaches succeed and other fail. Biochem Pharmacol. Sep. 1, 2010;80(5):624-37. doi: 10.1016/j.bcp.2010.04.029. Epub May 9, 2010.
Kanemaru et al., The circulating microRNA-221 level in patients with malignant melanoma as a new tumor marker. J Dermatol Sci. Mar. 2011;61(3):187-93. doi: 10.1016/j.jdermsci.2010.12.010. Epub Jan. 13, 2011.
Li et al., Characterization of microRNA expression in serous ovarian carcinoma. International Journal of Molecular Medicine. Aug. 2014;34(2):491-8. Epub Jun. 17, 2014.
Prakash et al., Gut microbiota: next frontier in understanding human health and development of biotherapeutics. Biologics. 2011;5:71-86. doi: 10.2147/BTT.S19099. Epub Jul. 11, 2011.
Stark et al., Characterization of the Melanoma miRNAome by Deep Sequencing. PLoS One. Mar. 12, 2010;5(3):e9685. doi: 10.1371/journal.pone.0009685. 9 pages.
Stark et al., miR-514a regulates the tumour suppressor NF1 and modulates BRAFi sensitivity in melanoma. Oncotarget. Jul. 10, 2015;6(19):17753-63. doi: 10.18632/oncotarget.3924.
Stark et al., The Prognostic and Predictive Value of Melanoma-related MicroRNAs Using Tissue and Serum: A MicroRNA Expression Analysis. EBioMedicine. May 12, 2015;2(7):671-80. doi: 10.1016/j.ebiom.2015.05.011.
Trinh et al., Ipilimumab in the treatment of melanoma. Expert Opin Biol Ther. Jun. 2012;12(6):773-82. doi: 10.1517/14712598.2012.675325. Epub Apr. 14, 2012.
Zhang et al., 5-Fluorouracil in combination with cisplatin alters the microRNA expression profile in the CNE nasopharyngeal carcinoma cell line. Mol Med Rep. Aug. 2012;6(2):303-8. doi: 10.3892/mmr.2012.917. Epub May 16, 2012.

* cited by examiner

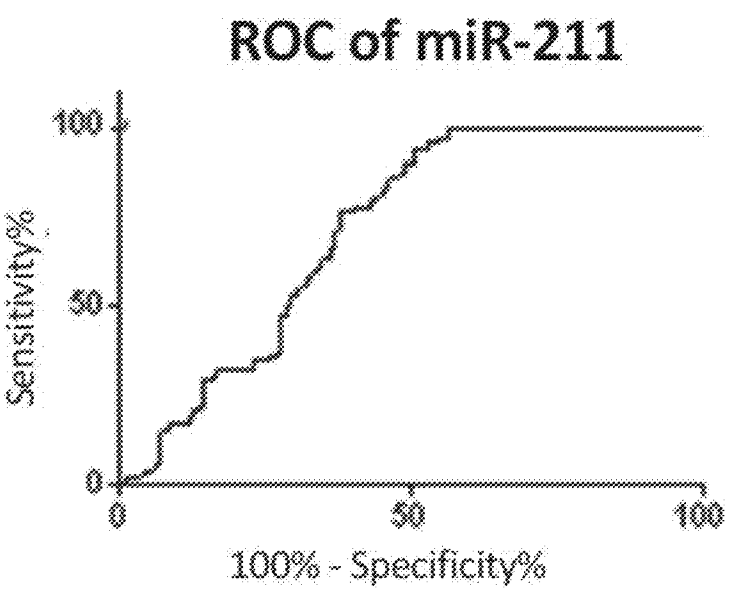
| Area under the ROC curve | |
|---|---|
| Area | 0.7129 |
| Std. Error | 0.03414 |
| 95% confidence interval | 0.6460 to 0.7799 |
| P value | < 0.0001 |
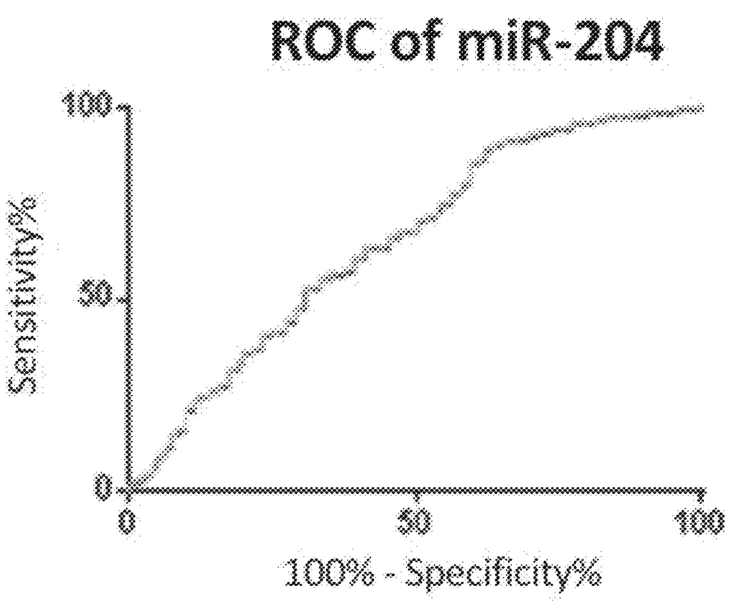
| Area under the ROC curve | |
|---|---|
| Area | 0.6442 |
| Std. Error | 0.03510 |
| 95% confidence interval | 0.5753 to 0.7130 |
| P value | < 0.0001 |
FIG. 7A ROC of miR-4487
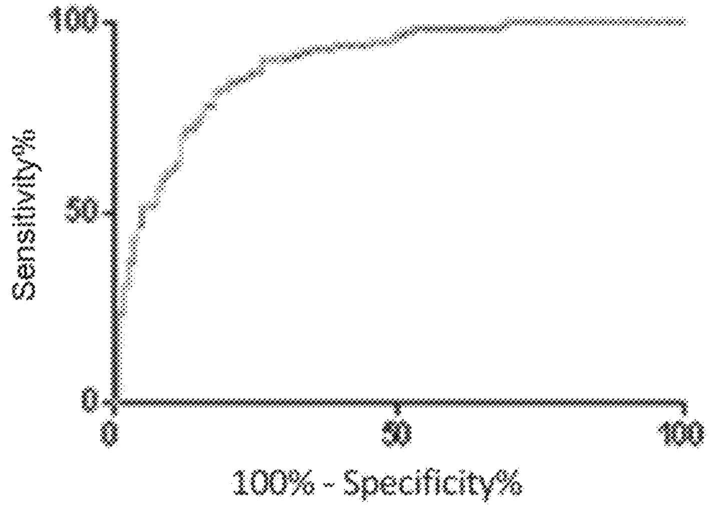
| Area under the ROC curve | |
|---|---|
| Area | 0.8878 |
| Std. Error | 0.02078 |
| 95% confidence interval | 0.8470 to 0.9285 |
| P value | < 0.0001 |
ROC of miR-4706
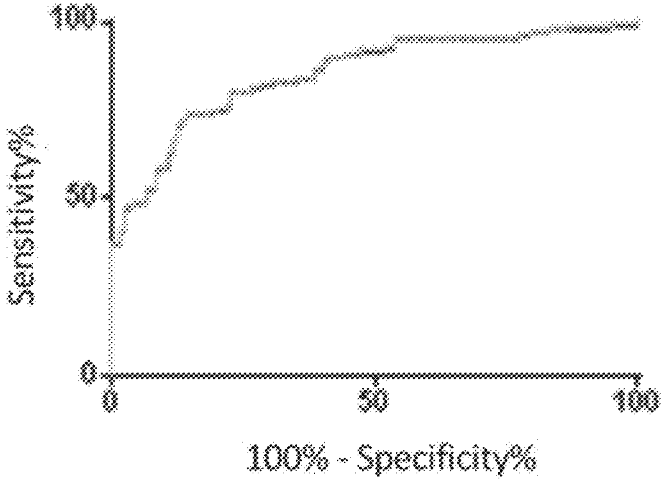
| Area under the ROC curve | |
|---|---|
| Area | 0.8540 |
| Std. Error | 0.02376 |
| 95% confidence interval | 0.8074 to 0.9006 |
| P value | < 0.0001 |
FIG. 7B

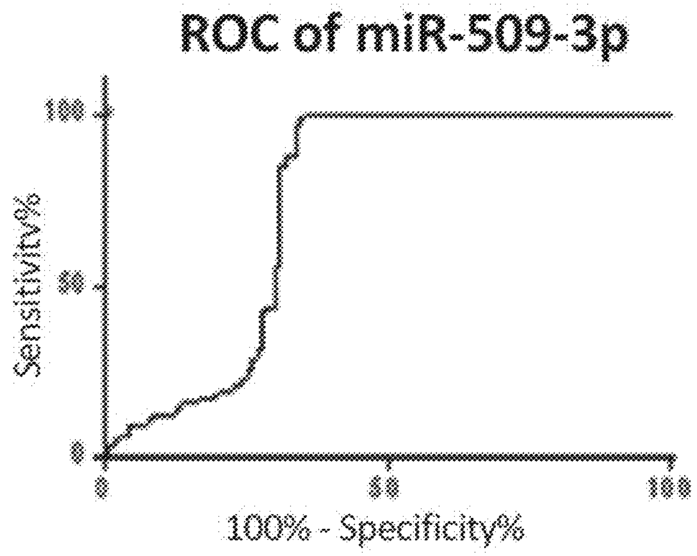
| Area under the ROC curve | |
|---|---|
| Area | 0.7407 |
| Std. Error | 0.03618 |
| 95% confidence interval | 0.6698 to 0.8117 |
| P value | < 0.0001 |
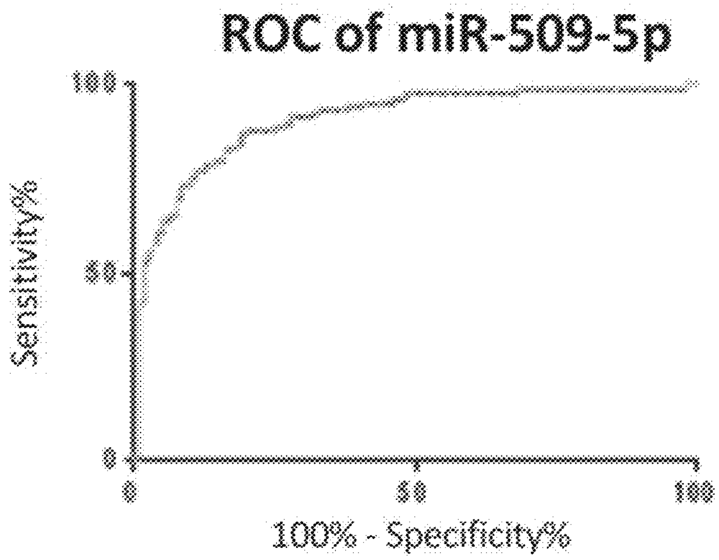
| Area under the ROC curve | |
|---|---|
| Area | 0.9051 |
| Std. Error | 0.01944 |
| 95% confidence interval | 0.8670 to 0.9432 |
| P value | < 0.0001 |
FIG. 7C ROC of miR-16
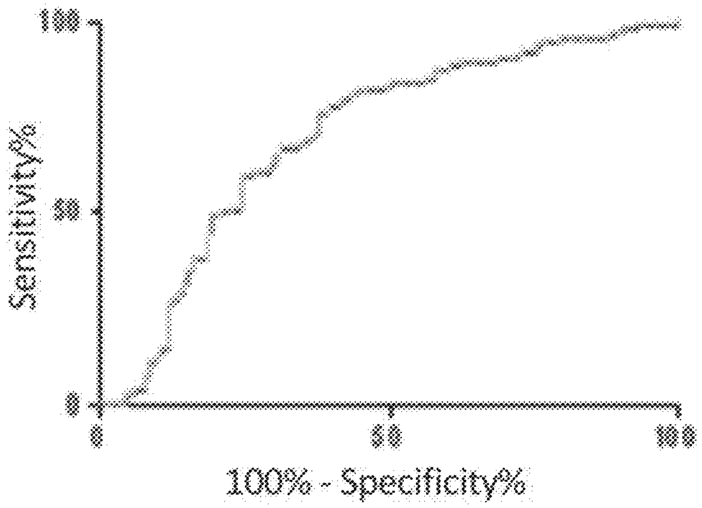
| Area under the ROC curve | |
|---|---|
| Area | 0.7016 |
| Std. Error | 0.03407 |
| 95% confidence interval | 0.6348 to 0.7684 |
| P value | < 0.0001 |
ROC of miR-4731
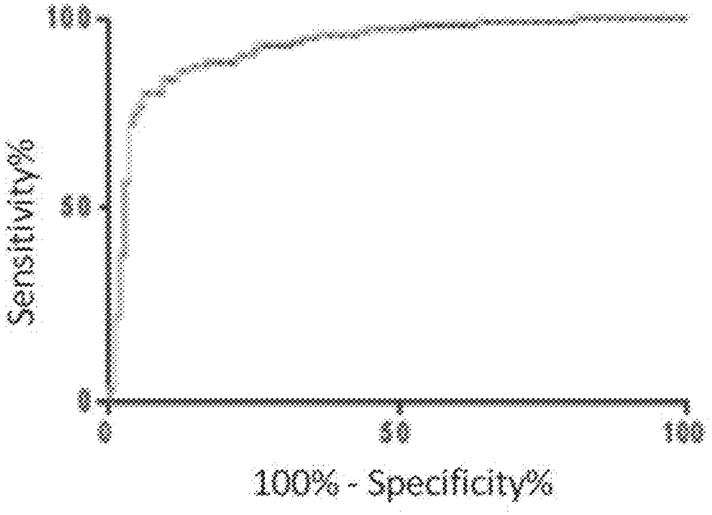
| Area under the ROC curve | |
|---|---|
| Area | 0.9269 |
| Std. Error | 0.01709 |
| 95% confidence interval | 0.8934 to 0.9604 |
| P value | < 0.0001 |
FIG. 7D

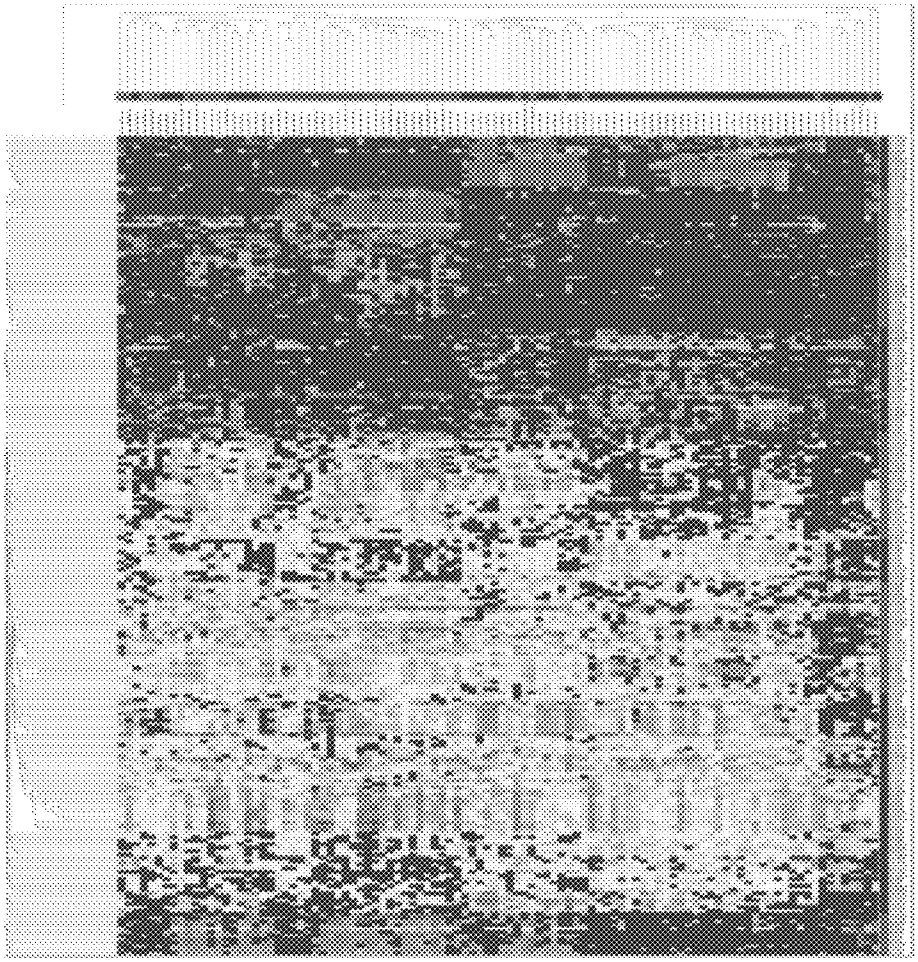

Legend – Hierarchical Combined Tree on All Samples

Color range

-4.7 0 4.7

Condition color by MELvsOTHER

- Control
- MEL-SERUM
- Melanoma
- Naevus
- OTHER
- UMM

Entity color by Regulation

- down
- up

Description

Created from Advanced Analysis operation: Clustering:
Entity List: Mann-Whitney unpaired [Melanoma] Vs [OTHER] P <= 0.05 >= 2.0 Interpretation: All Samples
Experiment: Normalized_raw <30setTo0.01_excludenormalPlasma
Clustering Algorithm: Hierarchical
Clustered By: Normalized intensity values
Clustered On: Entities and Conditions
Similarity Measure: Euclidean
Linkage Rule: Average
Cluster Within Conditions: 0

FIG. 8 mir-4487 is derived from the stem loop sequence of hsa-miR-4487 on Chr 11.

Mature Sequence

>hsa-miR-4487 MIMAT0019021
AGAGCUGGCUGAAGGGCAG

Stem Loop

>hsa-mir-4487 MI0016848 Coordinates (GRCh38)
chr11: 47400970-47401042 [+]
ACUGUCCUUCAGCCAGAGCUGGCUGAAGGGCAGAAGGGAACUGUCCUUCAGCCAGAGCUGGCUGAAGGGCAGA

Observed isomiR sequence (sequence variation) (http://www.mirbase.org/cgi-bin/get_read.pl?acc=MI0016848)

```
                                                         hsa-miR-4487       Count
ACUGUCCUUCAGCCAGAGCU.....................................................  1
....UCCUUCAGCCAGAGCUGGCU.................................................  1
.........CAGCCAGAGCUGGCUGAAGGGC..........................................  1
............CCAGAGCUGGCUGAAGGGCA.........................................  24
............CCAGAGCUGGCUGAAGGGCAG........................................  21
............CCAGAGCUGGCUGAAGGGC..........................................  2
............CCAGAGCUGGCUGAAGGGCAGAA......................................  2
.............CAGAGCUGGCUGAAGGGCAGA.......................................  54
.............CAGAGCUGGCUGAAGGGCAGAA......................................  24
..............AGAGCUGGCUGAAGGGCAGAA......................................  14
..............AGAGCUGGCUGAAGGGCAG........................................  13
..............AGAGCUGGCUGAAGGGCAGA.......................................  8
...............GAGCUGGCUGAAGGGCAGAA......................................  6
...............GAGCUGGCUGAAGGGCAGAAG.....................................  2
................AGCUGGCUGAAGGGCAGAAGG....................................  5
................AGCUGGCUGAAGGGCAGAA......................................  3
................AGCUGGCUGAAGGGCAGAAG.....................................  2
................AGCUGGCUGAAGGGCAGAAGGG...................................  1
.................GCUGGCUGAAGGGCAGAAGG....................................  8
.................GCUGGCUGAAGGGCAGAAGGGAACUGU.............................  1
.................GCUGGCUGAAGGGCAGAAG.....................................  1
..................CUGGCUGAAGGGCAGAAGG....................................  1
..................CUGGCUGAAGGGCAGAAGGGAA.................................  1
........................GAAGGGCAGAAGGGA..................................  1
..........................AGGGCAGAAGGGAACUGUC............................  1
...................................GGGAACUGUCCUUCAGCC....................  1
.................................................AGCCAGAGCUGGCUGAAGGGCA..  3
.................................................AGCCAGAGCUGGCUGAAGGGC...  2
...................................................CCAGAGCUGGCUGAAGGGCAGA  12
....................................................CAGAGCUGGCUGAAGGGCAG.  31
....................................................CAGAGCUGGCUGAAGGGCA..  21
....................................................CAGAGCUGGCUGAAG......  1
......................................................GAGCUGGCUGAAGGGCAGA  3
..........................................................UGGCUGAAGGGCAGA  1
ACUGUCCUUCAGCCAGAGCUGGCUGAAGGGCAGAAGGGAACUGUCCUUCAGCCAGAGCUGGCUGAAGGGCAGA
.(((((((((((((((..(((((((((((((((.......)))))))))))))))..))))))))))))))).  (-62.10)
```

FIG. 10 mir-4706 is derived from the stem loop sequence of hsa-miR-4706 on Chr 14.

Mature Sequence

>hsa-miR-4706 MIMAT0019806
AGCGGGGAGGAAGUGGGCGCUGCUU

Stem Loop

>hsa-mir-4706 MI0017339 Coordinates (GRCh38)
Chr14: 65044688-65044769 [+]
GCUACGGGGAGCGGGGAGGAAGUGGGCGCUGCUUCUGCGUUAUCUGGAAGGAGCAGCCCACUCCUGUCCUGGGCU
CUGUGGU

Observed isomiR sequences (sequence variation) (http://www.mirbase.org/cgi-bin/get_read.pl?acc=MI0017339)

```
          hsa-miR-4706                                                                  Count
.........AGCGGGGAGGAAGUGGGCGCUGCUU................................................   7
.........AGCGGGGAGGAAGUGGGCGCU....................................................   3
.........AGCGGGGAGGAAGUGGGCGCUGCU.................................................   2
GCUACGGGGAGCGGGGAGGAAGUGGGCGCUGCUUCUGCGUUAUCUGGAAGGAGCAGCCCACUCCUGUCCUGGGCUCUGUGGU
(((((((((..(((((((((.(((((((((.(((((.........))))).))).)))))))))).)))))..))))))))) (~47.70)
```

FIG. 11 mir-4731-5p is derived from the stem loop sequence of hsa-miR-4731 on Chr 17.

Mature Sequence

>hsa-miR-4731-5p MIMAT0019853
UGCUGGGGGCCACAUGAGUGUG

Stem Loop

>hsa-mir-4731 MI0017368 Coordinates (GRCh38)
Chr17: 15251627-15251696 [-]
CCCUGCCAGUGCUGGGGGCCACAUGAGUGUGCAGUCAUCCACACACAAGUGGCCCCCAACACUGGCAGGG

Observed isomiR sequences (sequence variation) (http://www.mirbase.org/cgi-bin/get_read.pl?acc=MI0017368)

```
         hsa-miR-4731-5p                  hsa-miR-4731-3p              Count
.........UGCUGGGGGCCACAUGAGUGU........................................   3
..........GCUGGGGGCCACAUGAGUGU........................................   5
CCCUGCCAGUGCUGGGGGCCACAUGAGUGUGCAGUCAUCCACACACAAGUGGCCCCCAACACUGGCAGGG
((((((((((.((((((((((.((.((((((........)))))).)).)))))))))).)))))))))) (-55.50)
```

FIG. 12 mir-16-5p is derived from the stem loop sequences of hsa-miR-16-1 on Chr 13 and hsa-miR-16-1 on Chr 3.

Mature Sequence
>hsa-mir-16-5p MIMAT0000069
UAGCAGCACGUAAAUAUUGGCG

Stem Loop
>hsa-mir-16-1 MI0000070 Coordinates (GRCh38)
chr13: 50048973-50049061 [-]
GUCAGCAGUGCCUUAGCAGCACGUAAAUAUUGGCGUUAAGAUUCUAAAAUUAUCUCCAGUAUUAACUGUGCUGCU
GAAGUAAGGUUGAC >hsa-mir-16-2 MI0000115 Coordinates (GRCh38)
chr3: 160404745-160404825 [+]
GUUCCACUCUAGCAGCACGUAAAUAUUGGCGUAGUGAAAUAUAUAUUAAACACCAAUAUUACUGUGCUGCUUUAG
UGUGAC

Observed isomiR sequences (sequence variation) (http://www.mirbase.org/cgi-bin/get_read.pl?acc=MI0000070)

```
              hsa-miR-16-5p                                   hsa-miR-16-1-2p          Count
............UUAGCAGCACGUAAAUAUUGGCG...................................................... 8
............UUAGCAGCACGUAAAUAU........................................................... 2
............UUAGCAGCACGUAAAUAUUGGC....................................................... 2
.............UAGCAGCACGUAAAUAUUGGCGUU....................................................610
.............UAGCAGCACGUAAAUAUU..........................................................402
.............UAGCAGCACGUAAAUA............................................................113
.............UAGCAGCACGUAAAUAUUGGCG...................................................... 55
.............UAGCAGCACGUAAAUAUUGGCGUUA................................................... 36
.............UAGCAGCACGUAAAUAUUG......................................................... 36
.............UAGCAGCACGUAAAUAUUGG........................................................ 27
.............UAGCAGCACGUAAAU............................................................. 16
.............UAGCAGCACGUAAAUAUUGGCGU..................................................... 12
.............UAGCAGCACGUAAAUAU........................................................... 10
.............UAGCAGCACGUAAAUAUUGGC....................................................... 5
.............UAGCAGCACGUAAAUAUUGGCGUUAAG................................................. 1
..............AGCAGCACGUAAAUAUUGGC....................................................... 65
..............AGCAGCACGUAAAUAUUGGCGU..................................................... 45
..............AGCAGCACGUAAAUAUUGG........................................................ 11
..............AGCAGCACGUAAAUAUU.......................................................... 2
..............AGCAGCACGUAAAUAUUGGCGUU.................................................... 2
..............AGCAGCACGUAAAUAUUGGCG...................................................... 1
...............GCAGCACGUAAAUAUUGGCG...................................................... 27
...............GCAGCACGUAAAUAUUGGC....................................................... 5
...............GCAGCACGUAAAUAUUGGCGU..................................................... 4
...............GCAGCACGUAAAUAUUGGCGUU.................................................... 1
................CAGCACGUAAAUAUUGGC....................................................... 23
................CAGCACGUAAAUAUUGGCG...................................................... 4
................CAGCACGUAAAUAUUGGCGU..................................................... 2
.................AGCACGUAAAUAUUGGCGU..................................................... 20
.................AGCACGUAAAUAUUGGC....................................................... 14
.................AGCACGUAAAUAUUGGCG...................................................... 2
.................AGCACGUAAAUAUUGG........................................................ 1
.................AGCACGUAAAUAUUG......................................................... 1
.................AGCACGUAAAUAUUGGCGUU.................................................... 1
..................GCACGUAAAUAUUGGC....................................................... 10
..................GCACGUAAAUAUUGG........................................................ 5
..................GCACGUAAAUAUUGGCGU..................................................... 4
..................GCACGUAAAUAUUGGCG...................................................... 3
...................CACGUAAAUAUUGGC....................................................... 43
...................CACGUAAAUAUUGGCG...................................................... 40
...................CACGUAAAUAUUGGCGU..................................................... 33
...................CACGUAAAUAUUGGCGUU.................................................... 3
....................ACGUAAAUAUUGGCG...................................................... 2
```

FIG. 13A

```
....................ACGUAAAUAUUGGCGUU....................................................  1
....................ACGUAAAUAUUGGCGU.....................................................  1
.....................CGUAAAUAUUGGCGU.....................................................  6
......................GUAAAUAUUGGCGUU....................................................  1
...................................UUAAGAUUCUAAAAUUAUCU..................................  1
...................................UUAAGAUUCUAAAAUUAU....................................  1
...................................UUAAGAUUCUAAAAUUA.....................................  1
.....................................................CUCCAGUAUUAACUGUGCUGCUGA............  1
.....................................................CUCCAGUAUUAACUGUGCUGCU..............  1
.......................................................CCAGUAUUAACUGUGCUGCUGA............ 37
.......................................................CCAGUAUUAACUGUGCUGCUGAA........... 25
.......................................................CCAGUAUUAACUGUGCUGCUG.............  8
.......................................................CCAGUAUUAACUGUGCUGC...............  1
........................................................CAGUAUUAACUGUGCUGCUGA............  1
.........................................................AGUAUUAACUGUGCUGCUGAA...........  2
.........................................................AGUAUUAACUGUGCUGCUG.............  1
GUCAGCAGUGCCUUAGCAGCACGUAAAUAUUGGCGUUAAGAUUCUAAAAUUAUCUCCAGUAUUAACUGUGCUGCUGAAGUAAGGUUGAC
{{{{{{..{{{.{{{{{{{{{{{{.{{{{{{{{.{.{{{..........}}}.}.}}}}}}}}.}}.}}}}}}}}}}.}}}..}}}}}} (-37.70)
```

FIG. 13B mir-211-5p is derived from the stem loop sequences of hsa-miR-211 which is located on Chr. 15.

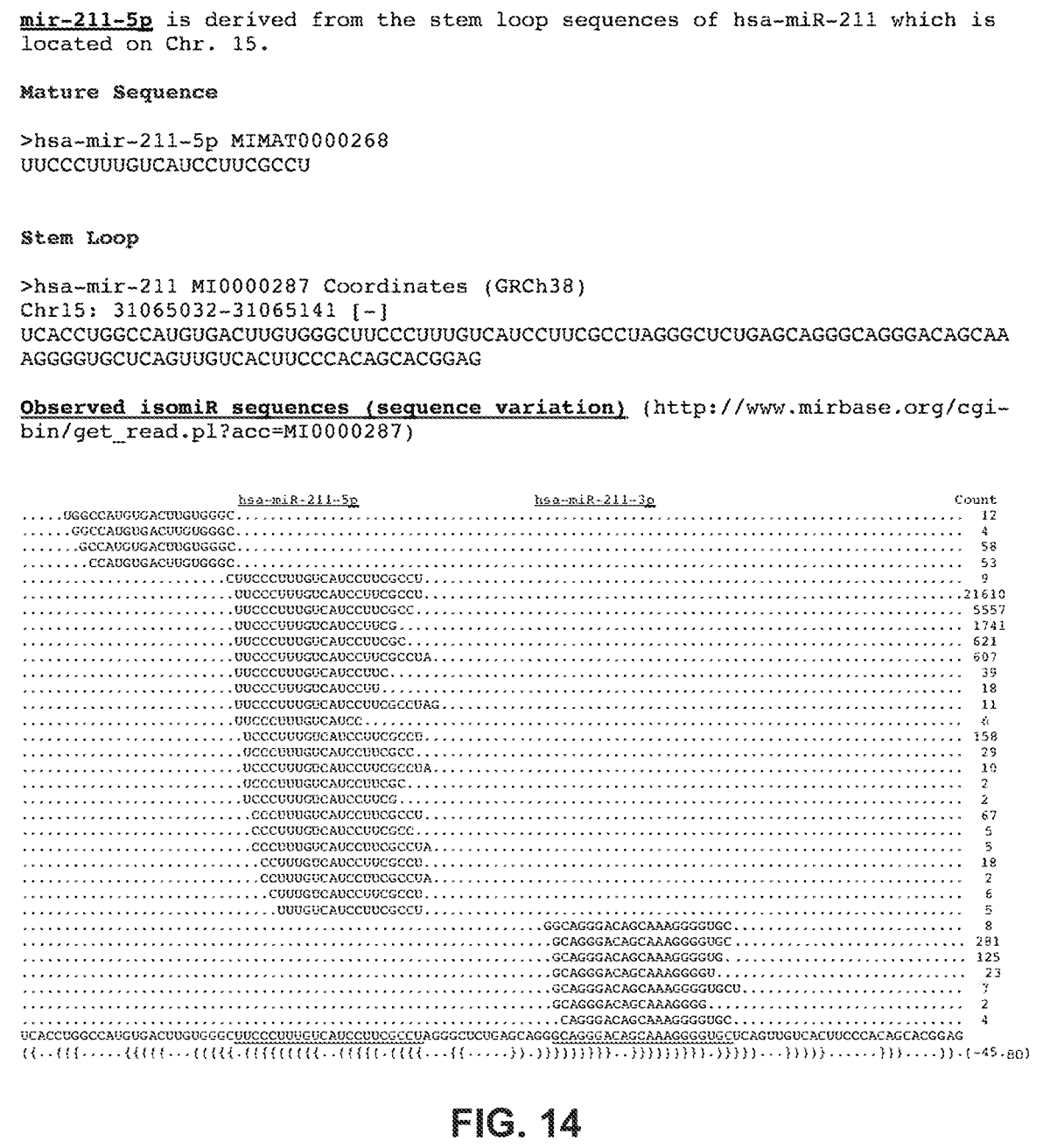

Mature Sequence

>hsa-mir-211-5p MIMAT0000268
UUCCCUUUGUCAUCCUUCGCCU

Stem Loop

>hsa-mir-211 MI0000287 Coordinates (GRCh38)
Chr15: 31065032-31065141 [-]
UCACCUGGCCAUGUGACUUGUGGGCUUCCCUUUGUCAUCCUUCGCCUAGGGCUCUGAGCAGGGCAGGGACAGCAAAGGGGUGCUCAGUUGUCACUUCCCACAGCACGGAG

Observed isomiR sequences (sequence variation) (http://www.mirbase.org/cgi-bin/get_read.pl?acc=MI0000287)

| hsa-miR-211-5p / hsa-miR-211-3p | Count |
|---|---|
| UGGCCAUGUGACUUGUGGGC | 12 |
| GGCCAUGUGACUUGUGGGC | 4 |
| GCCAUGUGACUUGUGGGC | 58 |
| CCAUGUGACUUGUGGGC | 53 |
| CUUCCCUUUGUCAUCCUUCGCCU | 9 |
| UUCCCUUUGUCAUCCUUCGCCU | 21610 |
| UUCCCUUUGUCAUCCUUCGCC | 5557 |
| UUCCCUUUGUCAUCCUUCG | 1741 |
| UUCCCUUUGUCAUCCUUCGC | 621 |
| UUCCCUUUGUCAUCCUUCGCCUA | 607 |
| UUCCCUUUGUCAUCCUUC | 39 |
| UUCCCUUUGUCAUCCUU | 18 |
| UUCCCUUUGUCAUCCUUCGCCUAG | 11 |
| UUCCCUUUGUCAUCC | 6 |
| UCCCUUUGUCAUCCUUCGCCU | 158 |
| UCCCUUUGUCAUCCUUCGCC | 29 |
| UCCCUUUGUCAUCCUUCGCCUA | 10 |
| UCCCUUUGUCAUCCUUCGC | 2 |
| UCCCUUUGUCAUCCUUCG | 2 |
| CCCUUUGUCAUCCUUCGCCU | 67 |
| CCCUUUGUCAUCCUUCGCC | 5 |
| CCCUUUGUCAUCCUUCGCCUA | 5 |
| CCUUUGUCAUCCUUCGCCU | 18 |
| CCUUUGUCAUCCUUCGCCUA | 2 |
| CUUUGUCAUCCUUCGCCU | 6 |
| UUUGUCAUCCUUCGCCU | 5 |
| GGCAGGGACAGCAAAGGGGUGC | 8 |
| GCAGGGACAGCAAAGGGGUGC | 281 |
| GCAGGGACAGCAAAGGGGUG | 125 |
| GCAGGGACAGCAAAGGGGU | 23 |
| GCAGGGACAGCAAAGGGGUGCU | 7 |
| GCAGGGACAGCAAAGGGG | 2 |
| CAGGGACAGCAAAGGGGUGC | 4 |

UCACCUGGCCAUGUGACUUGUGGGCUUCCCUUUGUCAUCCUUCGCCUAGGGCUCUGAGCAGGGCAGGGACAGCAAAGGGGUGCUCAGUUGUCACUUCCCACAGCACGGAG
(( . . ((( . . . . . ((((( . . . ((((( . ((((((((( . . ((((( . (((( . . . (( . . . . . )) . )))))))))) . . ))))))))) . ))))) . . . ))))) . . . . . . ))) . . . . )) . (-45.80)

FIG. 14

<u>mir-509-3p and miR-509-5p</u> are derived from the stem loop sequences hsa-mir-509-1, hsa-mir-509-2, and hsa-mir-509-3 which are located at three genomic locations on ChrX.

Mature Sequence

>hsa-miR-509-3p MIMAT0002881
UGAUUGGUACGUCUGUGGGUAG

>hsa-miR-509-5p MIMAT0004779
UACUGCAGACAGUGGCAAUCA

Stem Loop

>hsa-mir-509-1 MI0003196 Coordinates (GRCh38)
ChrX: 147260532-147260625 [-]
CAUGCUGUGUGUGGUACCCUACUGCAGACAGUGGCAAUCAUGUAUAAUUAAAAAUGAUUGGUACGUCUGUGGGUA
GAGUACUGCAUGACACAUG >hsa-mir-509-2 MI0005530 Coordinates (GRCh38)
ChrX: 147258760-147258850 [-]
CAUGCUGUGUGUGGUACCCUACUGCAGACAGUGGCAAUCAUGUAUAAUUAAAAAUGAUUGGUACGUCUGUGGGUA
GAGUACUGCAUGACAC >hsa-mir-509-3 MI0005717 Coordinates (GRCh38)
ChrX: 147259652-147259726 [-]
GUGGUACCCUACUGCAGACGUGGCAAUCAUGUAAUUAAAAAUGAUUGGUACGUCUGUGGGUAGAGUACUGCAU <u>Observed isomiR sequences (sequence variation)</u> (http://www.mirbase.org/cgi-bin/get_read.pl?acc=MI0003196)

```
                   hsa-miR-509-5p                   hsa-miR-509-3p              Count
CAUGCUGUGUGUGGUACCC........................................................................... 2
...................UACUGCAGACAGUGGCAAUCAUG.................................................... 5820
...................UACUGCAGACAGUGGCAAUCAU..................................................... 1411
...................UACUGCAGACAGUGGCAAUCA...................................................... 835
...................UACUGCAGACAGUGGCAAUCAUGU................................................... 202
...................UACUGCAGACAGUGGCAAUC....................................................... 112
...................UACUGCAGACAGUGGCAAU........................................................ 66
...................UACUGCAGACAGUGGCAA......................................................... 28
...................UACUGCAGACAGUGGCAAUCAUGUA.................................................. 7
...................UACUGCAGACAGUGGCAAUCAUGUAU................................................. 2
....................ACUGCAGACAGUGGCAAUCAUG.................................................... 40
....................ACUGCAGACAGUGGCAAUCA...................................................... 9
....................ACUGCAGACAGUGGCAAUCAU..................................................... 6
.....................CUGCAGACAGUGGCAAUCAU..................................................... 2
.....................CUGCAGACAGUGGCAAUCAUG.................................................... 2
....................................................AAUGAUUGGUACGUCUGUGGGUAGA................. 127
....................................................AAUGAUUGGUACGUCUGUGGGUAG.................. 66
.....................................................AUGAUUGGUACGUCUGUGGGUAG.................. 38
.....................................................AUGAUUGGUACGUCUGUGGGUAGA................. 32
......................................................UGAUUGGUACGUCUGUGGGUAGA................. 9115
......................................................UGAUUGGUACGUCUGUGGGUAG.................. 2092
......................................................UGAUUGGUACGUCUGUGGGUA................... 120
......................................................UGAUUGGUACGUCUGUGGGU.................... 49
......................................................UGAUUGGUACGUCUGUGGG..................... 35
......................................................UGAUUGGUACGUCUGUG....................... 2
.......................................................GAUUGGUACGUCUGUGGGUAGA................. 21
.......................................................GAUUGGUACGUCUGUGGGUAG.................. 2
........................................................AUUGGUACGUCUGUGGGUAGA................. 85
........................................................AUUGGUACGUCUGUGGGUAG.................. 6
........................................................AUUGGUACGUCUGUGGGUA................... 2
CAUGCUGUGUGUGGUACCCUACUGCAGACAGUGGCAAUCAUGUAUAAUUAAAAAUGAUUGGUACGUCUGUGGGUAGAGUACUGCAUGACACAUG
((((.((((((..((((.((((..(((((.(((.((((((.((....))...)))))).)))))))..).))).))))..))).))))))) (-40.90)
```

FIG. 15

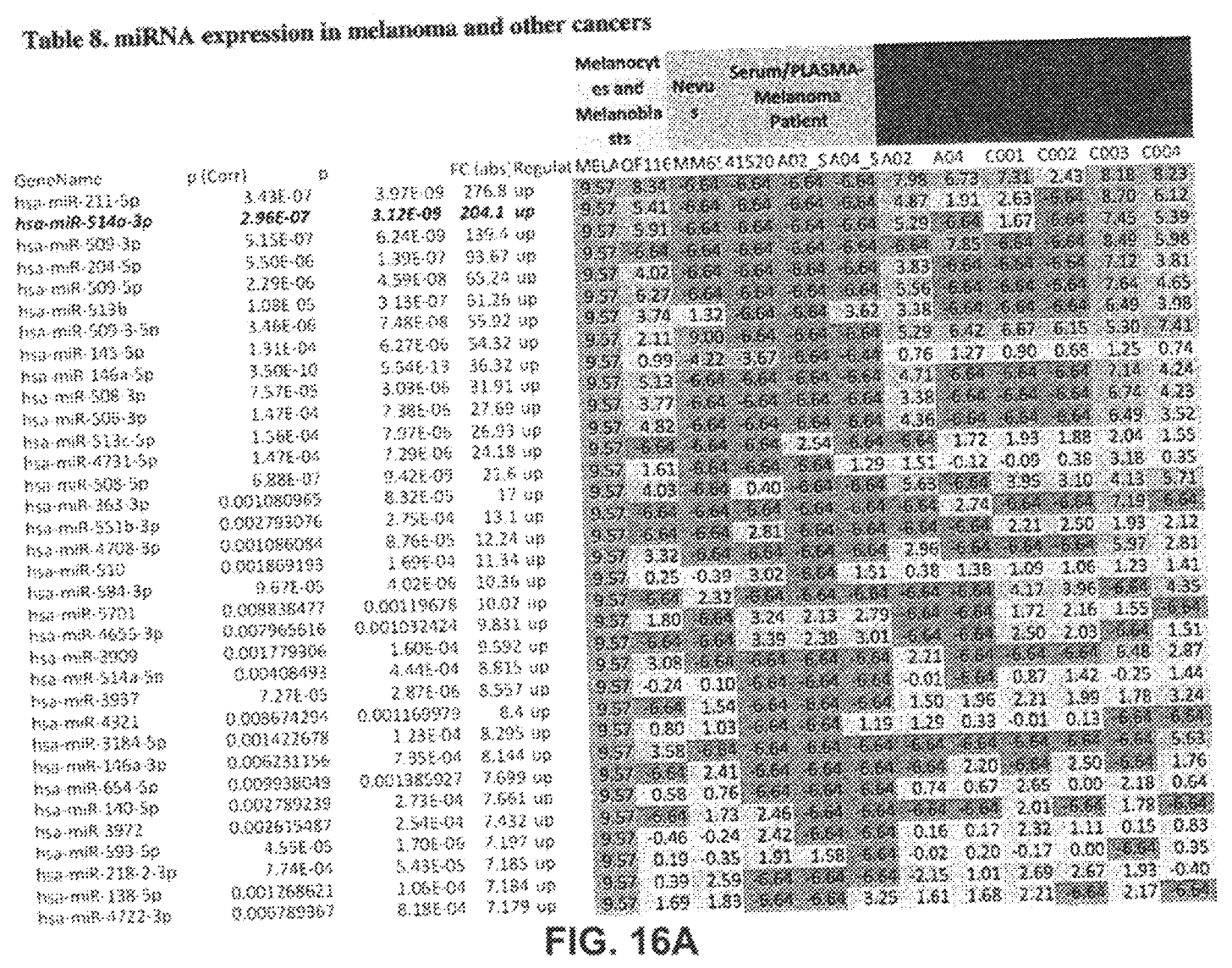

Table 8. miRNA expression in melanoma and other cancers

| | | | | | Melanocytes and Melanoblasts | Nevus | Serum/PLASMA-Melanoma Patient | | | | | | | | | |
|---|---|---|---|---|---|---|---|---|---|---|---|---|---|---|---|---|
| GeneName | p (Corr) | p | FC (abs) | Regulat | MELA | OF11 | MM6 | 41520 | A02_S | A04_S | A02 | A04 | C001 | C002 | C003 | C004 |
| hsa-miR-211-5p | 3.43E-07 | 3.97E-09 | 276.8 | up | 9.57 | 8.34 | 6.64 | 6.64 | 6.64 | 6.64 | 7.98 | 6.73 | 7.31 | 2.43 | 8.18 | 8.23 |
| ***hsa-miR-514a-3p*** | ***2.96E-07*** | ***3.12E-09*** | ***204.1*** | ***up*** | 9.57 | 5.41 | 6.64 | 6.64 | 6.64 | 6.64 | 4.87 | 1.91 | 2.63 | 6.64 | 8.70 | 6.12 |
| hsa-miR-509-3p | 9.15E-07 | 6.24E-09 | 139.4 | up | 9.57 | 5.91 | 6.64 | 6.64 | 6.64 | 6.64 | 5.29 | 6.64 | 1.67 | 6.64 | 7.45 | 5.39 |
| hsa-miR-204-5p | 5.50E-06 | 1.39E-07 | 93.67 | up | 9.57 | 6.64 | 6.64 | 6.64 | 6.64 | 6.64 | 6.64 | 7.85 | 6.64 | 6.64 | 8.49 | 5.98 |
| hsa-miR-509-5p | 2.29E-06 | 4.59E-08 | 65.24 | up | 9.57 | 4.02 | 6.64 | 6.64 | 6.64 | 6.64 | 3.83 | 6.64 | 6.64 | 6.64 | 7.12 | 3.81 |
| hsa-miR-513b | 1.08E-05 | 3.13E-07 | 61.26 | up | 9.57 | 6.27 | 6.64 | 6.64 | 6.64 | 6.64 | 3.56 | 6.64 | 6.64 | 6.64 | 7.64 | 4.65 |
| hsa-miR-509-3-5p | 3.46E-06 | 7.48E-08 | 55.92 | up | 9.57 | 3.74 | 1.32 | 6.64 | 6.64 | 3.62 | 3.38 | 6.64 | 6.64 | 6.64 | 6.49 | 3.98 |
| hsa-miR-143-5p | 1.91E-04 | 6.27E-06 | 54.32 | up | 9.57 | 2.11 | 9.00 | 6.64 | 6.64 | 6.64 | 5.29 | 6.42 | 6.67 | 6.15 | 5.30 | 7.41 |
| hsa-miR-146a-5p | 3.50E-10 | 5.54E-13 | 36.32 | up | 9.57 | 0.99 | 4.22 | 3.67 | 6.64 | 6.64 | 0.76 | 1.27 | 0.90 | 0.68 | 1.25 | 0.74 |
| hsa-miR-508-3p | 7.57E-05 | 3.09E-06 | 31.91 | up | 9.57 | 5.13 | 6.64 | 6.64 | 6.64 | 6.64 | 4.71 | 6.64 | 6.64 | 6.64 | 7.14 | 4.24 |
| hsa-miR-506-3p | 1.47E-04 | 7.38E-06 | 27.69 | up | 9.57 | 3.77 | 6.64 | 6.64 | 6.64 | 6.64 | 3.38 | 6.64 | 6.64 | 6.64 | 6.74 | 4.23 |
| hsa-miR-513c-5p | 1.56E-04 | 7.97E-06 | 26.93 | up | 9.57 | 4.82 | 6.64 | 6.64 | 6.64 | 6.64 | 4.36 | 6.64 | 6.64 | 6.64 | 6.49 | 3.52 |
| hsa-miR-4731-5p | 1.47E-04 | 7.29E-06 | 24.18 | up | 9.57 | 6.64 | 6.64 | 6.64 | 2.54 | 6.64 | 6.64 | 1.72 | 1.93 | 1.88 | 2.04 | 1.55 |
| hsa-miR-508-5p | 6.88E-07 | 9.42E-09 | 21.6 | up | 9.57 | 1.61 | 6.64 | 6.64 | 6.64 | 1.29 | 1.51 | -0.12 | -0.09 | 0.38 | 3.18 | 0.35 |
| hsa-miR-363-3p | 0.001080965 | 8.32E-05 | 17 | up | 9.57 | 4.03 | 6.64 | 0.40 | 6.64 | 6.64 | 5.63 | 6.64 | 3.95 | 3.10 | 4.13 | 5.71 |
| hsa-miR-551b-3p | 0.002793076 | 2.75E-04 | 13.1 | up | 9.57 | 6.64 | 6.64 | 6.64 | 6.64 | 6.64 | 6.64 | 2.74 | 6.64 | 6.64 | 7.19 | 6.64 |
| hsa-miR-4708-3p | 0.001086084 | 8.76E-05 | 12.24 | up | 9.57 | 6.64 | 6.64 | 2.81 | 6.64 | 6.64 | 6.64 | 6.64 | 2.21 | 2.50 | 1.93 | 2.12 |
| hsa-miR-510 | 0.001869193 | 1.69E-04 | 11.34 | up | 9.57 | 3.32 | 6.64 | 6.64 | 6.64 | 6.64 | 2.96 | 6.64 | 6.64 | 6.64 | 5.97 | 2.81 |
| hsa-miR-584-3p | 9.67E-05 | 4.02E-06 | 10.36 | up | 9.57 | 0.25 | -0.39 | 3.02 | 6.64 | 1.51 | 0.38 | 1.38 | 1.09 | 1.06 | 1.23 | 1.41 |
| hsa-miR-5701 | 0.008838477 | 0.00119678 | 10.02 | up | 9.57 | 6.64 | 2.32 | 6.64 | 6.64 | 6.64 | 6.64 | 6.64 | 4.17 | 3.96 | 6.64 | 4.35 |
| hsa-miR-4655-3p | 0.007965616 | 0.001032424 | 9.831 | up | 9.57 | 1.80 | 6.64 | 3.24 | 2.13 | 2.79 | 6.64 | 6.64 | 1.72 | 2.16 | 1.55 | 6.64 |
| hsa-miR-3909 | 0.001779306 | 1.60E-04 | 9.592 | up | 9.57 | 6.64 | 6.64 | 3.39 | 2.38 | 3.01 | 6.64 | 6.64 | 2.50 | 2.03 | 6.64 | 1.51 |
| hsa-miR-514a-5p | 0.00408493 | 4.44E-04 | 8.815 | up | 9.57 | 3.08 | 6.64 | 6.64 | 6.64 | 6.64 | 2.21 | 6.64 | 6.64 | 6.64 | 6.48 | 2.87 |
| hsa-miR-3937 | 7.27E-05 | 2.87E-06 | 8.557 | up | 9.57 | -0.24 | 0.10 | 6.64 | 6.64 | 6.64 | -0.01 | 6.64 | 0.87 | 1.42 | -0.25 | 1.44 |
| hsa-miR-4921 | 0.008674294 | 0.001169979 | 8.4 | up | 9.57 | 6.64 | 1.54 | 6.64 | 6.64 | 6.64 | 1.50 | 1.96 | 2.21 | 1.99 | 1.78 | 3.24 |
| hsa-miR-3184-5p | 0.001422678 | 1.23E-04 | 8.295 | up | 9.57 | 0.80 | 1.03 | 6.64 | 6.64 | 1.19 | 1.29 | 0.33 | -0.01 | 0.13 | 6.64 | 6.64 |
| hsa-miR-146a-3p | 0.006231156 | 7.35E-04 | 8.144 | up | 9.57 | 3.58 | 6.64 | 6.64 | 6.64 | 6.64 | 6.64 | 6.64 | 6.64 | 6.64 | 6.64 | 5.63 |
| hsa-miR-654-5p | 0.009938049 | 0.001385927 | 7.699 | up | 9.57 | 6.64 | 2.41 | 6.64 | 6.64 | 6.64 | 6.64 | 2.20 | 6.64 | 2.50 | 6.64 | 1.76 |
| hsa-miR-140-5p | 0.002789239 | 2.73E-04 | 7.661 | up | 9.57 | 0.58 | 0.76 | 6.64 | 6.64 | 6.64 | 0.74 | 0.67 | 2.65 | 0.00 | 2.18 | 0.64 |
| hsa-miR-3972 | 0.002615487 | 2.54E-04 | 7.432 | up | 9.57 | 6.64 | 1.73 | 2.46 | 6.64 | 6.64 | 6.64 | 6.64 | 2.01 | 6.64 | 1.78 | 6.64 |
| hsa-miR-593-5p | 4.55E-05 | 1.70E-06 | 7.197 | up | 9.57 | -0.46 | -0.24 | 2.42 | 6.64 | 6.64 | 0.16 | 0.17 | 2.32 | 1.11 | 0.15 | 0.83 |
| hsa-miR-218-2-3p | 7.74E-04 | 5.43E-05 | 7.185 | up | 9.57 | 0.19 | -0.35 | 1.91 | 1.58 | 6.64 | -0.02 | 0.20 | -0.17 | 0.00 | 6.64 | 0.35 |
| hsa-miR-138-5p | 0.001268621 | 1.06E-04 | 7.184 | up | 9.57 | 0.39 | 2.59 | 6.64 | 6.64 | 6.64 | -2.15 | 1.01 | 2.69 | 2.67 | 1.93 | -0.40 |
| hsa-miR-4722-3p | 0.006789367 | 8.19E-04 | 7.179 | up | 9.57 | 1.69 | 1.83 | 6.64 | 6.64 | 3.25 | 1.61 | 1.68 | 2.21 | 6.64 | 2.17 | 6.64 |

FIG. 16A

| | | | | | | | | | | | | | | | | |
|---|---|---|---|---|---|---|---|---|---|---|---|---|---|---|---|---|
| hsa-miR-658 | 0.010971099 | 0.001606937 | 6.931 | up | 9.57 | -6.64 | 1.96 | -6.64 | -6.64 | -6.64 | 1.94 | -6.64 | -6.64 | 2.82 | -6.64 | 2.92 |
| hsa-miR-3944-3p | 0.010202916 | 0.001440665 | 6.72 | up | 9.57 | -6.64 | 1.87 | 2.42 | 3.19 | 2.85 | -6.64 | 1.91 | 1.67 | 1.88 | -6.64 | -6.64 |
| hsa-miR-4539 | 0.021122124 | 0.003405358 | 6.615 | up | 9.57 | -6.64 | -6.64 | 3.68 | 3.59 | -6.64 | 1.87 | 1.65 | -6.64 | 1.76 | -6.64 | -6.64 |
| hsa-miR-146b-5p | 9.66E-07 | 1.42E-08 | 6.578 | up | 9.57 | 1.26 | -2.18 | -6.64 | -6.64 | -6.64 | 2.15 | 1.89 | 1.39 | 2.49 | 2.76 | 3.10 |
| hsa-miR-362-3p | 2.02E-04 | 1.08E-05 | 6.515 | up | 9.57 | 0.03 | -0.53 | -6.64 | -6.64 | -6.64 | 0.63 | 1.57 | 2.12 | -0.01 | 2.98 | 3.32 |
| hsa-miR-501-3p | 6.89E-07 | 9.19E-09 | 6.463 | up | 9.57 | -0.39 | -6.64 | 0.57 | 0.71 | -6.64 | 0.99 | 0.25 | 1.21 | 0.39 | 1.37 | 1.24 |
| hsa-miR-3907 | 7.04E-06 | 1.93E-07 | 6.438 | up | 9.57 | -0.23 | 0.04 | 1.44 | 0.56 | 2.10 | 0.00 | -0.51 | 0.35 | 0.91 | -0.27 | 0.98 |
| hsa-miR-3189-5p | 0.010122169 | 0.001418597 | 6.378 | up | 9.57 | -6.64 | 1.45 | -6.64 | -6.64 | 3.05 | -6.64 | -6.64 | -6.64 | 1.67 | 1.89 | -6.64 |
| hsa-miR-199b-5p | 0.01095315 | 0.001517919 | 6.023 | up | 9.57 | -6.64 | 6.13 | -6.64 | -6.64 | -6.64 | -6.64 | -6.64 | -6.64 | -6.64 | 4.37 | -6.64 |
| hsa-miR-4436b-5p | 0.029435895 | 0.00508692 | 5.612 | up | 9.57 | 3.15 | 1.87 | 3.31 | 2.65 | -6.64 | 1.57 | 1.86 | 2.01 | 1.92 | 2.32 | -6.64 |
| hsa-miR-548q | 0.00495142 | 5.61E-04 | 5.547 | up | 9.57 | 2.61 | -6.64 | -6.64 | 0.83 | -6.64 | 1.83 | 1.21 | 0.39 | 1.16 | 0.48 | -6.64 |
| hsa-miR-498 | 0.011229564 | 0.00165071 | 5.407 | up | 9.57 | 0.35 | -6.64 | -6.64 | -6.64 | -6.64 | -0.45 | -0.44 | 0.70 | 0.73 | -0.37 | -0.68 |
| hsa-miR-4781-5p | 0.014002807 | 0.002132145 | 5.305 | up | 9.57 | -6.64 | -6.64 | -6.64 | -6.64 | -6.64 | -6.64 | 2.65 | -6.64 | 1.67 | -6.64 | 1.55 |
| hsa-miR-5587-5p | 3.80E-04 | 2.30E-05 | 5.271 | up | 9.57 | -6.64 | -6.64 | 0.96 | 0.67 | -6.64 | -0.43 | -0.23 | 0.40 | 0.30 | -0.08 | -0.42 |
| hsa-miR-501-5p | 0.002221709 | 2.07E-04 | 5.114 | up | 9.57 | 0.25 | -6.64 | -6.64 | -6.64 | -6.64 | 1.46 | 0.94 | 2.29 | 0.29 | 2.26 | 2.65 |
| hsa-miR-4323 | 9.31E-04 | 7.02E-05 | 4.921 | up | 9.57 | 0.68 | -0.01 | -6.64 | -6.64 | 0.95 | 0.21 | 0.81 | 0.49 | 0.21 | 1.21 | 0.73 |
| hsa-miR-3944-5p | 0.001908161 | 1.74E-04 | 4.912 | up | 9.57 | -6.64 | 0.56 | 1.91 | 1.14 | 1.60 | 0.04 | 0.20 | 0.22 | 0.09 | -0.11 | -0.03 |
| hsa-miR-4665-5p | 0.04703079 | 0.008771813 | 4.908 | up | 9.57 | -6.64 | -6.64 | -6.64 | 3.14 | 3.85 | 1.73 | 2.02 | -6.64 | -6.64 | -6.64 | 1.51 |
| hsa-miR-4469 | 0.02695149 | 0.004558181 | 4.714 | up | 9.57 | -6.64 | 0.31 | 1.74 | 0.84 | 2.01 | -6.64 | -6.64 | 0.18 | 0.13 | 0.11 | -6.64 |
| hsa-miR-628-3p | 0.020250369 | 0.003232804 | 4.679 | up | 9.57 | 0.34 | 0.55 | 0.90 | -6.64 | -6.64 | 0.89 | 0.51 | 1.02 | 0.09 | 0.76 | 0.71 |
| hsa-miR-3619-3p | 0.008931357 | 0.001214062 | 4.414 | up | 9.57 | 0.33 | 0.00 | 2.66 | 0.37 | 1.17 | 0.40 | 0.45 | -6.64 | 0.30 | -0.12 | -6.64 |
| hsa-miR-20b-3p | 0.030173108 | 0.005262012 | 4.286 | up | 9.57 | 1.90 | -6.64 | -6.64 | -6.64 | -6.64 | 2.91 | -6.64 | -6.64 | -6.64 | -6.64 | 3.08 |
| hsa-miR-584-5p | 2.00E-06 | 3.68E-08 | 4.173 | up | 9.57 | 0.41 | -0.95 | -1.26 | -0.11 | -6.64 | -0.68 | 2.05 | 2.23 | 2.29 | 2.43 | 1.42 |
| hsa-miR-3194-3p | 0.00281164 | 2.83E-04 | 4.128 | up | 9.57 | 0.14 | 0.65 | 2.05 | 0.50 | 2.68 | 0.56 | 0.45 | -0.53 | -0.49 | -0.21 | -6.64 |
| hsa-miR-1914-5p | 0.00429963 | 4.75E-04 | 4.032 | up | 9.57 | -6.64 | -6.64 | -6.64 | -6.64 | 1.45 | -6.64 | -0.07 | -0.08 | 0.47 | -0.29 | -0.24 |
| hsa-miR-596 | 3.88E-04 | 2.39E-05 | 4.025 | up | 9.57 | -0.47 | -6.64 | -6.64 | -6.64 | -6.64 | 0.11 | 0.17 | 0.22 | 0.36 | 0.48 | -0.18 |
| hsa-miR-4665-3p | 5.11E-04 | 3.26E-05 | 4.01 | up | 9.57 | -0.11 | -0.38 | 1.40 | 1.39 | 1.86 | -0.11 | 0.40 | 0.17 | 0.90 | 0.41 | -0.07 |
| hsa-miR-557 | 0.002559185 | 2.45E-04 | 3.979 | up | 9.57 | -6.64 | -0.33 | -6.64 | -6.64 | -6.64 | -6.64 | -6.64 | 1.07 | 1.30 | -0.09 | 0.80 |
| hsa-miR-3677-3p | 0.046872903 | 0.008704409 | 3.971 | up | 9.57 | -6.64 | -6.64 | -6.64 | 2.76 | 3.72 | 1.59 | 1.97 | 1.76 | -6.64 | 1.89 | -6.64 |
| hsa-miR-646 | 0.028358638 | 0.004855931 | 3.962 | up | 9.57 | -6.64 | 1.66 | -6.64 | 2.12 | 2.93 | -6.64 | 1.61 | -6.64 | 1.76 | -6.64 | -6.64 |
| hsa-miR-602 | 4.35E-05 | 1.56E-06 | 3.929 | up | 9.57 | 0.36 | -0.91 | -6.64 | -6.64 | -6.64 | 0.28 | 0.24 | 0.51 | 1.01 | 0.30 | -0.41 |
| hsa-miR-660-5p | 4.69E-04 | 2.94E-05 | 3.817 | up | 9.57 | -0.28 | -0.46 | -6.64 | -6.64 | -6.64 | 0.76 | 1.52 | 1.81 | -0.58 | 2.63 | 2.54 |
| hsa-miR-4785 | 0.033194322 | 0.005928807 | 3.764 | up | 9.57 | -6.64 | -6.64 | 2.81 | 3.09 | -6.64 | -6.64 | 2.20 | -6.64 | 1.58 | 1.78 | 1.46 |
| hsa-miR-181a-3p | 0.022308715 | 0.003667186 | 3.537 | up | 9.57 | -0.42 | -6.64 | -6.64 | -6.64 | -6.64 | -6.64 | -6.64 | 1.93 | 0.60 | 1.25 | 1.53 |
| hsa-miR-5008-5p | 0.011545968 | 0.001703304 | 3.408 | up | 9.57 | -6.64 | -6.64 | 0.37 | 0.75 | -6.64 | -0.65 | -0.21 | 0.12 | 0.40 | 0.02 | -0.44 |
| hsa-miR-3176 | 1.96E-06 | 3.51E-08 | 3.344 | up | 9.57 | 1.59 | -1.09 | -1.96 | -2.90 | -1.12 | 1.22 | -0.04 | 1.08 | 1.41 | -0.14 | -0.10 |
| hsa-miR-500b | 4.14E-06 | 9.15E-08 | 3.307 | up | 9.57 | 0.05 | -1.32 | -6.64 | -6.64 | -6.64 | 0.86 | 0.93 | 2.03 | -0.01 | 1.81 | 2.03 |
| hsa-miR-500a-3p | 2.81E-06 | 5.76E-08 | 3.289 | up | 9.57 | 0.65 | -1.38 | -6.64 | -6.64 | -6.64 | 1.16 | 0.62 | 1.85 | -0.10 | 1.60 | 1.72 |
| hsa-miR-4467 | 1.43E-05 | 4.59E-07 | 3.27 | up | 9.57 | 1.26 | -0.79 | -6.64 | -0.54 | 0.74 | 0.73 | -0.70 | 0.20 | 1.16 | 0.46 | 0.66 |
| hsa-miR-1914-3p | 5.84E-04 | 3.84E-05 | 3.167 | up | 9.57 | -0.22 | -6.64 | -6.64 | -6.64 | 1.04 | 0.16 | 0.01 | 0.00 | 0.84 | -0.35 | -0.02 |

FIG. 16B

| | | | | | | | | | | | | | | | |
|---|---|---|---|---|---|---|---|---|---|---|---|---|---|---|---|
| hsa-miR-637 | 5.32E-04 | 3.42E-05 | 3.098 up | 9.57 | -0.43 | 0.56 | -6.64 | -6.64 | -6.64 | -0.16 | -0.22 | 0.23 | 1.44 | 0.34 | 0.12 |
| hsa-miR-3195 | 6.82E-10 | 3.25E-12 | 3.057 up | 9.57 | 1.79 | -0.61 | -0.59 | -2.10 | -0.68 | 1.11 | 0.65 | 0.32 | 1.28 | 0.65 | 0.71 |
| hsa-miR-612 | 0.018014142 | 0.002818862 | 2.969 up | 9.57 | 0.45 | -0.29 | -6.64 | -6.64 | -6.64 | 0.16 | -6.64 | 0.13 | 1.88 | -0.37 | 0.52 |
| hsa-miR-4654 | 0.04720147 | 0.008844766 | 2.916 up | 9.57 | -6.64 | -6.64 | -6.64 | 2.20 | -6.64 | -6.64 | -6.64 | -6.64 | -6.64 | -6.64 | 1.90 |
| hsa-miR-152 | 0.001604012 | 1.39E-04 | 2.904 up | 9.57 | 0.45 | 2.17 | -6.64 | -6.64 | -1.94 | -1.86 | 1.23 | -1.57 | 0.10 | 1.66 | 1.22 |
| hsa-miR-4707-3p | 2.78E-04 | 1.58E-05 | 2.89 up | 9.57 | 0.06 | -0.64 | 1.98 | 1.26 | 2.12 | -0.67 | -0.23 | 0.22 | 0.02 | -0.51 | -0.99 |
| hsa-miR-30b-3p | 0.047797843 | 0.009015572 | 2.87 up | 9.57 | -6.64 | -6.64 | -6.64 | -6.64 | -6.64 | 0.81 | -0.08 | 0.88 | 0.76 | 0.15 | 1.87 |
| hsa-miR-502-3p | 2.08E-06 | 4.05E-08 | 2.867 up | 9.57 | 0.27 | -1.33 | -6.64 | -0.40 | -6.64 | 1.07 | 0.32 | 1.86 | 0.13 | 1.70 | 1.81 |
| hsa-miR-4634 | 7.24E-08 | 5.72E-10 | 2.783 up | 9.57 | 0.08 | -1.43 | 0.67 | -0.48 | 0.02 | 0.77 | 0.22 | 0.73 | 1.24 | -0.04 | 0.05 |
| hsa-miR-4487 | 0.007933377 | 0.001024066 | 2.725 up | 9.57 | -6.64 | -0.22 | 0.89 | 0.84 | 1.79 | 1.51 | 0.10 | 0.56 | 0.35 | -0.05 | -6.64 |
| hsa-miR-636 | 0.03268774 | 0.005821104 | 2.652 up | 9.57 | -0.11 | 0.52 | 2.35 | 1.47 | -6.64 | -0.24 | 0.25 | -0.02 | 0.36 | 0.51 | -6.64 |
| hsa-miR-3196 | 1.22E-08 | 7.09E-11 | 2.634 up | 9.57 | 1.40 | -1.12 | -0.34 | -1.16 | -0.66 | 0.77 | 0.11 | 0.71 | 1.10 | -0.32 | -0.03 |
| hsa-miR-300a-5p | 1.92E-04 | 1.01E-05 | 2.592 up | 9.57 | 0.08 | -6.64 | -6.64 | -6.64 | -6.64 | 0.84 | 0.80 | 2.17 | 0.13 | 1.83 | 2.18 |
| hsa-miR-185-5p | 1.18E-05 | 3.55E-07 | 2.566 up | 9.57 | 0.58 | -0.86 | -6.64 | -6.64 | -6.64 | 1.75 | -0.04 | 2.13 | 1.81 | 1.07 | 2.46 |
| hsa-miR-4488 | 2.77E-07 | 2.77E-09 | 2.561 up | 9.57 | 1.51 | -1.08 | -0.16 | -2.08 | 0.42 | 1.08 | -0.12 | 0.34 | 0.97 | 0.46 | -0.42 |
| hsa-miR-513a-5p | 1.57E-05 | 5.28E-07 | 2.55 up | 9.57 | 1.45 | -0.23 | -6.64 | -1.85 | -6.64 | 0.90 | -1.84 | 0.26 | -0.06 | 2.62 | 1.65 |
| hsa-miR-663a | 1.75E-07 | 1.49E-09 | 2.544 up | 9.57 | 1.23 | -1.14 | -1.11 | -2.02 | -2.53 | 0.97 | 0.13 | 0.55 | 1.36 | 0.09 | 0.07 |
| hsa-miR-4783-5p | 6.75E-04 | 4.59E-05 | 2.468 up | 9.57 | -0.73 | -0.62 | -6.64 | -0.11 | -6.64 | -0.30 | 0.18 | 0.62 | 0.91 | 0.33 | 0.57 |
| hsa-miR-514b-5p | 4.14E-06 | 9.46E-08 | 2.452 up | 9.57 | 1.39 | 0.13 | -6.64 | 0.16 | -6.64 | 1.06 | -0.76 | 0.12 | -0.16 | 3.59 | 0.58 |
| hsa-miR-4497 | 3.24E-07 | 3.58E-09 | 2.424 up | 9.57 | 1.64 | -0.65 | -1.34 | -2.10 | -1.67 | 1.31 | -0.47 | 0.38 | 0.89 | 0.01 | -0.40 |
| hsa-miR-532-3p | 8.07E-04 | 5.87E-05 | 2.418 up | 9.57 | 0.76 | -1.29 | -6.64 | -1.25 | -6.64 | 0.97 | 0.96 | 1.23 | -0.05 | 1.99 | 1.64 |
| hsa-miR-4532 | 1.08E-08 | 5.66E-11 | 2.403 up | 9.57 | 0.47 | -1.36 | 0.14 | 1.74 | -1.03 | 0.32 | -0.23 | 0.12 | 0.64 | 0.79 | -0.67 |
| hsa-miR-140-3p | 2.94E-04 | 1.69E-05 | 2.38 up | 9.57 | 0.16 | -0.03 | -1.73 | -2.26 | -6.64 | 0.54 | 0.99 | 2.06 | 0.52 | 0.42 | -0.17 |
| hsa-miR-4706 | 0.029612198 | 0.005148591 | 2.311 up | 9.57 | -6.64 | -0.69 | 0.55 | 0.86 | 0.54 | -0.45 | -0.50 | 0.98 | 0.67 | -0.69 | 0.10 |
| hsa-miR-4306 | 9.11E-06 | 2.59E-07 | 2.3 up | 9.57 | 0.28 | -0.70 | -2.39 | 1.98 | 0.10 | 1.71 | -0.23 | 1.81 | 1.73 | 1.07 | 2.29 |
| hsa-miR-4440 | 0.013464825 | 0.002014758 | 2.268 up | 9.57 | -0.60 | 0.34 | 0.81 | 1.50 | 0.57 | -0.29 | -0.16 | 0.33 | 0.55 | -0.59 | 0.33 |
| hsa-miR-1469 | 1.21E-05 | 3.71E-07 | 2.237 up | 9.57 | 2.37 | -1.24 | -0.81 | -1.50 | 0.44 | 1.89 | 0.02 | 0.22 | 0.97 | -0.49 | -1.11 |
| hsa-miR-3180 | 1.03E-04 | 4.44E-06 | 2.207 up | 9.57 | -0.16 | -0.73 | 0.32 | 0.32 | 1.86 | -0.04 | -0.41 | 0.06 | 1.83 | 0.89 | -0.75 |
| hsa-miR-4758-3p | 0.007443091 | 9.27E-04 | 2.14 up | 9.57 | 0.29 | -0.47 | 1.60 | 1.07 | 2.03 | -0.01 | 0.00 | -0.23 | 0.33 | -0.10 | -6.64 |
| hsa-miR-211-3p | 0.01655979 | 0.002571768 | 2.137 up | 9.57 | 1.13 | -0.59 | 0.03 | 2.75 | 1.64 | 0.51 | -0.07 | 0.79 | 0.18 | 0.18 | 0.19 |
| hsa-miR-572 | 0.007835592 | 9.83E-04 | 2.122 up | 9.57 | 0.77 | -0.64 | 1.49 | -0.05 | 1.47 | -0.04 | -0.01 | 0.21 | 0.68 | -0.02 | -6.64 |
| hsa-miR-361-3p | 0.004367109 | 4.85E-04 | 2.082 up | 9.57 | -0.25 | -0.26 | -6.64 | -6.64 | -6.64 | 0.38 | 1.02 | 2.39 | 0.57 | 1.09 | 1.90 |
| hsa-miR-4466 | 4.49E-06 | 1.09E-07 | 2.079 up | 9.57 | 1.25 | -1.29 | 0.16 | -0.74 | 0.53 | 0.78 | -0.20 | 0.11 | 0.77 | -0.48 | -0.60 |
| hsa-miR-3940-5p | 7.03E-06 | 1.89E-07 | 2.072 up | 9.57 | 1.02 | -1.16 | 0.07 | -0.60 | 0.12 | 0.55 | -0.55 | -0.19 | 0.87 | -0.46 | -0.78 |
| hsa-miR-4707-5p | 7.75E-06 | 2.16E-07 | 2.063 up | 9.57 | 0.98 | -1.13 | -0.33 | -0.73 | 0.09 | 0.69 | -0.27 | 0.08 | 1.04 | -0.38 | -0.14 |
| hsa-miR-532-5p | 0.001257804 | 1.04E-04 | 2.05 up | 9.57 | -0.87 | -1.39 | -6.64 | -6.64 | -6.64 | 0.67 | 1.31 | 1.89 | 0.31 | 1.94 | 2.01 |
| hsa-miR-187-5p | 4.38E-05 | 1.62E-06 | 2.04 up | 9.57 | 1.80 | -0.56 | -6.64 | -0.32 | 0.47 | 1.05 | 2.21 | -0.34 | 1.37 | 0.25 | 0.56 |
| hsa-miR-33b-3p | 0.001779306 | 1.60E-04 | 2.03 up | 9.57 | -0.33 | 0.33 | 2.33 | 1.40 | 3.32 | 0.04 | 0.47 | -0.15 | -0.10 | -0.48 | -1.00 |
| hsa-miR-718 | 0.001672993 | 1.47E-04 | 2.02 up | 9.57 | -0.12 | -0.45 | 0.37 | 0.09 | -0.24 | -0.47 | 0.04 | 0.26 | 0.82 | -0.23 | -0.74 |
| hsa-miR-1538 | 0.022285916 | 0.003651697 | 2.002 up | 9.57 | -0.27 | -0.19 | -6.64 | 0.49 | 2.16 | 0.93 | -0.41 | 0.45 | 1.37 | -0.28 | -0.84 |

FIG. 16C

| | | | | | | | | | | | | | | | |
|---|---|---|---|---|---|---|---|---|---|---|---|---|---|---|---|
| hsa-miR-27b-3p | 0.001740683 | 1.55E-04 | 2.012 down | 9.57 | 0.80 | 1.58 | -3.02 | -6.64 | -4.72 | -1.56 | 0.06 | 0.11 | 0.65 | -0.37 | -0.50 |
| hsa-miR-3149 | 1.18E-04 | 5.33E-06 | 2.016 down | 9.57 | 1.06 | 0.06 | 4.54 | 2.04 | 3.16 | 0.49 | 0.91 | -0.92 | -1.82 | -0.06 | -1.15 |
| hsa-miR-3126-3p | 0.00501233 | 5.70E-04 | 2.052 down | 9.57 | 0.55 | -0.76 | 2.00 | 1.24 | 3.39 | 0.00 | 0.08 | -6.64 | -0.44 | 0.00 | -6.64 |
| hsa-miR-454-3p | 0.002884327 | 2.92E-04 | 2.117 down | 9.57 | 0.94 | -0.19 | -6.64 | -6.64 | -6.64 | 0.29 | 1.00 | 0.17 | -1.24 | 0.58 | -0.31 |
| hsa-miR-595 | 0.001086094 | 8.75E-05 | 2.123 down | 9.57 | 1.39 | -0.02 | 2.95 | 1.16 | -6.64 | 0.94 | 0.67 | -0.30 | -1.05 | 0.62 | -0.08 |
| hsa-miR-5011-5p | 2.97E-04 | 1.72E-05 | 2.128 down | 9.57 | -1.04 | 0.71 | -0.38 | -6.64 | -6.64 | -0.68 | -0.07 | -0.66 | -0.55 | 0.17 | 0.22 |
| hsa-miR-134 | 0.010971099 | 0.001605175 | 2.169 down | 9.57 | 0.47 | 1.96 | -6.64 | 1.53 | -6.64 | 0.13 | 0.70 | -0.80 | -0.11 | 0.41 | -6.64 |
| hsa-miR-4701-3p | 9.92E-05 | 4.18E-06 | 2.178 down | 9.57 | 1.37 | -0.51 | 3.54 | 2.42 | -6.64 | 0.36 | 0.53 | -0.27 | -6.64 | 0.10 | -0.53 |
| hsa-miR-331-3p | 9.31E-04 | 6.97E-05 | 2.205 down | 9.57 | -0.15 | -0.53 | -6.64 | -6.64 | -1.80 | 0.60 | 0.43 | 0.13 | -0.10 | 1.14 | -0.35 |
| hsa-miR-4489 | 0.00856133 | 0.001149056 | 2.226 down | 9.57 | -6.64 | 0.66 | -6.64 | 0.58 | 0.64 | -0.78 | 0.41 | -0.70 | -0.51 | -0.37 | -1.12 |
| hsa-miR-98 | 9.47E-04 | 7.18E-05 | 2.351 down | 9.57 | 0.88 | 0.60 | -6.64 | -6.64 | -6.64 | -1.42 | -0.18 | -0.22 | -2.14 | 2.05 | 1.01 |
| hsa-miR-196b-3p | 0.035311725 | 0.006362808 | 2.421 down | 9.57 | 0.85 | -0.18 | -6.64 | 0.55 | 2.03 | 0.59 | 0.07 | -0.28 | 0.35 | 0.46 | 0.61 |
| hsa-miR-505-3p | 0.030783074 | 0.005417042 | 2.51 down | 9.57 | 0.43 | 0.76 | -6.64 | -6.64 | -6.64 | 0.50 | 0.41 | -0.16 | -1.05 | 1.54 | 0.70 |
| hsa-miR-4639-3p | 0.046872903 | 0.008717668 | 2.578 down | 9.57 | -6.64 | -6.64 | -6.64 | 2.18 | -6.64 | -6.64 | -6.64 | -6.64 | -6.64 | -6.64 | -6.64 |
| hsa-miR-4753-5p | 0.004078888 | 4.41E-04 | 2.58 down | 9.57 | 0.26 | -0.28 | 2.30 | 0.20 | 0.17 | 0.29 | -0.01 | -6.64 | -0.69 | 0.43 | 0.21 |
| hsa-miR-568 | 6.07E-04 | 4.06E-05 | 2.589 down | 9.57 | 1.80 | 0.41 | 4.94 | 0.43 | -0.58 | 1.47 | 1.92 | -1.51 | -2.18 | 0.64 | -1.63 |
| hsa-miR-889 | 0.022174653 | 0.003621782 | 2.626 down | 9.57 | -6.64 | 1.99 | -6.64 | -6.64 | -6.64 | -6.64 | -6.64 | -6.64 | -6.64 | -6.64 | -6.64 |
| hsa-miR-3664-3p | 0.046872903 | 0.008717668 | 2.658 down | 9.57 | -6.64 | -6.64 | 3.67 | -6.64 | -6.64 | -6.64 | -6.64 | -6.64 | -6.64 | -6.64 | -6.64 |
| hsa-miR-1273f | 0.00429963 | 4.76E-04 | 2.662 down | 9.57 | -0.44 | -0.20 | 1.49 | 5.29 | 2.64 | -0.48 | -0.42 | 0.68 | -0.62 | -0.97 | 0.93 |
| hsa-miR-631 | 0.047797643 | 0.008991086 | 2.767 down | 9.57 | 1.93 | 0.44 | 0.65 | -6.64 | -6.64 | 1.65 | 1.08 | -6.64 | -0.01 | 0.75 | -0.34 |
| hsa-miR-135b-3p | 0.021434043 | 0.003489526 | 2.782 down | 9.57 | -0.37 | -0.25 | -6.64 | -6.64 | -6.64 | 0.17 | 0.63 | -0.13 | 1.19 | -0.04 | -6.64 |
| hsa-miR-3156-5p | 0.029612198 | 0.005148591 | 2.818 down | 9.57 | -0.62 | 0.55 | -6.64 | 3.27 | 0.49 | -0.27 | -0.05 | 0.05 | -0.30 | -0.43 | -0.22 |
| hsa-miR-4689 | 0.002804868 | 2.80E-04 | 2.844 down | 9.57 | 0.26 | 0.08 | -0.01 | -0.01 | 0.16 | -0.41 | -0.39 | -0.56 | -6.64 | -0.70 | -0.66 |
| hsa-miR-26b-5p | 2.04E-06 | 3.86E-08 | 2.913 down | 9.57 | 0.32 | 0.82 | -1.25 | -6.64 | -6.64 | 0.57 | 0.39 | -0.62 | -1.27 | 0.84 | -0.65 |
| hsa-miR-670 | 1.31E-04 | 6.20E-06 | 2.954 down | 9.57 | 1.47 | 0.10 | 2.61 | 0.74 | -6.64 | 0.65 | 0.78 | -0.39 | -0.73 | 0.22 | -0.71 |
| hsa-miR-4700-5p | 1.30E-04 | 5.95E-06 | 3.068 down | 9.57 | 1.36 | -0.60 | 2.32 | 0.79 | -6.64 | 0.62 | 0.56 | -0.42 | -6.64 | 0.23 | 0.13 |
| hsa-miR-16-2-3p | 0.005456461 | 6.27E-04 | 3.17 down | 9.57 | 0.26 | 0.29 | -1.18 | -6.64 | -6.64 | 0.80 | -0.46 | 0.99 | -1.05 | 0.04 | -0.94 |
| hsa-miR-1224-3p | 0.027130445 | 0.004602742 | 3.189 down | 9.57 | -6.64 | -6.64 | -6.64 | -6.64 | -6.64 | -6.64 | -6.64 | -6.64 | -6.64 | -6.64 | -6.64 |
| hsa-miR-4675 | 0.011764385 | 0.001741724 | 3.27 down | 9.57 | 1.20 | -0.15 | 0.12 | 0.88 | 1.68 | 0.81 | 1.25 | -0.68 | -0.91 | -0.35 | -6.64 |
| hsa-miR-23c | 4.38E-05 | 1.61E-06 | 3.371 down | 9.57 | 1.43 | 2.87 | -6.64 | -6.64 | -6.64 | 2.19 | 0.04 | 0.43 | 0.19 | 0.29 | -0.20 |
| hsa-miR-4468 | 0.007443091 | 9.29E-04 | 3.499 down | 9.57 | 1.18 | -0.16 | 0.74 | 0.39 | 1.24 | 0.19 | -0.07 | -0.01 | -6.64 | 0.58 | 0.01 |
| hsa-miR-182-3p | 0.004452876 | 4.97E-04 | 3.531 down | 9.57 | -6.64 | -6.64 | -6.64 | -6.64 | -6.64 | -6.64 | -6.64 | -6.64 | -6.64 | -6.64 | -6.64 |
| hsa-miR-136-3p | 0.009734832 | 0.001348926 | 3.623 down | 9.57 | -6.64 | 4.09 | -6.64 | -6.64 | -6.64 | -6.64 | -6.64 | -6.64 | -6.64 | -6.64 | -6.64 |
| hsa-miR-3667-5p | 2.33E-04 | 1.30E-05 | 3.667 down | 9.57 | 1.06 | 0.46 | -0.39 | 0.03 | -6.64 | 0.85 | 0.78 | -1.13 | -1.18 | 0.41 | 0.00 |
| hsa-miR-4435 | 0.001688552 | 1.49E-04 | 3.714 down | 9.57 | 0.97 | -0.30 | 2.73 | 1.61 | 1.85 | 0.58 | 0.64 | -6.64 | -6.64 | -0.01 | -6.64 |
| hsa-miR-3148 | 2.36E-04 | 1.33E-05 | 3.753 down | 9.57 | 1.86 | -0.02 | 3.32 | 3.19 | -6.64 | 1.18 | 1.20 | -0.90 | -6.64 | 0.62 | -0.49 |
| hsa-miR-26b-3p | 0.00789082 | 9.94E-04 | 3.76 down | 9.57 | -6.64 | -6.64 | -6.64 | -6.64 | -6.64 | -6.64 | -6.64 | -6.64 | -6.64 | -6.64 | -6.64 |
| hsa-miR-601 | 1.18E-05 | 3.53E-07 | 3.796 down | 9.57 | 1.15 | 0.71 | -6.64 | -0.28 | -6.64 | 0.82 | 0.97 | -1.01 | -2.14 | 0.04 | -1.78 |
| hsa-miR-3616-3p | 0.019740436 | 0.003120195 | 3.941 down | 9.57 | -6.64 | 0.54 | 0.25 | -6.64 | -6.64 | -6.64 | -0.24 | -6.64 | 0.02 | -0.48 | -6.64 |
| hsa-miR-3064-5p | 0.03839018 | 0.006965934 | 4.002 down | 9.57 | 2.61 | -6.64 | -6.64 | -6.64 | -6.64 | -6.64 | -6.64 | -6.64 | -6.64 | -6.64 | -6.64 |

FIG. 16D

| | | | | | | | | | | | | | | | | |
|---|---|---|---|---|---|---|---|---|---|---|---|---|---|---|---|---|
| hsa-miR-3127-5p | 0.021434043 | 0.003478941 | 4.026 | down | 9.57 | -6.64 | -6.64 | 2.09 | -6.64 | -6.64 | -6.64 | 0.69 | -6.64 | -0.02 | -0.44 | -0.63 |
| hsa-miR-4750 | 0.007443091 | 9.29E-04 | 4.045 | down | 9.57 | 0.53 | -6.64 | 0.39 | 0.20 | 0.79 | 0.16 | -6.64 | -6.64 | -0.19 | -0.46 | -0.24 |
| hsa-miR-4303 | 7.50E-04 | 5.18E-05 | 4.217 | down | 9.57 | 0.62 | -0.30 | -6.64 | 1.42 | 1.17 | 0.09 | 0.78 | -0.40 | -0.04 | -6.64 | 0.24 |
| hsa-miR-4277 | 0.019562139 | 0.003081706 | 4.243 | down | 9.57 | 2.01 | -0.35 | 2.36 | -6.64 | -6.64 | 1.25 | 1.08 | -6.64 | -6.64 | 0.08 | -6.64 |
| hsa-miR-200b-5p | 9.31E-04 | 6.99E-05 | 4.467 | down | 9.57 | -0.40 | 0.19 | 1.17 | 0.54 | 3.24 | 0.11 | 0.36 | 0.69 | -0.73 | -6.64 | -6.64 |
| hsa-let-7a-3p | 0.03159281 | 0.005576181 | 4.507 | down | 9.57 | -6.64 | 2.16 | -6.64 | -6.64 | -6.64 | 0.00 | -6.64 | 1.31 | 0.41 | 0.83 | 2.71 |
| hsa-miR-29c-5p | 0.018817035 | 0.002954413 | 4.759 | down | 9.57 | -6.64 | -6.64 | -6.64 | -6.64 | -6.64 | -6.64 | -6.64 | -6.64 | -6.64 | -6.64 | -6.64 |
| hsa-miR-15b-3p | 3.97E-05 | 1.40E-06 | 4.796 | down | 9.57 | -0.25 | -0.08 | -6.64 | -6.64 | -6.64 | 1.41 | 0.84 | -0.20 | -1.61 | 0.71 | -0.27 |
| hsa-miR-4712-3p | 0.008317743 | 0.001098604 | 4.874 | down | 9.57 | -6.64 | 1.29 | -6.64 | -6.64 | -6.64 | 0.08 | -6.64 | -0.54 | -0.59 | 0.22 | 0.66 |
| hsa-miR-374b-5p | 7.74E-04 | 5.45E-05 | 4.971 | down | 9.57 | 2.03 | 0.54 | -6.64 | -6.64 | -6.64 | 2.20 | 0.37 | -0.76 | -6.64 | 2.28 | 0.42 |
| hsa-miR-23b-5p | 0.010427405 | 0.001494338 | 5.084 | down | 9.57 | -6.64 | 2.71 | -6.64 | -6.64 | -6.64 | -6.64 | -6.64 | 1.63 | -6.64 | -6.64 | -6.64 |
| hsa-miR-192-5p | 0.008451228 | 0.001122081 | 5.302 | down | 9.57 | 0.03 | -6.64 | -6.64 | -6.64 | -6.64 | 1.57 | 1.26 | -6.64 | -0.50 | 1.30 | 1.58 |
| hsa-miR-374a-5p | 0.005488126 | 6.33E-04 | 5.316 | down | 9.57 | 0.42 | 1.97 | -6.64 | -6.64 | -6.64 | 1.26 | 1.74 | -6.64 | -6.64 | 3.14 | 0.12 |
| hsa-miR-625-3p | 6.00E-04 | 3.98E-05 | 5.362 | down | 9.57 | 0.68 | 0.15 | -6.64 | -6.64 | -6.64 | 0.25 | 0.28 | 0.07 | -6.64 | -6.64 | -6.64 |
| hsa-miR-654-3p | 0.040924497 | 0.007481962 | 5.409 | down | 9.57 | 2.88 | 5.20 | 4.04 | 2.42 | -6.64 | 2.30 | 2.10 | -6.64 | -6.64 | 1.35 | -6.64 |
| hsa-miR-3609 | 0.006150438 | 7.19E-04 | 5.481 | down | 9.57 | 2.01 | 0.25 | -6.64 | -6.64 | -6.64 | 1.92 | 1.54 | -0.26 | -6.64 | 1.96 | -0.18 |
| hsa-miR-1306-3p | 4.41E-04 | 2.74E-05 | 5.5 | down | 9.57 | 1.36 | -6.64 | 1.14 | 1.17 | -6.64 | 0.50 | 0.54 | 0.35 | -6.64 | -0.07 | 0.46 |
| hsa-miR-4644 | 7.74E-04 | 5.47E-05 | 5.509 | down | 9.57 | 0.39 | 0.03 | 5.94 | 2.38 | 2.19 | 0.19 | 0.08 | -6.64 | -6.64 | 0.30 | 1.09 |
| hsa-miR-103b | 0.013612635 | 0.002044047 | 5.532 | down | 9.57 | 1.41 | -6.64 | -6.64 | -6.64 | -6.64 | 1.22 | 1.61 | 0.09 | 0.33 | 0.23 | -6.64 |
| hsa-miR-4311 | 0.010701834 | 0.001550582 | 5.535 | down | 9.57 | 3.29 | -6.64 | 2.76 | 6.64 | -6.64 | 2.26 | 2.16 | -6.64 | -6.64 | 1.73 | 2.26 |
| hsa-miR-92a-1-5p | 0.032566432 | 0.005782343 | 5.653 | down | 9.57 | -6.64 | -6.64 | -6.64 | -6.64 | -6.64 | 2.52 | -6.64 | 1.85 | -6.64 | -6.64 | 2.83 |
| hsa-miR-934 | 0.004176745 | 4.58E-04 | 5.714 | down | 9.57 | -6.64 | -6.64 | -6.64 | -6.64 | -6.64 | -6.64 | -6.64 | 1.72 | -6.64 | -6.64 | 1.46 |
| hsa-miR-374c-5p | 0.002804868 | 2.80E-04 | 6.082 | down | 9.57 | 1.82 | 1.08 | -6.64 | -6.64 | -6.64 | 2.48 | 0.41 | -0.85 | -6.64 | 2.83 | 1.17 |
| hsa-miR-622 | 5.67E-06 | 1.46E-07 | 6.138 | down | 9.57 | -6.64 | 0.24 | 1.50 | 0.96 | 0.73 | -6.64 | -0.25 | -6.64 | 0.14 | -6.64 | -6.64 |
| hsa-miR-610 | 0.006735898 | 8.06E-04 | 6.325 | down | 9.57 | 2.81 | -6.64 | -6.64 | 5.87 | -6.64 | -6.64 | -6.64 | -6.64 | -6.64 | -6.64 | -6.64 |
| hsa-miR-224-3p | 8.00E-04 | 5.69E-05 | 6.373 | down | 9.57 | -6.64 | -6.64 | -6.64 | -6.64 | -6.64 | -6.64 | -6.64 | -6.64 | -6.64 | -6.64 | -6.64 |
| hsa-miR-181c-3p | 0.003249036 | 3.41E-04 | 6.809 | down | 9.57 | -6.64 | -6.64 | -6.64 | -6.64 | -6.64 | -6.64 | -6.64 | -6.64 | -6.64 | -6.64 | -6.64 |
| hsa-miR-4520a-3p | 0.022562997 | 0.003720874 | 6.89 | down | 9.57 | 2.57 | -6.64 | 3.20 | -6.64 | 3.61 | 1.85 | 1.60 | -6.64 | -6.64 | -6.64 | -6.64 |
| hsa-miR-194-5p | 0.010414282 | 0.001486971 | 6.899 | down | 9.57 | -0.19 | -0.52 | -6.64 | -6.64 | -6.64 | 1.20 | 1.54 | -6.64 | -0.35 | 1.85 | 1.15 |
| hsa-miR-7-1-3p | 0.013779393 | 0.002090867 | 7.003 | down | 9.57 | -0.10 | 0.03 | -6.64 | -6.64 | -6.64 | -0.42 | -0.11 | 0.19 | -6.64 | 0.50 | 1.82 |
| hsa-miR-31-5p | 0.003738492 | 4.00E-04 | 7.086 | down | 9.57 | 1.04 | 3.80 | -6.64 | -6.64 | -6.64 | -0.90 | -0.67 | -0.69 | -1.51 | -6.64 | -6.64 |
| hsa-miR-4474-5p | 0.00408493 | 4.46E-04 | 7.17 | down | 9.57 | 3.45 | -6.64 | 2.73 | -6.64 | -6.64 | 2.19 | -6.64 | -6.64 | -6.64 | -6.64 | -6.64 |
| hsa-miR-149-5p | 1.47E-04 | 7.24E-06 | 7.748 | down | 9.57 | 1.16 | 0.51 | -6.64 | -6.64 | -6.64 | -6.64 | -0.10 | -6.64 | 0.01 | 0.62 | -0.44 |
| hsa-miR-16-1-3p | 0.010708672 | 0.001557215 | 7.805 | down | 9.57 | 1.81 | -6.64 | -6.64 | -6.64 | -6.64 | 2.37 | 1.87 | 3.34 | 1.99 | 2.04 | -6.64 |
| hsa-miR-7-5p | 5.58E-08 | 4.12E-10 | 8.047 | down | 9.57 | -1.65 | 0.82 | -6.64 | -6.64 | -6.64 | -0.28 | 2.60 | -1.38 | 0.13 | -0.76 | 0.64 |
| hsa-miR-3170 | 5.75E-04 | 3.75E-05 | 8.304 | down | 9.57 | 0.39 | -6.64 | 6.98 | 3.69 | 1.59 | 0.38 | 0.68 | -6.64 | -6.64 | -6.64 | -6.64 |
| hsa-miR-3131 | 0.002804868 | 2.81E-04 | 8.681 | down | 9.57 | -6.64 | -6.64 | -6.64 | 2.26 | 3.34 | -6.64 | 1.82 | -6.64 | -6.64 | -6.64 | -6.64 |
| hsa-miR-2278 | 0.001324947 | 1.12E-04 | 8.703 | down | 9.57 | 3.15 | -6.64 | -6.64 | -6.64 | -6.64 | 2.44 | 1.63 | -6.64 | -6.64 | 2.07 | 1.88 |
| hsa-miR-1305 | 1.48E-05 | 4.76E-07 | 8.817 | down | 9.57 | 0.29 | -0.32 | 3.15 | 1.83 | -6.64 | -0.07 | 0.49 | 0.03 | -0.39 | -0.30 | -6.64 |
| hsa-miR-3146 | 0.001635823 | 1.43E-04 | 9.022 | down | 9.57 | -6.64 | -6.64 | -6.64 | -6.64 | -6.64 | -6.64 | -6.64 | -6.64 | -6.64 | -6.64 | -6.64 |

FIG. 16E

| | | | | | | | | | | | | | | | | |
|---|---|---|---|---|---|---|---|---|---|---|---|---|---|---|---|---|
| hsa-miR-27b-5p | 0.002927127 | 2.98E-04 | 9.261 down | 9.57 | 2.44 | 4.07 | -6.64 | -6.64 | -6.64 | -6.64 | -6.64 | 2.01 | 1.72 | -6.64 | -6.64 |
| hsa-miR-3713 | 0.006907172 | 8.44E-04 | 9.588 down | 9.57 | 3.58 | 1.58 | -6.64 | -6.64 | -6.64 | 2.00 | 2.10 | -6.64 | -6.64 | -6.64 | -6.64 |
| hsa-miR-297 | 0.01027078/ | 0.001461071 | 9.662 down | 9.57 | 3.27 | 1.50 | 2.65 | -6.64 | -6.64 | 2.25 | 1.67 | -6.64 | -6.64 | 2.29 | 2.46 |
| hsa-miR-617 | 1.49E-05 | 4.87E-07 | 10.13 down | 9.57 | 1.87 | -0.35 | -6.64 | -6.64 | -6.64 | 1.67 | 1.27 | -6.64 | -0.52 | 0.32 | -6.64 |
| hsa-miR-299-3p | 0.001144688 | 9.29E-05 | 10.3 down | 9.57 | -6.64 | 0.02 | -6.64 | -6.64 | -6.64 | -6.64 | 0.26 | -6.64 | -6.64 | -6.64 | -6.64 |
| hsa-miR-3125 | 1.56E-05 | 5.17E-07 | 10.46 down | 9.57 | 0.52 | -0.01 | -6.64 | -6.64 | 2.09 | 0.40 | 0.25 | -6.64 | -6.64 | 0.39 | 0.33 |
| hsa-miR-4768-3p | 3.71E-04 | 2.23E-05 | 11.12 down | 9.57 | 1.58 | -6.64 | 4.33 | 2.38 | -6.64 | -6.64 | -6.64 | -6.64 | -6.64 | -6.64 | 1.68 |
| hsa-miR-4719 | 0.00707513 | 8.69E-04 | 11.24 down | 9.57 | -6.64 | 2.69 | -6.64 | -6.64 | -6.64 | -6.64 | -6.64 | -6.64 | -6.64 | 1.55 | -6.64 |
| hsa-miR-3682-3p | 8.17E-05 | 3.31E-06 | 13.37 down | 9.57 | 1.96 | 0.07 | -6.64 | -6.64 | -6.64 | 1.41 | 1.63 | -6.64 | -6.64 | 0.88 | 0.13 |
| hsa-miR-1183 | 4.14E-06 | 9.60E-08 | 13.5 down | 9.57 | 1.22 | -6.64 | 1.83 | 0.35 | -6.64 | 0.09 | 0.60 | -6.64 | -6.64 | -6.64 | -6.64 |
| hsa-miR-200c-5p | 2.14E-04 | 1.17E-05 | 13.62 down | 9.57 | -6.64 | -6.64 | -6.64 | -6.64 | -6.64 | 1.66 | -6.64 | -6.64 | -6.64 | -6.64 | -6.64 |
| hsa-miR-2115-3p | 1.64E-04 | 8.45E-06 | 13.62 down | 9.57 | 2.63 | -6.64 | -6.64 | -6.64 | -6.64 | 1.83 | -6.64 | -6.64 | -6.64 | -6.64 | -6.64 |
| hsa-miR-1244 | 1.30E-05 | 4.04E-07 | 13.88 down | 9.57 | 0.45 | 1.19 | -6.64 | -6.64 | -6.64 | 1.02 | 1.84 | -6.64 | -6.64 | 0.02 | -0.38 |
| hsa-miR-10b-3p | 0.001257804 | 1.04E-04 | 15.86 down | 9.57 | 2.45 | -6.64 | -6.64 | -6.64 | -6.64 | -6.64 | -6.64 | -6.64 | -6.64 | 2.07 | -6.64 |
| hsa-miR-182-5p | 1.59E-10 | 1.67E-13 | 16.29 down | 9.57 | -1.36 | -6.64 | 0.46 | -0.55 | 1.73 | -2.14 | 0.38 | -6.64 | -1.88 | -2.48 | -6.64 |
| hsa-miR-206 | 3.85E-04 | 2.35E-05 | 18.04 down | 9.57 | 3.85 | -6.64 | 3.51 | -6.64 | -6.64 | 2.64 | 2.60 | -6.64 | -6.64 | -6.64 | -6.64 |
| hsa-miR-205-5p | 0.001083732 | 8.52E-05 | 19.47 down | 9.57 | -6.64 | 2.54 | -6.64 | -6.64 | -6.64 | -6.64 | 1.30 | -6.64 | 1.55 | -6.64 | -6.64 |
| hsa-miR-4672 | 1.31E-04 | 6.27E-06 | 22.66 down | 9.57 | 1.98 | 1.69 | 4.61 | 2.27 | -6.64 | 1.54 | 1.94 | -6.64 | -6.64 | 1.86 | -6.64 |
| hsa-miR-31-3p | 0.001083732 | 8.62E-05 | 22.98 down | 9.57 | -6.64 | 4.58 | -6.64 | -6.64 | -6.64 | -6.64 | -6.64 | -6.64 | -6.64 | -6.64 | -6.64 |
| hsa-miR-196b-5p | 1.03E-04 | 4.44E-06 | 23.31 down | 9.57 | 2.43 | -6.64 | -6.64 | -6.64 | -6.64 | -6.64 | 1.75 | -6.64 | -6.64 | -6.64 | 3.81 |
| hsa-miR-29b-2-5p | 4.74E-06 | 1.17E-07 | 24.81 down | 9.57 | -6.64 | -6.64 | -6.64 | -6.64 | -6.64 | -6.64 | -6.64 | -6.64 | -6.64 | -6.64 | -6.64 |
| hsa-miR-3120-3p | 9.80E-07 | 1.50E-08 | 25.58 down | 9.57 | -6.64 | -6.64 | -6.64 | -6.64 | 2.81 | -6.64 | -6.64 | -6.64 | -6.64 | -6.64 | -6.64 |
| hsa-miR-452-5p | 3.02E-06 | 6.36E-08 | 28.71 down | 9.57 | -6.64 | 2.16 | -6.64 | -6.64 | -6.64 | -6.64 | -6.64 | -6.64 | -6.64 | -6.64 | -6.64 |
| hsa-miR-215 | 3.54E-04 | 2.11E-05 | 30.11 down | 9.57 | 1.79 | -6.64 | 3.52 | -6.64 | -6.64 | 2.70 | 1.71 | -6.64 | -6.64 | 2.62 | 2.87 |
| hsa-miR-200a-5p | 4.47E-06 | 1.06E-07 | 31.41 down | 9.57 | -6.64 | 1.54 | -6.64 | -6.64 | -6.64 | 1.57 | -6.64 | -6.64 | 1.58 | -6.64 | -6.64 |
| hsa-miR-375 | 1.84E-05 | 6.29E-07 | 34.56 down | 9.57 | -6.64 | -6.64 | -6.64 | -6.64 | -6.64 | -6.64 | -6.64 | -6.64 | -6.64 | -6.64 | -6.64 |
| hsa-miR-335-3p | 9.59E-07 | 1.36E-08 | 40.53 down | 9.57 | 1.95 | 2.52 | -6.64 | -6.64 | -6.64 | 2.03 | -6.64 | 1.97 | -6.64 | -6.64 | -6.64 |
| hsa-miR-539-5p | 1.20E-06 | 2.03E-08 | 48.97 down | 9.57 | 3.33 | 2.99 | 3.36 | -6.64 | -6.64 | 2.30 | 2.22 | -6.64 | -6.64 | -6.64 | -6.64 |
| hsa-miR-224-5p | 1.05E-06 | 1.66E-08 | 93.72 down | 9.57 | -6.64 | 4.85 | -6.64 | -6.64 | -6.64 | -6.64 | -6.64 | -6.64 | -6.64 | -6.64 | -6.64 |
| hsa-miR-183-3p | 4.11E-09 | 1.73E-11 | 101 down | 9.57 | -6.64 | -6.64 | -6.64 | -6.64 | -6.64 | -6.64 | -6.64 | -6.64 | -6.64 | -6.64 | -6.64 |
| hsa-miR-96-5p | 1.74E-09 | 1.10E-10 | 120.5 down | 9.57 | -6.64 | -6.64 | -6.64 | -6.64 | -6.64 | -6.64 | -6.64 | -6.64 | -6.64 | -6.64 | -6.64 |
| hsa-miR-335-5p | 2.00E-07 | 1.89E-09 | 138.4 down | 9.57 | -6.64 | 2.14 | -6.64 | -6.64 | -6.64 | 3.40 | -6.64 | -6.64 | -6.64 | 4.90 | -6.64 |
| hsa-miR-141-3p | 1.08E-08 | 5.70E-11 | 206.6 down | 9.57 | -6.64 | -6.64 | -6.64 | -6.64 | -6.64 | -6.64 | -6.64 | -6.64 | -6.64 | -6.64 | -6.64 |
| hsa-miR-183-5p | 3.29E-11 | 1.73E-14 | 220.7 down | 9.57 | -6.64 | -6.64 | -6.64 | -6.64 | -6.64 | -6.64 | 0.50 | -6.64 | -6.64 | -6.64 | -6.64 |
| hsa-miR-200c-3p | 1.29E-06 | 2.24E-08 | 250.7 down | 9.57 | 1.66 | -6.64 | -6.64 | -6.64 | -6.64 | -6.64 | -6.64 | 2.15 | -6.64 | 1.69 | 2.21 |
| hsa-miR-203 | 2.10E-09 | 1.44E-10 | 273.7 down | 9.57 | -6.64 | -6.64 | -6.64 | -6.64 | -6.64 | -6.64 | -6.64 | -6.64 | -6.64 | -6.64 | -6.64 |
| hsa-miR-429 | 3.83E-10 | 9.84E-13 | 515.8 down | 9.57 | -6.64 | -6.64 | -6.64 | -6.64 | -6.64 | -6.64 | -6.64 | -6.64 | -6.64 | -6.64 | -6.64 |
| hsa-miR-200a-3p | 6.01E-10 | 1.90E-12 | 680.6 down | 9.57 | -6.64 | -6.64 | -6.64 | -6.64 | -6.64 | -6.64 | -6.64 | -6.64 | -6.64 | -6.64 | -6.64 |
| hsa-miR-200b-3p | 3.83E-10 | 1.01E-12 | 1717 down | 9.57 | -6.64 | -6.64 | -6.64 | -6.64 | -6.64 | -6.64 | -6.64 | -6.64 | -6.64 | -6.64 | -6.64 |

FIG. 16F

| CO06 | CO08 | CO11 | CO12 | CO13 | CO16 | CO17 | CO21 | CO22 | CO25 | CO27 | CO29 | CO37 | CO38 | CO42 | CO43 | CO44 | CO45 | CO50 | CO52 | CO54 | CO57 |
|---|---|---|---|---|---|---|---|---|---|---|---|---|---|---|---|---|---|---|---|---|---|
| 6.64 | 6.66 | 6.64 | 7.67 | 4.03 | -6.64 | 5.30 | 2.47 | 6.64 | 9.19 | 7.00 | 4.97 | 9.60 | -6.64 | 6.50 | -6.64 | -6.64 | 7.11 | 8.95 | 10.15 | 9.90 | -6.64 |
| 6.64 | 6.63 | 6.64 | 6.64 | 4.36 | -6.64 | 8.81 | 4.84 | -6.64 | 3.86 | 6.64 | 3.85 | 2.85 | 5.40 | 6.36 | -6.64 | 3.15 | 5.63 | 5.32 | 7.50 | -6.64 | 3.58 |
| 6.64 | 5.60 | -6.64 | -6.64 | 3.95 | -6.64 | 7.84 | 4.18 | -6.64 | 3.22 | 6.64 | 2.58 | 2.69 | 5.36 | 4.62 | -6.64 | 1.78 | 4.41 | 5.16 | 6.08 | 2.40 | 2.01 |
| 6.64 | 4.20 | 7.07 | 3.85 | 2.48 | 6.99 | 7.01 | 6.64 | 5.66 | 3.25 | 2.58 | 6.64 | 5.16 | 5.66 | 4.38 | 6.96 | 4.04 | 5.35 | -6.64 | 6.04 | -6.64 | 4.24 |
| 6.64 | 3.86 | -6.64 | -6.64 | 3.01 | -6.64 | 7.59 | 2.58 | -6.64 | 2.21 | 6.64 | 2.18 | 1.44 | 3.46 | 4.08 | -6.64 | 2.22 | 3.87 | 3.38 | 5.42 | -6.64 | 2.58 |
| 6.64 | 4.06 | -6.64 | -6.64 | 2.39 | -6.64 | 7.40 | 2.98 | 6.64 | 3.70 | 6.64 | 3.21 | 2.94 | 4.00 | 4.15 | -6.64 | 6.64 | 4.49 | 4.63 | 5.46 | -6.64 | -6.64 |
| 6.64 | 3.26 | -6.64 | 6.64 | 2.18 | -6.64 | 6.53 | 2.33 | -6.64 | 2.38 | -6.64 | 2.38 | 6.64 | 2.80 | 3.26 | -6.64 | 1.70 | 3.46 | 4.38 | 4.76 | -6.64 | 1.97 |
| 6.64 | 6.64 | 3.66 | 6.64 | 2.11 | 5.91 | 5.44 | 2.20 | 4.63 | 6.64 | 6.64 | 6.64 | 6.64 | 6.64 | 3.31 | -6.64 | -6.64 | 4.83 | 6.59 | 3.23 | -6.64 | 6.11 |
| 1.29 | 0.91 | -0.44 | 0.55 | 0.84 | 0.07 | -0.26 | 0.23 | 0.43 | 0.66 | 0.18 | 0.20 | 0.54 | 0.44 | 0.54 | 0.67 | -0.54 | 0.42 | 1.33 | 1.10 | 0.85 | -0.17 |
| 6.64 | 3.84 | -6.64 | 6.64 | 6.64 | -6.64 | 7.01 | 1.90 | 6.64 | 2.48 | -6.64 | 2.32 | 2.12 | 3.32 | 3.02 | -6.64 | -6.64 | 4.01 | 3.35 | 5.20 | -6.64 | -6.64 |
| 6.64 | 3.67 | -6.64 | -6.64 | 2.34 | -6.64 | 7.03 | 2.02 | -6.64 | 2.58 | -6.64 | 2.08 | 2.06 | 3.52 | 3.70 | -6.64 | 6.64 | 3.32 | 2.66 | 5.03 | -6.64 | -6.64 |
| 6.64 | 3.62 | -6.64 | -6.64 | 2.04 | -6.64 | 6.54 | 1.86 | -6.64 | 2.38 | -6.64 | 1.94 | 1.77 | 3.19 | 3.16 | -6.64 | 6.64 | 3.28 | 3.62 | 4.67 | -6.64 | -6.64 |
| 2.40 | 2.73 | -6.64 | 1.78 | 1.85 | 2.46 | 2.04 | 1.90 | 2.46 | 2.58 | 2.45 | 2.27 | -6.64 | 1.98 | 2.34 | 1.51 | 6.64 | 2.07 | 2.41 | 2.21 | -6.64 | -6.64 |
| 1.33 | 0.99 | -6.64 | 0.92 | 1.36 | 0.35 | 3.51 | 0.45 | 0.49 | 0.55 | 0.76 | 0.49 | -0.23 | 1.05 | 1.35 | -6.64 | 0.41 | 0.48 | -6.64 | 1.73 | -6.64 | -6.64 |
| 6.64 | 6.64 | 5.27 | -6.64 | 4.25 | -6.64 | 6.03 | 6.12 | -6.64 | -0.37 | -6.64 | 0.77 | 5.33 | 2.77 | 1.56 | -6.64 | 4.76 | 3.26 | 5.95 | 6.63 | 0.35 | 2.99 |
| -6.64 | 2.14 | 2.99 | -6.64 | 4.08 | 4.31 | 6.92 | 6.64 | 2.71 | -6.64 | 1.72 | -6.64 | -6.64 | 2.92 | 3.40 | 2.54 | 3.86 | 2.46 | 6.64 | -6.64 | 6.64 | 5.08 |
| 6.64 | 2.93 | -6.64 | 2.98 | 6.64 | -6.64 | -6.64 | 2.16 | 3.22 | 2.93 | 3.35 | 3.27 | 2.06 | -6.64 | 2.96 | 2.73 | -6.64 | 2.04 | -6.64 | 2.45 | 1.98 | -6.64 |
| 6.64 | 2.45 | -6.64 | -6.64 | 2.28 | -6.64 | 6.83 | -6.64 | 6.64 | 6.64 | 6.64 | 6.64 | 6.64 | 2.90 | 2.99 | -6.64 | 6.64 | 2.25 | 2.28 | 4.02 | -6.64 | 6.64 |
| -6.64 | 1.71 | 2.22 | 6.64 | 0.66 | 1.17 | 1.18 | 1.32 | -6.64 | 0.36 | -0.04 | -0.13 | 1.26 | 0.92 | -0.05 | 1.00 | 0.52 | 0.21 | 1.65 | 1.61 | 0.99 | 0.96 |
| 6.64 | 5.29 | -6.64 | 2.80 | 3.97 | 3.15 | -6.64 | 4.75 | 1.94 | 2.24 | 3.91 | 1.87 | -6.64 | 3.49 | 2.05 | 2.58 | 6.64 | 3.89 | 6.64 | 6.64 | 6.64 | 6.64 |
| 3.38 | 1.69 | 6.64 | 2.53 | 1.67 | 2.17 | -6.64 | 6.64 | -6.64 | -6.64 | 2.28 | 6.64 | 6.64 | 1.60 | 2.02 | -6.64 | 2.31 | 6.64 | 2.50 | 6.64 | 2.07 | 6.64 |
| 3.38 | 1.78 | -6.64 | 1.78 | 2.28 | 2.10 | 2.01 | 2.16 | 1.53 | 2.08 | 2.24 | -6.64 | 6.64 | 1.65 | 1.78 | 6.64 | 1.98 | 6.64 | 6.64 | 2.18 | 2.52 | 1.76 |
| 6.64 | 3.40 | 6.64 | 6.64 | 2.93 | -6.64 | 6.40 | 2.30 | -6.64 | -6.64 | -6.64 | 6.64 | 2.00 | 3.10 | 2.60 | -6.64 | 6.64 | 2.51 | 6.64 | 4.58 | -6.64 | -6.64 |
| 0.24 | 0.73 | -6.64 | 2.23 | 0.99 | 0.72 | 0.48 | 0.32 | 0.93 | 0.53 | 0.99 | 1.36 | 0.40 | 0.55 | 0.94 | 0.75 | -0.33 | 0.40 | -6.64 | 0.91 | -6.64 | 0.10 |
| 6.64 | 2.97 | 3.73 | 2.63 | -6.64 | 1.85 | 2.51 | 2.33 | 1.94 | 2.55 | 2.21 | 3.61 | 1.35 | 6.64 | 1.99 | 2.73 | 1.78 | 1.53 | 2.80 | 2.50 | 6.64 | 1.85 |
| 6.64 | -0.34 | -6.64 | 6.64 | -0.26 | -6.64 | -0.38 | 6.64 | 1.45 | -0.03 | 6.64 | -0.27 | 1.15 | 1.19 | -0.41 | 1.58 | 0.71 | 1.58 | 1.14 | -0.13 | 0.81 | 0.03 |
| 6.64 | 6.64 | 3.37 | 6.64 | 3.99 | 1.58 | 4.37 | 6.64 | 2.62 | 6.64 | 2.36 | -6.64 | 5.32 | 3.90 | 6.64 | 3.16 | -6.64 | 6.64 | 6.64 | -6.64 | -6.64 | 3.88 |
| 6.64 | 2.84 | -6.64 | 3.18 | 6.64 | 1.63 | 6.64 | 1.82 | 2.18 | 2.27 | 2.31 | 2.27 | 1.65 | 6.64 | 1.70 | 1.85 | 1.60 | 2.46 | 1.95 | -6.64 | -6.64 | -6.64 |
| -6.64 | 1.03 | 4.17 | -6.64 | 0.81 | 1.57 | 1.39 | 1.47 | -0.16 | -0.46 | 0.15 | -6.64 | 0.18 | 0.09 | -6.64 | 0.31 | 0.43 | 0.71 | 1.02 | 1.77 | -6.64 | 2.22 |
| 6.64 | 2.11 | -6.64 | 2.53 | 1.76 | 2.26 | 1.61 | -6.64 | -6.64 | 6.64 | 2.15 | -6.64 | 6.64 | 1.65 | 1.99 | 6.64 | 6.64 | 6.64 | 6.64 | 2.24 | -6.64 | 6.64 |
| 1.41 | 1.37 | -0.07 | 1.14 | 1.94 | 1.03 | 0.55 | 1.32 | 0.78 | -0.23 | -0.38 | 0.18 | 0.51 | -0.45 | 0.37 | 0.44 | 0.33 | -0.11 | 0.46 | 0.00 | 0.22 | 0.07 |
| 1.14 | -0.02 | 6.64 | 0.52 | 0.59 | 0.30 | 0.10 | -6.64 | -0.01 | 0.03 | 0.24 | 0.28 | -6.64 | 0.45 | -6.64 | 0.02 | 0.48 | 0.03 | 0.27 | 0.21 | 1.00 | 0.21 |
| 6.64 | 0.80 | 0.99 | -0.60 | 1.83 | 0.95 | 2.54 | 0.16 | 0.67 | -0.07 | -0.15 | -1.66 | -0.53 | 1.52 | 0.07 | 0.44 | 2.16 | -0.99 | 2.54 | 2.43 | -6.64 | 0.65 |
| -6.64 | 6.64 | -6.64 | 6.64 | 2.08 | 2.17 | 2.18 | 1.77 | 1.87 | 1.62 | 2.31 | -6.64 | 1.73 | 1.82 | -6.64 | 6.64 | 2.05 | -6.64 | 6.64 | 1.85 | -6.64 | 6.64 |

FIG. 16G

| | | | | | | | | | | | | | | | | | | | | | |
|---|---|---|---|---|---|---|---|---|---|---|---|---|---|---|---|---|---|---|---|---|---|
| -0.02 | 1.42 | -6.64 | 1.82 | 0.53 | -0.31 | -0.33 | 0.10 | 1.37 | 1.37 | 1.31 | 1.60 | 0.54 | 0.36 | 1.47 | 0.60 | 0.03 | 0.06 | 0.41 | 0.48 | -0.35 | -6.64 |
| 0.30 | 2.50 | -1.54 | 2.69 | -0.42 | -0.59 | 0.27 | -0.88 | 0.34 | 0.53 | 1.44 | 0.68 | 1.54 | 1.05 | 0.08 | 0.00 | 0.39 | 0.75 | 1.64 | 1.94 | 0.94 | -0.02 |
| -6.64 | 1.81 | -6.64 | 2.13 | 0.46 | -0.12 | -6.64 | 0.68 | 1.35 | 0.88 | 1.69 | 1.35 | 1.26 | 0.04 | 0.94 | 0.71 | -0.32 | 0.17 | 0.17 | 0.63 | 0.03 | -6.64 |
| 2.31 | 6.64 | 6.64 | 2.11 | -6.64 | -6.64 | 1.70 | -6.64 | -6.64 | -6.64 | -6.64 | -6.64 | -6.64 | -6.64 | -6.64 | -6.64 | -6.64 | -6.64 | 1.83 | -6.64 | -6.64 | -6.64 |
| -6.64 | 6.64 | 0.98 | -0.05 | 1.26 | 2.26 | 3.01 | -2.55 | 1.32 | 0.11 | -6.64 | -0.89 | -2.02 | 2.24 | 1.93 | 0.14 | 0.53 | 1.91 | 2.17 | 2.13 | -0.32 | 1.90 |
| 1.84 | 0.02 | -6.64 | 0.00 | 0.33 | 0.29 | -0.06 | -0.05 | 0.57 | 0.05 | 0.69 | 0.10 | -0.72 | 0.97 | 0.43 | -0.25 | 0.86 | 0.03 | 0.00 | 0.54 | 0.99 | -6.64 |
| -6.64 | 1.13 | 0.30 | 1.18 | 0.19 | 0.79 | 1.57 | 1.06 | 1.18 | 0.12 | 0.73 | 0.45 | 1.12 | 0.34 | 0.57 | 0.51 | -0.08 | -0.11 | 0.84 | 1.73 | -6.64 | 0.73 |
| 0.97 | 1.85 | 0.75 | 1.05 | 1.15 | 1.54 | 2.08 | 1.21 | 0.89 | 1.55 | -0.45 | -0.27 | 0.74 | 0.51 | 0.69 | 0.68 | 0.80 | 1.51 | 0.69 | 1.90 | -0.51 | 0.13 |
| 0.00 | 1.32 | -1.12 | 2.60 | 0.19 | 0.35 | 0.06 | -0.21 | 0.58 | 0.23 | 0.92 | 0.32 | 0.97 | -0.38 | 0.46 | 0.17 | 0.36 | 0.49 | 0.54 | 1.48 | 0.10 | -0.06 |
| 2.19 | 0.12 | -0.35 | 0.69 | -0.05 | 0.30 | 0.36 | 0.00 | 0.61 | -0.27 | 0.10 | -0.11 | -0.36 | 0.41 | 0.24 | 0.11 | 0.00 | 0.14 | -6.64 | 0.43 | -6.64 | 0.35 |
| 1.13 | 0.56 | -6.64 | 0.63 | 0.69 | 0.88 | 0.00 | 0.49 | 0.31 | 0.61 | 0.44 | 0.00 | -0.21 | 0.32 | 0.50 | -6.64 | 1.46 | -6.64 | 0.17 | 0.66 | 1.05 | -6.64 |
| 1.20 | 2.34 | -1.39 | 2.60 | 0.12 | 0.01 | -0.84 | -0.16 | 1.42 | -0.12 | 1.08 | 1.02 | 1.03 | 0.65 | 0.24 | 0.49 | 0.00 | 0.56 | 0.95 | 1.10 | 1.55 | -0.61 |
| 1.18 | 2.05 | 0.84 | 0.20 | 1.71 | 1.72 | 2.28 | 1.60 | 0.49 | 0.39 | -0.02 | -1.10 | 0.59 | 0.95 | 0.43 | 0.26 | 1.22 | 1.42 | 0.45 | 2.25 | -0.23 | 0.75 |
| -6.64 | 0.89 | -0.07 | 1.51 | 2.44 | 1.95 | 1.76 | 0.87 | -0.78 | 1.50 | 0.57 | 0.13 | 0.68 | 1.60 | 1.55 | -0.37 | 1.38 | 0.65 | 2.18 | 1.33 | 0.68 | 0.74 |
| 1.22 | 1.62 | -1.62 | 2.33 | -0.25 | 0.05 | -0.84 | -0.36 | 1.73 | -0.10 | 1.15 | 0.85 | 0.86 | 0.45 | 0.33 | 0.41 | 0.00 | 0.90 | 0.65 | 0.11 | 1.85 | -1.12 |
| 1.36 | 1.27 | -0.69 | 1.56 | 0.47 | -0.79 | 2.72 | 1.68 | 0.16 | 0.43 | 0.47 | 0.83 | 0.03 | 0.28 | 1.20 | 0.81 | -1.50 | 1.00 | 0.87 | 1.49 | 0.39 | -0.64 |
| -0.43 | 2.07 | -1.99 | 2.76 | 0.11 | 0.09 | -0.58 | -0.27 | 2.11 | 0.55 | 1.61 | 1.08 | 1.22 | 0.10 | 1.00 | 0.46 | 0.56 | 0.81 | 1.31 | 0.80 | 1.06 | -1.02 |
| 1.17 | 0.41 | -6.64 | 1.23 | 0.60 | -0.01 | 0.17 | 0.39 | 0.28 | 0.04 | 0.92 | 0.21 | -6.64 | 0.01 | 0.71 | -0.36 | 0.94 | -0.90 | 0.61 | 0.31 | 0.14 | -6.64 |
| 0.24 | 0.89 | -1.11 | 0.32 | 0.82 | -1.08 | 3.86 | 0.23 | 0.50 | 0.89 | 0.21 | 0.97 | 0.30 | 1.22 | 1.59 | -0.48 | -0.03 | 0.64 | 0.68 | 1.90 | 0.36 | -0.82 |
| 1.92 | 1.59 | -1.36 | 1.68 | 0.07 | 0.71 | -0.64 | -0.01 | 1.02 | 0.02 | 0.73 | 0.61 | 1.25 | 0.70 | 0.05 | 0.08 | -0.82 | 0.56 | 0.57 | 0.63 | 1.78 | -0.58 |
| -6.64 | 1.14 | 0.78 | 0.89 | 0.61 | 1.11 | 2.00 | 0.84 | 0.86 | 1.89 | -0.54 | -1.20 | 1.08 | 0.21 | 0.47 | 0.56 | 0.66 | 0.84 | 1.10 | 2.09 | -0.02 | 0.42 |
| 0.51 | 1.06 | -1.50 | 1.99 | -0.21 | 0.73 | -0.27 | 0.04 | 2.02 | -0.02 | 0.21 | 1.15 | 0.51 | 0.28 | 0.51 | -0.07 | 0.02 | 0.11 | 0.74 | 0.92 | 1.01 | -0.20 |
| -0.95 | 1.15 | 2.53 | -0.38 | 1.05 | 1.61 | 0.60 | 1.31 | 0.03 | -0.80 | 0.50 | -2.42 | -0.75 | 0.33 | -0.18 | 0.25 | 0.64 | 0.29 | 0.54 | 1.18 | -1.70 | 0.59 |
| 1.81 | 0.06 | -6.64 | 0.99 | 1.20 | 0.53 | -0.40 | 1.02 | 0.43 | -0.19 | 0.57 | 0.06 | -6.64 | 0.03 | 1.40 | -0.18 | 0.19 | -0.72 | -6.64 | -0.10 | 0.48 | -0.13 |
| -1.63 | 0.06 | -0.19 | 1.31 | 2.00 | 1.38 | 1.25 | 0.73 | -0.65 | 1.33 | 0.50 | 0.20 | 0.55 | 1.29 | 1.29 | 0.09 | 0.89 | 0.93 | 1.80 | 0.55 | 0.76 | 0.49 |
| 1.29 | 0.07 | -6.64 | 0.42 | -0.04 | -0.03 | -0.63 | 0.41 | 1.16 | 0.19 | 0.50 | 0.59 | 1.05 | -0.29 | 0.44 | 1.39 | 0.07 | 0.63 | -6.64 | 0.22 | 0.28 | -6.64 |
| -1.50 | 1.21 | -1.75 | 2.63 | -0.15 | -0.21 | -1.10 | -0.96 | 1.77 | -0.04 | 0.91 | 0.96 | 0.80 | 0.69 | 0.40 | -0.03 | 0.21 | 0.12 | 0.65 | 0.65 | 1.73 | -0.67 |
| 0.25 | 1.14 | 0.39 | 1.95 | 1.53 | 0.48 | -0.01 | -0.22 | 1.48 | 0.32 | 1.31 | 0.84 | -0.55 | 0.85 | 0.81 | 0.35 | 1.13 | -0.42 | -0.37 | 1.27 | 0.51 | -0.30 |
| 1.52 | 0.17 | -0.82 | -6.64 | -0.13 | 0.47 | -0.06 | 0.35 | -0.15 | -0.12 | 0.54 | -0.30 | -0.33 | -0.05 | 0.03 | 0.05 | 0.72 | -0.34 | 0.24 | 0.69 | 1.45 | -0.02 |
| 1.85 | 2.45 | -0.89 | 1.12 | 0.59 | -0.49 | -0.05 | -0.63 | 0.20 | 1.02 | 0.23 | 0.40 | 1.37 | 0.23 | 0.33 | -0.30 | -0.27 | -0.62 | 1.21 | 3.06 | 2.17 | -0.12 |
| -0.19 | 0.58 | -6.64 | 1.68 | 0.48 | 0.40 | -0.13 | -0.64 | 0.36 | 0.23 | 0.83 | 0.48 | -0.57 | 0.79 | 0.54 | -0.81 | 0.61 | -0.58 | 0.34 | 0.52 | 0.50 | -0.74 |
| -6.64 | 2.83 | 1.66 | 0.18 | -0.13 | 0.17 | 1.29 | 1.23 | 0.19 | 1.18 | 0.89 | -6.64 | 0.55 | -0.02 | 0.22 | -0.59 | 0.01 | 1.55 | 1.26 | 2.98 | -0.64 | 1.58 |
| 1.11 | 1.72 | -1.89 | 2.20 | 0.02 | -0.09 | -1.30 | -0.25 | 1.62 | -0.46 | 0.93 | 0.80 | 0.07 | 0.88 | -0.12 | 0.31 | 0.01 | 0.72 | 0.24 | -0.55 | 1.69 | -1.52 |
| 1.38 | 1.79 | -2.31 | 2.14 | -0.31 | -0.52 | -1.61 | -0.61 | 1.94 | -0.19 | 1.05 | 1.07 | 0.46 | 0.61 | 0.45 | 0.92 | -0.16 | 0.93 | -0.02 | -0.69 | 1.20 | -1.90 |
| 1.16 | 1.87 | -2.00 | 2.50 | -0.15 | -0.36 | -1.41 | -0.24 | 1.91 | -0.01 | 1.36 | 1.13 | 0.13 | 0.61 | 0.44 | 0.70 | 0.02 | 0.48 | 0.01 | -0.40 | 1.28 | -1.49 |
| -6.64 | 1.76 | 1.15 | 0.63 | 1.52 | 1.64 | 2.33 | 1.30 | 0.97 | 0.30 | -0.67 | -1.60 | -0.01 | 1.19 | 0.74 | 0.56 | 1.55 | 1.38 | 0.66 | 2.15 | -1.35 | 0.81 |
| -1.09 | 1.88 | -1.61 | 1.48 | -0.26 | -0.54 | -1.11 | -0.73 | 0.87 | 0.90 | 1.74 | 1.83 | 1.75 | 0.64 | 1.19 | 0.22 | 0.21 | 0.51 | 1.23 | 1.51 | 0.90 | -0.74 |
| 1.54 | -0.39 | -0.80 | -0.24 | -0.03 | 0.47 | -0.01 | -0.21 | 0.82 | -0.15 | -0.41 | -0.67 | 0.14 | 1.07 | -0.51 | 0.17 | 1.13 | 0.07 | -0.10 | 0.06 | 0.28 | 0.04 |
| 0.58 | 1.19 | -1.61 | 1.05 | 0.01 | 0.59 | -0.57 | -0.03 | 0.84 | 0.57 | 1.25 | 1.27 | -0.48 | 1.05 | 0.99 | -0.40 | 0.85 | -0.01 | 0.08 | 0.35 | 0.75 | -0.99 |
| 0.46 | 0.85 | -0.20 | 0.53 | 1.06 | 0.46 | 0.95 | 0.85 | 0.25 | -0.34 | 0.54 | 1.38 | -0.31 | -0.23 | 0.72 | 0.50 | 0.40 | -0.35 | -0.04 | 0.17 | -0.33 | 1.40 |

FIG. 16I

| | | | | | | | | | | | | | | | | | | | | | |
|---|---|---|---|---|---|---|---|---|---|---|---|---|---|---|---|---|---|---|---|---|---|
| -3.86 | -1.31 | 0.47 | -0.79 | 0.23 | 1.10 | -0.34 | -0.03 | -0.02 | -0.97 | 0.09 | -1.01 | -0.87 | -0.30 | -0.58 | 0.56 | -1.17 | -0.72 | 0.61 | -1.81 | 3.12 | 0.26 |
| -0.95 | -0.61 | 0.34 | -0.99 | -1.61 | -0.58 | -0.17 | -0.22 | -1.47 | 0.69 | -1.22 | -0.98 | 0.08 | -1.81 | -1.34 | -0.31 | -0.12 | -0.61 | 0.57 | -0.02 | 0.70 | 0.68 |
| 2.87 | -6.64 | 0.05 | -0.82 | 0.10 | -1.70 | -1.77 | -1.60 | -1.23 | -1.05 | -0.57 | -0.39 | -0.63 | -1.68 | -0.17 | -0.86 | 0.29 | -0.69 | -0.93 | -1.41 | 1.55 | -0.55 |
| -0.90 | -2.07 | 1.19 | -2.22 | -1.77 | -1.04 | 0.89 | -0.72 | -1.00 | 0.47 | -1.01 | -1.78 | 0.85 | -1.69 | -1.39 | -0.34 | 1.69 | 0.45 | 0.37 | 0.85 | 0.16 | -0.40 |
| -0.60 | -0.34 | 0.58 | -6.64 | -1.45 | -0.67 | -0.20 | -0.17 | -0.77 | 0.32 | -1.17 | -0.71 | 0.52 | -1.68 | -1.43 | 0.02 | -0.92 | 0.14 | 1.08 | -0.30 | 0.61 | 0.42 |
| -6.64 | -1.10 | -0.52 | -1.18 | -0.95 | -1.65 | -0.40 | -0.48 | -0.53 | 0.18 | -0.82 | 0.78 | -0.09 | -1.34 | -0.36 | 1.13 | -1.40 | -0.63 | 0.20 | -0.36 | -0.28 | -1.23 |
| -6.64 | -0.59 | 1.10 | -0.48 | -0.62 | -0.20 | -0.53 | -0.87 | -0.53 | 0.40 | -0.88 | 0.00 | 0.17 | -0.23 | -0.78 | 0.00 | -0.26 | 0.29 | -0.62 | 0.20 | 0.21 | 1.03 |
| 1.01 | -1.07 | 0.38 | -1.01 | -1.04 | -0.48 | -1.07 | 0.14 | -0.30 | -0.18 | -0.69 | -0.73 | -0.44 | -0.99 | -1.53 | -0.19 | -1.19 | -0.11 | 0.25 | -6.64 | 1.15 | 0.00 |
| -6.64 | 0.23 | 0.21 | -0.22 | -0.99 | 0.00 | 1.64 | 0.25 | -0.04 | 0.08 | 0.45 | -2.20 | -0.66 | -0.09 | -1.06 | -1.54 | 0.32 | -0.77 | 0.97 | 1.19 | -0.91 | 0.81 |
| 0.66 | -6.64 | 0.23 | 0.29 | -0.91 | -0.68 | -0.45 | -0.55 | -0.56 | 0.92 | -0.25 | 2.37 | -1.31 | -0.86 | 0.69 | 0.69 | -1.10 | 0.20 | -6.64 | -0.67 | -6.64 | 0.33 |
| -6.64 | -6.64 | 1.59 | 0.10 | -1.14 | -0.59 | 0.44 | -0.45 | -1.17 | 0.14 | 1.24 | -0.84 | -1.35 | -0.13 | -0.71 | 0.98 | -1.23 | -1.56 | 1.27 | -0.33 | -0.64 | 0.40 |
| -6.64 | -6.64 | 0.40 | -0.31 | -6.64 | 0.31 | -0.11 | -6.64 | -6.64 | 0.10 | 0.07 | 0.16 | 0.51 | -6.64 | -0.05 | 0.34 | -0.06 | -0.01 | 0.48 | 0.07 | -6.64 | 0.98 |
| -6.64 | -0.19 | 0.69 | -1.31 | 0.10 | 0.60 | 0.53 | 0.48 | -6.64 | 0.28 | 0.64 | -6.64 | -6.64 | -0.74 | -1.16 | -0.33 | -6.64 | 0.19 | 0.44 | -0.08 | -6.64 | 0.94 |
| -6.64 | 2.53 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -6.64 | -0.55 | 0.56 | -6.64 | -0.77 | -0.38 | 0.01 | -6.64 | -6.64 | -0.15 | -0.20 | -0.43 | -0.19 | -0.71 | -6.64 | 0.57 | -0.84 | 0.08 | -0.01 | -0.20 | 0.81 | 1.16 |
| -2.82 | -1.34 | 1.11 | -1.78 | -2.65 | -0.62 | 0.15 | -1.16 | -1.97 | 1.27 | -1.87 | -0.84 | 0.79 | -1.51 | -1.86 | 0.12 | -0.20 | 0.11 | 0.75 | -0.03 | 1.16 | 1.15 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | 3.48 |
| -6.64 | 0.53 | 0.08 | -0.23 | -6.64 | -0.01 | 0.04 | 0.74 | -0.06 | -0.16 | -0.47 | -0.01 | -0.04 | -0.19 | -0.80 | 0.12 | -6.64 | 0.07 | 0.93 | 0.36 | -6.64 | -0.19 |
| -6.64 | 0.01 | 0.10 | -6.64 | -6.64 | 0.32 | -0.24 | -6.64 | -6.64 | 0.73 | 0.26 | -0.32 | 0.84 | 0.10 | -6.64 | -0.20 | 0.46 | -6.64 | 1.48 | 0.43 | -6.64 | 0.16 |
| -6.64 | -0.66 | -0.81 | -0.09 | 0.16 | 0.12 | 0.02 | -0.06 | 0.02 | 1.04 | -0.55 | 1.66 | -0.50 | 0.06 | 0.79 | 0.72 | 0.21 | 1.39 | -6.64 | -0.23 | 0.14 | -0.40 |
| -6.64 | -6.64 | -0.61 | -0.14 | -0.09 | -6.64 | -6.64 | 0.01 | 0.10 | -0.28 | -0.12 | 1.01 | -0.20 | -0.38 | 0.53 | 0.06 | -0.49 | -0.13 | -6.64 | -6.64 | -0.13 | -0.15 |
| -0.62 | -6.64 | -0.33 | -6.64 | -0.39 | -1.21 | -6.64 | -0.23 | -0.29 | 0.67 | -0.12 | 1.82 | -0.97 | 0.14 | 0.36 | 0.24 | -1.10 | 0.11 | -0.88 | -6.64 | 0.94 | -6.64 |
| -6.64 | 2.21 | 0.34 | -0.48 | -1.56 | -1.37 | 0.02 | -0.41 | -0.47 | 1.13 | -0.02 | -1.04 | 0.13 | -3.17 | -1.77 | -0.11 | -2.08 | -0.06 | 1.41 | -0.30 | -0.06 | -0.07 |
| -6.64 | -0.37 | 0.63 | -6.64 | -6.64 | -0.99 | -0.79 | -0.85 | -0.63 | 0.14 | -0.68 | -0.52 | 0.16 | -0.63 | -6.64 | 0.42 | -6.64 | 0.41 | -0.08 | -6.64 | 0.45 | -0.77 |
| 0.48 | -0.88 | 0.25 | -6.64 | -6.64 | -0.98 | -0.63 | 0.21 | -0.70 | -0.39 | -0.64 | -0.55 | -0.19 | -6.64 | -6.64 | 0.17 | -6.64 | 0.18 | -0.35 | -0.68 | 0.78 | 0.51 |
| -6.64 | 0.51 | 1.21 | -0.18 | 1.30 | 0.87 | -0.06 | 0.65 | -6.64 | 0.34 | 0.45 | -6.64 | 0.12 | -6.64 | -1.10 | -0.87 | -0.60 | -0.15 | 1.71 | 0.88 | -0.45 | 1.20 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| 0.10 | -6.64 | 0.93 | -6.64 | -6.64 | -0.11 | 0.45 | -0.55 | -0.87 | -0.51 | -6.64 | -6.64 | -6.64 | -0.44 | -6.64 | 0.20 | 0.34 | 0.28 | 0.80 | -6.64 | 0.03 | -0.25 |
| -6.64 | -2.86 | 1.56 | 0.17 | -1.06 | 0.48 | -0.46 | -1.38 | -0.21 | -0.38 | 0.40 | -0.62 | 0.55 | -1.60 | -1.31 | 1.38 | -6.64 | -1.17 | 0.87 | -2.88 | -6.64 | 0.62 |
| 0.96 | -6.64 | 0.12 | -6.64 | -6.64 | -6.64 | 0.32 | -0.41 | -6.64 | -0.22 | -0.41 | 0.24 | 0.03 | -6.64 | -6.64 | 0.27 | -6.64 | -0.26 | 0.54 | -6.64 | 1.29 | 0.49 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -6.64 | -1.03 | 0.73 | -0.81 | -6.64 | -0.92 | -0.48 | -6.64 | -0.94 | -0.08 | -1.13 | -0.14 | -0.21 | -6.64 | -6.64 | 0.77 | -0.83 | 0.60 | 0.90 | -0.70 | 0.08 | 0.16 |
| 0.38 | -6.64 | 0.55 | -6.64 | -6.64 | -0.21 | 0.34 | -0.70 | -0.27 | -0.06 | -6.64 | -6.64 | 0.44 | -6.64 | -0.72 | 0.08 | 0.36 | 0.08 | 0.78 | -0.34 | 0.41 | 0.27 |
| -6.64 | -0.38 | 0.91 | -1.07 | -6.64 | -0.94 | -0.33 | -0.25 | -6.64 | -0.74 | -1.35 | -1.27 | 0.23 | -1.33 | -6.64 | 0.37 | -0.93 | 0.30 | 1.09 | -1.13 | 0.44 | 0.41 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | 2.00 | -6.64 | -6.64 | -6.64 |
| -6.64 | -6.64 | 0.71 | -6.64 | -6.64 | -1.06 | -0.32 | -2.16 | -1.27 | 0.17 | -1.81 | -0.70 | -0.69 | -1.18 | -2.58 | 0.45 | -1.18 | 0.94 | -0.23 | -1.60 | 0.79 | 0.12 |
| 0.59 | -6.64 | -0.02 | -0.39 | -0.28 | -6.64 | -6.64 | -6.64 | -0.42 | 0.81 | -6.64 | 2.51 | -6.64 | -6.64 | 0.75 | 0.74 | -6.64 | 0.36 | -6.64 | -6.64 | 0.05 | 0.22 |
| -6.64 | -6.64 | 2.04 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | 2.03 | 1.67 |

FIG. 16J

| | | | | | | | | | | | | | | | | | | | | | |
|---|---|---|---|---|---|---|---|---|---|---|---|---|---|---|---|---|---|---|---|---|---|
| -6.64 | -6.64 | 3.46 | -6.64 | -6.64 | 2.61 | -6.64 | -6.64 | -6.64 | -6.64 | -6.64 | -6.64 | -6.64 | -6.64 | -6.64 | 1.51 | -6.64 | -6.64 | 2.63 | -6.64 | -6.64 | 1.89 |
| -6.64 | -6.64 | 1.55 | -6.64 | -6.64 | -6.64 | -6.64 | -6.64 | 2.29 | -6.64 | -6.64 | 2.35 | -6.64 | -6.64 | -6.64 | 1.59 | -6.64 | 1.75 | -6.64 | -6.64 | -6.64 | -6.64 |
| -6.64 | 2.00 | 2.63 | -6.64 | -6.64 | -6.64 | -6.64 | -6.64 | -6.64 | -6.64 | -6.64 | -6.64 | 2.65 | -6.64 | -6.64 | 2.03 | -6.64 | 1.79 | -6.64 | -6.64 | -6.64 | 1.89 |
| -6.64 | -6.64 | 1.17 | -6.64 | -6.64 | -6.64 | -6.64 | -6.64 | -6.64 | 0.55 | -6.64 | 1.15 | 1.03 | -0.45 | -6.64 | 1.16 | -0.58 | 0.20 | 0.19 | -6.64 | 0.60 | -0.26 |
| -6.64 | -6.64 | -6.64 | -6.64 | -6.64 | -6.64 | -6.64 | -6.64 | -6.64 | -6.64 | -6.64 | 1.25 | -6.64 | 0.69 | -6.64 | 0.60 | -6.64 | -6.64 | -6.64 | -6.64 | 0.94 | -6.64 |
| -6.64 | -6.64 | 0.34 | -6.64 | -6.64 | -6.64 | -6.64 | -6.64 | -6.64 | -6.64 | -6.64 | 0.12 | 0.00 | -6.64 | -6.64 | 0.59 | -0.19 | -0.16 | -6.64 | -6.64 | 0.49 | 0.36 |
| -6.64 | -6.64 | 1.33 | -6.64 | -6.64 | -6.64 | -6.64 | -6.64 | -6.64 | -6.64 | -6.64 | -6.64 | 2.15 | -6.64 | -6.64 | 1.51 | -6.64 | -6.64 | -6.64 | -6.64 | -6.64 | 3.01 |
| -6.64 | -6.64 | 1.95 | -6.64 | -6.64 | -6.64 | -6.64 | -6.64 | -6.64 | 2.56 | -6.64 | 4.98 | -6.64 | -6.64 | 2.12 | 2.60 | -6.64 | 2.51 | -6.64 | -6.64 | -6.64 | -6.64 |
| -6.64 | -6.64 | 1.13 | -6.64 | -6.64 | -6.64 | -6.64 | -6.64 | -6.64 | -6.64 | -6.64 | 0.37 | 0.79 | -6.64 | -6.64 | 0.79 | -6.64 | 0.43 | 0.41 | -6.64 | -6.64 | 0.34 |
| -6.64 | -6.64 | 0.28 | -6.64 | -6.64 | -0.35 | -0.25 | -6.64 | 0.25 | -0.32 | -6.64 | 0.04 | -0.42 | -6.64 | -6.64 | 0.78 | -6.64 | 0.77 | -6.64 | -6.64 | -0.09 | -6.64 |
| -6.64 | -6.64 | -6.64 | -6.64 | -6.64 | 1.72 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -6.64 | -6.64 | 1.59 | -6.64 | 1.63 | -6.64 | -6.64 | -6.64 | -6.64 | 1.87 | -6.64 | 2.01 | -6.64 | -6.64 | -6.64 | -6.64 | -6.64 | -6.64 | -6.64 | -6.64 | -6.64 | 1.67 |
| -6.64 | -6.64 | 1.92 | -6.64 | -6.64 | -6.64 | -1.31 | -6.64 | -6.64 | 0.46 | -6.64 | -6.64 | 1.28 | -6.64 | -6.64 | -0.41 | -6.64 | -0.48 | 1.44 | 1.67 | 2.05 | 1.48 |
| -6.64 | -6.64 | 4.09 | -6.64 | -6.64 | -6.64 | 1.21 | -6.64 | -6.64 | -6.64 | -6.64 | -6.64 | 2.17 | -6.64 | -6.64 | -6.64 | -6.64 | 1.79 | -6.64 | -6.64 | -6.64 | 2.31 |
| -0.77 | -6.64 | -1.32 | -2.41 | -2.21 | -1.78 | -2.24 | -6.64 | 0.76 | -6.64 | -0.19 | -2.37 | -1.63 | -1.85 | -1.59 | -0.65 | -1.64 | -2.29 | -2.16 | -2.85 | -0.13 | 0.32 |
| -6.64 | -6.64 | 2.67 | -6.64 | -6.64 | -6.64 | -6.64 | -6.64 | -6.64 | -6.64 | -6.64 | -6.64 | -6.64 | -6.64 | -6.64 | -6.64 | -6.64 | 1.58 | -6.64 | -6.64 | -6.64 | -6.64 |
| 3.39 | -6.64 | -6.64 | 2.07 | -6.64 | -6.64 | -6.64 | -6.64 | 1.68 | -6.64 | 2.10 | 1.54 | -6.64 | -6.64 | 1.37 | -6.64 | 1.28 | 1.33 | -6.64 | -6.64 | -6.64 | -6.64 |
| -6.64 | -6.64 | 2.93 | -6.64 | -6.64 | -6.64 | -6.64 | -6.64 | -6.64 | -6.64 | -6.64 | -6.64 | -6.64 | -6.64 | -6.64 | -6.64 | -6.64 | 1.53 | -6.64 | -6.64 | -6.64 | 3.29 |
| -6.64 | -6.64 | 4.46 | -6.64 | -6.64 | -6.64 | 1.56 | 4.10 | -6.64 | -6.64 | 4.03 | -6.64 | -6.64 | -6.64 | -6.64 | -6.64 | -6.64 | -6.64 | -6.64 | -6.64 | -6.64 | 6.00 |
| -6.64 | -6.64 | 2.53 | -6.64 | -6.64 | -6.64 | 3.27 | -6.64 | 1.75 | -6.64 | -6.64 | -6.64 | 1.40 | -6.64 | -6.64 | 2.03 | -6.64 | 3.19 | 2.18 | -6.64 | -6.64 | 2.67 |
| -6.64 | -6.64 | 2.07 | -6.64 | -6.64 | -6.64 | 1.82 | -6.64 | -6.64 | -6.64 | -6.64 | -6.64 | -6.64 | -6.64 | -6.64 | -6.64 | -6.64 | -6.64 | -6.64 | 2.63 | -6.64 | 1.63 |
| -6.64 | -6.64 | 1.63 | -6.64 | -6.64 | -6.64 | -6.64 | -6.64 | -6.64 | -6.64 | -6.64 | -6.64 | -6.64 | -6.64 | -6.64 | -6.64 | 1.94 | -6.64 | -6.64 | -6.64 | -6.64 | 1.63 |
| -6.64 | -6.64 | 1.42 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -6.64 | -6.64 | 3.83 | -6.64 | -6.64 | -6.64 | -6.64 | -6.64 | -6.64 | 3.61 | -6.64 | -6.64 | 1.87 | -6.64 | -6.64 | 1.73 | -6.64 | 1.79 | 4.61 | -6.64 | -6.64 | 3.43 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -6.64 | -6.64 | 2.10 | -6.64 | -6.64 | -6.64 | -6.64 | -6.64 | -6.64 | 2.51 | -6.64 | 2.53 | 1.80 | -6.64 | -6.64 | 1.93 | -6.64 | 2.71 | -6.64 | -6.64 | -6.64 | 2.45 |
| -6.64 | -6.64 | 2.47 | -6.64 | -6.64 | -6.64 | -6.64 | -6.64 | -6.64 | -6.64 | -6.64 | -6.64 | -6.64 | -6.64 | -6.64 | -6.64 | -6.64 | 1.82 | 2.11 | -6.64 | -6.64 | -6.64 |
| -6.64 | -6.64 | 3.65 | -6.64 | -6.64 | -6.64 | 2.24 | -6.64 | -6.64 | -6.64 | 3.15 | 2.67 | -6.64 | -6.64 | -6.64 | 2.39 | -6.64 | -6.64 | -6.64 | -6.64 | -6.64 | 2.85 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -6.64 | -6.64 | -6.64 | -6.64 | -6.64 | -6.64 | -6.64 | -6.64 | 2.79 | -6.64 | 1.72 | -6.64 | -6.64 | -6.64 | -6.64 | -6.64 | -6.64 | -6.64 | -6.64 | -6.64 | -6.64 | 2.15 |
| -6.64 | -6.64 | 3.66 | -6.64 | -6.64 | -6.64 | -6.64 | -6.64 | -6.64 | -6.64 | -6.64 | -6.64 | 1.61 | -6.64 | -6.64 | -6.64 | -6.64 | -6.64 | -6.64 | -6.64 | 2.94 | 4.23 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -6.64 | -6.64 | -6.64 | -6.64 | -6.64 | -6.64 | -6.64 | -6.64 | 1.61 | -6.64 | 1.07 | -6.64 | -0.79 | -0.13 | -6.64 | -0.11 | -6.64 | -6.64 | -6.64 | -6.64 | -6.64 | 1.15 |
| -6.64 | 1.65 | 2.07 | -6.64 | -6.64 | 1.58 | 1.82 | -6.64 | 2.73 | -6.64 | -6.64 | 1.79 | -6.64 | -6.64 | 1.92 | -6.64 | -6.64 | -6.64 | 1.87 | 2.18 | -6.64 | -6.64 |
| -6.64 | -6.64 | -6.64 | 1.87 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | 2.07 | -6.64 | -6.64 | -6.64 |

FIG. 16L

| CD58 | CD60 | CD62 | CD65 | CD67 | CD71 | CD74 | CD76 | CD77 | CD78 | CD79 | CD80 | CD81 | CD83 | CD84 | CD86 | CD88 | CD89 | CD91 | CD92 | CD94 | CD96 | CD97 |
|---|---|---|---|---|---|---|---|---|---|---|---|---|---|---|---|---|---|---|---|---|---|---|
| 3.57 | 7.98 | 5.18 | 2.34 | -6.64 | -6.64 | 3.25 | -6.64 | 1.54 | 1.86 | 5.70 | 2.03 | 5.02 | 1.81 | 4.48 | -6.64 | 6.45 | 4.74 | 1.81 | -6.64 | 1.56 | -6.64 | -6.64 |
| -6.64 | 6.10 | 2.50 | 3.19 | -6.64 | 4.18 | 4.39 | 4.26 | 4.45 | -6.64 | 4.51 | 2.46 | 5.35 | -6.64 | 5.89 | -6.64 | 3.31 | 5.85 | 6.30 | -6.64 | 7.13 | -6.64 | 2.51 |
| -6.64 | 6.14 | 2.83 | 3.01 | -6.64 | 2.16 | 4.63 | 3.94 | 3.71 | -6.64 | 3.27 | 2.97 | 4.96 | -6.64 | 5.60 | -6.64 | 2.76 | 5.65 | 4.92 | -6.64 | 6.54 | -6.64 | -6.64 |
| -6.64 | 4.61 | 6.62 | 4.75 | -6.64 | 3.45 | 7.02 | 5.51 | 4.59 | -6.64 | 2.82 | 5.54 | 3.22 | -6.64 | -6.64 | -6.64 | 3.95 | 3.23 | 6.69 | -6.64 | -6.64 | 5.48 | 7.90 |
| -6.64 | 4.75 | -6.64 | 1.92 | -6.64 | 2.07 | 3.33 | 2.92 | 2.95 | -6.64 | 2.41 | 2.04 | 3.20 | -6.64 | 3.60 | -6.64 | 1.66 | 3.17 | 4.35 | -6.64 | 3.51 | -6.64 | -6.64 |
| -6.64 | 5.49 | -6.64 | -6.64 | -6.64 | 2.80 | 3.69 | 3.73 | 3.06 | -6.64 | 3.60 | -6.64 | 3.57 | -6.64 | 4.39 | -6.64 | 2.95 | 4.80 | 3.21 | -6.64 | 6.42 | -6.64 | -6.64 |
| -6.64 | 5.87 | -6.64 | 1.83 | -6.64 | 2.43 | 3.39 | 2.79 | 2.73 | -6.64 | 2.41 | 1.83 | 3.28 | -6.64 | 4.58 | 2.30 | 1.65 | 3.34 | 3.98 | -6.64 | 5.43 | -6.64 | 1.67 |
| 6.10 | -6.64 | 2.89 | 4.38 | 6.45 | 4.75 | -6.64 | 3.43 | 2.98 | 7.95 | 1.93 | 2.46 | -6.64 | -6.64 | 4.55 | -6.64 | -6.64 | 6.42 | -6.64 | 6.42 | -6.64 | 4.74 | -6.64 |
| 1.00 | 1.69 | 1.10 | 0.38 | -2.21 | -0.02 | 0.24 | -2.32 | 0.38 | 0.20 | -0.05 | 0.43 | 0.78 | -1.58 | 1.23 | -6.64 | 0.02 | 1.34 | 0.85 | -0.37 | 1.19 | -1.81 | 0.81 |
| -6.64 | 4.97 | -6.64 | -6.64 | -6.64 | 1.48 | 2.45 | 2.64 | 2.77 | -6.64 | 2.36 | -6.64 | 2.78 | -6.64 | 4.14 | -6.64 | 1.64 | 4.46 | 4.67 | -6.64 | 5.12 | -6.64 | -6.64 |
| -6.64 | 4.05 | -6.64 | 2.70 | -6.64 | -6.64 | 2.49 | 2.21 | 2.32 | -6.64 | 2.74 | -6.64 | 1.83 | -6.64 | 2.81 | 3.20 | 1.57 | 3.59 | 4.14 | -6.64 | 5.18 | -6.64 | -6.64 |
| -6.64 | 4.27 | -6.64 | -6.64 | -6.64 | -6.64 | 2.83 | 2.15 | 1.93 | -6.64 | 2.49 | -6.64 | 2.17 | -6.64 | 3.33 | -6.64 | 1.56 | 3.91 | 3.92 | -6.64 | 5.44 | -6.64 | -6.64 |
| -6.64 | 2.20 | -6.64 | 1.75 | -6.64 | -6.64 | 2.19 | 1.99 | -6.64 | 1.63 | 3.30 | -6.64 | 2.03 | 1.89 | 1.72 | 2.32 | 1.59 | 2.20 | -6.64 | -6.64 | -6.64 | 1.92 | -6.64 |
| 0.02 | 2.45 | -6.64 | 0.24 | -6.64 | 0.15 | 1.10 | 0.69 | -6.64 | -6.64 | -0.14 | 0.31 | 1.23 | -6.64 | 1.30 | 0.93 | 0.28 | 0.67 | 1.53 | 0.25 | 2.02 | 0.32 | 0.23 |
| -6.64 | -6.64 | 3.33 | 3.02 | -0.46 | 3.37 | 0.59 | 5.84 | 5.83 | -6.64 | 2.00 | 4.66 | -6.64 | -6.64 | -6.64 | -6.64 | 2.67 | 2.44 | 3.28 | -6.64 | -0.32 | 2.64 | 1.53 |
| 2.41 | 1.93 | -6.64 | -6.64 | -6.64 | 4.52 | 3.50 | -6.64 | -6.64 | -6.64 | -6.64 | 2.06 | -6.64 | -6.64 | -6.64 | -6.64 | -6.64 | 2.83 | 4.15 | -6.64 | 3.87 | -6.64 | 4.39 |
| 2.29 | 2.40 | -6.64 | 2.21 | 1.51 | 2.62 | 2.67 | 1.73 | 1.78 | -6.64 | 2.41 | -6.64 | -6.64 | -6.64 | -6.64 | -6.64 | 2.89 | 2.84 | -6.64 | 2.26 | 1.51 | 2.94 | 2.55 |
| -6.64 | 3.91 | -6.64 | -6.64 | -6.64 | -6.64 | 2.45 | 2.51 | -6.64 | -6.64 | 2.20 | -6.64 | 1.96 | -6.64 | 2.48 | -6.64 | -6.64 | 1.65 | 2.94 | 1.58 | 4.30 | -6.64 | -6.64 |
| 0.70 | 0.17 | -6.64 | 0.99 | 0.24 | 1.70 | -6.64 | -6.64 | 0.66 | -6.64 | -6.64 | 0.89 | 0.26 | 0.10 | 2.07 | -6.64 | -0.25 | 0.73 | 0.52 | -6.64 | 1.60 | -6.64 | 0.04 |
| -6.64 | -6.64 | -6.64 | 2.92 | 1.93 | -6.64 | 3.73 | 1.64 | 3.12 | -6.64 | 2.02 | -6.64 | -6.64 | -6.64 | -6.64 | -6.64 | 3.59 | 1.81 | -6.64 | 3.61 | 1.95 | 2.37 | 3.44 |
| -6.64 | 1.89 | 2.47 | 1.99 | -6.64 | 1.97 | 2.59 | 1.81 | -6.64 | -6.64 | -6.64 | 1.61 | 2.04 | -6.64 | 2.35 | 2.43 | 1.85 | -6.64 | 2.23 | 1.85 | -6.64 | 2.45 | 1.58 |
| 2.58 | -6.64 | -6.64 | 2.94 | -6.64 | -6.64 | 2.22 | -6.64 | -6.64 | 2.05 | -6.64 | 2.05 | 2.13 | -6.64 | 1.68 | 2.75 | -6.64 | 1.51 | 1.87 | -6.64 | -6.64 | 2.00 | 1.67 |
| -6.64 | 2.69 | -6.64 | -6.64 | -6.64 | -6.64 | 1.97 | 1.51 | -6.64 | -6.64 | -6.64 | -6.64 | -6.64 | -6.64 | 2.07 | -6.64 | -6.64 | -6.64 | 3.61 | -6.64 | 4.89 | -6.64 | -6.64 |
| -0.11 | 0.42 | -6.64 | -0.10 | 0.38 | 0.94 | 1.01 | 0.62 | 0.08 | 0.14 | 1.25 | -0.18 | 0.76 | -6.64 | -0.09 | -6.64 | 1.21 | 1.31 | -0.05 | 0.63 | -6.64 | 1.16 | 1.03 |
| -6.64 | 1.89 | 2.38 | -6.64 | 2.89 | -6.64 | -6.64 | -6.64 | 2.03 | -6.64 | 2.72 | -6.64 | 1.72 | -6.64 | 1.58 | -6.64 | 1.93 | 2.65 | -6.64 | -6.64 | -6.64 | -6.64 | -6.64 |
| 0.96 | 0.59 | 1.56 | 0.67 | 0.45 | 1.33 | 0.82 | 0.28 | 0.27 | 2.07 | -0.28 | 1.19 | -0.03 | 0.45 | 0.57 | 1.16 | 0.35 | 1.35 | -0.19 | 0.41 | 0.09 | 0.28 | 1.84 |
| -6.64 | -6.64 | 2.18 | -6.64 | -6.64 | -6.64 | -6.64 | -6.64 | 2.03 | -6.64 | -6.64 | -6.64 | -6.64 | -6.64 | -6.64 | -6.64 | -6.64 | 3.39 | 2.15 | -6.64 | 5.74 | -6.64 | 2.35 |
| -6.64 | -6.64 | -6.64 | 2.42 | 1.69 | -6.64 | 1.67 | -6.64 | 1.58 | -6.64 | 3.40 | -6.64 | -6.64 | -6.64 | -6.64 | -6.64 | 2.39 | 2.08 | -6.64 | -6.64 | -6.64 | 2.04 | -6.64 |
| -6.64 | 0.88 | -6.64 | 2.19 | 0.42 | 4.45 | -6.64 | -0.11 | 2.79 | 0.02 | -6.64 | 1.87 | -6.64 | 1.62 | 1.02 | -6.64 | -6.64 | -6.64 | 0.27 | -0.32 | 3.95 | 0.08 | 0.49 |
| -6.64 | 1.78 | -6.64 | 1.65 | -6.64 | 1.62 | -6.64 | -6.64 | -6.64 | -6.64 | 2.17 | 1.57 | 1.91 | -6.64 | 2.43 | -6.64 | -6.64 | -6.64 | -6.64 | -6.64 | -6.64 | -6.64 | -6.64 |
| -6.64 | -0.04 | -6.64 | 0.56 | -0.41 | 0.83 | -0.05 | -0.15 | 0.35 | -6.64 | 0.69 | -0.11 | -0.17 | 1.04 | 0.18 | 0.93 | 0.40 | 0.70 | -0.03 | 0.06 | 1.05 | -0.07 | 0.91 |
| -6.64 | 0.06 | 0.11 | 0.52 | 0.05 | -0.18 | 0.28 | -0.07 | -6.64 | 0.68 | 0.09 | 0.45 | -0.11 | 0.37 | 0.37 | -6.64 | -0.05 | 0.22 | 0.25 | -0.21 | 0.00 | 0.00 | -0.01 |
| 0.14 | 0.12 | 0.02 | 0.90 | 0.81 | -0.56 | 1.10 | -0.86 | 0.67 | 0.20 | 0.42 | 1.35 | -0.67 | 1.00 | -6.64 | -6.64 | -1.51 | -0.94 | 1.01 | 0.77 | 2.60 | 0.51 | -0.10 |
| -6.64 | 1.73 | 1.91 | -6.64 | -6.64 | 2.19 | 1.65 | 1.77 | -6.64 | 2.25 | 2.60 | 2.00 | 1.78 | 2.70 | 2.14 | -6.64 | -6.64 | 1.95 | -6.64 | -6.64 | -6.64 | -6.64 | 2.40 |

FIG. 16M

| | | | | | | | | | | | | | | | | | | | | | | |
|---|---|---|---|---|---|---|---|---|---|---|---|---|---|---|---|---|---|---|---|---|---|---|
| -6.64 | 1.73 | -6.64 | 2.60 | 2.22 | -6.64 | 1.63 | 1.77 | 2.26 | -6.64 | 3.70 | -6.64 | -6.64 | -6.64 | -6.64 | -6.64 | 2.96 | 2.77 | -6.64 | 1.58 | -6.64 | 2.04 | 1.83 |
| -6.64 | 1.97 | -6.64 | -6.64 | -6.64 | -6.64 | -6.64 | 1.64 | -6.64 | 2.61 | 1.66 | 1.65 | 2.57 | 1.86 | 2.35 | 2.48 | -6.64 | 1.95 | -6.64 | -6.64 | -6.64 | 1.75 | -6.64 |
| 2.35 | 1.82 | -6.64 | 1.99 | 1.65 | -6.64 | 1.98 | -6.64 | 1.54 | -6.64 | -6.64 | 2.02 | 1.70 | 1.99 | -6.64 | 3.53 | -6.64 | 1.60 | -6.64 | 1.92 | 1.54 | 2.11 | 1.71 |
| 0.96 | 2.30 | 2.01 | 0.68 | -1.20 | 1.48 | 1.11 | 1.35 | 1.10 | 0.25 | -0.20 | 1.00 | 1.23 | 2.25 | 2.19 | -6.64 | 3.36 | 2.25 | -0.07 | 1.00 | 1.32 | 0.41 | 3.60 |
| 0.11 | 1.88 | 0.89 | 1.02 | -0.78 | 1.21 | -6.64 | 0.05 | 2.08 | -6.64 | -6.64 | -0.18 | -0.54 | 1.13 | 1.37 | -6.64 | -0.34 | 0.88 | 2.19 | -6.64 | 3.51 | -6.64 | 1.26 |
| 1.01 | 1.04 | 0.19 | 1.59 | -6.64 | -0.70 | 0.68 | -0.03 | -0.25 | -6.64 | -0.10 | -0.04 | 0.00 | -6.64 | 0.26 | 0.83 | 0.09 | 0.53 | 0.97 | -0.02 | 1.55 | -0.07 | 0.61 |
| 0.34 | 0.20 | 0.81 | 0.83 | 0.05 | 1.28 | 1.01 | 0.28 | -0.42 | 0.28 | -0.06 | 0.24 | 0.79 | 0.67 | 0.26 | 0.83 | -0.20 | 0.77 | -0.48 | 0.90 | -6.64 | -0.45 | 1.37 |
| 1.75 | 1.93 | -6.64 | 2.10 | -6.64 | 1.53 | 1.78 | -6.64 | -6.64 | -6.64 | -6.64 | 2.15 | -6.64 | -6.64 | -6.64 | 2.39 | -6.64 | -6.64 | -6.64 | -6.64 | -6.64 | 1.75 | 1.62 |
| -6.64 | -6.64 | -6.64 | -6.64 | -6.64 | -6.64 | 2.32 | 2.15 | 2.39 | 2.61 | 1.78 | 3.13 | -6.64 | -6.64 | -6.64 | -6.64 | -6.64 | -6.64 | -6.64 | -6.64 | -6.64 | -6.64 | -6.64 |
| -6.64 | 1.86 | 2.00 | 2.30 | -6.64 | -6.64 | -6.64 | -6.64 | 1.49 | -6.64 | 2.49 | 1.97 | -6.64 | 1.28 | 2.07 | -6.64 | -6.64 | 1.69 | -6.64 | -6.64 | -6.64 | 2.18 | 1.87 |
| 0.46 | 0.86 | -6.64 | -0.02 | 0.34 | -6.64 | 0.60 | 0.24 | 0.60 | -6.64 | 1.45 | -6.64 | 0.31 | 1.89 | -6.64 | -6.64 | 2.18 | 0.05 | 1.21 | 1.06 | 0.30 | 0.32 | -6.64 |
| 0.64 | 1.16 | 1.07 | 0.30 | 0.19 | 0.41 | 0.88 | 0.95 | -0.70 | 0.34 | 0.63 | -6.64 | 0.25 | 0.06 | -0.38 | -6.64 | 1.80 | 0.58 | 0.03 | 1.17 | -0.32 | 0.74 | -0.17 |
| -6.64 | -6.64 | -6.64 | -6.64 | -6.64 | -6.64 | -6.64 | -6.64 | -6.64 | -6.64 | 2.05 | -6.64 | -6.64 | -6.64 | -6.64 | -6.64 | 2.01 | 1.73 | -6.64 | -6.64 | 3.42 | -6.64 | -6.64 |
| 0.91 | 0.89 | 0.41 | 1.49 | -0.65 | -0.59 | 1.14 | 0.43 | -6.64 | 0.36 | 0.49 | -0.64 | -0.19 | -6.64 | -6.64 | 1.28 | 0.58 | 0.57 | 0.17 | 0.38 | -0.23 | 1.21 | 0.35 |
| 0.74 | 1.26 | 1.17 | 1.77 | -6.64 | -6.64 | 0.03 | -0.44 | 0.05 | -6.64 | -0.47 | -0.38 | -0.43 | -6.64 | 0.04 | -6.64 | -6.64 | 1.41 | 1.34 | -6.64 | 2.40 | -6.64 | -6.64 |
| -6.64 | 0.76 | 0.48 | -6.64 | -6.64 | 0.92 | 0.31 | -6.64 | -6.64 | 0.18 | -0.06 | 0.24 | 0.87 | 0.36 | 0.51 | -6.64 | 0.23 | 0.36 | -6.64 | -6.64 | -6.64 | -6.64 | 0.39 |
| -6.64 | 0.26 | -6.64 | 0.21 | -6.64 | 0.36 | 0.43 | 0.10 | -6.64 | -0.08 | 0.75 | 0.07 | 0.73 | -6.64 | 0.43 | 1.70 | 0.19 | 0.02 | -6.64 | -6.64 | -6.64 | 0.21 | 0.53 |
| -6.64 | 1.73 | -6.64 | 1.75 | -6.64 | -6.64 | 1.70 | -6.64 | -6.64 | 2.05 | -6.64 | 1.94 | 2.40 | -6.64 | 2.26 | 2.32 | -6.64 | -6.64 | -6.64 | -6.64 | -6.64 | 1.88 | -6.64 |
| 0.35 | 0.71 | 1.87 | 1.36 | -6.64 | 0.44 | 1.06 | 0.66 | -6.64 | 0.52 | -6.64 | 1.06 | 0.96 | -6.64 | 0.68 | 2.12 | -6.64 | 0.01 | -6.64 | 0.58 | -6.64 | 1.12 | 0.77 |
| -6.64 | -0.35 | -6.64 | -6.64 | 0.56 | 0.45 | 0.25 | 0.22 | 0.82 | 1.85 | 0.77 | -0.09 | 0.56 | 1.20 | 0.65 | -6.64 | -0.37 | 0.88 | -6.64 | -0.32 | 0.69 | -6.64 | 0.69 |
| -0.01 | 0.20 | 0.84 | 0.30 | 0.09 | 0.13 | 0.03 | 0.08 | -0.14 | 0.63 | -0.06 | 0.47 | 0.80 | 0.52 | 0.79 | 1.19 | -6.64 | 0.47 | -0.02 | -6.64 | 0.00 | 0.31 | 0.56 |
| -6.64 | -6.64 | 2.11 | -6.64 | -6.64 | -6.64 | -6.64 | 1.73 | 2.73 | -6.64 | -6.64 | 2.16 | -6.64 | -6.64 | -6.64 | -6.64 | -6.64 | -6.64 | -6.64 | -6.64 | -6.64 | -6.64 | -6.64 |
| 2.15 | 1.83 | 0.18 | 2.82 | 0.79 | 1.92 | 0.56 | -0.01 | 0.63 | 0.67 | -0.26 | 1.78 | 2.12 | -1.39 | 3.10 | -1.44 | -0.42 | 1.06 | 1.37 | 0.86 | 2.30 | 1.29 | -0.18 |
| 0.18 | 0.10 | 0.53 | 0.75 | 0.36 | 0.00 | 0.57 | -0.60 | 0.58 | 2.20 | 0.85 | 0.68 | 0.92 | 1.86 | 0.89 | 1.07 | -6.64 | 0.65 | -0.12 | -0.44 | 1.37 | 0.09 | 1.02 |
| 0.11 | 0.66 | 0.51 | 0.33 | -6.64 | -0.26 | 0.31 | 0.34 | -6.64 | 0.41 | -0.26 | 0.36 | 0.76 | 0.28 | 0.48 | -6.64 | 0.33 | -0.15 | -6.64 | 0.36 | -6.64 | 0.47 | 0.21 |
| -6.64 | 0.31 | -6.64 | 0.82 | -0.42 | 0.01 | 0.47 | 0.01 | -0.49 | -6.64 | 0.37 | 0.25 | -0.18 | 0.50 | 0.12 | 0.73 | 0.65 | 0.61 | -6.64 | 0.39 | -0.10 | 0.96 | 0.29 |
| -0.17 | 0.84 | -0.16 | 0.84 | -6.64 | 0.18 | 0.39 | -0.47 | -6.64 | -0.06 | -0.05 | 0.52 | 0.82 | 0.53 | 0.91 | 1.46 | 0.59 | 0.01 | -6.64 | 0.31 | -0.55 | 0.97 | -0.06 |
| 1.19 | 0.85 | 1.19 | 1.24 | -0.09 | 0.17 | 1.43 | 0.78 | -0.12 | -0.01 | 0.06 | -0.13 | 0.53 | -6.64 | -0.23 | -6.64 | 0.95 | 1.11 | -6.64 | 0.94 | -0.37 | 0.96 | 0.54 |
| -6.64 | 1.69 | -6.64 | -6.64 | -6.64 | -6.64 | -6.64 | -6.64 | -6.64 | 1.63 | -6.64 | 1.73 | 2.30 | -6.64 | 1.93 | -6.64 | -6.64 | -6.64 | -6.64 | -6.64 | -6.64 | -6.64 | -6.64 |
| -6.64 | -6.64 | -6.64 | 2.07 | -6.64 | -6.64 | -6.64 | -6.64 | -6.64 | -6.64 | 1.82 | -6.64 | 1.70 | -6.64 | 1.81 | 3.51 | -6.64 | -6.64 | -6.64 | -6.64 | -6.64 | -6.64 | -6.64 |
| -0.35 | 0.30 | 0.66 | 1.14 | -0.21 | -0.27 | -0.57 | -0.25 | -0.31 | -6.64 | -0.02 | 0.05 | -0.26 | 0.42 | 0.26 | 0.22 | 0.88 | 0.19 | -0.09 | 0.63 | -0.64 | 0.93 | 0.23 |
| -0.30 | 2.05 | 0.72 | 1.30 | -0.67 | 0.78 | -0.89 | 0.50 | 1.74 | -1.65 | -0.25 | 0.20 | -0.07 | 0.19 | 1.28 | -6.64 | -0.58 | 1.24 | 2.23 | -1.79 | 3.24 | -6.64 | 0.68 |
| -6.64 | -6.64 | -6.64 | -6.64 | -6.64 | -6.64 | -6.64 | -6.64 | -6.64 | -6.64 | -6.64 | 1.69 | -6.64 | -6.64 | 1.89 | -6.64 | -6.64 | -6.64 | -6.64 | -6.64 | -6.64 | -6.64 | -6.64 |
| -6.64 | -6.64 | -6.64 | 1.28 | 1.03 | 2.02 | 0.00 | -6.64 | 1.90 | 1.03 | -6.64 | 0.27 | 0.00 | 0.77 | 1.06 | -6.64 | -0.28 | 0.48 | 0.03 | 0.55 | 1.14 | 0.00 | 2.63 |
| 0.72 | 0.68 | 0.74 | 1.23 | -0.46 | -0.14 | 0.77 | -0.15 | -6.64 | 0.01 | -0.70 | 0.35 | 0.69 | -0.43 | 0.43 | 0.78 | -0.01 | -0.19 | -0.38 | 0.43 | -0.40 | 0.91 | -0.19 |
| 1.44 | 0.67 | 0.94 | 1.19 | -1.06 | -1.01 | 0.85 | -0.80 | -0.19 | 0.48 | 1.86 | -0.51 | 0.64 | 1.28 | -1.14 | -1.39 | 1.27 | 1.68 | -0.62 | 0.00 | 0.75 | 1.08 | -1.23 |
| 1.20 | 1.28 | 1.14 | 1.97 | 0.37 | -0.25 | 0.37 | -0.08 | 0.99 | -0.36 | -0.58 | 0.31 | 0.26 | -0.89 | 0.92 | 0.04 | -0.96 | 0.89 | 1.75 | -6.64 | 2.51 | -0.77 | -0.25 |
| 0.08 | 1.56 | 1.54 | 2.03 | -1.09 | 0.17 | 0.10 | -0.22 | 1.03 | -0.72 | -0.74 | 0.38 | 0.05 | -0.29 | 1.15 | -1.00 | -1.02 | 0.91 | 1.59 | -1.05 | 2.58 | -1.48 | 0.47 |
| 0.80 | 0.76 | 0.06 | 0.78 | -0.21 | 0.87 | 0.43 | 0.19 | -0.03 | -0.04 | -0.36 | -0.03 | 0.63 | 0.64 | -6.64 | -0.24 | 1.70 | 0.92 | -0.72 | 0.36 | -0.54 | 0.90 | 0.47 |
| 0.28 | 0.73 | -0.05 | 0.47 | -6.64 | -0.30 | 0.72 | 0.27 | -0.15 | 0.40 | 0.20 | 0.51 | 0.96 | -0.03 | 0.38 | -6.64 | 0.38 | 0.69 | -6.64 | 0.18 | -6.64 | 0.78 | -0.14 |

FIG. 16N

| | | | | | | | | | | | | | | | | | | | | | | |
|---|---|---|---|---|---|---|---|---|---|---|---|---|---|---|---|---|---|---|---|---|---|---|
| 0.30 | 0.85 | -6.64 | 0.51 | 0.19 | 0.63 | 0.51 | 0.82 | -0.33 | -6.64 | 1.02 | -0.24 | 0.55 | -0.50 | 0.01 | -6.64 | 1.39 | 0.50 | -6.64 | 0.29 | -6.64 | 1.00 | 0.52 |
| 1.73 | 0.62 | 0.54 | 1.12 | -0.83 | -0.52 | -0.12 | -0.43 | -0.21 | 0.31 | 1.05 | 0.17 | 0.66 | 1.64 | 0.43 | 0.55 | 1.70 | 1.29 | -0.40 | 0.03 | 0.84 | 0.40 | -0.42 |
| -0.07 | 0.08 | -0.52 | 0.52 | 0.40 | 0.28 | 0.21 | -0.08 | 0.49 | -0.58 | -0.04 | -6.64 | 0.32 | -0.63 | -0.20 | -6.64 | 1.81 | 0.94 | -0.89 | 0.83 | 0.07 | 0.86 | 0.51 |
| 2.02 | 1.65 | -6.64 | -6.64 | -6.64 | -6.64 | 1.78 | -6.64 | -6.64 | 1.63 | -6.64 | -6.64 | -6.64 | -6.64 | -6.64 | -6.64 | 1.56 | -6.64 | -6.64 | -6.64 | -6.64 | -6.64 | -6.64 |
| -1.95 | -1.39 | 2.27 | 0.90 | -1.13 | 1.95 | 2.02 | -0.98 | 0.54 | 2.03 | 0.53 | 1.71 | 1.43 | 0.75 | 1.48 | -6.64 | -0.72 | -0.62 | 2.37 | -0.20 | 1.96 | -1.48 | 1.73 |
| 0.57 | 0.22 | 0.68 | 1.12 | -0.85 | 0.17 | 0.92 | 0.07 | -0.45 | 0.25 | -0.15 | 0.39 | 0.57 | -0.43 | 0.64 | 2.02 | -0.22 | 0.42 | -0.14 | 0.29 | -0.54 | 0.74 | 0.38 |
| 0.00 | 0.32 | -6.64 | -6.64 | 0.49 | -6.64 | -6.64 | -6.64 | 1.09 | -6.64 | 0.14 | -0.09 | -6.64 | -6.64 | -0.14 | -6.64 | 0.16 | 0.97 | 0.13 | -6.64 | 1.76 | -0.16 | -6.64 |
| 0.75 | 1.57 | 1.50 | 2.01 | -1.20 | 0.03 | -0.04 | -0.19 | 0.91 | -1.42 | -0.59 | 0.08 | -0.44 | -0.65 | 0.78 | 0.08 | -0.64 | 1.01 | 1.49 | -0.97 | 2.58 | -1.12 | 0.30 |
| 0.17 | -0.39 | 0.33 | 0.72 | -1.02 | -0.88 | 0.17 | -0.96 | -0.44 | -0.98 | 0.17 | -0.05 | -0.38 | 0.10 | 0.05 | 1.52 | 1.44 | 0.49 | -0.10 | 0.03 | -0.25 | 1.02 | -0.21 |
| 0.07 | 0.15 | -6.64 | 0.59 | 0.26 | -6.64 | 0.85 | 0.51 | -0.31 | -0.12 | 0.27 | 0.27 | 0.16 | -6.64 | 0.21 | 1.36 | -0.24 | 0.07 | -6.64 | 0.21 | -6.64 | 0.35 | 0.15 |
| -0.04 | 0.85 | 0.57 | 0.95 | -6.64 | -6.64 | -6.64 | 0.16 | -6.64 | -0.01 | 0.02 | 0.80 | 0.86 | 0.18 | 0.64 | -6.64 | 0.13 | -0.06 | -6.64 | -0.19 | -6.64 | 0.06 | -0.20 |
| 1.04 | 0.23 | 0.52 | 0.97 | -0.56 | -0.81 | 0.41 | 0.00 | -0.55 | 0.11 | 1.07 | -0.40 | 0.20 | 0.65 | -0.55 | 0.43 | 1.76 | 0.93 | -0.07 | 0.13 | 0.00 | 0.59 | -0.39 |
| 0.97 | 1.19 | 0.99 | 1.90 | -6.64 | -0.69 | 0.45 | -0.33 | 0.86 | -0.61 | -1.05 | 0.56 | 0.80 | -0.70 | 0.98 | -6.64 | -6.64 | 0.80 | 1.80 | -6.64 | 2.67 | -6.64 | -0.25 |
| -0.07 | 1.14 | 1.34 | 1.83 | -1.24 | -0.61 | 0.88 | -0.90 | 0.49 | 0.04 | -0.16 | 0.75 | 1.44 | -0.62 | 1.10 | -6.64 | -0.22 | 1.62 | 1.33 | -0.74 | 2.70 | -1.48 | -0.79 |
| 0.97 | 0.70 | 0.62 | 0.69 | -0.43 | -0.44 | 0.55 | 0.37 | -0.62 | 0.24 | 0.91 | -0.40 | 0.24 | 1.02 | -0.75 | -0.10 | 1.65 | 0.88 | 0.00 | 0.27 | -0.10 | 0.70 | -0.16 |
| -0.27 | 1.67 | -0.88 | 0.34 | -0.68 | -1.24 | 1.22 | 0.50 | -0.02 | -0.86 | 1.00 | -0.49 | 0.66 | 2.14 | 0.80 | -1.49 | 1.58 | 1.44 | 0.73 | 0.30 | 1.72 | -0.14 | 0.47 |
| 1.22 | 0.49 | 0.89 | 0.99 | -0.56 | -0.36 | 0.39 | -0.20 | -0.34 | -0.17 | 1.41 | -0.48 | 0.06 | 0.91 | -0.25 | -6.64 | 1.76 | 0.77 | -0.52 | 0.16 | 0.30 | 0.98 | -0.32 |
| -0.13 | 0.51 | 0.17 | 0.75 | -6.64 | -0.11 | 0.64 | 0.19 | -0.76 | 0.51 | 0.03 | 0.38 | 0.66 | -0.06 | 0.61 | -6.64 | 0.27 | 0.15 | -6.64 | 0.65 | -6.64 | 0.95 | 0.02 |
| -0.96 | 2.42 | -0.24 | -0.22 | 0.04 | 0.29 | 1.33 | 1.41 | 0.07 | -0.03 | 0.82 | -0.23 | 0.72 | 1.04 | 1.10 | -6.64 | 0.29 | 1.27 | 1.47 | 0.43 | 2.06 | -0.10 | -0.04 |
| 1.21 | 0.18 | 0.41 | 0.57 | -0.83 | -1.56 | 0.86 | 0.04 | -0.52 | 0.56 | 1.24 | -0.03 | 0.43 | 1.01 | -0.75 | 1.71 | 1.04 | 0.86 | 0.02 | 0.09 | -0.14 | 0.65 | -0.39 |
| 0.59 | 1.88 | 1.16 | 0.96 | -1.54 | 0.57 | -0.52 | 0.02 | 0.43 | -1.04 | -0.84 | 0.28 | 0.38 | -0.16 | 0.50 | -6.64 | -0.71 | 0.84 | 1.55 | -1.04 | 2.41 | -6.64 | 0.75 |
| 1.01 | -0.10 | 0.26 | 0.31 | -0.91 | -0.67 | 0.50 | 0.24 | -0.74 | 0.71 | 1.39 | 0.38 | -0.31 | 0.25 | -0.04 | 0.12 | 0.88 | 0.17 | 0.24 | -0.21 | -0.24 | 0.69 | 0.24 |
| -1.00 | 1.21 | -0.07 | 3.20 | 0.16 | 3.12 | 0.57 | 0.19 | 1.88 | 0.60 | 1.59 | 2.42 | 0.58 | -0.05 | 1.70 | -6.64 | -1.32 | 0.04 | 0.53 | 0.39 | 2.67 | 0.97 | 0.40 |
| 1.13 | -0.14 | 0.01 | 0.98 | -0.65 | 0.84 | 1.15 | 0.28 | -0.38 | 0.09 | -0.60 | -0.31 | 0.14 | 0.87 | -0.56 | 1.35 | -0.57 | 0.05 | 0.61 | 0.73 | -0.82 | 0.68 | 0.39 |
| -0.21 | 0.90 | 1.11 | 1.39 | -1.14 | -0.74 | 0.93 | -0.38 | 0.11 | 0.24 | -0.44 | 0.10 | 1.35 | -1.16 | 1.01 | -1.72 | 0.28 | 1.29 | 1.11 | -0.68 | 2.36 | -1.21 | -0.54 |
| 0.54 | 0.17 | -6.64 | 1.05 | -0.41 | -6.64 | 0.16 | -0.64 | 0.08 | -0.36 | 0.98 | -0.05 | -0.25 | -0.31 | 0.24 | 0.83 | 2.19 | 0.15 | -6.64 | -0.52 | -0.39 | 0.61 | 0.84 |
| 1.37 | 0.00 | 0.94 | 0.33 | -0.76 | -0.51 | 0.24 | 0.36 | -0.27 | 1.27 | 1.72 | 0.15 | 0.26 | 1.26 | -0.72 | -6.64 | 1.51 | 0.63 | 0.46 | 0.23 | -0.79 | 0.97 | -0.81 |
| 1.43 | 0.82 | 1.61 | 0.64 | -0.82 | 0.04 | 0.58 | 0.06 | 0.00 | 0.24 | -0.49 | 0.18 | 0.31 | -0.32 | -0.03 | 0.71 | 1.38 | -0.10 | -0.57 | 0.56 | -0.29 | 0.82 | -0.20 |
| 0.27 | -0.13 | 0.69 | 0.59 | -0.31 | 0.18 | 0.30 | 0.12 | -0.67 | -0.15 | -0.67 | 0.55 | 0.30 | 0.08 | 0.74 | 1.81 | -0.24 | -0.09 | 0.68 | -0.03 | -6.64 | 0.78 | 0.61 |
| 0.56 | 0.92 | -0.17 | -0.15 | -0.36 | -0.08 | 0.49 | -0.03 | -0.95 | 0.43 | -0.83 | -0.01 | 0.16 | -6.64 | -0.25 | 1.08 | 0.21 | -0.26 | -0.52 | 0.17 | -0.66 | -0.27 | -0.34 |
| -6.64 | 0.49 | 0.70 | 0.42 | -0.68 | 0.32 | 0.35 | 0.53 | -0.88 | 0.26 | -0.35 | 0.53 | 0.42 | 0.14 | 0.63 | 0.23 | 0.17 | -0.42 | -0.71 | 0.48 | -0.64 | 0.72 | -0.29 |
| -0.01 | -0.26 | 0.33 | 1.26 | 0.30 | 0.43 | 0.32 | -1.43 | 1.25 | -0.14 | -1.22 | 0.10 | 0.44 | -0.50 | 1.49 | -6.64 | -0.98 | 0.89 | 0.50 | -1.23 | 1.89 | -1.00 | 0.78 |
| 0.88 | 0.29 | 0.86 | 0.69 | -0.38 | -0.55 | 0.53 | 0.36 | -0.66 | 0.40 | 0.25 | -0.01 | 0.44 | 0.97 | -0.60 | 0.63 | 1.53 | 0.47 | -0.05 | 0.56 | -0.63 | 0.46 | -0.43 |
| 0.67 | 0.48 | 0.16 | 0.39 | -0.40 | -0.17 | 0.53 | 0.67 | -0.92 | 0.08 | 0.68 | -0.52 | 0.43 | 0.43 | -0.52 | 1.08 | 2.03 | 0.58 | 0.02 | 0.40 | -0.66 | 0.89 | 0.25 |
| 0.85 | 0.28 | 0.69 | 0.72 | -0.49 | -0.14 | 0.82 | 0.43 | -0.59 | 0.05 | 0.27 | -0.21 | 0.57 | 0.52 | -0.52 | 0.57 | 1.87 | 0.38 | -0.02 | 0.64 | -0.96 | 0.93 | 0.16 |
| 0.71 | 1.52 | 1.12 | 1.52 | -0.75 | 0.14 | -0.22 | -0.01 | 1.16 | -0.40 | -0.86 | 0.44 | 0.66 | 0.34 | 0.81 | -6.64 | -1.09 | 0.80 | 1.79 | -1.03 | 2.61 | -1.60 | 0.65 |
| 0.37 | 0.82 | 0.78 | 0.46 | -1.09 | 0.10 | 0.79 | 0.43 | -1.06 | 0.61 | 0.67 | -0.13 | 0.91 | 0.70 | -0.05 | -1.12 | 1.66 | 0.49 | -0.50 | 0.44 | -0.39 | 1.02 | 0.29 |
| -0.03 | 0.18 | 0.03 | 0.67 | -0.17 | 0.86 | 0.30 | 0.28 | 0.35 | 1.54 | 0.76 | 0.69 | 1.13 | 1.12 | 0.74 | 1.57 | -0.54 | 0.71 | -0.13 | -0.30 | 0.42 | 0.53 | 0.80 |
| 0.53 | 0.78 | 1.32 | 1.17 | -0.59 | -0.43 | 1.29 | 0.46 | -1.25 | 0.50 | 0.05 | 0.10 | 0.69 | -0.02 | 0.36 | -0.34 | 0.48 | 0.39 | -0.68 | 0.78 | -0.35 | 0.99 | -0.24 |
| 0.47 | 0.05 | -6.64 | 1.31 | -0.15 | -0.58 | 0.52 | -0.27 | -0.09 | -0.20 | 0.03 | 0.28 | -0.09 | -6.64 | 0.15 | -6.64 | 0.14 | 0.49 | -6.64 | 0.59 | -0.28 | 1.05 | 0.27 |

FIG. 16O

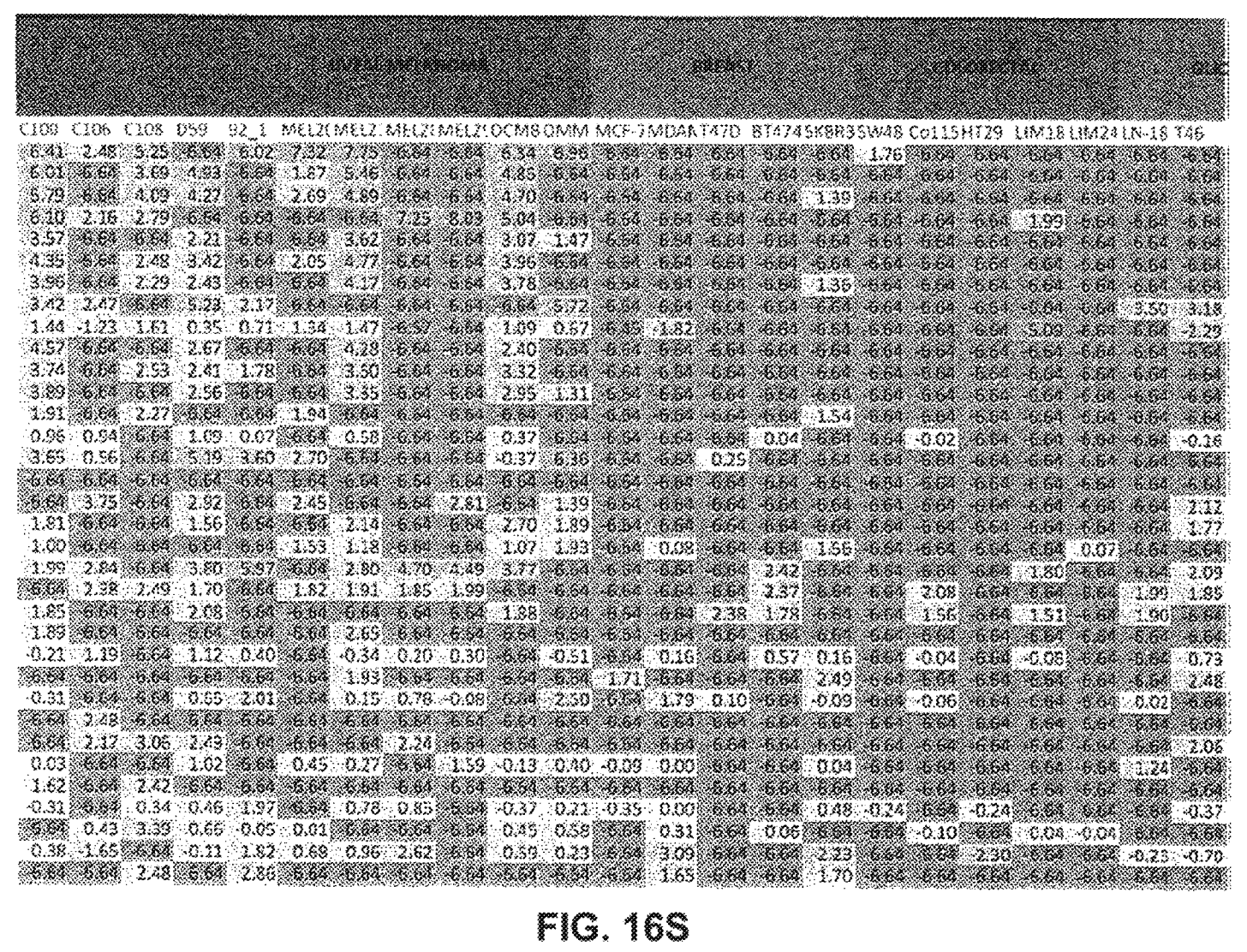

| C109 | C106 | C108 | D59 | 92_1 | MEL2( | MEL2 | MEL2( | MEL2( | OCM8 | OMM | MCF-7 | MDAI | T47D | BT474 | SKBR3 | SW48 | Co115 | HT29 | LIM18 | LIM24 | LN-18 | T46 |
|---|---|---|---|---|---|---|---|---|---|---|---|---|---|---|---|---|---|---|---|---|---|---|
| 6.41 | 2.48 | 3.25 | -6.64 | 6.02 | 7.32 | 7.75 | -6.64 | -6.64 | 6.34 | 6.96 | -6.64 | -6.64 | -6.64 | -6.64 | -6.64 | 1.76 | -6.64 | -6.64 | -6.64 | -6.64 | -6.64 | -6.64 |
| 6.01 | -6.64 | 3.69 | 4.83 | -6.64 | 1.87 | 5.46 | -6.64 | -6.64 | 4.86 | -6.64 | -6.64 | -6.64 | -6.64 | -6.64 | -6.64 | -6.64 | -6.64 | -6.64 | -6.64 | -6.64 | -6.64 | -6.64 |
| 5.79 | -6.64 | 4.09 | 4.27 | -6.64 | 2.69 | 4.89 | -6.64 | -6.64 | 4.70 | -6.64 | -6.64 | -6.64 | -6.64 | -6.64 | 1.39 | -6.64 | -6.64 | -6.64 | -6.64 | -6.64 | -6.64 | -6.64 |
| 6.10 | 2.16 | 2.79 | -6.64 | -6.64 | -6.64 | -6.64 | 7.25 | 8.09 | 5.04 | -6.64 | -6.64 | -6.64 | -6.64 | -6.64 | -6.64 | -6.64 | -6.64 | -6.64 | 1.93 | -6.64 | -6.64 | -6.64 |
| 3.57 | -6.64 | -6.64 | 2.21 | -6.64 | -6.64 | 3.62 | -6.64 | -6.64 | 3.07 | 1.47 | -6.64 | -6.64 | -6.64 | -6.64 | -6.64 | -6.64 | -6.64 | -6.64 | -6.64 | -6.64 | -6.64 | -6.64 |
| 4.35 | -6.64 | 2.48 | 3.42 | -6.64 | 2.05 | 4.77 | -6.64 | -6.64 | 3.96 | -6.64 | -6.64 | -6.64 | -6.64 | -6.64 | -6.64 | -6.64 | -6.64 | -6.64 | -6.64 | -6.64 | -6.64 | -6.64 |
| 3.96 | -6.64 | 2.29 | 2.43 | -6.64 | -6.64 | 4.17 | -6.64 | -6.64 | 3.78 | -6.64 | -6.64 | -6.64 | -6.64 | -6.64 | 1.36 | -6.64 | -6.64 | -6.64 | -6.64 | -6.64 | -6.64 | -6.64 |
| 3.42 | 2.47 | -6.64 | 5.23 | 2.17 | -6.64 | -6.64 | -6.64 | -6.64 | -6.64 | 5.72 | -6.64 | -6.64 | -6.64 | -6.64 | -6.64 | -6.64 | -6.64 | -6.64 | -6.64 | -6.64 | 3.50 | 3.18 |
| 1.44 | -1.23 | 1.61 | 0.35 | 0.71 | 1.34 | 1.47 | -6.57 | -6.64 | 1.09 | 0.67 | -6.35 | -1.82 | -6.64 | -6.64 | -6.64 | -6.64 | -6.64 | -6.64 | -5.09 | -6.64 | -6.64 | -2.29 |
| 4.57 | -6.64 | -6.64 | 2.67 | -6.64 | -6.64 | 4.28 | -6.64 | -6.64 | 2.40 | -6.64 | -6.64 | -6.64 | -6.64 | -6.64 | -6.64 | -6.64 | -6.64 | -6.64 | -6.64 | -6.64 | -6.64 | -6.64 |
| 3.74 | -6.64 | 2.53 | 2.41 | 1.78 | -6.64 | 3.50 | -6.64 | -6.64 | 3.32 | -6.64 | -6.64 | -6.64 | -6.64 | -6.64 | -6.64 | -6.64 | -6.64 | -6.64 | -6.64 | -6.64 | -6.64 | -6.64 |
| 3.89 | -6.64 | -6.64 | 2.56 | -6.64 | -6.64 | 3.35 | -6.64 | -6.64 | 2.95 | 1.31 | -6.64 | -6.64 | -6.64 | -6.64 | -6.64 | -6.64 | -6.64 | -6.64 | -6.64 | -6.64 | -6.64 | -6.64 |
| 1.91 | -6.64 | 2.27 | -6.64 | -6.64 | 1.94 | -6.64 | -6.64 | -6.64 | -6.64 | -6.64 | -6.64 | -6.64 | -6.64 | -6.64 | 1.54 | -6.64 | -6.64 | -6.64 | -6.64 | -6.64 | -6.64 | -6.64 |
| 0.96 | 0.94 | -6.64 | 1.09 | 0.07 | -6.64 | 0.58 | -6.64 | -6.64 | 0.37 | -6.64 | -6.64 | -6.64 | -6.64 | 0.04 | -6.64 | -6.64 | -0.02 | -6.64 | -6.64 | -6.64 | -6.64 | -0.16 |
| 3.65 | 0.56 | -6.64 | 5.39 | 3.60 | 2.70 | -6.64 | -6.64 | -6.64 | -0.37 | 6.36 | -6.64 | -6.64 | 0.25 | -6.64 | -6.64 | -6.64 | -6.64 | -6.64 | -6.64 | -6.64 | -6.64 | -6.64 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -6.64 | 3.75 | -6.64 | 2.92 | -6.64 | 2.45 | -6.64 | -6.64 | 2.81 | -6.64 | 1.39 | -6.64 | -6.64 | -6.64 | -6.64 | -6.64 | -6.64 | -6.64 | -6.64 | -6.64 | -6.64 | -6.64 | 2.12 |
| 1.81 | -6.64 | -6.64 | 1.56 | -6.64 | -6.64 | 2.14 | -6.64 | -6.64 | 2.70 | 1.89 | -6.64 | -6.64 | -6.64 | -6.64 | -6.64 | -6.64 | -6.64 | -6.64 | -6.64 | -6.64 | -6.64 | 1.77 |
| 1.00 | -6.64 | -6.64 | -6.64 | -6.64 | 1.53 | 1.18 | -6.64 | -6.64 | 1.07 | 1.93 | -6.64 | 0.08 | -6.64 | -6.64 | 1.56 | -6.64 | -6.64 | -6.64 | -6.64 | 0.07 | -6.64 | -6.64 |
| 1.99 | 2.84 | -6.64 | 3.80 | 5.97 | -6.64 | 2.80 | 4.70 | 4.49 | 3.77 | -6.64 | -6.64 | -6.64 | -6.64 | 2.42 | -6.64 | -6.64 | -6.64 | -6.64 | 1.80 | -6.64 | -6.64 | 2.09 |
| -6.64 | 2.38 | 2.49 | 1.70 | -6.64 | 1.82 | 1.91 | 1.85 | 1.99 | -6.64 | -6.64 | -6.64 | -6.64 | -6.64 | 2.37 | -6.64 | -6.64 | 2.08 | -6.64 | -6.64 | -6.64 | 1.99 | 1.85 |
| 1.85 | -6.64 | -6.64 | 2.08 | -6.64 | -6.64 | -6.64 | -6.64 | -6.64 | 1.88 | -6.64 | -6.64 | -6.64 | 2.38 | 1.78 | -6.64 | -6.64 | 1.56 | -6.64 | 1.51 | -6.64 | 1.90 | -6.64 |
| 1.89 | -6.64 | -6.64 | -6.64 | -6.64 | -6.64 | 2.69 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -0.21 | 1.19 | -6.64 | 1.12 | 0.40 | -6.64 | -0.34 | 0.20 | 0.30 | -6.64 | -0.51 | -6.64 | 0.16 | -6.64 | 0.57 | 0.16 | -6.64 | -0.04 | -6.64 | -0.08 | -6.64 | -6.64 | 0.73 |
| -6.64 | -6.64 | -6.64 | -6.64 | -6.64 | -6.64 | 1.93 | -6.64 | -6.64 | -6.64 | -6.64 | 1.71 | -6.64 | -6.64 | -6.64 | 2.49 | -6.64 | -6.64 | -6.64 | -6.64 | -6.64 | -6.64 | 2.48 |
| -0.31 | -6.64 | -6.64 | 0.65 | 2.01 | -6.64 | 0.15 | 0.78 | -0.08 | -6.64 | 2.30 | -6.64 | 1.79 | 0.10 | -6.64 | -0.09 | -6.64 | -0.06 | -6.64 | -6.64 | -6.64 | -0.02 | -6.64 |
| -6.64 | 2.48 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -6.64 | 2.17 | 3.06 | 2.49 | -6.64 | -6.64 | -6.64 | 2.24 | -6.64 | -6.64 | -6.64 | -6.64 | -6.64 | -6.64 | -6.64 | -6.64 | -6.64 | -6.64 | -6.64 | -6.64 | -6.64 | -6.64 | 2.06 |
| 0.03 | -6.64 | -6.64 | 1.02 | -6.64 | 0.45 | 0.27 | -6.64 | 1.59 | -0.13 | 0.40 | -0.09 | 0.00 | -6.64 | -6.64 | 0.04 | -6.64 | -6.64 | -6.64 | -6.64 | -6.64 | 1.24 | -6.64 |
| 1.62 | -6.64 | 2.42 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -0.31 | -6.64 | 0.34 | 0.46 | 1.97 | -6.64 | 0.78 | 0.85 | -6.64 | -0.37 | 0.21 | -0.35 | 0.00 | -6.64 | -6.64 | 0.48 | -0.24 | -6.64 | -0.24 | -6.64 | -6.64 | -6.64 | -0.37 |
| -6.64 | 0.43 | 3.39 | 0.66 | -0.05 | 0.01 | -6.64 | -6.64 | -6.64 | 0.45 | 0.59 | -6.64 | 0.31 | -6.64 | 0.06 | -6.64 | -6.64 | -0.10 | -6.64 | 0.04 | -0.04 | -6.64 | -6.64 |
| 0.38 | -1.65 | -6.64 | -0.11 | 1.82 | 0.69 | 0.96 | 2.62 | -6.64 | 0.59 | 0.23 | -6.64 | 3.09 | -6.64 | -6.64 | 2.23 | -6.64 | -6.64 | 2.30 | -6.64 | -6.64 | -0.23 | -0.70 |
| -6.64 | -6.64 | 2.48 | -6.64 | 2.86 | -6.64 | -6.64 | -6.64 | -6.64 | -6.64 | -6.64 | -6.64 | 1.65 | -6.64 | -6.64 | 1.70 | -6.64 | -6.64 | -6.64 | -6.64 | -6.64 | -6.64 | -6.64 |

FIG. 16S

| | | | | | | | | | | | | | | | | | | | | | | |
|---|---|---|---|---|---|---|---|---|---|---|---|---|---|---|---|---|---|---|---|---|---|---|
| -0.05 | 1.64 | -0.07 | 0.78 | 0.96 | 0.11 | -6.64 | 0.25 | 0.06 | -0.06 | -6.64 | 0.51 | -0.13 | -6.64 | 0.74 | -0.30 | -0.78 | -0.12 | -6.64 | -0.38 | -0.52 | -6.64 | 1.06 |
| 1.66 | 1.24 | -0.16 | 1.21 | 1.95 | 2.00 | 0.20 | -0.33 | 0.00 | 0.84 | 0.53 | -1.39 | -1.56 | -0.74 | -0.51 | -1.51 | -1.62 | -0.49 | 2.15 | 2.04 | 0.53 | -1.45 | -0.76 |
| -0.39 | 1.24 | -6.64 | 0.21 | 1.68 | 0.23 | 0.39 | -6.64 | 1.04 | -6.64 | -6.64 | -0.58 | 0.54 | -6.64 | 1.08 | 1.22 | -1.11 | 0.78 | -6.64 | -0.78 | -6.64 | -6.64 | 0.86 |
| -6.64 | -6.64 | -6.64 | -6.64 | -6.64 | -6.64 | -6.64 | 2.52 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -1.76 | -1.65 | 0.37 | -1.27 | -0.96 | 1.59 | -2.26 | 0.96 | 1.68 | 1.62 | -1.63 | 0.11 | -1.11 | 0.04 | -3.08 | -3.25 | -0.89 | -6.64 | -1.48 | -3.32 | -2.52 | 1.34 | -0.01 |
| -0.20 | 0.81 | 0.46 | 0.58 | 0.22 | -0.46 | -0.04 | 1.14 | 0.76 | -0.05 | -6.64 | -0.18 | 0.29 | -0.71 | 0.24 | -6.64 | -6.64 | 0.22 | -6.64 | -6.64 | -0.16 | -0.32 | -0.35 |
| 1.24 | -6.64 | -6.64 | -6.64 | 0.65 | 1.90 | 1.00 | 0.26 | -6.64 | 0.59 | 0.84 | 0.21 | -6.64 | -0.02 | -6.64 | -6.64 | 0.34 | -6.64 | 0.63 | 0.56 | 0.47 | 0.01 | 0.27 |
| 1.99 | -6.64 | -0.15 | 2.08 | -0.83 | -0.03 | 1.05 | -0.82 | -6.64 | 1.17 | 1.24 | -0.16 | 1.32 | 0.94 | -0.42 | -1.15 | -0.21 | -0.23 | -0.52 | 0.11 | 0.58 | -6.64 | -1.63 |
| 0.49 | 1.36 | -0.12 | 1.31 | 1.44 | 0.56 | 0.14 | 0.69 | 0.00 | 0.65 | -0.75 | -0.99 | -0.98 | -1.66 | -0.34 | -6.64 | -1.80 | -1.70 | -1.24 | -1.43 | 0.18 | -0.75 | -0.20 |
| -0.08 | 0.91 | 0.14 | 0.28 | -0.17 | -0.05 | -6.64 | -6.64 | -6.64 | 0.13 | -0.10 | -0.40 | 0.28 | -0.18 | 0.27 | -0.09 | -6.64 | -0.39 | -0.27 | -0.35 | 0.12 | -6.64 | -0.21 |
| 0.24 | -6.64 | 0.87 | 0.69 | 0.52 | 0.04 | -6.64 | -0.04 | -6.64 | -6.64 | -6.64 | -0.17 | 0.24 | -0.01 | 0.39 | 0.05 | -6.64 | 0.68 | -0.49 | -6.64 | 0.09 | -6.64 | -0.02 |
| 0.53 | 1.54 | 0.30 | 1.45 | 1.37 | 1.37 | 0.17 | 0.48 | 0.17 | 0.71 | 0.76 | -1.15 | -1.22 | -1.61 | -1.01 | -0.97 | -1.23 | -1.35 | -1.59 | -1.34 | -0.73 | -1.62 | -0.12 |
| 1.44 | -6.64 | -6.64 | 2.05 | 0.17 | -0.26 | 0.72 | -6.64 | -6.64 | 1.55 | -1.05 | 0.03 | -0.59 | 1.44 | -0.07 | -0.87 | -1.08 | 0.02 | -0.48 | 0.14 | 0.75 | -6.64 | -6.64 |
| 1.19 | -1.35 | 0.94 | 0.15 | 0.31 | 0.47 | 0.64 | -0.46 | -0.29 | 1.56 | 1.02 | 0.39 | -0.83 | -0.63 | -0.34 | 0.11 | -0.90 | -0.54 | 0.71 | 0.14 | -0.15 | -0.41 | 1.78 |
| 0.44 | 1.58 | 0.40 | 1.22 | 1.49 | 1.17 | -0.03 | 0.36 | 0.12 | 0.52 | 0.32 | -0.95 | -1.28 | -2.18 | -0.92 | -1.30 | -1.29 | -1.57 | 1.94 | -1.06 | -0.24 | -1.92 | -0.21 |
| 0.66 | -0.29 | 0.86 | 1.05 | -0.17 | -0.44 | 1.08 | 1.27 | 0.23 | 1.10 | 0.24 | -1.30 | 0.24 | -1.83 | -0.05 | -0.14 | -0.91 | -1.41 | -0.92 | -0.48 | -0.89 | -2.00 | 0.02 |
| 0.93 | 1.29 | 0.53 | 1.41 | 1.58 | 1.09 | -0.02 | 0.23 | -0.17 | 0.28 | 0.11 | -0.83 | -1.24 | -1.79 | -0.67 | -1.71 | -0.98 | -1.02 | 1.53 | -1.33 | 0.06 | -2.37 | 0.19 |
| 0.26 | 1.33 | -6.64 | 0.62 | 0.54 | 0.35 | -6.64 | 0.94 | 0.03 | -0.31 | -6.64 | -0.20 | 0.11 | -6.64 | 0.78 | -6.64 | -0.69 | 0.62 | -6.64 | -6.64 | -0.60 | -0.63 | 0.34 |
| 0.82 | 1.01 | -6.64 | -0.07 | 0.17 | 0.03 | 0.83 | -0.12 | 0.76 | 1.02 | -1.83 | -0.77 | -6.64 | -1.30 | 0.24 | -1.49 | -0.77 | -0.20 | -1.14 | -0.71 | -0.82 | -1.37 | 0.51 |
| 0.70 | 1.89 | 0.66 | 1.02 | 1.66 | 2.12 | -0.07 | 0.89 | 0.06 | 0.57 | 0.82 | -0.85 | -0.96 | -1.35 | -0.69 | -1.00 | -1.18 | -2.03 | 2.15 | -1.52 | -0.60 | -1.57 | -0.59 |
| 1.50 | -6.64 | -6.64 | 1.49 | -0.37 | -0.02 | 1.18 | -0.97 | -1.25 | 0.45 | -1.87 | -0.10 | -1.00 | 1.14 | -0.38 | -0.76 | 0.44 | -0.66 | -0.24 | 1.14 | 1.01 | -6.64 | -6.64 |
| 0.79 | 2.39 | -0.57 | 2.02 | 0.96 | 1.16 | -0.18 | 0.87 | 0.08 | 0.24 | 0.37 | -1.20 | -1.22 | 1.69 | -0.47 | -1.70 | -0.39 | -0.61 | 1.80 | -1.63 | -0.95 | -1.06 | 0.05 |
| 0.97 | -2.48 | -1.43 | 1.93 | -0.04 | 0.48 | -0.63 | 0.19 | 0.97 | 0.13 | -0.61 | -0.08 | 0.56 | -0.87 | -1.52 | -0.37 | -2.27 | -0.39 | -0.91 | -0.71 | -0.86 | 0.56 | -0.62 |
| -0.40 | 1.05 | -6.64 | 0.27 | -0.12 | -6.64 | -0.60 | 0.34 | 0.67 | 0.30 | -1.04 | -0.36 | -0.01 | 0.77 | 0.62 | -6.64 | -0.01 | 0.23 | -0.56 | -0.69 | -0.16 | -6.64 | -0.01 |
| 0.73 | -1.18 | 1.18 | 0.12 | -0.02 | -0.38 | 0.64 | -0.50 | -0.24 | 1.58 | 0.19 | 0.32 | -0.63 | -1.03 | -0.15 | -0.04 | -1.31 | -0.28 | 0.59 | 0.26 | -0.38 | -0.18 | -1.36 |
| 0.07 | 1.02 | 1.58 | 0.15 | 0.04 | -0.45 | 0.44 | -0.55 | -6.64 | -0.30 | -0.41 | -0.24 | -6.64 | 0.70 | 0.03 | -6.64 | -0.73 | -0.15 | -0.35 | 0.56 | -0.38 | -6.64 | 0.19 |
| 0.23 | 2.69 | 0.32 | 1.57 | 1.32 | 2.61 | -0.01 | 0.35 | 0.23 | 0.93 | 2.06 | -1.04 | -1.38 | -1.83 | -0.50 | -1.59 | -0.65 | -0.68 | 1.74 | -1.71 | 0.31 | -1.21 | -0.06 |
| -0.02 | 1.87 | -6.64 | 0.70 | 1.03 | -0.06 | -0.65 | -0.98 | 0.24 | 0.78 | 1.59 | -0.62 | -0.03 | 0.15 | 0.22 | -0.54 | -0.77 | 0.55 | -0.79 | -0.60 | -0.78 | -0.29 | -0.08 |
| -0.18 | 0.19 | 0.66 | 0.43 | 0.43 | -0.27 | 0.35 | 0.23 | 0.09 | 0.68 | -0.42 | 0.00 | 0.07 | -0.43 | 0.50 | -0.27 | -6.64 | -0.23 | -0.41 | 0.03 | -0.22 | 0.24 | 0.20 |
| 0.66 | 1.63 | -0.59 | 0.05 | 0.82 | 1.65 | 0.10 | 0.01 | -6.64 | 0.27 | 0.81 | -0.42 | -0.01 | 0.43 | 0.59 | -0.22 | -0.37 | 0.41 | -6.64 | -0.04 | -0.56 | 0.03 | -0.08 |
| 0.00 | 2.50 | -6.64 | 2.36 | 0.00 | 1.08 | 0.13 | -0.06 | 0.15 | -6.64 | -0.41 | -0.34 | 0.18 | -0.63 | -0.01 | -0.08 | -0.79 | 0.47 | -6.64 | -6.64 | -0.58 | -0.23 | 0.09 |
| 2.70 | -0.80 | -6.64 | 2.28 | -0.25 | -1.21 | 0.58 | -0.16 | 0.02 | 0.41 | -0.69 | 0.01 | -0.57 | -1.02 | -1.18 | -1.27 | -0.57 | -6.64 | 0.42 | 0.52 | -0.19 | -0.54 | -0.48 |
| 0.29 | 2.29 | 0.37 | 1.30 | 1.44 | 1.51 | -0.62 | 0.52 | 0.29 | 0.98 | 0.45 | -0.98 | -0.63 | -1.50 | -0.45 | -0.97 | 1.18 | -0.74 | -1.60 | -1.41 | -0.89 | -1.10 | -0.27 |
| 0.10 | 1.66 | 0.62 | 0.72 | 1.16 | 0.55 | -0.18 | 0.11 | 0.29 | 0.59 | -0.05 | -0.96 | -0.72 | -2.31 | -0.63 | -0.68 | -1.39 | -0.84 | 1.52 | -0.76 | -1.41 | -0.99 | 0.15 |
| 0.05 | 2.10 | 0.17 | 1.12 | 1.45 | 0.74 | -0.48 | 0.09 | 0.48 | 0.71 | 0.05 | -1.17 | -0.69 | -1.30 | -0.35 | -1.52 | -1.14 | -0.52 | -1.32 | -1.03 | -0.95 | -1.33 | 0.20 |
| 1.36 | -6.64 | -6.64 | 2.06 | 0.01 | 0.51 | 1.07 | -0.19 | -1.01 | 1.18 | -0.19 | 0.09 | -0.59 | 1.60 | -0.17 | -0.24 | 0.55 | 0.87 | -0.01 | 0.39 | 1.03 | -6.64 | -6.64 |
| 1.87 | 0.52 | -0.80 | 1.03 | 1.31 | -0.27 | -0.46 | -0.04 | 0.87 | -1.51 | -1.26 | -0.04 | -0.73 | -0.74 | 0.13 | 2.35 | -0.19 | -0.14 | 1.28 | -0.95 | -0.16 | -0.72 | 0.28 |
| -0.13 | -0.09 | 0.10 | 0.18 | 2.16 | -0.76 | 0.17 | 1.09 | -0.15 | 0.02 | -0.22 | -0.43 | 0.81 | -0.69 | -0.08 | 1.34 | -0.83 | -0.03 | -1.20 | -0.42 | -0.15 | -0.03 | -0.38 |
| 0.33 | 1.87 | -6.64 | 0.86 | 1.22 | 0.50 | -0.60 | 0.17 | 0.59 | -6.64 | -1.24 | -0.12 | -0.04 | -0.15 | 0.81 | -0.93 | -0.29 | 0.93 | -0.82 | -1.52 | -0.40 | -6.64 | 0.17 |
| 0.13 | 0.70 | -0.56 | 0.17 | -0.10 | -6.64 | -0.40 | 0.60 | 0.63 | -0.22 | -0.64 | -0.40 | 0.31 | 0.50 | 0.27 | 0.22 | -6.64 | -0.33 | -0.38 | 0.01 | 0.17 | 0.02 | 1.22 |

FIG. 16U

| | | | | | | | | | | | | | | | | | | | | | | |
|---|---|---|---|---|---|---|---|---|---|---|---|---|---|---|---|---|---|---|---|---|---|---|
| -1.04 | -6.64 | -2.04 | -0.04 | -1.30 | -2.10 | -1.34 | 1.21 | 1.53 | -1.79 | -3.09 | 1.48 | 1.08 | 2.06 | 1.51 | 1.53 | 2.21 | -0.26 | 0.70 | -0.15 | -1.16 | 1.08 | 0.01 |
| 0.26 | -6.64 | 2.56 | -1.48 | -1.59 | 1.03 | -0.02 | -0.36 | -0.58 | -0.51 | 0.07 | 0.76 | 0.30 | 1.40 | -0.87 | 0.23 | 0.81 | -2.10 | 0.35 | 0.31 | 0.39 | 1.06 | -0.52 |
| -1.26 | 1.27 | 0.55 | -0.06 | -1.57 | 0.29 | -0.82 | 0.10 | 0.01 | -0.63 | -1.40 | 0.14 | 0.14 | 0.35 | 0.83 | -1.96 | 0.68 | 1.31 | 0.00 | 1.92 | -0.39 | 1.40 | -0.51 |
| 0.84 | -6.64 | -0.84 | -0.73 | -1.50 | 2.70 | 1.55 | -1.52 | -1.09 | -0.57 | 0.85 | 3.62 | 1.14 | 2.75 | 2.41 | -1.37 | 0.65 | 0.47 | 1.56 | 0.47 | 1.48 | 1.56 | -1.77 |
| 0.51 | -6.64 | 1.50 | -1.37 | -1.62 | 1.11 | 0.66 | -0.53 | -0.61 | -0.29 | -0.33 | 1.04 | 0.20 | 1.30 | -1.45 | 0.50 | 1.10 | -6.64 | 0.80 | 1.22 | 0.42 | 0.56 | -0.41 |
| -0.12 | -6.64 | -6.64 | 0.70 | -1.21 | -0.62 | -0.82 | 0.53 | 0.32 | 0.18 | -6.64 | 0.60 | 0.49 | -0.90 | 0.60 | -1.39 | -0.65 | 0.40 | -0.45 | 1.06 | -0.20 | 0.59 | 0.43 |
| 0.29 | 1.45 | -0.82 | -0.83 | -0.30 | 1.87 | 0.04 | -0.83 | -6.64 | -0.71 | 0.77 | 0.11 | 0.35 | 0.17 | 0.50 | 1.65 | 0.48 | -0.44 | -0.18 | -0.23 | 0.23 | 0.92 | 1.09 |
| 0.19 | -0.48 | 1.12 | -0.86 | -0.73 | 0.94 | -0.02 | 0.00 | 0.38 | -0.38 | -0.37 | 1.30 | 0.71 | 1.75 | -0.38 | 0.08 | 1.54 | -0.38 | 0.81 | 1.22 | 0.63 | 0.83 | -0.64 |
| -0.02 | -6.64 | -6.64 | 0.25 | -0.52 | 0.57 | 0.98 | -0.35 | 0.45 | -0.24 | -0.82 | 1.23 | 0.79 | 1.95 | 1.04 | 0.42 | 0.36 | -0.20 | 0.61 | 0.61 | 1.41 | 0.34 | -1.69 |
| -0.79 | -6.64 | -0.47 | -0.27 | -6.64 | 0.75 | -0.07 | -6.64 | -0.16 | -0.33 | 0.16 | -0.18 | 0.48 | -0.27 | 0.96 | -0.12 | -0.02 | 0.46 | -0.18 | -0.13 | 0.44 | 1.43 | 0.86 |
| -0.08 | -6.64 | 0.54 | -0.01 | -6.64 | 2.15 | -2.52 | -1.96 | -0.96 | -2.24 | -6.64 | 2.33 | 2.06 | -6.64 | 1.04 | 0.40 | 1.43 | -0.10 | 2.24 | 1.36 | 1.31 | -1.71 | -0.22 |
| 0.57 | -6.64 | 0.12 | -6.64 | -6.64 | -6.64 | -6.64 | -6.64 | -6.64 | -6.64 | 0.34 | 0.22 | -0.17 | -6.64 | -0.02 | -6.64 | 0.70 | -0.15 | 1.04 | 3.52 | 0.21 | 0.29 | -0.16 |
| -0.14 | -6.64 | -6.64 | 0.07 | 0.57 | 1.04 | 0.52 | 0.01 | -6.64 | 0.61 | -6.64 | 2.02 | 0.55 | -0.59 | -6.64 | -6.64 | 0.29 | -6.64 | 0.27 | 1.62 | 1.34 | -0.04 | -1.32 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | 1.49 | -6.64 | -6.64 | -6.64 | -6.64 |
| -0.05 | -0.05 | -0.35 | -0.40 | -0.15 | 0.47 | 0.23 | 0.12 | 0.66 | 0.29 | -0.49 | 0.01 | 0.41 | -0.04 | -0.37 | -0.79 | -0.03 | -0.48 | 0.46 | 0.59 | 0.40 | 0.48 | 0.60 |
| -0.31 | -6.64 | 3.01 | -1.74 | -2.98 | 2.08 | -0.26 | -0.72 | -0.45 | -0.28 | 0.19 | 1.03 | 0.41 | 1.47 | -0.96 | -0.24 | 1.54 | -2.08 | 0.43 | 1.14 | 0.25 | 1.78 | -0.84 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 |
| -6.64 | -6.64 | -6.64 | -6.64 | -6.64 | 3.32 | -6.64 | -6.64 | -6.64 | -6.64 | 2.41 | -6.64 | -6.64 | -6.64 | -6.64 | -6.64 | 2.69 | -6.64 | 1.94 | -6.64 | -6.64 | -6.64 | -6.64 |
| -0.15 | -6.64 | 0.87 | -0.96 | 0.46 | -0.21 | 0.47 | 0.69 | 0.18 | 0.88 | 0.07 | 0.16 | -0.09 | -0.05 | -0.24 | 0.27 | -0.30 | -0.33 | 0.44 | 0.05 | 0.68 | 0.44 | -0.46 |
| 0.01 | -6.64 | 0.46 | -0.07 | -6.64 | 1.49 | -0.15 | -6.64 | -6.64 | -6.64 | -6.64 | 0.42 | 0.39 | -0.22 | -6.64 | -0.28 | 0.89 | -0.30 | 0.61 | 0.52 | 0.85 | -6.64 | -0.08 |
| -6.64 | 1.19 | -6.64 | -6.64 | -0.34 | -0.13 | -0.36 | 0.28 | 1.53 | 0.77 | -0.27 | 0.22 | 0.44 | -0.30 | 1.95 | 1.72 | -0.20 | 1.25 | -0.50 | -0.73 | 0.58 | 1.23 | 0.29 |
| -0.30 | -6.64 | 1.38 | -0.10 | -6.64 | 0.56 | -0.72 | -0.11 | 0.75 | 0.17 | 0.15 | -0.03 | 0.45 | 0.42 | 1.26 | -0.92 | 0.17 | 0.50 | -0.09 | -0.03 | 0.10 | 0.86 | 1.25 |
| -0.59 | 0.36 | 1.09 | -1.10 | -6.64 | 0.35 | -0.70 | -0.10 | 1.52 | -0.67 | -0.87 | 0.78 | -1.14 | 0.48 | 1.71 | 0.36 | 0.52 | 1.69 | 0.25 | -0.01 | 0.14 | 0.42 | 0.61 |
| 0.52 | -6.64 | 0.55 | -0.32 | -3.20 | 0.28 | 0.67 | -1.42 | -0.10 | -0.21 | -2.20 | 2.23 | 0.52 | 0.75 | 1.00 | 0.84 | 0.94 | 1.06 | 1.84 | 2.51 | 1.64 | 1.09 | -0.41 |
| -0.03 | -6.64 | 2.19 | -0.79 | -6.64 | 1.21 | 0.59 | -6.64 | -6.64 | -0.22 | -0.14 | 1.06 | 0.03 | 0.80 | -6.64 | -0.60 | 1.38 | -6.64 | 0.67 | 0.97 | 0.40 | 0.80 | 0.03 |
| -0.18 | -6.64 | 0.14 | -0.74 | -6.64 | 1.01 | 0.98 | -0.29 | 0.17 | -0.42 | -0.51 | 0.38 | 0.75 | 1.18 | -0.02 | -0.08 | 0.91 | -0.39 | 0.28 | 0.66 | 0.60 | 0.60 | -0.47 |
| 2.15 | -6.64 | -6.64 | -1.00 | -6.64 | 0.80 | 0.17 | 0.09 | -6.64 | -0.04 | -0.52 | 2.13 | -0.20 | 1.58 | -0.96 | -0.41 | 1.28 | -0.88 | 1.00 | 0.88 | 1.32 | 0.29 | 0.68 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | 1.89 | 1.69 | -6.64 | -6.64 | -6.64 | -6.64 | -6.64 |
| 0.28 | -6.64 | 1.34 | -6.64 | -0.21 | 2.22 | -6.64 | 0.29 | -6.64 | -0.12 | 0.60 | 0.45 | 0.98 | 0.35 | -0.77 | -0.55 | 1.18 | -6.64 | -0.22 | -0.45 | 1.13 | 1.48 | -0.89 |
| -1.90 | -6.64 | -6.64 | -0.96 | -2.36 | -6.64 | -1.40 | 0.79 | 1.98 | -3.08 | -6.64 | 2.15 | 1.72 | 1.93 | 1.38 | 1.51 | 2.40 | -1.11 | 1.23 | 1.45 | -0.66 | 1.68 | 0.19 |
| 0.49 | -6.64 | 0.92 | -0.53 | -6.64 | 0.66 | 0.19 | -6.64 | 0.47 | -6.64 | -6.64 | 0.13 | -0.39 | 1.01 | -0.09 | -0.37 | 0.40 | -0.17 | 0.56 | 0.71 | 0.20 | -6.64 | -0.32 |
| -6.64 | -6.64 | -6.64 | -6.64 | -6.64 | -6.64 | -6.64 | -6.64 | -6.64 | -6.64 | 1.33 | -6.64 | -6.64 | -6.64 | -6.64 | -6.64 | 2.34 | -6.64 | 2.12 | 2.13 | 2.09 | -6.64 | -6.64 |
| -6.64 | -6.64 | -6.64 | -6.64 | -6.64 | -6.64 | -6.64 | -6.64 | -6.64 | -6.64 | -6.64 | -6.64 | -6.64 | -6.64 | -6.64 | 2.26 | -6.64 | -6.64 | -6.64 | -6.64 | -6.64 | -6.64 | 2.33 |
| 0.13 | -6.64 | 0.56 | -6.64 | -6.64 | 1.30 | 0.27 | -0.17 | -0.08 | 0.12 | 0.11 | 0.44 | 0.69 | -0.04 | -0.58 | -0.12 | 0.69 | -1.03 | 0.56 | 0.17 | 1.07 | 1.64 | -0.17 |
| -0.50 | -6.64 | 1.55 | -0.12 | -6.64 | 0.79 | -6.64 | 0.03 | -6.64 | -6.64 | -6.64 | 0.54 | -0.18 | 0.55 | -0.57 | -6.64 | 1.35 | -0.69 | 0.40 | 1.89 | 0.48 | 0.82 | -0.32 |
| 0.49 | -6.64 | 1.34 | -6.64 | -1.20 | 1.79 | 0.46 | -0.24 | -6.64 | -0.97 | 0.14 | 1.29 | 0.61 | 1.10 | -6.64 | 0.07 | 1.67 | -6.64 | 0.81 | 1.02 | 0.46 | 1.35 | -0.95 |
| -6.64 | -6.64 | -6.64 | -6.64 | -6.64 | -6.64 | -6.64 | -6.64 | -6.64 | -6.64 | 1.32 | 1.80 | -6.64 | -6.64 | -6.64 | -6.64 | 2.02 | -6.64 | 2.19 | 2.10 | -6.64 | -6.64 | -6.64 |
| -0.21 | -6.64 | 1.13 | -1.37 | -6.64 | 1.86 | -0.27 | -0.75 | 0.26 | -0.14 | 0.23 | 0.67 | 1.54 | 1.23 | -0.86 | 0.01 | 1.24 | -1.29 | 0.59 | 0.26 | 1.29 | 2.40 | -0.60 |
| -6.64 | 0.53 | -6.64 | -0.13 | -6.64 | 0.17 | -6.64 | -0.33 | 0.43 | 0.49 | -0.72 | 0.16 | 0.60 | 0.02 | 0.72 | -6.64 | 0.19 | 0.45 | -0.71 | 0.07 | -0.23 | 2.62 | 0.95 |
| -6.64 | -6.64 | -6.64 | -6.64 | 1.81 | 2.08 | -6.64 | -6.64 | -6.64 | 2.43 | 2.82 | 2.08 | -6.64 | 2.23 | -6.64 | -6.64 | 2.67 | -6.64 | -6.64 | 2.46 | -6.64 | 1.96 | -6.64 |

FIG. 16V

| | | | | | | | | | | | | | | | | | | | | | |
|---|---|---|---|---|---|---|---|---|---|---|---|---|---|---|---|---|---|---|---|---|---|
| 0.99 | -1.73 | 0.70 | 0.87 | 1.72 | 1.17 | 1.01 | 0.98 | 0.94 | 0.96 | 0.04 | -0.68 | -0.57 | -0.53 | -2.28 | -0.72 | 0.60 | 0.50 | 0.73 | 0.83 | -0.58 | 0.72 |
| 1.68 | 0.73 | 0.79 | -0.49 | 1.03 | 0.52 | 0.18 | -0.20 | 0.01 | 0.44 | 0.59 | -0.87 | -0.09 | 0.40 | 0.66 | 2.39 | 0.92 | 0.38 | 0.85 | 0.74 | 1.14 | 0.22 |
| 1.56 | -0.34 | 0.75 | 1.52 | 0.45 | -0.69 | -0.33 | -1.27 | 0.13 | 0.04 | 1.18 | -0.30 | -0.07 | -0.80 | 1.65 | 1.62 | 0.99 | 1.35 | 1.87 | 1.24 | 1.20 | -0.16 |
| 0.72 | 0.57 | 1.85 | 0.14 | 0.41 | 0.73 | 1.46 | -0.56 | -1.88 | -0.26 | 0.07 | -1.37 | -0.12 | -0.09 | -1.67 | 1.59 | 1.81 | 0.22 | 1.03 | 0.68 | 0.07 | 0.69 |
| 1.09 | 0.59 | 0.62 | -0.45 | 0.90 | 0.41 | 0.37 | 0.33 | 0.51 | 0.37 | 1.08 | -0.75 | -0.21 | 0.38 | -0.19 | 1.74 | 1.01 | -0.09 | 1.22 | 0.45 | 0.83 | 0.17 |
| 0.89 | 0.59 | -1.09 | 1.44 | 0.48 | 1.60 | 0.08 | 0.68 | 0.40 | 0.83 | 0.46 | 1.00 | 0.15 | 0.40 | 0.90 | 0.31 | 0.78 | -0.46 | 0.27 | 1.50 | 0.43 | 0.72 |
| 1.77 | 0.75 | 1.98 | 2.03 | 0.30 | 0.63 | -0.73 | -0.02 | 1.48 | -0.54 | -0.05 | 0.15 | -0.04 | 1.40 | -6.64 | 1.98 | -0.67 | -1.20 | 0.05 | 0.43 | 0.10 | 0.42 |
| 1.53 | 1.03 | 0.54 | -0.76 | 1.40 | 0.60 | 0.74 | -0.05 | 0.08 | 0.26 | 1.12 | -0.07 | 0.72 | -0.59 | 1.10 | 1.87 | 0.87 | -0.49 | 1.16 | 0.96 | 1.14 | -0.14 |
| -0.57 | -0.46 | 0.41 | 0.99 | -0.04 | 0.69 | 1.05 | 0.64 | 0.97 | 2.25 | -0.74 | 0.00 | 1.23 | 0.54 | -1.87 | 0.75 | 1.27 | -0.42 | 0.51 | -0.37 | 0.05 | 1.09 |
| 0.74 | 1.29 | 0.60 | 0.08 | 1.26 | -0.34 | 0.29 | -0.98 | -0.08 | -0.19 | 0.25 | -0.23 | 0.84 | 0.61 | 3.60 | 2.77 | 0.06 | 1.63 | 0.28 | 2.20 | 0.19 | -0.33 |
| 0.69 | -6.64 | 0.88 | 0.94 | 0.84 | 1.62 | 1.37 | 0.56 | -0.62 | 1.14 | 0.61 | -1.34 | 0.90 | 1.46 | 1.37 | 0.81 | 0.69 | -0.04 | -0.15 | 0.33 | 0.75 | 1.05 |
| 2.29 | 0.35 | 0.83 | 4.06 | 0.33 | -0.47 | -0.33 | -0.08 | 0.51 | 0.37 | 0.64 | -0.33 | -6.64 | -0.19 | -6.64 | 0.99 | 1.06 | 0.07 | 1.34 | 0.61 | 0.49 | 1.37 |
| 1.05 | 0.82 | 0.73 | -0.26 | 1.42 | 0.31 | 1.00 | 1.56 | 1.23 | 1.38 | -0.50 | -6.64 | -0.37 | 0.96 | -0.34 | -0.68 | 0.85 | -0.10 | 1.01 | -0.05 | 1.47 | 0.88 |
| -6.64 | -6.64 | -6.64 | 2.44 | 2.34 | -6.64 | -6.64 | -6.64 | -6.64 | -6.64 | -6.64 | -6.64 | -6.64 | 1.53 | -6.64 | -6.64 | -6.64 | -6.64 | 2.25 | -6.64 | 2.10 | -6.64 |
| 0.84 | 0.31 | 0.30 | -1.03 | 1.02 | 0.70 | -0.38 | 0.11 | 0.09 | -0.02 | 0.87 | -0.01 | 0.37 | -0.21 | 0.21 | 0.38 | 0.81 | -0.07 | 0.96 | 1.47 | 0.68 | 0.24 |
| 2.36 | 1.26 | 1.69 | 0.94 | 1.87 | 0.49 | -0.15 | -0.64 | 1.01 | 0.18 | 1.27 | -0.81 | -0.09 | 0.12 | 1.67 | 3.24 | 1.33 | 0.53 | 1.83 | 1.19 | 1.97 | -0.10 |
| -6.64 | -6.64 | 2.60 | 3.75 | -6.64 | -6.64 | -6.64 | 2.24 | 3.16 | -6.64 | -6.64 | -6.64 | -6.64 | -6.64 | 2.39 | -6.64 | -6.64 | -6.64 | -6.64 | -6.64 | -6.64 | -6.64 |
| 1.94 | -6.64 | 2.81 | -6.64 | -6.64 | 1.91 | -6.64 | -6.64 | -6.64 | -6.64 | -6.64 | -6.64 | -6.64 | -6.64 | -6.64 | -6.64 | -6.64 | -6.64 | -6.64 | 3.07 | -6.64 | -6.64 |
| 0.04 | 0.26 | -0.95 | 0.04 | 0.29 | 0.25 | 0.32 | 0.08 | -0.75 | 0.36 | 0.99 | 0.39 | 0.38 | 0.08 | 0.34 | 0.61 | -0.03 | 0.18 | 0.23 | 0.36 | 0.01 | 0.31 |
| -6.64 | 0.49 | 1.43 | 0.54 | -0.19 | 0.19 | 0.32 | 0.23 | 1.01 | 0.89 | 0.83 | -0.15 | -6.64 | 0.71 | -6.64 | 1.09 | 1.28 | 0.13 | 0.92 | -6.64 | 1.16 | 0.39 |
| -6.64 | 1.06 | -0.18 | 0.37 | 0.92 | 0.42 | 0.38 | 0.08 | 1.77 | -0.21 | 0.52 | 1.02 | 0.34 | 1.69 | 0.75 | 1.23 | -0.37 | -0.01 | -0.06 | 1.54 | -0.16 | 0.01 |
| -0.02 | 0.81 | -0.31 | -0.94 | 0.60 | 0.28 | 0.24 | -0.77 | -0.75 | 0.77 | 0.19 | 0.75 | 1.56 | 0.32 | 0.02 | 0.40 | 0.19 | -0.60 | -0.18 | 1.31 | 0.19 | 0.47 |
| 0.69 | 1.37 | -0.21 | -0.28 | 1.19 | 0.58 | 0.01 | -0.41 | -0.04 | -0.30 | 0.65 | 0.15 | 0.80 | 0.65 | 1.41 | -0.52 | 0.68 | -0.19 | 0.66 | 1.32 | 0.64 | -1.10 |
| 0.84 | -0.17 | 1.11 | -0.39 | 0.75 | 1.57 | 1.22 | 0.83 | -0.53 | 1.01 | 1.18 | -0.87 | 1.74 | 1.03 | 0.58 | 0.66 | 0.61 | 0.04 | 1.16 | 0.44 | 1.06 | 1.06 |
| 1.33 | 0.99 | -0.19 | 0.17 | 0.93 | 0.54 | 0.51 | 0.46 | 0.67 | 0.63 | 1.19 | -6.64 | 0.51 | 0.10 | 0.55 | 1.58 | 1.31 | -6.64 | 1.11 | 0.76 | 1.15 | -0.20 |
| 1.01 | 1.05 | -0.05 | -0.93 | 1.42 | 0.51 | -0.21 | -0.16 | 0.43 | -0.02 | 0.83 | -0.43 | 0.88 | -0.26 | 1.15 | 1.05 | 1.00 | 0.25 | 1.08 | 1.31 | 1.16 | -0.17 |
| 0.52 | -0.80 | 1.35 | 0.95 | 0.05 | 1.62 | 0.76 | 0.44 | -0.18 | 0.91 | 0.86 | -0.15 | -0.31 | 0.18 | -6.64 | 0.32 | 1.40 | -0.29 | 0.72 | 0.04 | 2.16 | 1.30 |
| -6.64 | -6.64 | 1.92 | 2.14 | -6.64 | 1.49 | -6.64 | -6.64 | -6.64 | -6.64 | -6.64 | -6.64 | -6.64 | -6.64 | -6.64 | -6.64 | -6.64 | 1.58 | 1.83 | -6.64 | 1.76 | -6.64 |
| 1.33 | 1.02 | 0.95 | -6.64 | 1.60 | 1.44 | -0.07 | -0.10 | 0.16 | 0.21 | 0.22 | -0.04 | 0.80 | -6.64 | 0.25 | 1.79 | 0.32 | -0.66 | 0.35 | 1.03 | 1.46 | 0.09 |
| 1.79 | -1.79 | 0.70 | 1.47 | 1.63 | 2.21 | 1.10 | 2.22 | 0.81 | 0.86 | 0.35 | -1.00 | -0.04 | 0.27 | -6.64 | 2.77 | 0.96 | 0.66 | 1.51 | 1.59 | -0.05 | 1.06 |
| 1.30 | 0.92 | 0.87 | -6.64 | 0.60 | -0.04 | -0.14 | 0.57 | 0.10 | -0.01 | 0.50 | -0.19 | 0.16 | 0.09 | 1.49 | 1.70 | 0.77 | 0.03 | 0.89 | 0.95 | 0.19 | -0.04 |
| -6.64 | -6.64 | 2.38 | -6.64 | -6.64 | -6.64 | -6.64 | 2.52 | -6.64 | -6.64 | -6.64 | -6.64 | -6.64 | 1.78 | -6.64 | -6.64 | -6.64 | -6.64 | -6.64 | -6.64 | -6.64 | -6.64 |
| -6.64 | -6.64 | 3.25 | 5.71 | -6.64 | -6.64 | -6.64 | -6.64 | 6.64 | -6.64 | -6.64 | -6.64 | -6.64 | 3.10 | -6.64 | -6.64 | -6.64 | -6.64 | -6.64 | -6.64 | -6.64 | -6.64 |
| 1.61 | 1.00 | 1.15 | -0.76 | 1.48 | 1.15 | -0.80 | 0.75 | 1.01 | -0.09 | 1.00 | -0.40 | 0.40 | -0.30 | 0.43 | 1.73 | 1.73 | -0.54 | 1.58 | 2.17 | 1.39 | 0.20 |
| 1.63 | 0.12 | 1.16 | 1.35 | 0.70 | -0.21 | 0.02 | -0.39 | 0.46 | 0.23 | 1.02 | -0.37 | 0.01 | -0.20 | 0.37 | 1.07 | 0.91 | 0.51 | 1.35 | 0.84 | 1.07 | -0.06 |
| 1.34 | 1.04 | 0.96 | -1.13 | 1.53 | 1.04 | 0.31 | 0.43 | 0.76 | 0.61 | 1.35 | -0.86 | -0.10 | 0.02 | 0.78 | 2.42 | 1.34 | -6.64 | 1.46 | 1.12 | 1.40 | 0.09 |
| -6.64 | -6.64 | 1.87 | -6.64 | -6.64 | -6.64 | -6.64 | 2.19 | -6.64 | -6.64 | -6.64 | -6.64 | 3.33 | -6.64 | -6.64 | -6.64 | -6.64 | -6.64 | -6.64 | -6.64 | -6.64 | 1.65 |
| 2.19 | 1.04 | 1.08 | -0.50 | 1.67 | 0.98 | -0.22 | 0.53 | 0.99 | 0.65 | 0.64 | -0.77 | 0.67 | 0.25 | 1.08 | 3.17 | 1.83 | 0.34 | 1.51 | 2.23 | 1.84 | 0.13 |
| 0.80 | 1.44 | 0.83 | -0.29 | 1.50 | -0.09 | -0.08 | -6.64 | -0.11 | -6.64 | 0.32 | -0.42 | 1.19 | 0.30 | 2.89 | 2.92 | 0.90 | 2.02 | 0.73 | 2.72 | 0.16 | -6.64 |
| 2.53 | -6.64 | 1.44 | -6.64 | -6.64 | -6.64 | -6.64 | 1.54 | -6.64 | -6.64 | -6.64 | -6.64 | 1.86 | -6.64 | -6.64 | 2.42 | -6.64 | -6.64 | 1.82 | -6.64 | 2.05 | -6.64 |

FIG. 16BB

SEQUENCE LISTING

<160> NUMBER OF SEQ ID NOS: 7

<210> SEQ ID NO 1
<211> LENGTH: 19
<212> TYPE: RNA
<213> ORGANISM: Homo sapiens

<400> SEQUENCE: 1
agagcuggcu gaagggcag 19

<210> SEQ ID NO 2
<211> LENGTH: 25
<212> TYPE: RNA
<213> ORGANISM: Homo sapiens

<400> SEQUENCE: 2
agcggggagg aagugggcgc ugcuu 25

<210> SEQ ID NO 3
<211> LENGTH: 22
<212> TYPE: RNA
<213> ORGANISM: Homo sapiens

<400> SEQUENCE: 3
ugcugggggc cacaugagug ug 22

<210> SEQ ID NO 4
<211> LENGTH: 22
<212> TYPE: RNA
<213> ORGANISM: Homo sapiens

<400> SEQUENCE: 4
uagcagcacg uaaauauugg cg 22

<210> SEQ ID NO 5
<211> LENGTH: 22
<212> TYPE: RNA
<213> ORGANISM: Homo sapiens

<400> SEQUENCE: 5
uucccuuugu cauccuucgc cu 22

<210> SEQ ID NO 6
<211> LENGTH: 22
<212> TYPE: RNA
<213> ORGANISM: Homo sapiens

-continued

```
<400> SEQUENCE: 6

ugauugguac gucugugggu ag                                             22


<210> SEQ ID NO 7
<211> LENGTH: 21
<212> TYPE: RNA
<213> ORGANISM: Homo sapiens

<400> SEQUENCE: 7

uacugcagac aguggcaauc a                                              21
```

METHOD OF TREATING, DIAGNOSING AND MONITORING MELANOMA UTILIZING MICRO-RNAS

CROSS REFERENCE TO RELATED APPLICATIONS

This is a continuation of U.S. patent application Ser. No. 15/506,545, filed Feb. 24, 2017, which is the § 371 U.S. National Stage of International Application No. PCT/AU2015/050487, filed Aug. 24, 2015, which was published in English under PCT Article 21(2), which in turn claims the benefit of AU Application No. 2014903347, filed Aug. 25, 2014, which is incorporated by reference herein in its entirety.

TECHNICAL FIELD

THIS INVENTION relates to the prognosis, diagnosis and/or treatment of cancers. More particularly, this invention relates to determining expression levels of one or more micro-RNAs correlated with melanoma in a biological sample from a subject.

BACKGROUND

Melanomas are among the most commonly occurring cancers. Incidence rates in Australia[2] and the USA[3] reveal more than 11,400 (in 2010) and 76,000 (estimated in 2014) new cases respectively, with more than 1,500 (in 2011) and 9,700 (estimated in 2014) respectively, dying annually of advanced disease. Current staging criteria are based on melanoma progression from an early stage lesion, confined to the epidermis (stage 0) followed by a series of early stages of local invasion (I and II) before moving to the regional lymph nodes (stage III) and finally metastasizing to distal sites (stage IV). The overall 5-year survival for melanoma is 91%. However, if distal metastasis occurs (AJCC ih ed stage IV), cure rates are <15%[1]. Hence, melanoma must be detected in earlier stages to maximize the chances of patient survival. Therefore, the ability to rapidly identify predictors of melanoma progression in patients would therefore be a significant clinical tool.

For many years, melanoma progression markers have been studied intensively with varying levels of success. Serum lactate dehydrogenase (LDH) levels have been reported to be elevated in melanoma patients and have been integrated into current staging regimens[1]. Despite the high sensitivity and specificity of serum LDH levels in stage II patients (95% and 83% respectively), performance of this marker has been found to be reduced as disease progresses (stage III, 57% and 87%, respectively)4-[8]. In an earlier study of stage N patients, sensitivity and specificity was increased to 79% and 92% respectively[4-8]. S-lO0B, a calcium binding protein, is another serological marker found to be elevated in stage III and IV melanoma patients[10,11]. The proportion of patients with elevated S-100B levels has been measured in all stages of disease which vary dependent somewhat upon stage: 0-9% in stage I/II, 5-98% in stage III, and 40-100% in stage IV (reviewed in ref 12). However, serum S100B is not routinely used in the clinic, highlighting that the current serological methods of progression detection, whilst relatively specific, are inadequate due to somewhat variable sensitivity to detect all stages of disease. To date, there are no biomarkers that are sensitive or specific enough to be beneficial for early diagnosis of melanoma. The use of a blood test ('circulating' biomarkers) for early detection of melanoma, prior to distant metastases, could improve treatment and outcomes for melanoma patients.

In order for a circulating biomarker to be effective, it needs to be not only highly sensitive and specific; it also needs to be highly stable and resistant to degradation. In recent years, circulating microRNAs (miRNAs) have been studied intensively for their utility as biomarkers in a wide range of malignancies and disorders[13-15]. miRNAs are small (20-22 nt) non-coding RNAs which function primarily is to regulate gene expression in a sequence specific manner and to act as positive or negative regulators of protein levels in the cell. More recently, tumour cells have been shown experimentally to release miRNAs directly into the circulation[16] contained primarily in micro-vesicles or exosomes (extracellular vesicles), or bound to AGO2 which is part of the miRNA-mediated silencing complex[13-15]. Due to the 'encapsulation' of these miRNAs in serum or plasma, they are highly resistant to degradation from RNases (highly concentrated in the blood) thus their potential usefulness as a 'biomarker' is relatively high. Not only are they resistant to degradation, they are also inherently stable with many studies highlighting their resistance to extended storage conditions and changes in pH and temperature[13-15].

To date, the identification of circulating melanoma-specific miRNAs has been limited to a small number of studies[17, 18]. Most recently Friedman et al. (2012) screened 355 miRNAs in sera from 80 melanoma patients using a previously characterised panel of serum-expressed miRNAs[18]. The authors found that a five-miRNA signature was able to classify the patients into high and low recurrence risk. Although this study highlighted the potential use of this subset of miRNAs for diagnostic purposes, it only assessed ~17% of all known miRNAs (there are now >2000 miRNAs in miRBase). In addition, the panel of miRNAs selected for validation was not assessed for its specificity to melanoma. Whilst this panel addresses an important question, it is limited to prior diagnosis of melanoma and could not be used to identify the presence of unknown primaries or unidentified metastases. Accordingly, there remains a need for biomarkers, such as miRNA biomarkers, that are useful in the diagnosis, prognosis, therapeutic response monitoring and/or disease monitoring in melanoma patients. Specifically, the use of such biomarkers may address the outstanding clinical needs for more sensitive tools to screen for recurrence following treatment and prognostic tools to guide treatment decisions for patients with advanced disease.

SUMMARY

MicroRNAs represent an important class of biomarkers that provide opportunities for clinical translation. The invention is broadly directed to a method of diagnosis, prognosis, therapeutic response monitoring and/or disease response monitoring of melanoma.

More particularly, the inventors have discovered specific miRNA biomarkers that have proved to be useful in the diagnosis, prognosis and/or disease monitoring of melanoma. Subsequently, methods have been developed to diagnose and/or monitor disease progression in subjects with melanoma as well as to provide an indication of disease prognosis. Furthermore, the inventors have discovered that particular miRNA biomarkers may serve as a prognostic marker with respect to treatment response.

In a first aspect, the invention provides a method of determining whether or not a subject has melanoma, including:

determining an expression level of one or more miRNA biomarkers in a biological sample from a subject, wherein the one or more miRNA biomarkers are selected from the group consisting of miRNA-4487, miRNA-4706 and miRNA-4731, or a fragment or variant thereof, and wherein melanoma is detected if said expression level of one or more miRNA biomarkers, is altered or modulated in the biological sample.

In a second aspect, the invention provides a method of determining the prognosis of a subject with melanoma, including:

determining an expression level of one or more miRNA biomarkers in a biological sample obtained from the subject, wherein the one or more miRNA biomarkers are selected from the group consisting of miRNA-4487, miRNA-4706 and miRNA-4731, or a fragment or variant thereof to thereby evaluate the prognosis of melanoma in the subject.

Suitably, if the expression level of said one or more miRNA biomarkers is altered or modulated in the biological sample, the prognosis may be negative or positive.

In one embodiment, the prognosis is used, at least in part, to determine whether the subject would benefit from treatment of melanoma.

In one embodiment, the prognosis is used, at least in part, to develop a treatment strategy for the subject.

In one embodiment, the prognosis is used, at least in part, to determine disease progression in the subject.

In one embodiment, the prognosis is defined as an estimated time of survival.

In one embodiment, the method of this aspect further includes determining suitability of the subject for treatment based, at least in part, on the prognosis.

In one embodiment of the first and second aspects, the method further comprises determining a disease stage and/or grade for melanoma based on the expression level of the one or more miRNA biomarkers.

In one embodiment of the first and second aspects, the expression level of the one or more miRNA biomarkers is determined before, during and/or after treatment.

In a third aspect, the invention provides a method of treating melanoma in a subject including:

determining an expression level of one or more miRNA biomarkers in a biological sample from the subject, before, during and/or after treatment of melanoma, wherein the one or more miRNA biomarkers are selected from the group consisting of miRNA-4487, miRNA-4706 and miRNA-473, or a fragment or variant thereof, and based on the determination made, initiating, continuing, modifying or discontinuing a treatment of melanoma.

In a fourth aspect, the invention provides a method of evaluating treatment efficacy of melanoma in a subject including:

determining an expression level of one or more miRNA biomarkers in a biological sample from the subject before, during and/or after treatment, wherein the one or more miRNA biomarkers are selected from the group consisting of miRNA-4487, miRNA-4706 and miRNA-4731, or a fragment or variant thereof; and determining whether or not the treatment is efficacious according to whether said expression level of one or more miRNA biomarkers is altered or modulated in the subject's biological sample.

In one embodiment of the third and fourth aspects, the method further comprises selecting a treatment for melanoma based on the expression level of the miRNA biomarkers.

In particular embodiments, the method of the first, second, third and fourth aspects further comprises measuring an expression level of one or more additional miRNA biomarkers selected from the group consisting of miRNA-16, miRNA-211, miRNA-509-3p and miRNA-509-5p, or a fragment or variant thereof.

In particular embodiments of the method of the first, second, third and fourth aspects, an expression level of a protein or nucleic acid biomarker may also be determined. Suitably, the protein or nucleic acid biomarker is selected from the group consisting of serum lactate dehydrogenase (LDH), S-100B, tyrosinase, melanoma-inhibiting activity (MIA), tumour-associated antigen 90 immune complex (TA901C), C-reactive protein, galectin-3, melanoma, associated antigen, interleukin-8, matrix metalloprotease (MMP)-1, MMP-3 and YKL-40.

In particular embodiments of the method of the first, second, third and fourth aspects, the biological sample comprises tissue, blood, serum, plasma or cerebrospinal fluid. Typically, the miRNAs described herein are obtainable from a non-cellular source. Accordingly, the biological sample is, comprises, or is obtained from a non-cellular source. To this end, the biological sample may be serum, plasma, or cerebrospinal fluid, although without limitation thereto.

Suitably, the subject referred to herein is a mammal. Preferably, the subject is a human.

As used herein, except where the context requires otherwise, the term "comprise" and variations of the term, such as "comprising", "comprises" and "comprised", are not intended to exclude further elements, components, integers or steps but may include one or more unstated further elements, components, integers or steps.

It will be appreciated that the indefinite articles "a" and "an" are not to be read as singular indefinite articles or as otherwise excluding more than one or more than a single subject to which the indefinite article refers. For example, "a" cell includes one cell, one or more cells and a plurality of cells.

BRIEF DESCRIPTION OF THE FIGURES

FIGS. 7A-7D. ROC curves derived from the data presented in Table 5 for the MELmir-8 panel which were those that showed high significance (P<0.0001) between stage IV vs controls. All members of the 'MELmir-7' panel have AUC scores >0.7. Using this cut-off, miR-204 is excluded/

FIG. 8. Unsupervised hierarchical cluster tree (Euclidean similarity with average linkage) of all miRNA genes and samples (Tables 7 and 8) Distinct separation can be observed for most melanoma (cutaneous) samples (brown) compared with other solid malignancies (green): Controls (melanocytes and melanoblasts) (red), uveal melanoma (UMM) (pink), melanoma patient-derived serum (blue) and nevocyte (grey) are also present in the tree.

FIG. 11. The nucleic acid sequence and observed sequence variation of miRNA-4706.

FIG. 12. The nucleic acid sequence and observed sequence variation of miRNA-4731.

FIGS. 13A-13B. The nucleic acid sequence and observed sequence variation of miRNA-16.

FIG. 14. The nucleic acid sequence and observed sequence variation of miRNA-211.

FIG. 15. The nucleic acid sequence and observed sequence variation of miRNA-509-3p and miRNA-509-5p.

BRIEF DESCRIPTION OF THE SEQUENCES

Figure 1:
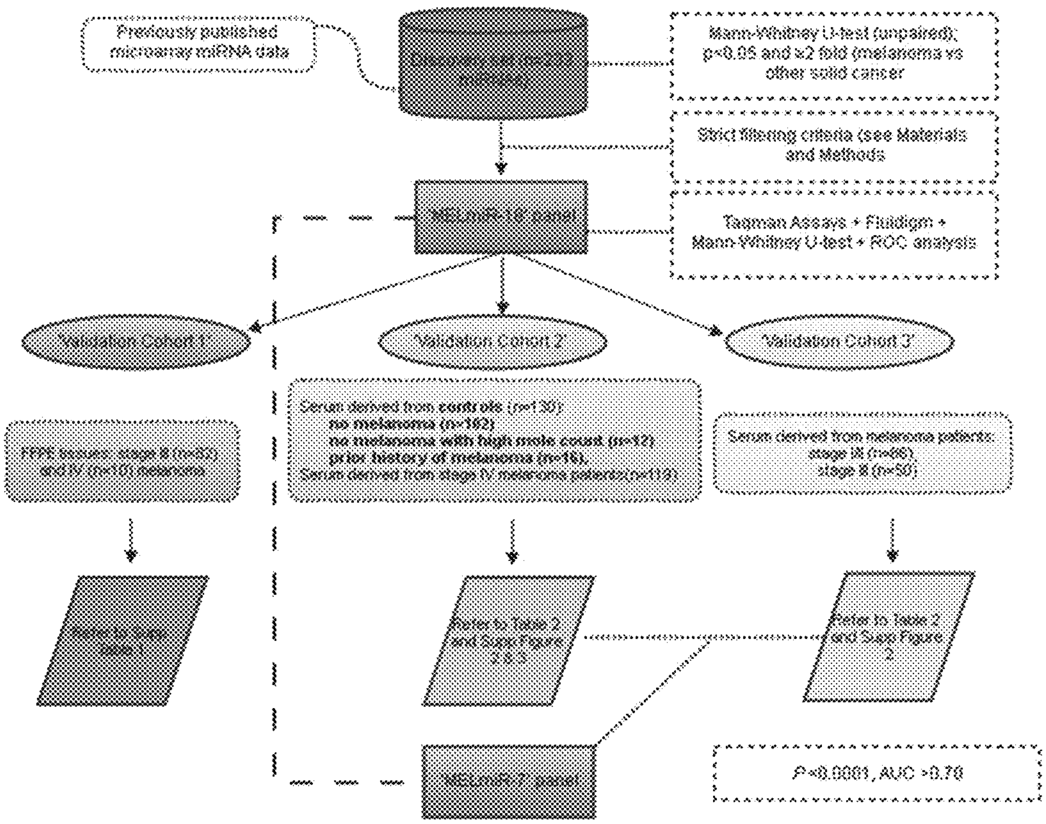
FIG. 1. 'Melanoma-specific' miRNAs were first identified in a 'Discovery set' of 233 miRNAs. The 'MELmiR-18' panel was measured firstly in an independent cohort of FFPE melanoma tissues ('Validation Cohort 1'). These data are summarised if Table 4. The 'MELmiR-18' panel was then measured ('Validation Cohorts 2 and 3') in two cohorts of serum derived front controls in comparison to AJCC staged melanoma patients (stages I-IV). These data are summarised in Table 2 and FIGS. 6 and 7. The 'MELmiR-7' panel was identified and carried forward in subsequent analysis as each miRNA member achieved high significance ($P<0.0001$) and an AUC score >0.70 in the 'Validation Cohort 2 and 3' comparison.

SEQ ID NO: 1=nucleic acid sequence miRNA-4487 of FIG. 10 (mature sequence of miRNA-4487)

SEQ ID NO: 2=nucleic acid sequence miRNA-4706 of FIG. 11 (mature sequence of miRNA-4706)

SEQ ID NO: 3=nucleic acid sequence miRNA-4731 of FIG. 12 (mature sequence of 15 miRNA-4731-5p)

SEQ ID NO: 4=nucleic acid sequence miRNA-16 of FIG. 13 (mature sequence of miRNA-16-5p)

SEQ ID NO: 5=nucleic acid sequence miRNA-211 of FIG. 14 (mature sequence of miRNA-211-5p)

SEQ ID NO: 6=nucleic acid sequence miRNA-509-3p of FIG. 15 (mature sequence of miRNA-509-3p)

SEQ ID NO: 7=nucleic acid sequence miRNA-509-5p of FIG. 15 (mature sequence of miRNA-509-5p)

The Sequence Listing is submitted as an ASCII text file in the form of the file named Sequence_Listing.txt, which was created on Jul. 6, 2021, and is 1,387 bytes, which is incorporated by reference herein.

DETAILED DESCRIPTION

The present invention is predicated, at least in part, on the surprising discovery that a novel panel of micro RNAs (miRNAs or miRs) may provide a scrum-based prognostic and/or diagnostic biomarker for melanoma. In this regard, the inventors demonstrate herein that the panel may be used to monitor disease progression in melanoma patients, particularly in those patients with metastatic disease. Accordingly, the miRNAs disclosed herein may also have utility in methods of treating and/or evaluating treatment efficacy in melanoma patients.

In an aspect, the invention provides a method of determining whether or not a subject has melanoma, including:

determining an expression level of one or more miRNA biomarkers in a biological sample from a subject, wherein the one or more miRNA biomarkers are selected from the group consisting of miRNA-4487, miRNA-4706 and miRNA-4731, and wherein melanoma is detected if said expression level of one or more miRNA biomarkers, is altered or modulated in the biological sample.

As generally used herein, the terms "cancer", "tumour", "malignant" and "malignancy" refer to diseases or conditions, or to cells or tissues associated with the diseases or conditions, characterized by aberrant or abnormal cell proliferation, differentiation and/or migration often accompanied by an aberrant or abnormal molecular phenotype that includes one or more genetic mutations or other genetic changes associated with oncogenesis, expression of tumour markers, loss of tumour suppressor expression or activity and/or aberrant or abnormal cell surface marker expression.

"Melanoma", as used herein, refers to the malignant proliferation of melanocytes. The term "melanoma" is used, unless stated otherwise, in the broadest sense and refers to all stages and all forms of the cancer, such as malignant, metastatic (regional or distant), cutaneous, uveal and recurrent melanoma. As would be understood by the skilled artisan, this includes those subjects with melanoma that may be asymptomatic and/or a diagnosis of melanoma has not been provided or is ambiguous and yet the subject does indeed have melanoma.

The term "determining" includes any form of measurement, and includes determining if an element is present or not. As used herein, the terms "determining", "measuring", "evaluating", "assessing" and "assaying" are used interchangeably and include quantitative and qualitative determinations. Determining may be relative or absolute. "Determining the presence q/" includes determining the amount of something present (e.g., an miRNA and/or protein biomarker), and/or determining whether it is present or absent.

As would be, understood by the skilled person, the expression level of the one or more miRNA biomarkers is deemed to be "altered" or "modulated" when the amount or expression level of the respective miRNA biomarker is increased or up regulated or decreased or down regulated, as defined herein.

In one embodiment, melanoma is detected if the one or more miRNA biomarkers are at a reduced level, down regulated or absent in the biological sample. In an alternative embodiment, melanoma is detected if the one or more miRNA biomarkers are at an increased level, up regulated or present in the biological sample.

By "enhanced", "increased" or "up regulated" as used herein to describe the expression level of miRNA, protein and/or nucleic acid biomarkers, refers to the increase in and/or amount or level of one or more miRNA, protein and/or nucleic acid biomarkers, including variants, in a biological sample when compared to a control or reference sample or a further biological sample from a subject. The expression level of a biomarker may be relative or absolute. In some embodiments, the expression level of the one or more miRNA, protein and/or nucleic acid biomarkers is increased if its level of expression is more than about 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400% or at least about 500% higher than the level of expression of the corresponding miRNA, protein and/or nucleic acid biomarkers in a control sample or further biological sample from a subject.

The terms, "reducer" and "down regulated", as used herein to describe the expression level of miRNA, protein and/or nucleic acid biomarkers, refer to a reduction in and/or amount or level of one or more miRNA, protein and/or nucleic acid biomarkers, including variants, in a biological sample when compared to a control or reference sample or further biological sample from a subject. The expression level of a biomarker may be relative or absolute. In some embodiments, the expression level of one or more miRNA, protein and/or nucleic acid biomarkers is reduced or down regulated if its level of expression is more than about 95%, 90%, 80%, 70%, 60%, 50%, 40%, 30%, 20% or 10%, or even less than about 5%, 4%, 3%, 2%, 1%, 0.5%, 0.1%, 0.01%, 0.00% or 0.0001% of the level of expression of the corresponding miRNA, protein and/or nucleic acid biomarkers in a control sample or further biological sample from a subject.

The term "control sample" typically refers to a biological sample from a healthy or non-diseased individual not having melanoma. In one embodiment, the control sample may be from a subject known to be free of melanoma. Alternatively, the control sample may be from a subject in remission from melanoma. The control sample may be a pooled, average or an individual sample. An internal control is a marker from the same biological sample being tested.

Suitably, the expression level of any combination of the miRNA biomarkers miRNA-4487, miRNA-4706 and miRNA-4731 in a biological sample may be determined, including for example: miRNA-4487 and miRNA-4706; miRNA-4487 and miRNA-4731; miRNA-4706 and miRNA-4731; or miRNA-4487, miRNA-4706 and miRNA-4731.

In one embodiment the method of determining whether or not a subject has melanoma includes determining the expression level of a further miRNA biomarker in addition to miRNA-4487, miRNA-4706 and miRNA-4731 in a biological sample from the subject, wherein the miRNA biomarkers are selected from the following group: miRNA-16, miRNA-211, miRNA-509-3p and miRNA-509-5p, and wherein melanoma may be detected if at least one of the miRNA biomarkers is at an altered or modulated level or expression in the biological sample when compared to a control or reference sample. By way of example, an increase in the level or up regulation in the biological sample of a further biomarker, such as miRNA-15 and/or miRNA-211, may indicate the presence of melanoma in the subject. Further, a decrease in the level, down regulation or absence in the biological sample of a further biomarker, such as miRNA-509-3p and/or miRNA-509-5p, may indicate the presence of melanoma in the subject.

It will be appreciated that the methods of the invention include methods of determining the expression level of the one or more miRNA biomarkers alone or in combination with one or more protein and/or nucleic acid biomarkers which have been identified as being diagnostic for melanoma. In certain embodiments, the expression level of one or more protein and/or nucleic acid biomarkers may also be determined. In this regard, the one or more protein and/or nucleic acid biomarkers may include, for example, serum lactate dehydrogenase (LDH), S-100B, tyrosinase, VEGF, bFGF, ICAM-1, matrix metalloproteases (MMPs; e.g., MMP-1 and MMP-3), cytokines and/or their receptors (e.g., IL-6, IL-8, IL-10), ILA molecules. TuM2-PK, apoptosis markers (e.g., Fas/CD95) karyopherin-alpha2, MCMs (minichromosome maintenance proteins), melanoma-inhibiting activity (MIA), tumour-associated antigen 90 immune complex (TA901C), C-reactive protein, galectin-3, melanoma associated antigens (e.g., MAGE proteins), YKL-40, geminin and PCNA, albeit without limitation thereto. Additional diagnostic and prognostic protein and nucleic acid biomarkers for melanoma have been described previously, as reviewed in DIAGNOSTIC AND PROGNOSTIC BIOMARKERS AND THERAPEUTIC TARGETS IN MELANOMA Ed. Murphy, M. J., (Humana Press, 2012), which is incorporated by reference herein.

The expression level of the one or more miRNA, protein and/or nucleic acid biomarkers may be determined by any method known in the art. By way of example, the expression level of miRNA biomarkers may be determined by hybridization-based techniques (e.g., Northern blots, in situ hybridization, RT-PCR, and microarrays), amplification-based techniques (e.g., real-time quantitative PCR; gold nanoparticle-initiated silver enhancement) and cloning-based techniques (e.g., miRAGE).

Suitably, when the expression level of the one or more miRNA biomarkers and/or one or more protein and/or nucleic acid biomarkers are determined, they can be derived from the same or different samples. For example, the expression level of the one or more miRNA biomarkers can be determined in a blood derived sample and the expression level of a protein biomarker can be determined in a tissue sample.

In particular embodiments, the biological sample comprises tissue, blood, serum, plasma or cerebrospinal fluid. Typically, the miRNAs described herein are obtainable from a non-cellular source. Accordingly, the biological sample is, comprises, or is obtained from a non-cellular source. To this end, the biological sample may be serum, plasma, or cerebrospinal fluid, although without limitation thereto.

In some embodiments, the method of determining whether or not a subject has melanoma may be performed in "high throughput" diagnostic tests or procedures such as performed by commercial pathology laboratories or in hospitals. Furthermore or alternatively, the method of the present aspect may be used to confirm a diagnosis of melanoma, including metastatic and recurrent melanoma, such as that initially detected by a different or alternative diagnostic test or procedure.

It would be further appreciated, that such methods of determining miRNA expression in the biological sample from a melanoma patient may have potential utility in characterising disease progression and/or severity of a given patient. Additionally, such methods may be used for selecting patients for particular treatments.

In one embodiment, the method determines whether the subject has metastatic melanoma.

As used herein, "metastasis" or "metastatic", refers to the migration or transfer of malignant tumour cells, or neoplasms, via the circulatory or lymphatic systems or via natural body cavities, typically from the primary focus of tumour, cancer or a neoplasia to a distant site in the body, and the subsequent development of one or more secondary tumours or colonies thereof in the one or more new locations. "Metatases" refers to the secondary tumours or colonies formed as a result of metastasis and encompasses micro-metastases as well as regional and distant metastases.

In one embodiment, the method determines whether the subject has recurrent melanoma.

In another aspect, the invention provides a method of determining the prognosis of a subject with melanoma, including:

determining an expression level of one or more miRNA biomarkers in a biological sample obtained from the subject, wherein the one or more miRNA biomarkers are selected from the group consisting of miRNA-4487, miRNA-4706 and miRNA-4731, to thereby evaluate the prognosis of melanoma in the subject.

Suitably, if the expression level of said one or more miRNA biomarkers, is altered or modulated in the biological sample, the prognosis may be negative or positive.

The terms "prognosis" and "prognostic" are used herein to include making a prognosis, which can provide for predicting a clinical outcome (with or without medical treatment), selecting an appropriate course of treatment (or whether treatment would be effective) and/or monitoring a current treatment and potentially changing the treatment. This may be at least partly based on determining expression levels of one or more miRNA biomarkers by the methods of the invention, which may be in combination with determining the expression levels of additional protein and/or other nucleic acid biomarkers. A prognosis may also include a prediction, forecast or anticipation of any lasting or permanent physical or psychological effects of melanoma suffered by the subject after the melanoma has been successfully treated or otherwise resolved. Furthermore, prognosis may include one or more of determining metastatic potential or occurrence, therapeutic responsiveness, implementing appropriate treatment regimes, determining the probability, likelihood or potential for melanoma recurrence after therapy and prediction of development of resistance to established-therapies (e.g., chemotherapy). It would be appreciated that a positive prognosis typically refers to a beneficial clinical outcome or outlook, such as long-term survival without recurrence of the subject's melanoma, whereas a negative prognosis typically refers to a negative clinical outcome or outlook, such as cancer recurrence or progression.

"Resistance" as used herein refers to a diminished or failed response of an organism, disease, tissue or cell to the intended effectiveness of a treatment, such as a chemical or drug. Resistance to a treatment can be already present at diagnosis or the start of treatment (i.e., intrinsic resistance) or it can develop with or after treatment (i.e., acquired resistance).

As described herein, the expression levels of miRNA-4487, miRNA-4706 and miR-4731 are typically decreased or down regulated upon the initial development of melanoma in a subject. The expression levels of these miRNAs, however, may be shown to be altered or modulated (i.e., they may increase and/or decrease) with disease progression, such as progression from Stage I/II to Stage III or Stage IV melanoma and front Stage III to Stage IV melanoma, despite typically remaining decreased or down regulated when compared to a control sample or level of expression.

In this regard, an increase or up regulation of the level in the biological sample of miRNA-4487 in a subject with Stage I/II or Stage III melanoma, may indicate a positive prognosis for the subject, such as disease remission or regression, or alternatively it may indicate a negative prognosis for the subject, such as disease progression to Stage IV melanoma. Further, a decrease or down regulation of the level in the biological sample of miRNA-4487 in, a subject with Stage I/II melanoma may indicate a negative prognosis for the subject, such as disease progression to Stage III melanoma.

An increase or up regulation of the level in the biological sample of miRNA-4706 in a subject with Stage I/II or Stage III melanoma, may indicate a positive prognosis for the subject, such as disease regression or remission, or alternatively it may indicate a negative prognosis for the subject, such as disease progression to Stage III or Stage IV melanoma.

An increase or up regulation of the level in the biological sample of miRNA-4731 in a subject with Stage III melanoma, may indicate a positive prognosis for the subject, such as disease regression or remission, or alternatively it may indicate a negative prognosis for the subject, such as disease progression to Stage 11.1 melanoma. Further, a decrease or down regulation of the level in the biological sample of miRNA-4731 in a subject with Stage III melanoma may indicate a negative prognosis for the subject, such as disease progression to Stage IV melanoma. Additionally, an increase or up regulation of the level in the biological sample of miRNA-4731 in a subject with Stage III or IV melanoma, may indicate a positive prognosis for the subject, such as disease regression or remission.

In one embodiment, the method further comprises measuring an expression level of one or more additional miRNA biomarkers selected from the group consisting of miRNA-16, miRNA-211, miRNA-509-3p and miRNA-509-5p.

In this regard, an increase or up regulation of the level in the biological sample of an additional biomarker, such as miRNA-16 and/or miRNA-211, may indicate a negative prognosis for the subject. Further, a decrease or down regulation of the level in the biological sample of an additional biomarker, such as miRNA-509-3p and/or miRNA-509-5p may indicate a negative prognosis for the subject. Additionally, a decrease or down regulation of the level in the biological sample of miRNA-16 in a subject with Stage III melanoma, may indicate a positive prognosis for the subject, such as disease regression or remission, or alternatively it may indicate a negative prognosis for the subject, such as disease progression to Stage IV melanoma.

In certain embodiments, the expression level of one or more protein and/or nucleic acid biomarkers, as hereinbefore described, may also be determined.

In particular embodiments, the biological sample comprises tissue, blood, serum, plasma or cerebrospinal fluid. Preferably, the biological sample comprises serum, plasma, or cerebrospinal fluid, although without limitation thereto.

In one embodiment, the method further comprises determining a disease stage and/or grade for the subject's melanoma based on the expression level of the one or more miRNA biomarkers. In this regard, the method may be used to determine whether the subject's melanoma has metastasized regionally, such as to lymph nodes (i.e., Stage III melanoma), and/or distantly to other parts of the subject's body (i.e., Stage IV melanoma).

In one embodiment, the expression level of the one or more miRNA biomarkers is determined before, during and/or after treatment.

In one embodiment, the prognosis is used, at least in part, to determine whether the subject would benefit from treatment of the melanoma.

In one embodiment, the prognosis is used, at least in part, to develop a treatment strategy for the subject.

In one embodiment, the prognosis is used, at least in part, to determine disease progression or recurrence in the subject.

In one embodiment, the prognosis is defined as an estimated time of survival.

In one embodiment, the method of this aspect further includes determining suitability of the subject for treatment based, at least in part, on the prognosis.

In a further aspect, the invention provides a method of treating melanoma in a subject including:

determining an expression level of one or more miRNA biomarkers in a biological sample from a subject, before, during and/or after treatment of melanoma, wherein the one or more miRNA biomarkers are selected from the group consisting of miRNA-4487, miRNA-4706, miRNA-4731 and based on the determination made, initiating, continuing, modifying or discontinuing a treatment of melanoma.

As used herein, "treating", "treat" or "treatment," refers to a therapeutic intervention, course of action or protocol that at least ameliorates a symptom of melanoma after the cancer and/or its symptoms have at least started to develop. As used herein, "preventing", "prevent" or "prevention" refers to therapeutic intervention, course of action or protocol initiated prior to the onset of cancer and/or a symptom of cancer so as to prevent, inhibit or delay development or progression of the cancer or the symptom.

In one embodiment, the method further comprises measuring an expression level of one or more additional miRNA biomarkers selected from the group consisting of miRNA-16, miRNA-211, miRNA-509-3p and miRNA-509-5p.

In certain embodiments, the expression level of one or more protein and/or nucleic acid biomarkers, as herein before described, may also be determined.

In particular embodiments, the biological sample comprises tissue, blood, serum, plasma or cerebrospinal fluid. Preferably, the biological sample comprises serum, plasma, or cerebrospinal fluid, although without limitation thereto.

In one embodiment, the method further comprises selecting a treatment for melanoma based on the expression level of the miRNA biomarkers.

It will be appreciated that the method of treating melanoma may include administration of one or more other therapeutic agents that facilitate melanoma treatment or prevention. By way of example only, these include: chemotherapeutic agents such as paclitaxel, doxorubicin, methotrexate, irinotecan, dacarbazine, temozolomide and cisplatin, although without limitation thereto; biotherapeutic agents such as anti-PD-1 antibodies (e.g. Nivolumab) and anti-CTLA4 antibodies (e.g., Ipilimumab), although without limitation thereto; and/or molecularly targeted agents such as MAPK pathway (i.e., RAS-RAF-MEK-ERK signalling) inhibitors and phosphatidylinositol 3-kinase (PI3K)/protein kinase B (AKT)/mammalian target of rapamycin (mTOR) pathway inhibitors, although without limitation thereto.

In one embodiment, the method further comprises selecting a treatment for melanoma based on the expression level of the miRNA biomarkers.

In yet another aspect, the invention provides a method of evaluating treatment efficacy of melanoma in a subject including:

determining an expression level of one or more miRNA biomarkers in a biological sample from the subject before, during and/or after treatment, wherein the one or more miRNA biomarkers are selected from the group consisting of miRNA-4487, miRNA-4706 and miRNA-4731; and determining whether or not the treatment is efficacious according to whether said expression level of one or more miRNA biomarkers is altered or modulated in the subjects biological sample.

As noted earlier, the expression levels of miRNA-4487, miRNA-4706 and miRNA-4731, may increase and/or decrease with disease progression, despite typically remaining decreased or down regulated when compared to a control sample.

In this regard, an increase or up regulation of the level in the biological sample of miRNA-4487 in a subject with Stage I/II or Stage III melanoma undergoing treatment, may indicate disease remission or regression in the subject, and as such the treatment is efficacious, or alternatively it may indicate disease progression to Stage IV melanoma and the treatment is inefficacious. Further, a decrease or down regulation of the level in the biological sample of miRNA-4487 in a subject with Stage I/II melanoma undergoing treatment may indicate disease progression to Stage 111 melanoma and the treatment is inefficacious.

An increase or up regulation of the level in the biological sample of miRNA-4706 in a subject with Stage I/II or Stage III melanoma undergoing treatment, may indicate disease regression or remission and the treatment is efficacious, or alternatively it may indicate disease progression to Stage III or Stage IV melanoma and the treatment is inefficacious.

An increase or up regulation of the level in the biological sample of miRNA-4731 in a subject with Stage I/II melanoma undergoing treatment, may indicate disease regression or remission and the treatment is efficacious, or alternatively it may indicate disease progression to Stage III melanoma and the treatment is inefficacious. Further, a decrease or down regulation of the level in the biological sample of miRNA-4731 in a subject with Stage III melanoma undergoing treatment may indicate disease progression to Stage IV melanoma and the treatment is inefficacious. Additionally, an increase or up regulation of the level in the biological sample of miRNA-4731 in a subject with Stage 111 or IV melanoma undergoing treatment, may indicate disease regression or remission and the treatment is efficacious.

In one embodiment, the method further comprises measuring the expression level of one or more additional miRNA biomarkers selected from the group consisting of miRNA-16, miRNA-211, miRNA-509-3p and miRNA-509-5p. In this regard, a decrease or down regulation of the level in the biological sample of an additional biomarker, such as miRNA-16 and/or miRNA-211, may indicate the treatment is efficacious. Additionally, for miRNA-16, a decrease or down regulation of its expression level in the biological sample from a subject with Stage I/II or III melanoma, may indicate disease progression to Stage IV melanoma and the treatment is inefficacious. Further, an increase in the level or up regulation in the biological sample of an additional biomarker, such as miRNA-509-3p and/or miRNA-509-5p, may indicate the treatment is efficacious.

In certain embodiments, the expression level of one or more protein and/or nucleic acid biomarkers, as herein before described, may also be determined.

In particular embodiments, the biological sample comprises tissue, blood, serum, plasma or cerebrospinal fluid. Preferably, the biological sample comprises serum, plasma, or cerebrospinal fluid, although without limitation thereto.

It would be appreciated by the skilled artisan that the methods of present invention also include within their scope fragments and variants of the miRNA biomarkers described herein.

In this regard, a miRNA "fragment" includes a nucleic acid sequence that constitutes less than 100%, but at least 20%, 30%, 40%, 50%, 60%, 70%, 80%, 90% or 95% of said miRNA sequence. In particular embodiments, a miRNA fragment may comprise, for example, at least 10, 11, 12, 13, 14, 15, 16, 17, 18, 19, 20, 21, 22, 23 and 24 contiguous nucleotides of said miRNA biomarkers.

As used herein, "variant" refers to those miRNAs described herein that have one or more nucleic acids deleted, added or substituted by different nucleotides. In particular embodiments, a miRNA variant may comprise, for example, 1, 2, 3, 4, 5, 6, 7, 8 or 9 nucleotide deletions, additions and/or substitutions. In this regard, it is well known in the art that miRNAs can demonstrate some degree of variation from their respective reference miRNA sequence. By way of example and referring to FIGS. 11-15, it will be appreciated that the nucleotide sequences of SEQ ID NOS: 1-7 are "canonical" or preferred sequences and that there may be significant variability with respect to the length of the nucleotide sequence of each miRNA biomarker, in particular.

In some embodiments, a diagnostic, prognostic and/or treatment expression level of the one or more miRNA biomarkers described herein is correlated to melanoma by merely its presence or absence. In other embodiments, a threshold level of a diagnostic, prognostic and or treatment expression level of the one or more miRNA biomarkers can be established, and the level of the one or more miRNA biomarkers in a subject's biological sample can simply be compared to the threshold level.

In some embodiments, multiple time points prior to, during and/or after treatment of a subject with melanoma may be selected to determine the expression level of the one or more miRNA biomarkers, with or without other biomarkers, to determine a diagnosis, prognosis or treatment efficacy. For example, the expression level of the one or more miRNA biomarkers with or without additional specific miRNA biomarkers, protein biomarkers and/or nucleic acid biomarkers can be determined at an initial time point and then again at one, two, three or more time points.

Suitably, the time points may be selected throughout a treatment cycle or over a desired time period. Over a desired time period, for example, the time points may be prior to treatment, mid way through treatment and/or after treatment has been completed. Suitably, an altered or modulated expression level, such as a decrease or reduction in the expression level, of the one or more miRNA biomarkers, such as miRNA-4487, miRNA-4706 and/or miRNA-4731, may be utilised by the methods of the invention from the first to second and/or third time points may provide a poor prognosis for a subject with melanoma. Alternatively, an altered or modulated expression level, such as an increase or upregulation in the expression level, of the one or more miRNA biomarkers, such as miRNA-4487, miRNA-4706 and/or miRNA-4731, utilised by the methods of the invention from the first to second and/or third time points may provide a positive prognosis for a subject with melanoma.

As would be appreciated by the skilled artisan, the alteration or modulation in expression level of the one or more miRNA biomarkers may also be related to the severity, stage, recurrence or progression of melanoma and/or the efficacy of the treatment. By way of example, differences in the expression levels of the one or more miRNA biomarkers may be used to delineate stage III (i.e., regional metastatic) from stage IV (i.e., distant metastatic) melanoma patients. In addition, differences in the expression levels of the one or more miRNA biomarkers may be used to delineate stage I/II (i.e., non-metastatic) from stage III/IV (i.e., metastatic) melanoma patients.

In one embodiment, biological samples may be sourced and/or collected from a subject at diagnosis and then prior to each cycle of treatment. Suitably, there may be any number of treatment cycles, depending on the subject and the nature and/or stage of melanoma, including but not limited to 1, 2, 3, 4, 5, 6, 7, 8, 9, 10, 15 and/or 20 cycles. The treatment cycles may be close together, spread out over a period of time and/or intense cycles at defined time points over a period of time, or any combination of the above.

In further embodiments, samples may be taken both during treatment and/or after treatment has been completed. Suitably, samples may be sourced from a subject at any time point after treatment has been completed, examples of which include 1, 2, 3, 4, 5, 10, 15, 20, 25 and/or 30 days post treatment, 1, 2 and/or 3 weeks post treatment and/or 1, 3, 6 and/or 9 months post treatment and/or 1, 2, 3, 4, 5, 10, 15, 20 and/or 30 years post treatment. The treatment may be completed once the subject is in remission or after at least one or more treatment cycles, depending on the subject and the melanoma.

In some embodiments, subjects are sampled every three to six months and/or every year post treatment. It will be understood by a person of skill in the art that a subject may be in remission or may have non-responsive or relapsed melanoma. If subjects have non-responsive or relapsed disease, then monitoring may be more frequent.

In one embodiment, a decrease or no change in the expression level of the one or more miRNA biomarkers, such as miRNA-4487, miRNA-4706 and/or miRNA-4731, in a second, third, fourth and/or fifth etc., biological sample from a subject collected either after treatment or during treatment as compared to the expression level in a First earlier sample, may indicate progression of melanoma or failure of the treatment, such as the presence and/or development of resistance.

In one embodiment, an increase in the expression level of the one or more miRNA biomarkers, such as miRNA-4487, miRNA-4706 and/or miRNA-4731, in a second, third, fourth and/or fifth etc., biological sample from a subject collected either after treatment or during treatment as compared to the expression level in a first earlier sample, may indicate that the treatment is efficacious.

The methods described herein may be suitable for any biological sample from a subject. In particular embodiments, the biological sample is or comprises tissue, blood, serum, plasma or cerebrospinal fluid. Typically, the miRNAs are obtainable from a non-cellular source. Accordingly, the biological sample is, comprises, or is obtained from a non-cellular source. The biological sample may be serum, plasma, or cerebrospinal fluid, although without limitation thereto.

Additionally, the one or more biomarkers described herein may be used in in vitro assays of response by subject-derived test cells or tissue to predict an in vitro response to the treatment. As such, the one or more biomarkers described herein, may be used, for example, to predict and monitor how particular subjects with melanoma respond to therapeutic intervention with the treatment. A biomarker expression pattern correlating with sensitivity or resistance of cells following exposure of the cells to the treatment may provide a useful tool for screening one or more tumour samples from the subject before treatment. The screening allows a prediction of cells of a biological sample of the melanoma exposed to the treatment, based on the expression results of the one or more biomarkers, as to whether or not the melanoma, and hence a patient harbouring the melanoma, will or will not respond to the treatment.

It would be understood that the methods described herein may be applicable to any mammal. In particular embodiments, the term "mammal" includes but is not limited to humans, performance animals (such as horses, camels, greyhounds), livestock (such as cows, sheep, horses) and companion animals (such as cats and dogs). Preferably, the subject is a human.

So that the present invention may be more readily understood and put into practical effect, the skilled person is referred to the following non-limiting examples.

Example 1

Materials and Methods

Patient Specimen Details and Inclusion Criteria

VALIDATION Cohort 1. Stage III melanoma tissues ("PAH-tissue") were obtained from a prospective database of stage IIIA-C cutaneous melanoma patients, presenting to the Princess Alexandra Hospital (PAH) Melanoma Unit and affiliated private hospitals, which has been maintained since 1997. Permission to collect and use information was approved by the hospital ethics committee (HREX Reference number: HREX/11/QPAH/650; SSA reference number: SSA/11/QPAH/694). Formalin-fixed paraffin embedded (FFPE) tumour samples from 72 patients who met these criteria were reviewed according to the AJCC staging system for cutaneous melanoma seventh edition[1] by an experienced melanoma pathologist. Pathologic and treatment-related variables were prospectively recorded.

Stage III and IV melanoma tissues 'MIA-tissue' were obtained from a prospective database of melanoma patients, presenting to the Melanoma institute Australia (formerly Sydney Melanoma Unit) and affiliated private hospitals, which has been maintained since 1967. Cases and corresponding available FFPE tissue specimens were selected that fell into one of the following three categories, (1) diagnosed with distant metastatic melanoma and survived less than 1 year. (2) diagnosed with distant metastatic melanoma and survived greater than 5 years, and (3) diagnosed with regional lymph node metastasis. Informed written consent was obtained for each patient under approved protocols (Protocol No X10-0305 &HREC/10/RPAH/539 and Protocol No X10-0300 HREC/10/RPAH/530) governed by the Human Research Ethics Committee of the Royal Prince Alfred Hospital (Sydney NSW, Australia)

VALIDATION Cohort 2 and 3. Sera from 'Healthy Controls' were ascertained from a large cohort of participants collected as part of the Australian Cancer Study (ACS) (QIMR Berghofer HREC approved project no, P399). As part of the ACS, potential controls were randomly selected from the Australian Electoral Roll (enrolment is compulsory). Controls were prospectively sampled from within strata of age (in 5 year age-groups) and state of residence. Of 3,258 potentially eligible control participants, 41 could not be contacted and 175 were excluded because they were deceased (16), too ill (61), or unable to read or write in English (98). Of 3,042 controls meeting the inclusion criteria, 1680 (55%) gave their consent to take part. Completed questionnaires were returned by 1580 controls (48% of all potentially eligible controls selected from the roll). See Table 1 for participant descriptive statistics.

Sera from 'High nevus count' and 'History of melanoma' participants were prospectively collected from cohorts who were enrolled in a large study titled: 'Pigmentation genotypes and phenotypic correlations with dermoscopic naevus types and distribution'. These samples were included as 'controls' to determine the level of expression measurable in sera derived from patients with a high melanocyte burden. All study participants were enrolled in the following human ethics approved projects: QIMR HREC/P1237. The Metro South Health District HREC/09/QPAH/162, and UQ HREC approval number is 2009001590. Participants with a history of melanoma were recruited through the Melanoma Unit and Dermatology Department of the Princess Alexandra Hospital, Brisbane, Queensland. Australia, between May 2012 and November 2012. Control participants, with no personal history of melanoma, were recruited from the Brisbane Twin Naevus Study between August 2012 and November 2012. All participants had 16-panel full-body images and dermoscopic images of significant naevi recorded[21]. Significant naevi were defined as naevi greater than or equal to 5 mm on all body sites except the scalp, buttocks, mucosal surfaces and genitals, and greater than or equal to 2 mm on the back of both males and females and on the legs of females. All significant naevi were classified by the predominant dermoscopic pattern (reticular, globular, or non-specific), colour, and profile (flat, raised, domed or papillomatous). See Table 1 for participant descriptive statistics.

Sera from Stage I/II and IV melanoma patients (staged according to the current AJCC staging manual[1]) had blood drawn and serum stored as part of a large prospectively collected cohort from the university department of dermatology in Tubingen, Germany ('Tubingen' cohort). Biobanking and the usage of corresponding patient data for this study was approved by the Ethics Committee, University of Tübingen (approvals 657/2012BO2). An additional cohort of patients was obtained from the Melanoma Institute of Australia, Sydney ('MIA' cohort). Patients were staged I-IV according to the current AJCC staging guidelines[1]. Informed written consent was obtained for each patient under approved protocols (Protocol No X10-0305 &HREC/10/RPAH/539 and Protocol No X10-0300 HREC/10/RPAH/530) governed by the Human Research Ethics Committee of the Royal Prince Alfred Hospital (Sydney NSW, Australia).

Total RNA extraction from 'Validation cohort 1': FFPE tissue. The extraction of total RNA from FFPE tissue was performed using miRNeasy FFPE Kits (QIAGEN). A sterile disposable biopsy punch (BPP-20F; Kai Medical, Japan) was used to retrieve tumour content from blocks that had been scored and marked for content via H&E histological staining. This process allowed for minimal stromal contamination. This kit is specifically designed to reverse the formalin crosslinking of RNA, efficiently releasing RNA from tissue sections, while avoiding significant RNA degradation.

Total RNA extraction from 'Validation cohorts 2 and 3': serum. Total RNA was extracted from serum following the manufacturer's protocol using the miRNeasy Serum/Plasma Kits (QIAGEN) which efficiently purify RNA from up to 200 μl serum or plasma. As there is currently no consensus as to which miRNA should be used as an endogenous control[15], a synthetic miRNA mimic (miRNeasy Serum/Plasma Spike-In Control: *C. elegans* miR-39 miRNA mimic) was spiked into each sample ($5.6\times10^8$ copies/200 μl) to allow for normalization of expression data.

Selection criteria for 'melanoma-specific' miRNAs. In our previously published miRNA microarray data[20] we found a total of 233/1898 miRNAs ('Discovery' set) (FIG. 1) that were differentially expressed (DE: P≤0.05 and ≥2 fold) between a group of cutaneous melanoma cell lines (n=55) as compared to a group of other (non-melanoma) solid malignancies (n=34). We then applied filtering criteria to the 233 DE miRNAs to identify which miRNAs would be suitable to measure in patient derived serum. The following strict criteria were used to filter the 'Discovery' set: ≥15 fold higher expression in cutaneous melanoma vs 'other' solid malignancies (n=14/14), or ≥2 fold higher expression in cutaneous melanoma vs 'other' solid malignancies with no detectable expression in melanocytes or melanoblasts (n=3/6). In addition, miR-16, which is known to be highly expressed in blood, was also included as a control. This identified an 18 miRNA panel ('MELmiR-18') that consisted of: miR-211-5p, miR-514a-3p, miR-509-3p, miR-204-5p, miR-509-5p, miR-513b, miR-145-5p, miR-146a-5p, miR-508-3p, miR-506-3p, miR-513c-5p, miR-4731-5p, miR-508-5p, miR-363-3p, miR-4487, miR-4469, miR-4706, and hsa-miR-16. This panel was carried forward for validation in independent cohorts of patient derived sera and subsequent correlation with panel analysis, in FFPE of melanoma tumours.

Reverse transcription and PreAmnplification using custom primer and assay pools. The standard TaqMan® MicroRNA Assay protocol calls for an individual gene specific reverse transcription (RT) reaction for each assay, however in order to maximize the full capability of the Biomark HD (Fluidigm) system, we developed a modified protocol (User bulletin publication part number 4465407, revision date January 2013 (Rev. C)). Briefly, a custom RT primer pool consisting of equal amounts of miRNA-specific RT primer plus an additional pool of the corresponding TaqMan® MicroRNA Assay (PreAmp Primer Pool) were used to pre-amplify the RT reaction. The TaqMan® PreAmp Master Mix was used to amplify small amounts of cDNA reactions (this was specifically designed to avoid amplification bias). The RT protocol was as per manufacturers guidelines and the PreAmplification protocol was modified in the following way: total reaction volume was scaled down to OL (2.5 μL of RT-product, 5 μL of TaqMan PreAmp Master Mix (2×), and 1.5 μL of PreAmp Printer Pool) with a total of 14 cycles used in the PreAmplification.

qRT-PCR using the Fluidigm® 96.96 Dynamic Array™ and BioMark™ HD. The 96.96 Dynamic™ Array on the Fluidigm system allows simultaneous measurement of 96 assays with 96 samples totaling 9216 reactions with minimal cDNA and (2.7 ul) assay (2.5 ul) input. The Dynamic Array has an on-chip network of microfluidic channels, chambers and valves that automatically assemble individual PCR reactions. The BioMark system has the ability to detect a single copy in a 6.75 nl reaction volume, a feat not possible with conventional real-time PCR instruments (5 ul minimum volume). In this way, it is possible to combine up to 96 primer assays to create a high throughput, specific and highly sensitive custom miRNA expression panel, which maximizes the information that can be obtained from each RNA sample. This ultra-sensitivity allows for confidence in its ability to detect subtle changes in gene expression—a requirement for serum miRNA detection.

qRT-PCR analysis to determine the median normalized Ct expression value. The expression of the 'MELmiR-18' panel (FIG. 1) was assayed in each sample with at least 4 replicate Taqman assays to determine their expression. Firstly, real-time expression data was analyzed and extracted using Fluidigm's Real-Time PCR Analysis software using default parameters (Quality Threshold=0.65, Baseline Correction Method=Linear, and Ct Threshold Method=Auto (Global)). The combined data from all 96.96 Dynamic Array runs were then combined in Microsoft Excel so as to perform global normalization (median normalized Ct value method)[22]. Firstly, the average C value was determined for each sample-assay combination (including the synthetic spike-in control cel-miR-39). The normalization factor was then derived by subtracting the mean cel-miR-39 Ct value of each sample from median cel-miR-39 Ct value of all samples. The median normalized Ct value was then calculated by adding the normalization factor to the averaged Ct value of each sample-assay combination.

For the FFPE samples, again, the average Ct value was determined for each sample-assay combination (including the endogenous control RNU-6). The normalization factor was then derived by subtracting the mean RNU-6 Ct value of a positive control sample with known quantity (151n) of total RNA (added to the initial cDNA reaction) from each RNU-6 assay-sample combination. The median normalized Ct value was then calculated by adding the normalization factor to the averaged Ct value of each sample-assay combination.

Statistical Analysis. All data analysis (Mann-Whitney U test, ROC analysis, and Binary Logistic Regression) was performed in Graph Pad Prism 6 or SPSS for Windows, version 21.0 (Statistical Package for the Social Sciences, SPSS, Inc., Chicago, IL) with median-normalized Ct expression values using default parameters.

Figure 2:
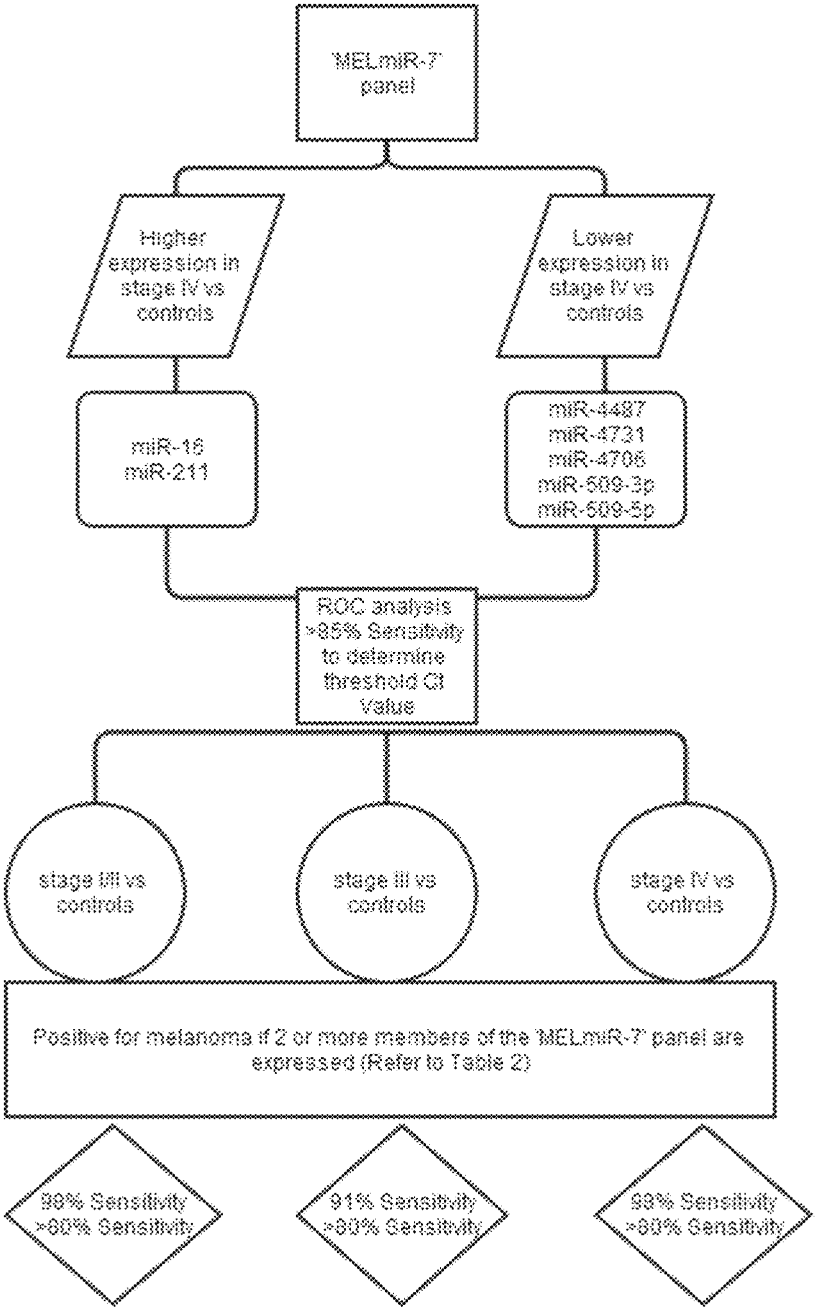
FIG. 2. The diagnostic decision tree summarises the utility of the 'MELmiR-7' panel in a diagnostic setting. The 'MELmiR-7' panel achieves very high sensitivity and specificity when a diagnostic score of 2-7 is attained (see Table 2 for further details).

Diagnostic inclusion criteria. To maximize the chances of having a positive signal expressed in the patients serum, only the combined stage IV cohorts were used (n=119; 'TUBINGEN' and 'MIA') to compare against disease-free 'controls' (n=130; no history of melanoma or nevi, prior history of melanoma, high nevus count with no melanoma). Initially, all members of the 'MELmiR-18' panel underwent a simple Mann-Whitney U test to identify the highly significant (p.<0.0001) miRNAs to be included in the next step (FIG. 1). Those miRNAs that met these criteria then underwent ROC analysis to determine their Area under the Curve (AUC) (FIGS. 1 and 2). The miRNAs that had an AUC≥0.70 ('MELmiR-7' panel) were interrogated further to classify the median-normalized Ct values as 'high' or 'low' expression for diagnostic test purposes along with survival analysis. AUC scores≥0.7 were deemed to be diagnostically useful[23]. Interpretation of Ct expression values used to determine ROC curves were evaluated with an arbitrary cut-off of '85% sensitivity'. Those that were greater than this cut-off were classed as 'high' and those that were below were 'low'. Binary Logistic Regression (SPSS for Windows, version 21.0 (Statistical Package for the Social Sciences, SPSS, Inc., Chicago, IL) analysis was also performed to provide further justification of the inclusion or exclusion of particular miRNAs in the MELmiR-7 panel.

Diagnostic Score assignment. For those miRNAs that met the criteria for inclusion in the diagnostic panel (FIGS. 1 and 2), the patient was given a diagnostic score (ranging from 0-7) determined by the number of miRNAs that were present as 'high' and 'low' (graphing of Ct values as part of the Mann-Whitney U test allowed a visual determinant of the stage IV cohort being higher or lower than the 'control' cohort for each miRNA) or 'normal' (most like the 'control' cohort). To be deemed positive for melanoma, the patients sample must have had a score≥2 (max 7). A negative test was a score of 0 or 1.

Diagnostic test evaluation. The following, formulas were used to determine diagnostic test ability:

Positive Predictive Value (PPV) or Precision=True Positive (TP)/(TP+False Positive (FP))

Negative Predictive Value (NPV)=True Negative (TN)/(False Negative (FN)+TN)

Sensitivity=TP/(TP+FN)

Specificity=TN/(FP+TN)

False Positive Rate=1−Specificity

False Negative Rate=1−Sensitivity

Power=Sensitivity

Likelihood Ratio Positive=Sensitivity/1−Specificity

Likelihood Ratio Negative=1−Sensitivity/Specificity

Diagnostic Odds Ratio (DOR)=(TP/FN)/(FP/TN)

Survival Curve analysis. All Kaplan Meier curves were drawn in Graph Pad Prism 6 using date of last follow-up to compare to date of diagnosis (stage IV) to determine survival years and Alive/Dead status. 'High' and 'Low' categories were derived as discussed. P values were determined using the Mantel-Cox (Log-rank) test and the Hazard Ratio (HR) and Confidence Intervals (CI) were determined by the Mantel-Haenszel test. Serum LDH and S100B data were available from routine testing carried out in the 'Tubingen' cohort.

Results

Validation of 'melanoma-specific' miRNA expression in an independent cohort of stage III and stage IV FFPE melanoma tumors shows significant differences between stages. The 'MELmiR-18' panel (see Materials and Methods for selection criteria) was assessed (along with the endogenous control RNU-6) in a retrospective collection ('Validation Cohort 1') of FFPE melanoma tissues derived from stage III melanoma patients (n=82) and stage IV melanoma patients (n=10) (FIG. 1). Each assay had a serial dilution of a positive control sample (known expression for all miRNAs in panel) that had a total input of 1 ng, 3 ng, 15 ng, and 45 ng in the original cDNA reaction. The BioMark RD Real-time PCR system (Fluidigm) was used to maximize the chances for miRNA detection. Detectable expression was observed in all dilutions of the positive control (except miR-4469 which had assay failure) as well as being expressed to varying degrees in the FFPE tissue-derived RNA. Grouping of the samples into stages (III vs IV) allowed for statistically significant separation (p.0.031-p<0.0001) in 13/18 miRNAs with 4/18 (miR-145-5p, miR-363-3p, miR-4706, and miR-514b) being non-significant (ns). The most strongly significant miRNA was miR-4731 (p<0.0001) followed by miR-4487 (p.0.001) followed by most of the members of the miR-506-514-cluster (Table 4 and FIG. 5). Subsequent ROC analysis (stage III vs IV) confirmed the Mann-Whitney U tests where all previously identified significant miRNAs also had 'good' to 'strong' AUC scores ranging from 0.709-0.854, (Table 4). The highest AUC scores were 0.854 (miR-4731) and 0.821 (miR-4487). Members of the miR-506-514 cluster had AUC scores ranging from (0.709-0.793) with the highest scores being shared by miR-508-3p and miR-509-5p.

Circulating miRNA expression, is readily detectable in serum using a high-throughput ultra-sensitive method of detection. The same MELmiR-18' panel was then assessed (along with a spiked-in *C. elegans* (cel-miR-39) miRNA for normalization purposes) in a large series of retrospective and prospective cohorts of patient sera ('Validation Cohort 2') with varied stages of disease: no melanoma (n=102), no melanoma but high mole count (n=12), prior history of melanoma (n=16), and stage IV melanoma patients (n=119) (FIG. 1). An ultra-sensitive, high-throughput method of detection (Biomark, HD, Fluidigm in combination with TaqMan® MicroRNA Assays, Life Technologies) was used to maximize the chance of detecting low abundance miRNAs which may have been present in the specimens. In miRNA derived from serum, detectable expression was measured in 13/18 miRNAs (Table 2) with 5/18 miRNAs showing no detectable expression. Those miRNAs that had no expression included: miR-4469, miR-508-3p, miR-508-5p, miR-513b, and miR-513c (data not shown), in the 1.3/18 miRNAs having detectable expression, eight (miR-16, miR-204-5p, miR-211-5p, miR-4487, miR-4706, miR-4731, miR-509-3p, and miR-509-5p) of these showed highly significant differences (Mann-Whitney U-test: p<0.0001) between 'controls' (no melanoma, no melanoma but high mole count, and a prior history of melanoma) and patients with stage IV disease (Tables 2 and 5 shows the p values and AUC scores when compared to healthy controls alone). Importantly, the eight highly significant (p<0,0001) miRNAs represented in FIG. 5 show that miR-16 and miR-211-5p have increased expression in melanoma cases compared to controls and the remainder have lower expression as compared to controls.

Table 2 also highlights the significance of the 0.13 detectable miRNAs in relation to stage I/II (n=86) vs. 'controls' along with stage 111 (n=50) vs. 'controls' ('Validation Cohort 3'). It is important, to note that the same highly significant miRNAs (except miR-211-5p) that discriminated stage IV vs. 'controls' are also able to discriminate the lesser stages.

Circulating 'melanoma-specific' miRNA expression shows significant differences between stages of melanoma. Highly significant expression (Man-Whitney U-test p<0.0001) differences were also observed between stage III vs. stage IV melanoma patients along with stages I/II vs. stage IV melanoma patients (Table 2 and FIG. 6).

A panel of 7 miRNAs has the ability to diagnose melanoma with high sensitivity and specificity. Receiver operating characteristic (ROC) curve analysis revealed which of the highly significant miRNAs (Table 2) have the potential to be used for diagnostic/prognostic purposes (FIG. 2). Particular attention is paid to those miRNAs that were able to detect all stages of disease (stages I-IV) (Table 2). The following miRNAs fitted these criteria: miR-16, miR-211-5p, miR-4487, miR-4706, miR-4731, miR-509-3p, and miR-509-5p ('MELmiR-7'). FIG. 7 shows all of the ROC curves associated with stage IV vs. 'controls'.

Analysis of the ROC curve data (see Materials and Methods) was used to categorise expression levels into 'high' or 'low' vs. 'controls', or 'normal' (control-like) (FIG. 2). A diagnostic score was then applied to each sample (see Materials and Methods) which ranged from 0 or 1 (low likelihood of melanoma) and 2-7 (high likelihood of melanoma). Upon applying the derived diagnostic score, the 'MELmiR-7' panel was evaluated as a group. We found that it had the ability to diagnose melanoma (independent of stage), when ≥2 miRNAs were expressed (96% sensitivity and ≥80% specificity) (Table 3). The sensitivity of the 'MELmiR-7' panel increases to 98% when stage IV is compared to 'controls' (FIG. 2). Table 3 provides a summary of the effectiveness of the 'MELmiR-' panel in relation to other stages (see Materials and Methods), particularly for the Diagnostic Odds Ratio (DOR). This ratio was used to determine the lowest diagnostic score possible for the 'MELmiR-7' panel yet still maintaining very high sensitivity and specificity.

The 'MELmiR-7' panel is more sensitive then serum LDH and S100B in diagnosing stage IV melanoma patients. Stage IV melanoma patients ('TUBINGEN' cohort) had serum LDH and S100B levels determined as part of their standard of care regimen. Elevated levels of serum LDH and S100B were found in 39% (27/69) and 63% (43/68) of these patients (data not shown). In the same patients, the 'MELmiR-7' achieved 96% (66/69) sensitivity and ≥80% specificity. Specificity could not be determined for serum LDH and S100B as 'controls' were not assayed.

Figure 3:
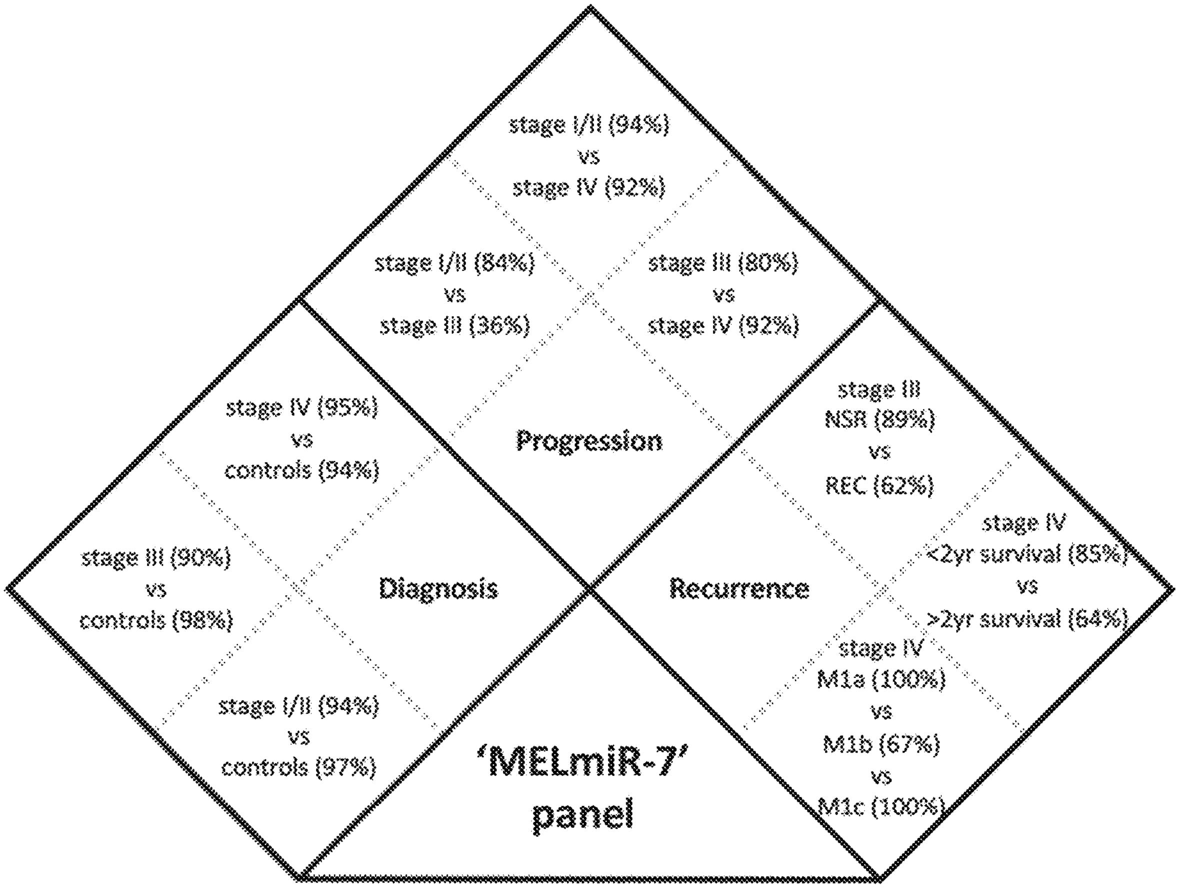
FIG. 3. Predictions derived from Binary Logistic Regression (BLR) analysis are summarised. This represents the versatility of the 'MELmiR-7' panel for not only diagnosis of melanoma, but also for its predictive power for progression and recurrence of disease.

Binary logistic regression models predicts the accuracy of the MELmiR-7 panel. In regression analysis, using just the median normalised Ct values, high predictive accuracy was achieved when using a binary logistic regression model (stepwise backwards conditional) which was able to classify stage IV melanoma and 'controls' 95% and 94% respectively (FIG. 3). The same accuracy was achieved when in a stepwise fashion; miR-16 and miR-4487 were left out of the model (Table 6). When stage III were compared to 'controls', the highest level of accuracy (90% and 99% respectively) was achieved when miR-4731 and miR-509-3p were left out of the model (Table 5). Likewise, when stage I/II were compared to 'controls', the same level of predictive accuracy was maintained following 3 stepwise iterations. The highest percentages were 94% and 97% prediction when miR-211-5p and miR-4731 were left out of the model.

Binary logistic regression models predict recurrence in stage III melanoma patients using the MELmiR-7 panel. Interestingly, when stage III patients were compared to stage IV patients using the same regression model, the complete MELmiR-7 panel achieves an accuracy of 80% (40/50) prediction of stage III vs. 92% prediction of stage IV (FIG. 3). Closer inspection of the stage III patients (at time of blood collection) that were misclassified (according to the regression model) as stage IV (10/50) revealed that 60% (6/10) subsequently developed stage IV recurrence. The combinations of stage III vs. stage IV and stage I/II vs. stage IV can be seen in Table 6.

In stage III melanoma patients with known dates of disease recurrence (stage IV diagnosis) following blood-draw (Median follow-up=20 months, Progression free survival=15.7 months), binary logistic regression was able to predict recurrence in 8/13 (62%) patients and no sign of recurrence (NSR) in 33/37 (89%) patients (FIG. 3). The prediction of NSR was increased to 95% (35/37) when only miR-16, miR-4731, and miR-509-5p were measured (see Table 6 for all possible iterations) however prediction for recurrence was reduced to 54% (7/13).

Binary logistic regression models predict short and long survival in stage IV patients using the MELmiR-7 panel. Stage IV melanoma patients can be classified as short (<2 years) and long (>2 years) survivors using the 'MELmiR-7' panel. Using binary logistic regression models, short and long survivors have a prediction of 85% (57/67) and 64% (33/52) respectively (FIG. 3). The highest level of prediction for short survivors increases to 88% (59/67) when only miR-211-5p, miR-4706, miR-4731, and miR-miR-509-5p are measured (see Table 6 for all possible iterations).

Figure 4:
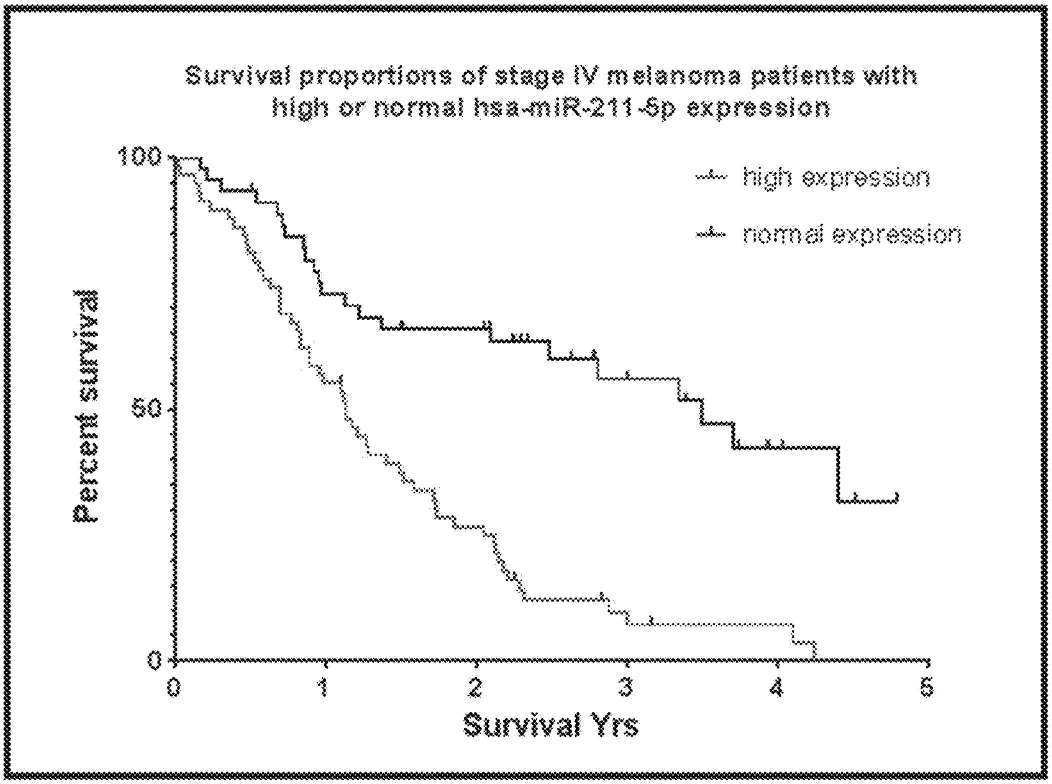
FIG. 4. Expression levels of miR-211-5p were assigned as high or normal expression based upon the comparison of stage IV melanoma with controls (FIG. 1). Using ROC analysis, high expression was determined if the median-normalised CT value was >85% sensitive. The Kaplan-Meier curve shows clear separation between high and normal miR-211-Sp expressers median survival being 1.1 years vs. 3.5 years (HR 3.2, 95% CI 2.02-5.14, p<0.0001).
Figure 5A:
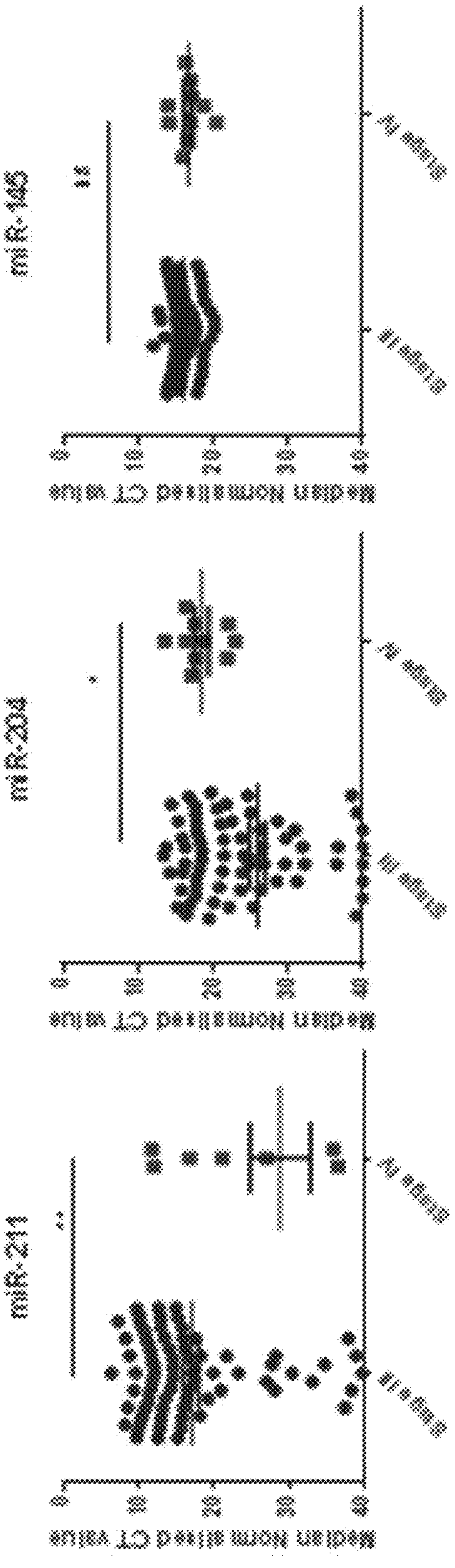
FIGS. 5A-5G. Graphical representation of the data presented in Table 4 for stage TIT and TV FEPE tissues following a Mann-Whitney U test (unpaired). ns=no significance; *=P 0.05-0.01; =P<0.01; *=P<0.001; ****=P<0.0001.
Figure 5B:
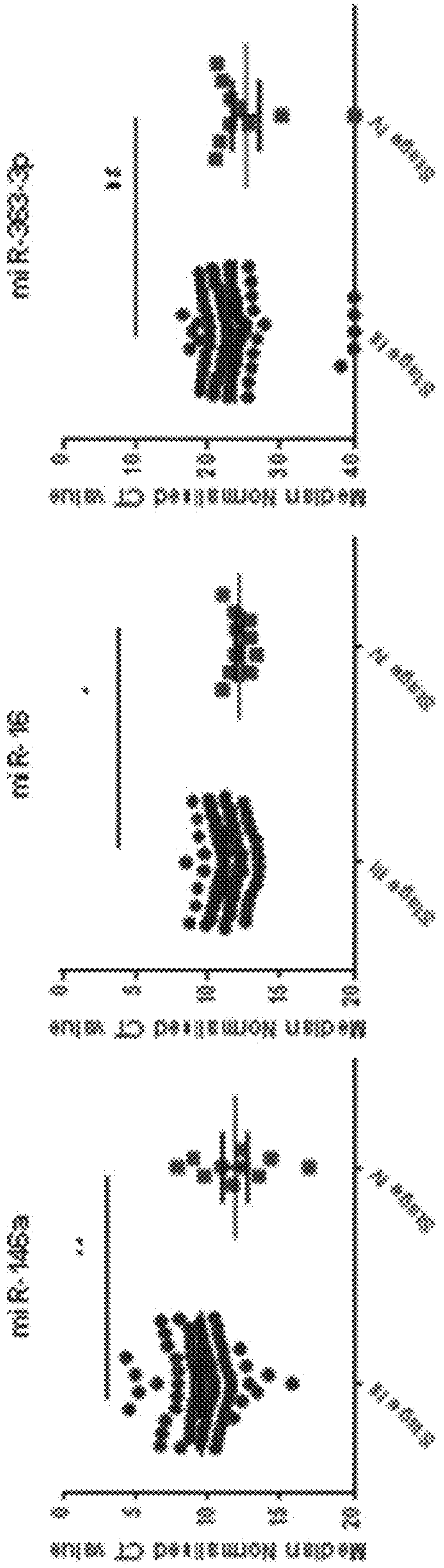
Figure 5C:
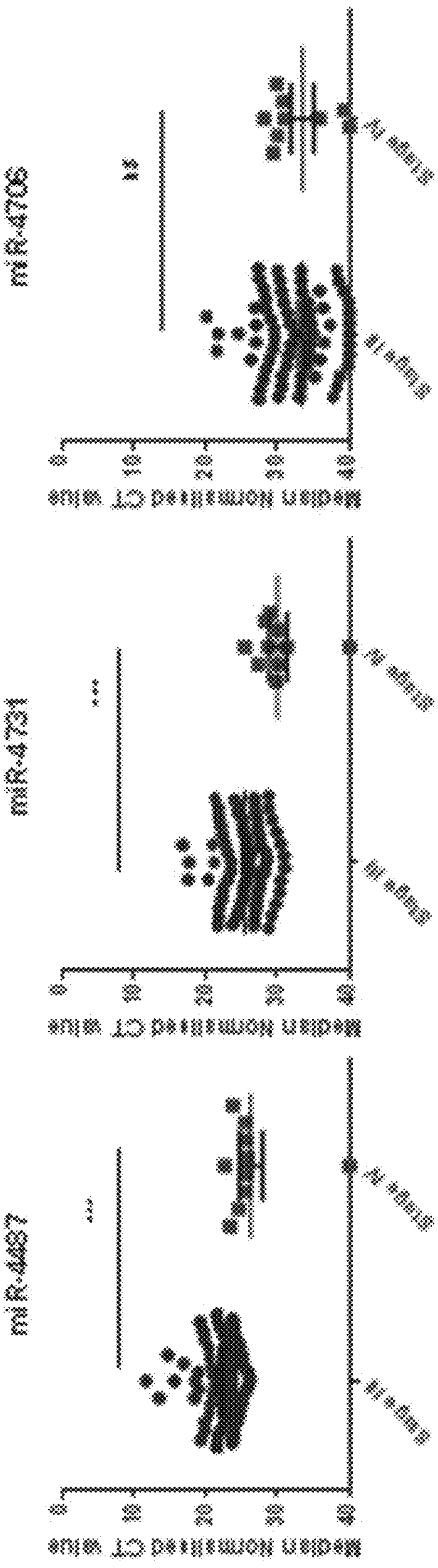
Figure 5D:
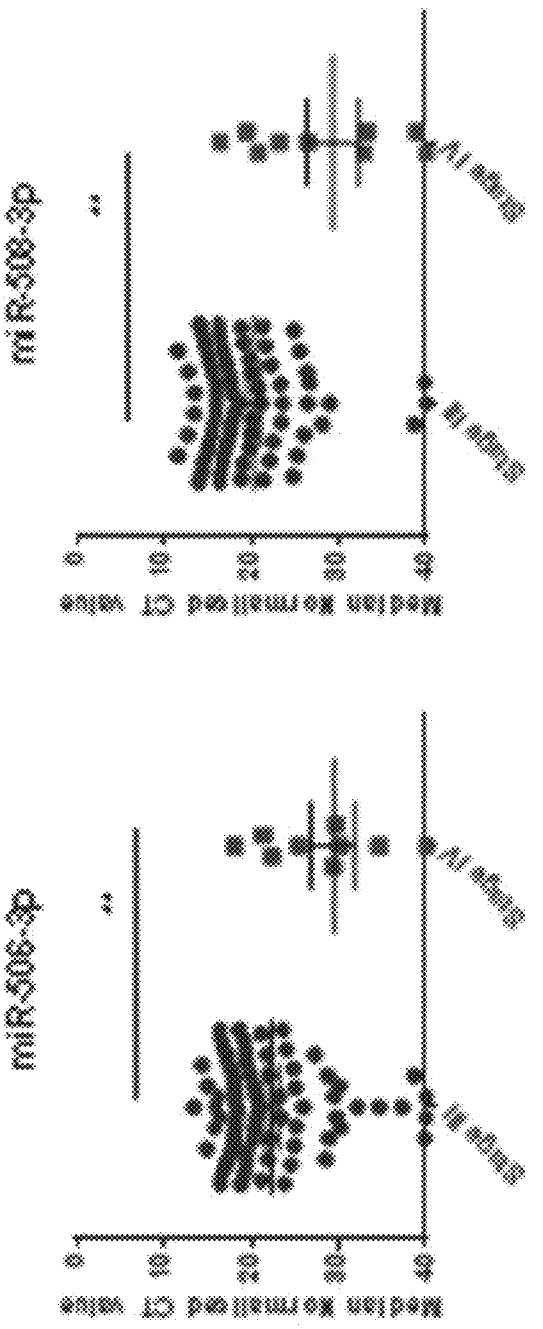
Figure 5E:
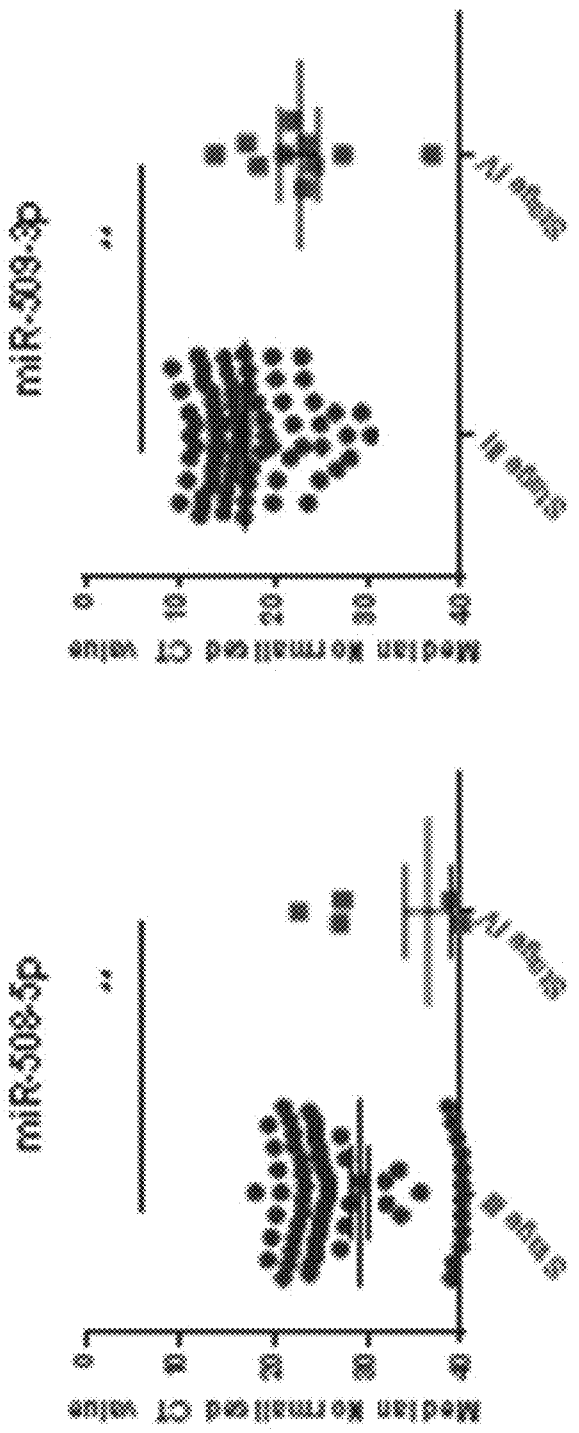
Figure 5F:
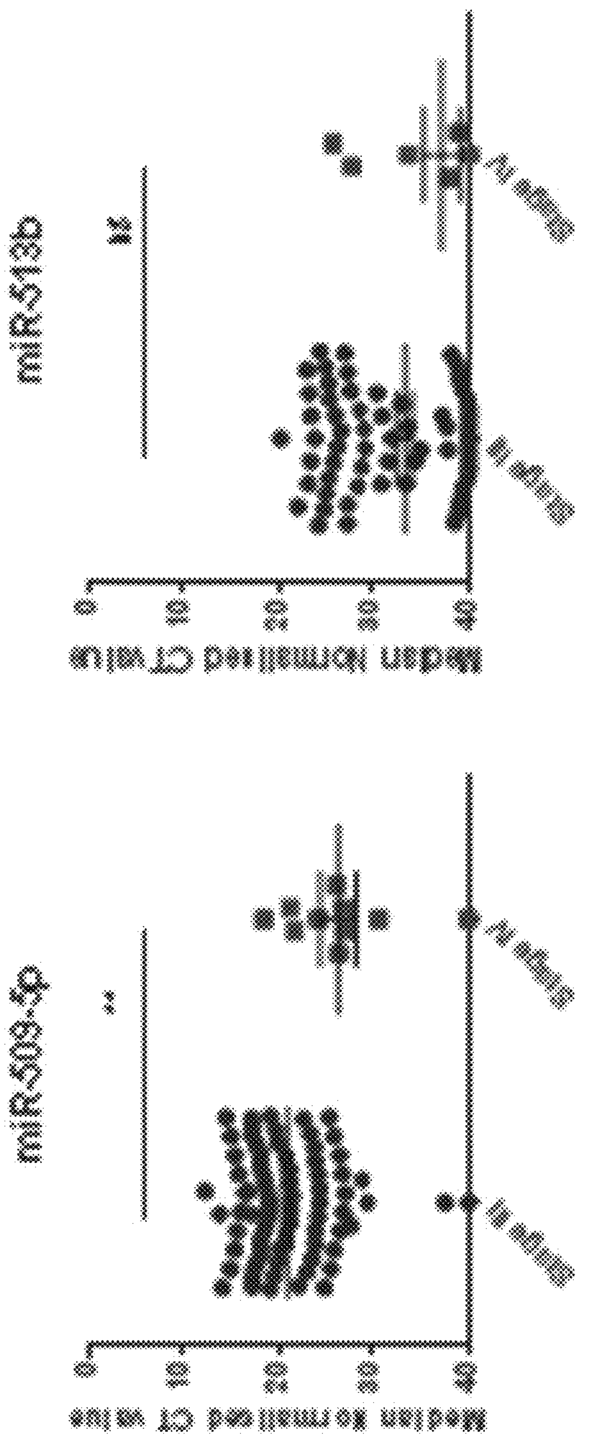
Figure 5G:
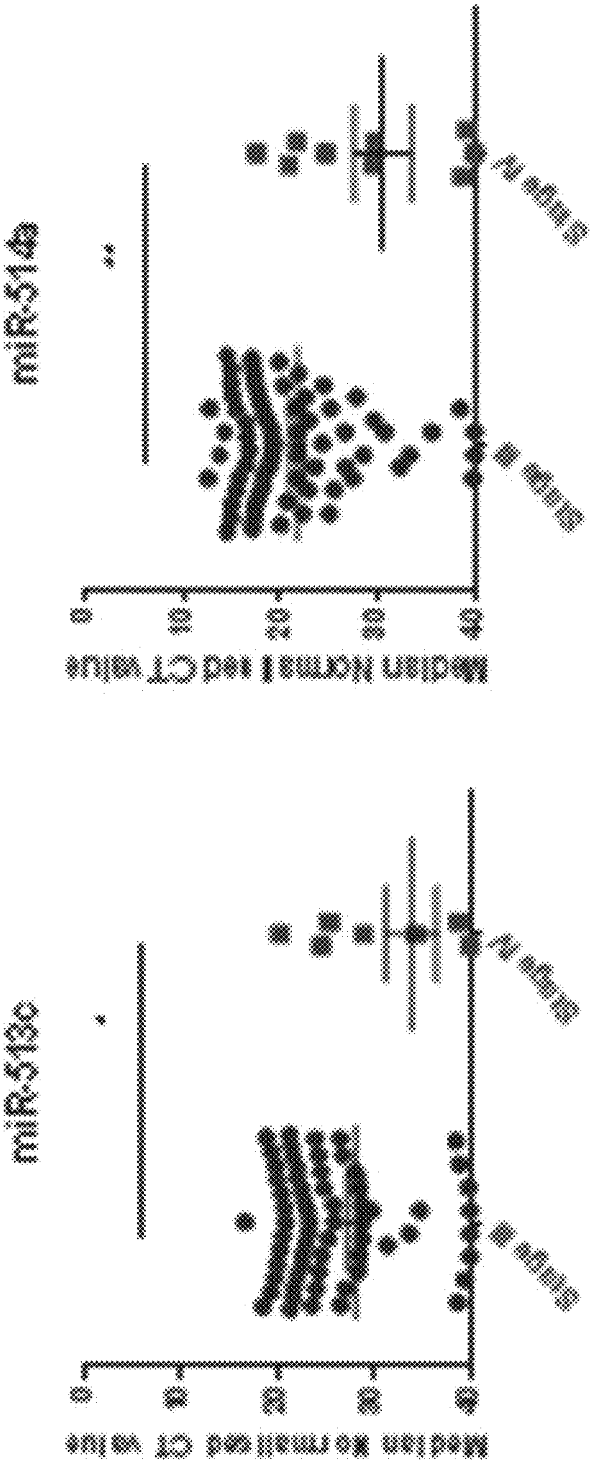
Figure 6A:
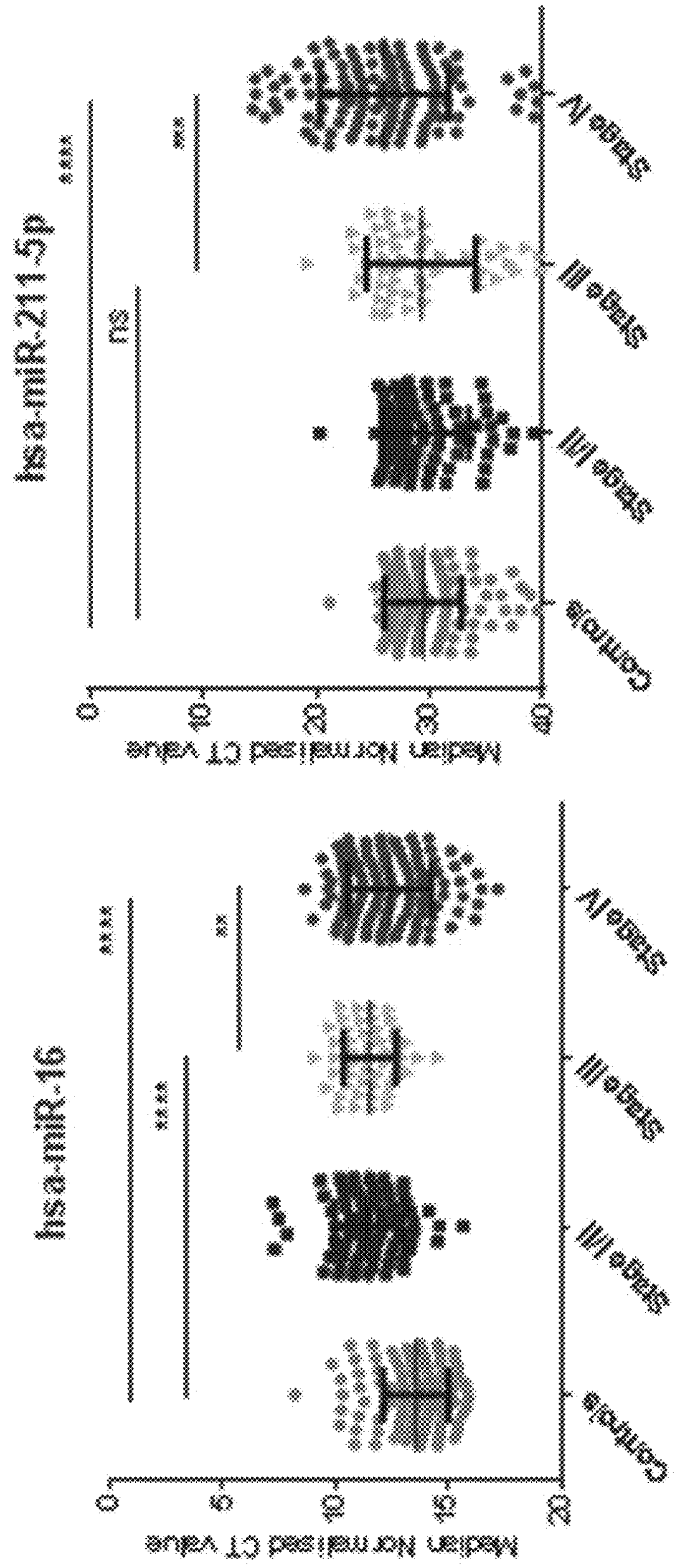
FIGS. 6A-6D. Graphical representation of the data presented in Table 5 for the MELmir-8 panel which were those that showed high significance (P<0.0001) between stage IV vs controls following a Mann-Whitney U test (unpaired). ns=no significance; *=P 0.05-0.01; =P<0.01; *=P<0.001; ****=P<0.0001.
Figure 6B:
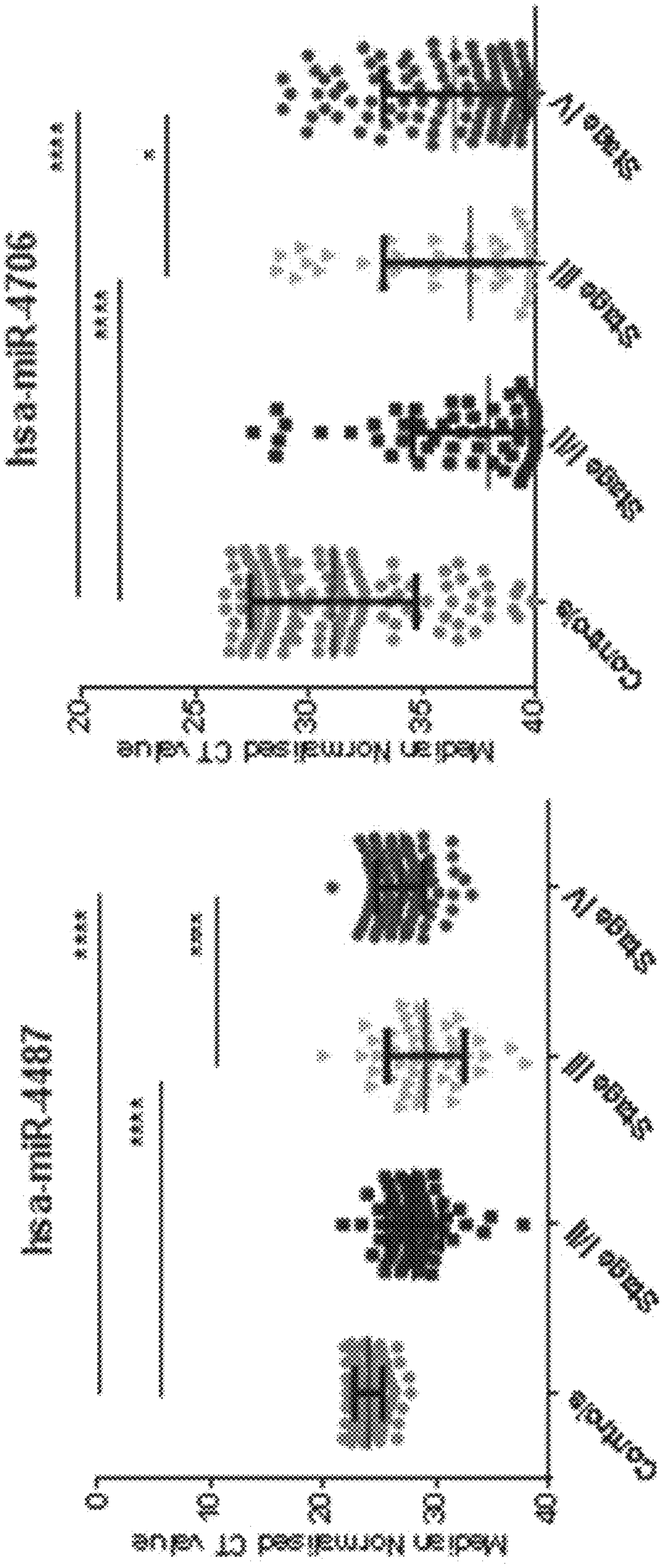
Figure 6C:
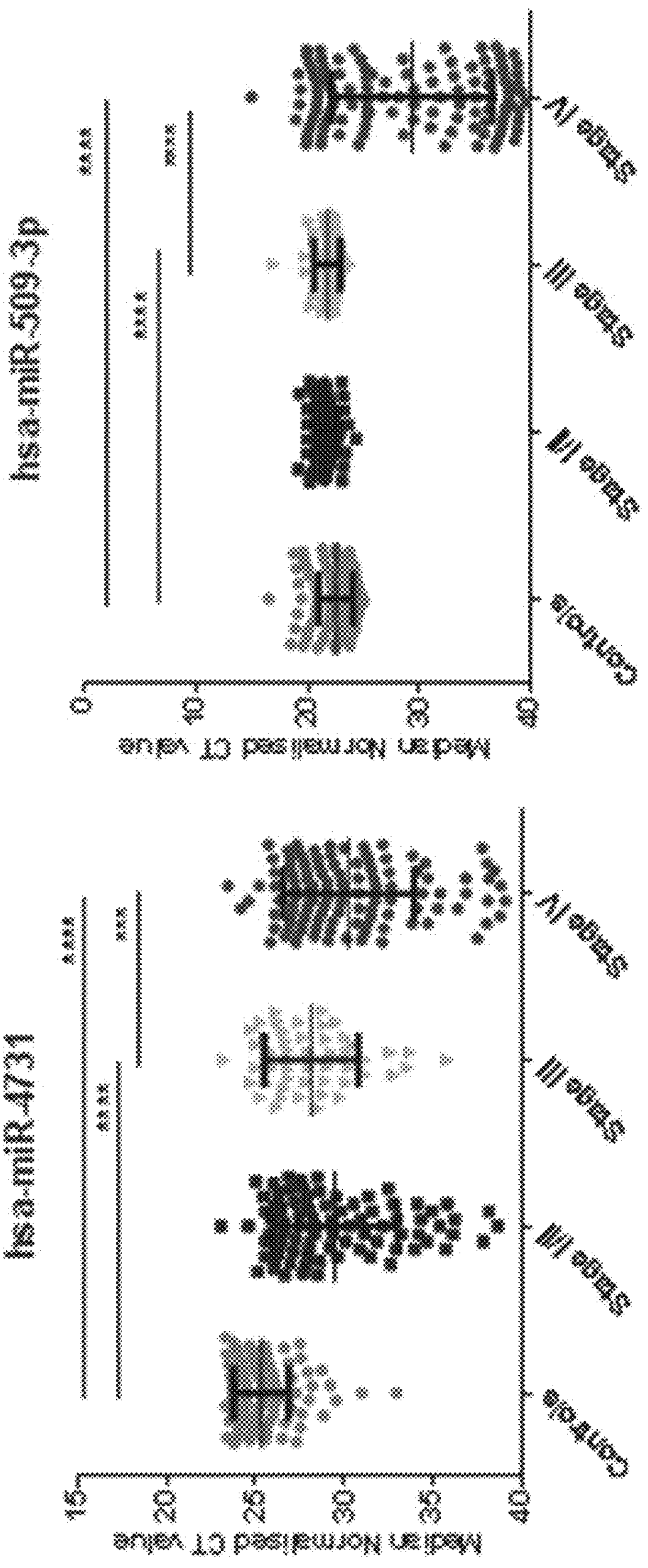
Figure 6D:
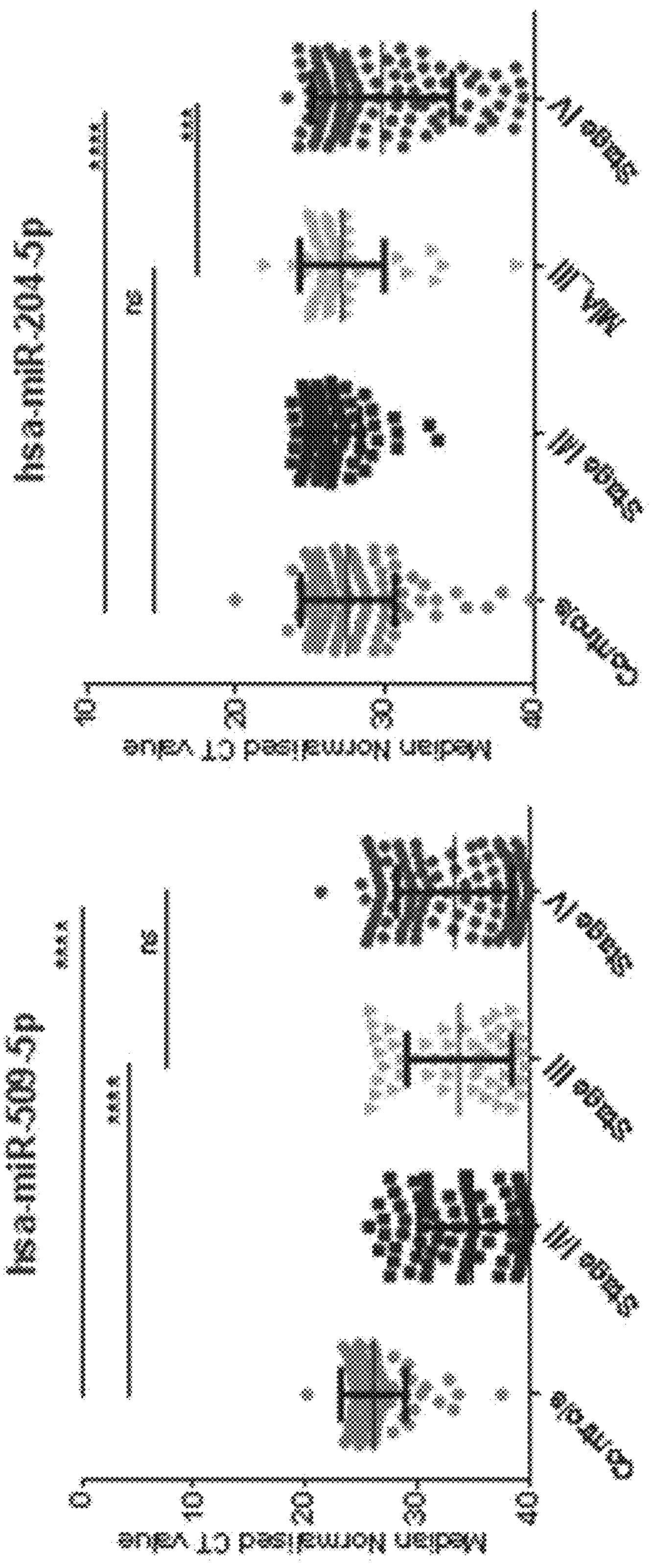

Binary logistic regression models predict M1a-c stage in stage IV melanoma patients using the MELmir-7 panel. Stage IV patients are classed as M1a, M1b, and M1c, depending upon the site of distal metastasis. In stage IV patients (MIA cohort; n=40) previously classed as M1a-c at last follow-up, using binary logistic regression, the MELmiR-7 panel was able to predict M1a in 14/14 (100%) cases and M1b in 4/6 (67%) cases respectively (FIG. 3). Prediction of M1b was increased to 83% (5/6) and was decreased to 93% (13/14) for M1a, when only miR-16, miR4487, miR-4706, miR-4731, and miR-509-3p were expressed. When M1b was compared to M1c, the complete MELmiR-7 panel was able to predict 4/6 (67%) and 15116 (94%) cases respectively. However, when M1a cases were compared to M1c, 100% prediction was achieved respectively (FIG. 3) (see Table 6 for all possible iterations) miRNA expression is strongly associated with survival in stage IV patients. The individual miRNAs from the 'MELmiR-7' panel identified following ROC analysis were then assessed for their prognostic ability in terms of survival using date of last follow-up data along with alive/dead from melanoma status (up to 5 years post stage IV diagnosis). One miRNA, miR-211-5p, showed statistically significant association with survival of stage IV patients. Kaplan-Meier survival curve analysis identified high miR-211 expression as the most strongly significant predictor of survival, with median survival being 1.1 years vs. 3.5 years (HR 3.2, 95% CI 2.02-5.14, p<0.0001) (FIG. 4) for high and normal miR-21 i-5p expression.

Additionally, for the stage IV patients (Tubingen cohort) that had S1001B (n=67) and serum LDH (n=69) status available, median survival times observed for elevated S100B, serum LDH, and miR-211-5p, was 1.21, 1.22, and 1.26 years respectively (data not shown).

Discussion

The linear progression model for melanoma has been in place for many years and by and large, most of the observable tumors fit into this framework. Staging of melanoma adheres to strict guidelines devised by the American Joint Committee on Cancer (AJCC) 1 and is based upon evidence-based gross observation and currently available serological markers (eg serum LDH). This is a highly effective system and dictates the level of treatments which are offered to melanoma patients. However, this model which does not take into account the presence of metastatic disease unobservable to the treating physician by conventional methods (e.g. palpation, CT scans). Currently, there are no serological tests available that are sensitive enough to detect the presence of melanoma in a patient before it manifests into 'observable' disease.

We have successfully confirmed the expression of a 'melanoma-specific' panel of miRNAs that are not only diagnostically accurate in FFPE tissue, distinguishing stage III from stage IV turnouts, but also, via a minimally-invasive blood test, a proportion of these miRNAs ('MELmiR-7') allow for highly accurate diagnosis and prognosis of melanoma patients (independent of AJCC stage).

miRNAs are commonly found in the circulation and have been associated with cancer progression[13, 14]. miRNAs are also inherently resistant to degradation (if contained within exosomes or bound to AGO2)13-15 and are readily detectable in serum and plasma, using precise methods of isolation and detection. Using a comprehensive approach to identify a panel of miRNAs (MELmiR-18)[20] that could be deemed 'melanoma-specific', combined with using an ultra-sensitive method of detection, we have successfully identified a highly sensitive (96%) and specific (≥80%) diagnostic panel of seven miRNAs ('MELmiR-7' including: miR-16, miR-211-5p, miR-509-3p, miR-509-5p, mir-4487, miR-4731-5p, and miR-4706) which have the ability to correctly diagnose melanoma (n=242) independent of AJCC stages I-AV. Most importantly, the sensitivity increases to 98% in stage IV patients (n=119) when 2 or more miRNAs are expressed as compared to 'controls'. In fact, the panel also achieved high sensitivity and specificity in stage I/II (98% and ≥80% respectively) as well as stage III (91% and ≥79% respectively) thus paving the way for early diagnosis to be achieved.

There is currently an unmet need for a highly specific and predictive serum biomarker of melanoma burden, as for many years the consensus whether or not to use currently available serological markers (S100B and serum LD-1) is often disputed due to the ranges of sensitivity and specificities that some studies have reported[1-8, 10-12]. As such, dependent upon the local treatment regimen, these are not commonly used. Despite the lack of consensus for sensitivity and specificity, a recent study did find that elevated levels of S100B were able to predict survival times in unresectable melanoma patients[24].

We have subsequently found that elevated expression levels of miR-211-5p (a member of our MELmiR-7 panel) have the ability to predict prognosis in stage IV melanoma patients. Interestingly in the same group of patients, these survival data mirror those found for S100B, thus making the MELmir-7 panel not only highly sensitive as a diagnostic panel, but also highly informative in terms of prognosis.

Stage IV patients are further categorized into M-stage which is given according to where the tumor has metastasized (M1a: skin, subcutaneous, or distant lymph nodes; M1b: lung; and M1c: other visceral metastases or any distant metastasis with elevated serum LDH)1. We have found that the MELmir-7 panel allows for 100% discrimination between M1a and M1c. These data are highly suggestive of the level of MELmiR-7 panel expression being relative to the presence of tumour in the circulation. This panel would therefore be ideally suited to monitor tumour progression in patients diagnosed with late stage disease (IV) following treatment to enable a change in therapy following a subsequent recurrence. In addition, in a cohort of stage III melanomas (MIA) with known dates of recurrence, the MELmiR-7 panel was able to predict recurrence in 62% of patients and confirm no sign of recurrence (NSR) in 89% of patients.

According to the AJCC Staging committee, stage III melanoma patients have a 50% chance of survival beyond 5 years 1; these patients also remain the most difficult to provide effective treatments/surveillance regimens and accurate survival estimates. Melanoma patients diagnosed with stage III disease have tumours thar have spread to regional lymph nodes or have developed in-transit metastases or satellites but have no evidence of distant metastasis. The treatment for stage III melanoma relies heavily on the accuracy of the clinical staging of the disease and (which can vary across melanoma centres) as the most effective treatment is surgical removal of the affected lymph nodes/satellites 25. Following treatment, stage III patients are subjected to a series of standard physical examinations including computer tomography (CT) scans and serum LDH/S100B (depending on treatment centre) testing every 3 months for the first year, every 4 months in the second year, every 6 months in the third-fifth year, and then yearly for every subsequent year after 5 years. The frequency of these tests is deemed necessary for early detection of distant metastases; however this causes a significant burden to both the patient and the healthcare system. To alleviate this burden, the MELmiR-7 panel could be offered to patients to complement physical examination. If the diagnostic score for melanoma positivity has changed from earlier measurements, then this may indicate the presence of disease recurrence and as such, these patients may qualify earlier for adjuvant, systemic, or targeted therapies that would otherwise be only offered to stage IV patients. The use of this miRNA panel in this manner has the potential to greatly increase the chances of survival by earlier and more precise detection of the presence of metastases.

In terms of prognosis, miR-211-5p measurement may also allow better triaging of patients diagnosed with stage IV disease, into good and poor prognosis which would be highly informative for not only the treating clinician but also for the quality of life of the patients.

TABLE 1

Descriptive statistics of all cohorts used within the study

| Prognostic factors | | Healthy Controls n (%) | High Nevus Count n (%) | History of Melanoma n (%) | Tubingen Cohort Stage I/II n (%) | MIA Cohort Stage I/II n (%) | Combined Stage I/II n (%) | MIA Cohort Stage III n (%) | Tubingen Cohort Stage IV n (%) | MIA Cohort Stage IV n (%) | Combined Stage IV n (%) |
|---|---|---|---|---|---|---|---|---|---|---|---|
| | Totals | **102 (100)** | **12 (100)** | **16 (100)** | **52 (100)** | **34 (100)** | **86 (100)** | **50 (100)** | **79 (100)** | **40 (100)** | **119 (100)** |
| Sex | Male | **50 (49)** | **2 (17)** | **7 (44)** | 19 (37) | 20 (59) | **39 (45)** | **32 (64)** | 48 (61) | 28 (70) | **76 (64)** |
| | Female | **52 (51)** | **10 (83)** | **9 (56)** | 33 (63) | 14 (41) | **47 (55)** | **18 (36)** | 31 (39) | 12 (30) | **43 (36)** |
| Age at | 20-30 | **4 (4)** | **8 (67)** | **1 (6)** | 3 (6) | 3 (9) | **6 (7)** | **2 (4)** | 3 (4) | 1 (2) | **4 (3)** |
| blood | 31-40 | **5 (5)** | **4 (33)** | — | 2 (4) | 2 (6) | **4 (5)** | **3 (6)** | 3 (4) | — | **3 (3)** |
| draw | 41-50 | **28 (27)** | — | **2 (13)** | 12 (23) | 2 (6) | **14 (16)** | **6 (12)** | 19 (24) | 5 (12) | **24 (20)** |
| | 51-60 | **19 (19)** | — | **6 (38)** | 10 (19) | 10 (29) | **20 (23)** | **15 (30)** | 19 (24) | 9 (23) | **28 (24)** |
| | 61+ | **46 (45)** | — | **7 (44)** | 25 (48) | 17 (50) | **42 (49)** | **24 (48)** | 35 (44) | 26 (63) | **60 (50)** |
| Histological | SSM | — | — | — | 19 (36) | — | **19 (22)** | — | 34 (43) | — | **34 (29)** |
| subtype of | Nodular | — | — | — | 14 (27) | — | **14 (16)** | — | 18 (23) | — | **18 (15)** |
| primary | LMM | — | — | — | 4 (8) | — | **4 (5)** | — | — | — | — |
| | ALM | — | — | — | 2 (4) | — | **2 (2)** | — | 6 (7) | — | **6 (5)** |
| | Unknown | — | — | **16 (100)** | 13 (25) | 34 (100) | **47 (55)** | **50 (100)** | 21 (27) | 40 (100) | **61 (51)** |

TABLE 1-continued

Descriptive statistics of all cohorts used within the study

| Prognostic factors | | Healthy Controls n (%) | High Nevus Count n (%) | History of Melanoma n (%) | Tubingen Cohort Stage I/II n (%) | MIA Cohort Stage I/II n (%) | Combined Stage I/II n (%) | MIA Cohort Stage III n (%) | Tubingen Cohort Stage IV n (%) | MIA Cohort Stage IV n (%) | Combined Stage IV n (%) |
|---|---|---|---|---|---|---|---|---|---|---|---|
| Breslow's | ≤1 mm | — | — | — | 3 (6) | — | **3 (3)** | — | 18 (23) | — | **18 (15)** |
| thickness | 1.01-2 mm | — | — | — | 32 (61) | — | **32 (37)** | — | 12 (15) | — | **12 (10)** |
| of | 2.01-4 mm | — | — | — | 11 (21) | — | **11 (13)** | — | 20 (25) | — | **20 (17)** |
| primary | >4 mm | — | — | — | 5 (10) | — | **5 (6)** | — | 16 (20) | — | **16 (13)** |
| | Unknown | — | — | **16 (100)** | 1 (2) | 34 (100) | **34 (41)** | **50 (100)** | 13 (16) | 40 (100) | **43 (36)** |
| M staging | M1a | — | — | — | — | — | — | — | 19 (24) | 15 (38) | **34 (29)** |
| | M1b | — | — | — | — | — | — | — | 16 (20) | 9 (18) | **25 (21)** |
| | M1c | — | — | — | — | — | — | — | 44 (56) | 16 (28) | **60** |
| Serum LDH | Elevated | — | — | — | — | — | — | — | 27 (34) | 7 (18) | **34 (29)** |
| | Normal | — | — | — | — | — | — | — | 42 (53) | 5 (12) | **47 (40)** |
| | Unknown | — | — | — | — | — | — | — | 10 (13) | 28 (70) | **38 (32)** |
| S100B | Elevated | — | — | — | — | | | | 43 (54) | — | **45 (38)** |
| | Normal | — | — | — | — | | | | 25 (32) | — | **25 (21)** |
| | Unknown | — | — | — | — | | | | 11 (14) | 40 (100) | **55 (46)** |
| Cause of | Alive | — | **12 (100)** | **16 (100)** | 48 (92) | 30 (88) | **78 (91)** | **32 (64)** | 15 (19) | 20 (50) | **35 (29)** |
| Death | Melanoma | — | — | — | 2 (4) | 4 (12) | **6 (7)** | **15 (30)** | 62 (78) | 20 (50) | **82 (69)** |
| | Other Ca. | — | — | — | 1 (2) | — | **1 (1)** | — | 1 (1) | — | **1 (1)** |
| | Not Ca. | — | — | — | — | — | — | — | — | — | — |
| | Unknown | — | — | — | 1 (2) | — | **1 (1)** | **3 (6)** | 1 (1) | — | **1 (1)** |
| | Missing data | **102** | — | — | — | — | — | — | | | |

Bolded texts are the cohorts that were used in the analysis

TABLE 2

Table 2 showing Mann-Whitney U test P values and AUC scores for 13 detectable miRNAs in serum derived from melanoma patients and controls

| Comparison | Sample numbers | Test | hsa-miR-145 | hsa-miR-146a | hsa-miR-16 | hsa-miR-204 | hsa-miR-211 | hsa-miR-363-3p | hsa-miR-4487 | hsa-miR-4706 | hsa-miR-4731 | hsa-miR-506-3p | hsa-miR-509-3p | hsa-miR-509-5p | hsa-miR-514a-3p |
|---|---|---|---|---|---|---|---|---|---|---|---|---|---|---|---|
| Controls vs. stage I/II | n = 130 | Mann-Whitney U test | *** | **** | **** | * | ns | *** | **** | **** | **** | **** | **** | **** | **** |
| | n = 86 | ROC Analysis AUC score | 0.64 | **0.73** | ***0.85*** | 0.59 | 0.50 | 0.65 | ***0.95*** | ***0.90*** | ***0.90*** | 0.66 | ***0.75*** | ***0.95*** | **0.74** |
| Controls vs. stage III | n = 130 | Mann-Whitney U test | ns | ** | **** | ns | ns | * | **** | **** | **** | ** | **** | **** | **** |
| | n = 50 | ROC Analysis AUC score | 0.57 | 0.65 | ***0.86*** | 0.52 | 0.55 | 0.62 | ***0.93*** | ***0.86*** | ***0.85*** | 0.67 | ***0.72*** | ***0.93*** | **0.70** |
| Controls vs. stage IV | n = 130 | Mann-Whitney U test | ns | ** | **** | **** | **** | ns | **** | **** | **** | ns | **** | **** | ** |
| | n = 119 | ROC Analysis AUC score | 0.51 | 0.60 | ***0.70*** | 0.64 | ***0.71*** | 0.54 | ***0.89*** | ***0.85*** | ***0.93*** | 0.57 | ***0.74*** | ***0.91*** | 0.60 |

TABLE 2-continued

Table 2 showing Mann-Whitney U test P values and AUC scores for 13 detectable miRNAs in serum derived from melanoma patients and controls

| Comparison | Sample numbers | Test | hsa-miR-145 | hsa-miR-146a | hsa-miR-16 | hsa-miR-204 | hsa-miR-211 | hsa-miR-363-3p | hsa-miR-4487 | hsa-miR-4706 | hsa-miR-4731 | hsa-miR-506-3p | hsa-miR-509-3p | hsa-miR-509-5p | hsa-miR-514a-3p |
|---|---|---|---|---|---|---|---|---|---|---|---|---|---|---|---|
| Stage III vs. stage IV | n = 50 | Mann-Whitney U test | ns | ns | ** | *** | *** | ** | **** | * | *** | **** | **** | ns | **** |
| | n = 119 | ROC Analysis AUC score | 0.55 | 0.52 | 0.64 | 0.67 | 0.67 | 0.66 | **0.73** | 0.61 | 0.67 | **0.71** | **0.78** | 0.51 | **0.77** |
| Stage I/II vs. stage IV | n = 86 | Mann-Whitney U test | *** | ** | ** | **** | **** | **** | **** | **** | ns | **** | **** | ** | **** |
| | n = 119 | ROC Analysis AUC score | 0.64 | 0.63 | 0.63 | **0.72** | **0.71** | 0.68 | 0.67 | **0.70** | 0.57 | 0.69 | **0.79** | 0.61 | **0.80** |

ns = no significance;
* = P 0.05-0.01;
** = P < 0.01;
*** = P < 0.001;
**** = P <0.0001.
Italicize text represents miRNAs that are both highly significant and have a high AUC score relating to all stages of melanoma.
Underlining represents AUC scores that offer good-high diagnostic potential

TABLE 3

Summaries of diagnostic test statistics generated when AJCC staged melanoma is compared with controls.

| MELmiR-panel | MELANOMA | | Stage I/II | | Stage III | | Stage IV | |
|---|---|---|---|---|---|---|---|---|
| Diagnostic Score | ≥2 | ≥3 | ≥2 | ≥3 | ≥2 | ≥3 | ≥2 | ≥3 |
| Sensitivity | **96%** | **91%** | **98%** | **92%** | **91%** | **86%** | **98%** | **93%** |
| Specificity | **80%** | **90%** | **80%** | **90%** | **80%** | **90%** | **80%** | **90%** |
| False Positive Rate | 20% | 10% | 20% | 10% | 20% | 10% | 20% | 10% |
| False Negative Rate | 4% | 9% | 2% | 8% | 9% | 14% | 2% | 7% |
| Positive Predictive Value (PPV) | 89% | 94% | 72% | 85% | 60% | 77% | 78% | 89% |
| Negative Predictive Value (PPV) | 93% | 84% | 98% | 95% | 96% | 94% | 98% | 94% |
| Likelihood Ratio Positive | 4.75 | 8.84 | 4.83 | 8.94 | 4.49 | 8.33 | 4.82 | 8.99 |
| Likelihood Ratio Negative | 0.05 | 0.10 | 0.03 | 0.08 | 0.11 | 0.15 | 0.03 | 0.08 |
| Diagnostic Odds Ratio (DOR) | **100.45** | **92.08** | **169.39** | **105.48** | **39.39** | **54.17** | **156.26** | **114.59** |

TABLE 4

Table showing Mann-Whitney U test P values and AUC scores for 17 detectable miRNAs in FFPE tissue derived from melanoma patients.

| Comparison | Sample Numbers | Test | hsa miR-145 | hsa miR-146a | hsa miR-16 | hsa miR-204 | hsa miR-211 | hsa miR-363-3p | hsa miR-4487 | hsa miR-4706 | hsa miR-4731 | hsa miR-506-3p | hsa miR-508-3p | hsa miR-508-5p | hsa miR-509-3p | hsa miR-509-5p | hsa miR-513b | hsa miR-513c | hsa miR-514a-3p |
|---|---|---|---|---|---|---|---|---|---|---|---|---|---|---|---|---|---|---|---|
| Stage III vs stage IV | n = 82 | Mann Whitney U test | ns | ** | * | * | ** | ns | ** | ns | *** | ** | ** | ** | ** | ** | ns | * | ** |

TABLE 4-continued

Table showing Mann-Whitney U test P values and AUC scores for 17 detectable miRNAs in FFPE tissue derived from melanoma patients.

| Comparison | Sample Numbers | Test | hsa miR-145 | hsa miR-146a | hsa miR-16 | hsa miR-204 | hsa miR-211 | hsa miR-363-3p | hsa miR-4487 | hsa miR-4706 | hsa miR-4731 | hsa miR-506-3p | hsa miR-508-3p | hsa miR-508-5p | hsa miR-509-3p | hsa miR-509-5p | hsa miR-513b | hsa miR-513c | hsa miR-514a-3p |
|---|---|---|---|---|---|---|---|---|---|---|---|---|---|---|---|---|---|---|---|
| | n = 10 | ROC Analysis AUC score | nd | **0.75** | **0.73** | **0.74** | **0.78** | nd | **0.82** | nd | **0.85** | **0.78** | **0.79** | **0.78** | **0.77** | **0.79** | nd | **0.71** | **0.79** |

nd = not defined.
ns = no significance:
* = P 0.05-0.01:
** = P < 0.01:
*** P < 0.001:
**** P < 0.0001.
Bolding represents miRNAs that are both highly significant and have a high AUC score relating to all stages of melanoma.
Underline represents AUC scores that offer good-high diagnostic potential.

TABLE 5

Table showing Mann-Whitney U test P values and AUC scores for 13 detectable miRNAs in serum derived from melanoma patients and healthy controls.

| Comparison | Sample Numbers | Test | hsa miR-145 | hsa miR-146a | hsa miR-16 | hsa miR-204 | hsa miR-211 | hsa miR-363-3p | hsa miR-4487 | hsa miR-4706 | hsa miR-4731 | hsa miR-506-3p | hsa miR-509-3p | hsa miR-509-5p | hsa miR-514a-3p |
|---|---|---|---|---|---|---|---|---|---|---|---|---|---|---|---|
| Healthy Controls vs Stage I/II | n = 102 | Mann Whitney U test | **** | **** | **** | **** | ns | **** | **** | **** | **** | **** | **** | **** | **** |
| | n = 86 | ROC Analysis AUC score | **0.74** | **0.88** | **0.93** | 0.68 | 0.53 | **0.72** | **0.94** | **0.90** | **0.91** | **0.72** | **0.90** | **0.95** | **0.78** |
| Healthy Controls vs Stage III | n = 102 | Mann Whitney U test | ns | **** | **** | * | ns | **** | **** | **** | **** | **** | **** | **** | **** |
| | n = 50 | ROC Analysis AUC score | 0.52 | **0.79** | **0.95** | 0.61 | 0.57 | 0.69 | **0.92** | **0.86** | **0.86** | **0.72** | **0.87** | **0.92** | **0.74** |
| Healthy Controls vs Stage IV | n = 102 | Mann Whitney U test | * | **** | **** | * | **** | ns | **** | **** | **** | ns | **** | **** | * |
| | n = 119 | ROC Analysis AUC score | 0.58 | **0.72** | **0.78** | 0.59 | **0.73** | 0.52 | **0.88** | **0.85** | **0.94** | 0.48 | **0.70** | **0.90** | 0.59 |

nd = not defined.
ns = no significance:
* = P 0.05-0.01:
** = P < 0.01:
*** P < 0.001:
**** P < 0.0001.
Bolding represents miRNAs that are both highly significant and have a high AUC score relating to all stages of melanoma.
Underline represents AUC scores that offer good-high diagnostic potential.

TABLE 6

Tables were compiled following Binary Logistic Regression analysis performed in SPSS for Windows. version 21.0. To represent the overall analysis performed for each cohort. only the "classification table" and the "variables in the equation" are shown.

Controls vs Stage I/II
Classification Table[a]

| Observed | | | Predicted: Cohorts: Controls | Predicted: Cohorts: Stage I/II | Predicted: Percentage Correct |
|---|---|---|---|---|---|
| Step 1 | Cohorts | Controls | 126 | 4 | 96.9 |
| | | Stage I/II | 5 | 81 | 94.2 |
| | Overall Percentage | | | | 95.8 |
| Step 2 | Cohorts | Controls | 126 | 4 | 96.9 |
| | | Stage I/II | 5 | 81 | 94.2 |
| | Overall Percentage | | | | 95.8 |
| Step 3 | Cohorts | Controls | 126 | 4 | 96.9 |
| | | Stage I/II | 5 | 81 | 94.2 |
| | Overall Percentage | | | | 95.8 |

[a]The cut value is .500

Variables in the Equation

| | | B | S.E. | Wald | df | Sig. | Exp(B) |
|---|---|---|---|---|---|---|---|
| Step 1[a] | miR16 | −1.270 | .444 | 8.169 | 1 | .004 | .281 |
| | miR211 | .025 | .110 | .052 | 1 | .820 | 1.025 |
| | miR4487 | 1.164 | .305 | 14.579 | 1 | .000 | 3.204 |
| | miR4706 | .137 | .114 | 1.453 | 1 | .228 | 1.147 |
| | miR4731 | .171 | .246 | .487 | 1 | .485 | 1.187 |
| | miR509.3p | −.629 | .358 | 3.096 | 1 | .079 | .533 |
| | miR509.5p | .297 | .088 | 11.266 | 1 | .001 | 1.346 |
| | Constant | −19.668 | 7.505 | 6.867 | 1 | .009 | .000 |
| Step 2[a] | miR16 | −1.244 | .427 | 8.506 | 1 | .004 | .288 |
| | miR4487 | 1.160 | .304 | 14.543 | 1 | .000 | 3.188 |
| | miR4706 | .129 | .108 | 1.436 | 1 | .231 | 1.138 |
| | miR4731 | .185 | .239 | .002 | 1 | .438 | 1.203 |
| | miR509.3p | .611 | .344 | 3.159 | 1 | .076 | .543 |
| | miR509.5p | .299 | .088 | 11.585 | 1 | .001 | 1.348 |
| | Constant | −19.677 | 7.474 | 6.931 | 1 | .008 | .000 |
| Step 3[a] | miR16 | −1.248 | .416 | 8.996 | 1 | .003 | .287 |
| | miR4487 | 1.218 | .304 | 16.009 | 1 | .000 | 3.380 |
| | miR4706 | .165 | .101 | 2.670 | 1 | .102 | 1.179 |
| | miR509.3p | −.576 | .336 | 2.936 | 1 | .087 | .562 |
| | miR509.5p | .278 | .082 | 11.623 | 1 | .001 | 1.321 |
| | Constant | −17.449 | 6.719 | 6.745 | 1 | .009 | .000 |

[a]Variable(s) entered on step 1: miR16, miR211, miR4487, miR4706, miR4731, miR509.3p, miR509.5p.

Controls vs Stage III
Classification Table[a]

| Observed | | | Predicted: Cohorts: Controls | Predicted: Cohorts: Stage III | Predicted: Percentage Correct |
|---|---|---|---|---|---|
| Step 1 | Cohorts | Controls | 127 | 3 | 97.7 |
| | | Stage III | 5 | 45 | 90.0 |
| | Overall Percentage | | | | 95.0 |
| Step 2 | Cohorts | Controls | 127 | 3 | 97.7 |
| | | Stage III | 5 | 45 | 90.0 |
| | Overall Percentage | | | | 95.6 |
| Step 3 | Cohorts | Controls | 128 | 2 | 98.5 |
| | | Stage III | 5 | 45 | 90.0 |
| | Overall Percentage | | | | 96.1 |
| Step 4 | Cohorts | Controls | 129 | 1 | 99.2 |
| | | Stage III | 6 | 44 | 88.0 |
| | Overall Percentage | | | | 96.1 |
| Step 5 | Cohorts | Controls | 129 | 1 | 99.2 |
| | | Stage III | 6 | 44 | 88.0 |
| | Overall Percentage | | | | 96.1 |

TABLE 6-continued

Tables were compiled following Binary Logistic Regression analysis performed in SPSS for Windows. version 21.0. To represent the overall analysis performed for each cohort. only the "classification table" and the "variables in the equation" are shown.

| | | | | | |
|---|---|---|---|---|---|
| Step 6 | Cohorts | Controls | 129 | 2 | 98.5 |
| | | Stage III | 6 | 44 | 88.0 |
| | Overall Percentage | | | | 95.6 |

[a]The cut value is .500

Variables in the Equation

| | | B | S.E. | Wald | df | Sig. | Exp(B) |
|---|---|---|---|---|---|---|---|
| Step 1[a] | miR16 | −1.531 | .479 | 10.210 | 1 | .001 | .216 |
| | miR211 | .139 | .096 | 2.101 | 1 | .147 | 1.149 |
| | miR4487 | .938 | .329 | 8.146 | 1 | .004 | 2.555 |
| | miR4706 | .158 | .129 | 1.494 | 1 | .222 | 1.171 |
| | miR4731 | −.118 | .289 | .167 | 1 | .683 | .889 |
| | miR509.3p | −.118 | .362 | .107 | 1 | .744 | .889 |
| | miR509.5p | .090 | .091 | .984 | 1 | .321 | 1.094 |
| | Constant | −12.453 | 6.711 | 3.443 | 1 | .064 | .000 |
| Step 2[a] | miR16 | −1.620 | .404 | 16.060 | 1 | .000 | .198 |
| | miR211 | .135 | .094 | 2.029 | 1 | .154 | 1.144 |
| | miR4487 | .935 | .328 | 8.110 | 1 | .004 | 2.548 |
| | miR4706 | .161 | .128 | 1.590 | 1 | .207 | 1.175 |
| | miR4731 | −.109 | .287 | .143 | 1 | .705 | .897 |
| | miR509.5p | .084 | .088 | .905 | 1 | .341 | 1.087 |
| | Constant | −13.915 | 5.181 | 7.213 | 1 | .007 | .000 |
| Step 3[a] | miR16 | −1.595 | .394 | 15.340 | 1 | .000 | .203 |
| | miR211 | .120 | .091 | 1.910 | 1 | .100 | 1.134 |
| | miR4487 | .860 | .250 | 11.804 | 1 | .001 | 2.362 |
| | miR4706 | .144 | .118 | 1.490 | 1 | .222 | 1.155 |
| | miR509.5p | .099 | .078 | 1.593 | 1 | .207 | 1.104 |
| | Constant | −14.800 | 4.740 | 9.748 | 1 | .002 | .000 |
| Step 4[a] | miR16 | −1.537 | .379 | 16.455 | 1 | .000 | .215 |
| | miR211 | .086 | .086 | 1.011 | 1 | .315 | 1.090 |
| | miR4487 | 1.029 | .239 | 18.610 | 1 | .000 | 2.799 |
| | miR509.5p | .103 | .077 | 1.815 | 1 | .178 | 1.109 |
| | Constant | −13.936 | 4.632 | 9.052 | 1 | .003 | .000 |
| Step 5[a] | miR16 | −1.431 | .343 | 17.440 | 1 | .000 | .239 |
| | miR4487 | 1.056 | .241 | 19.245 | 1 | .000 | 2.876 |
| | miR509.5p | .097 | .076 | 1.624 | 1 | .203 | 1.102 |
| | Constant | −13.081 | 4.559 | 8.234 | 1 | .004 | .000 |
| Step 6[a] | miR16 | −1.497 | .332 | 20.273 | 1 | .000 | .224 |
| | miR4487 | 1.160 | .226 | 27.243 | 1 | .000 | 3.255 |
| | Constant | −12.700 | 4.451 | 8.142 | 1 | .004 | .000 |

[a]Variable(s) entered on step 1: miR16, miR211, miR4487, miR4706, miR4731, miR509.3p, miR509.5p.

Controls vs Stage IV

Classification Table[a]

| | | | Predicted | | |
|---|---|---|---|---|---|
| | | | Cohorts | | Percentage |
| Observed | | | Controls | Stage IV | Correct |
| Step 1 | Cohorts | Controls | 122 | 8 | 93.8 |
| | | Stage IV | 6 | 113 | 95.0 |
| | Overall Percentage | | | | 94.4 |
| Step 2 | Cohorts | Controls | 122 | 8 | 93.8 |
| | | Stage IV | 7 | 112 | 94.1 |
| | Overall Percentage | | | | 94.0 |
| Step 3 | Cohorts | Controls | 122 | 8 | 93.8 |
| | | Stage IV | 6 | 113 | 95.0 |
| | Overall Percentage | | | | 94.4 |

[a]The cut value is .500

Variables in the Equation

| | | B | S.E. | Wald | df | Sig. | Exp(B) |
|---|---|---|---|---|---|---|---|
| Step 1[a] | miR509.5p | .388 | .090 | 18.622 | 1 | .000 | 1.474 |
| | mir16 | .298 | .319 | .873 | 1 | .350 | 1.347 |
| | miR211 | −.491 | .101 | 23.846 | 1 | .000 | .612 |
| | miR4487 | .183 | .279 | .434 | 1 | .510 | 1.201 |
| | miR4706 | .233 | .099 | 5.488 | 1 | .019 | 1.262 |
| | miR4731 | .938 | .245 | 14.669 | 1 | .000 | 2.555 |
| | miR509.3p | .321 | .103 | 9.737 | 1 | .002 | 1.379 |
| | Constant | −47.261 | 10.728 | 19.409 | 1 | .000 | .000 |

TABLE 6-continued

Tables were compiled following Binary Logistic Regression analysis performed in SPSS for Windows. version 21.0. To represent the overall analysis performed for each cohort. only the "classification table" and the "variables in the equation" are shown.

| | | | | | | | |
|---|---|---|---|---|---|---|---|
| Step 2[a] | miR509.5p | .402 | .088 | 20.744 | 1 | .000 | 1.498 |
| | miR16 | .280 | .306 | .835 | 1 | .361 | 1.323 |
| | miR211 | −.494 | .100 | 24.343 | 1 | .000 | .610 |
| | miR4706 | .238 | .099 | 5.728 | 1 | .017 | 1.268 |
| | miR4731 | 1.018 | .217 | 22.041 | 1 | .000 | 2.768 |
| | miR509.3p | .308 | .094 | 10.761 | 1 | .001 | 1.361 |
| | Constant | −44.729 | 9.547 | 21.951 | 1 | .000 | .000 |
| Step 3[a] | miR509.5p | .398 | .088 | 20.659 | 1 | .000 | 1.489 |
| | miR211 | −.484 | .098 | 24.197 | 1 | .000 | .616 |
| | miR4706 | .237 | .097 | 5.930 | 1 | .014 | 1.267 |
| | miR4731 | 1.002 | .218 | 21.113 | 1 | .000 | 2.724 |
| | miR509.3p | .297 | .093 | 10.262 | 1 | .001 | 1.345 |
| | Constant | −40.322 | 7.744 | 27.109 | 1 | .000 | .000 |

[a]Variable(s) entered on step 1: miR509.5p, miR16, miR211, miR4487, miR4706, miR4731, miR509.3p.

Stage I/II vs Stage III

Classification Table[a]

| | Observed | | Predicted | | |
|---|---|---|---|---|---|
| | | | Cohorts | | Percentage |
| | | | Stage I/II | Stage III | Correct |
| Step 1 | Cohorts | Stage I/II | 73 | 13 | 84.9 |
| | | Stage III | 32 | 18 | 35.0 |
| | Overall Percentage | | | | 68.0 |
| Step 2 | Cohorts | Stage I/II | 73 | 13 | 84.9 |
| | | Stage III | 32 | 18 | 36.0 |
| | Overall Percentage | | | | 66.9 |
| Step 3 | Cohorts | Stage I/II | 76 | 10 | 88.4 |
| | | Stage III | 35 | 15 | 30.0 |
| | Overall Percentage | | | | 66.9 |
| Step 4 | Cohorts | Stage I/II | 75 | 11 | 87.2 |
| | | Stage III | 33 | 17 | 34.0 |
| | Overall Percentage | | | | 67.6 |
| Step 5 | Cohorts | Stage I/II | 76 | 10 | 68.4 |
| | | Stage III | 32 | 18 | 36.0 |
| | Overall Percentage | | | | 69.1 |

[a]The cut value is .500

Variables in the Equation

| | | B | S.E. | Wald | df | Sig. | Exp(B) |
|---|---|---|---|---|---|---|---|
| Step 1[a] | miR16 | −.157 | .159 | .982 | 1 | .322 | .854 |
| | miR211 | −.004 | .048 | .006 | 1 | .937 | .996 |
| | miR4487 | .305 | .097 | 10.001 | 1 | .002 | 1.357 |
| | miR4706 | −.003 | .065 | .931 | 1 | .335 | .939 |
| | miR4731 | −.188 | .077 | 5.886 | 1 | .015 | .829 |
| | miR509.3p | .178 | .200 | .770 | 1 | .380 | 1.192 |
| | miR509.5p | −.083 | .046 | 3.193 | 1 | .074 | .920 |
| | Constant | −.532 | 4.284 | .015 | 1 | .901 | .587 |
| Step 2[a] | miR16 | −.160 | .156 | 1.057 | 1 | .304 | .652 |
| | miR4487 | .306 | .096 | 10.266 | 1 | .001 | 1.359 |
| | miR4706 | −.062 | .065 | .926 | 1 | .336 | .939 |
| | miR4731 | −.188 | .077 | 5.934 | 1 | .015 | .823 |
| | miR509.3p | .173 | .197 | .772 | 1 | .380 | 1.189 |
| | miR509.5p | −.083 | .046 | 3.258 | 1 | .071 | .920 |
| | Constant | −.572 | 4.253 | .018 | 1 | .993 | .564 |
| Step 3[a] | miR16 | −.124 | .150 | .083 | 1 | .408 | .883 |
| | miR4487 | .318 | .095 | 11.225 | 1 | .001 | 1.375 |
| | miR4706 | −.054 | .064 | .709 | 1 | .400 | .948 |
| | miR4731 | −.195 | .077 | 6.422 | 1 | .011 | .823 |
| | miR509.5p | −.080 | .046 | 3.066 | 1 | .080 | .923 |
| | Constant | 2.191 | 2.892 | .574 | 1 | .449 | 8.944 |

TABLE 6-continued

Tables were compiled following Binary Logistic Regression analysis performed in SPSS for Windows. version 21.0. To represent the overall analysis performed for each cohort. only the "classification table" and the "variables in the equation" are shown.

| | | | | | | | |
|---|---|---|---|---|---|---|---|
| Step 4[a] | miR4487 | .295 | .088 | 11.120 | 1 | .001 | 1.342 |
| | miR4706 | −.043 | .062 | .479 | 1 | .489 | .958 |
| | miR4731 | −.193 | .077 | 6.354 | 1 | .012 | .825 |
| | miR509.5p | −.080 | .046 | 3.055 | 1 | .080 | .923 |
| | Constant | .953 | 2.467 | .149 | 1 | .099 | 2.594 |
| Step 5[a] | miR4487 | .284 | .086 | 10.781 | 1 | .001 | 1.328 |
| | miR4731 | −.212 | .072 | 8.549 | 1 | .003 | .809 |
| | miR509.5p | −.087 | .044 | 3.816 | 1 | .051 | .917 |
| | Constant | .430 | 2.370 | .033 | 1 | .856 | 1.537 |

[a]Variable(s) entered on step 1: miR16, miR211, miR4487, miR4706, miR4731, miR509.3p, miR509.5p.

Stage I/II vs Stage IV

Classification Table[a]

| Observed | | | Predicted | | |
|---|---|---|---|---|---|
| | | | Cohorts | | Percentage |
| | | | Stage I/II | Stage IV | Correct |
| Step 1 | Cohorts | Stage I/II | 81 | 5 | 94.2 |
| | | Stage IV | 10 | 109 | 91.6 |
| | Overall Percentage | | | | 92.7 |
| Step 2 | Cohorts | Stage I/II | 82 | 4 | 95.3 |
| | | Stage IV | 10 | 109 | 91.6 |
| | Overall Percentage | | | | 93.2 |
| Step 3 | Cohorts | Stage I/II | 79 | 7 | 91.9 |
| | | Stage IV | 11 | 108 | 90.8 |
| | Overall Percentage | | | | 91.2 |
| Step 4 | Cohorts | Stage I/II | 79 | 8 | 90.7 |
| | | Stage IV | 12 | 107 | 89.9 |
| | Overall Percentage | | | | 90.2 |

[a]The cut value is .500

Variables in the Equation

| | | B | S.E. | Wald | df | Sig. | Exp(B) |
|---|---|---|---|---|---|---|---|
| Step 1[a] | miR16 | .979 | .217 | 20.407 | 1 | .000 | 2.661 |
| | miR211 | −.350 | .076 | 21.463 | 1 | .000 | .705 |
| | miR4487 | −.479 | .156 | 9.156 | 1 | .002 | .623 |
| | miR4706 | −.065 | .086 | .570 | 1 | .450 | .937 |
| | miR4731 | .170 | .101 | 2.851 | 1 | .091 | 1.185 |
| | miR509.3p | .905 | .217 | 17.470 | 1 | .000 | 2.473 |
| | miR509.5p | −.035 | .065 | .291 | 1 | .589 | .966 |
| | Constant | −11.035 | 5.856 | 3.552 | 1 | .050 | .000 |
| Step 2[a] | miR16 | .954 | .213 | 20.579 | 1 | .000 | 2.823 |
| | miR211 | −.361 | .073 | 24.365 | 1 | .000 | .697 |
| | miR4487 | −.450 | .157 | 9.378 | 1 | .002 | .619 |
| | miR4706 | −.093 | .080 | 1.095 | 1 | .295 | .620 |
| | miR4731 | .163 | .090 | 2.718 | 1 | .090 | 1.177 |
| | miR509.3p | .900 | .216 | 17.203 | 1 | .000 | 2.460 |
| | Constant | −10.566 | 2.773 | 3.350 | 1 | .067 | .000 |
| Step 3[a] | miR16 | .054 | .210 | 20.657 | 1 | .000 | 2.596 |
| | miR211 | −.373 | .073 | 26.848 | 1 | .000 | .680 |
| | miR4487 | −.506 | .155 | 10.657 | 1 | .001 | .603 |
| | miR4731 | .147 | .096 | 2.347 | 1 | .126 | 1.159 |
| | miR509.3p | .888 | .214 | 17.196 | 1 | .000 | 2.430 |
| | Constant | −11.773 | 5.668 | 4.314 | 1 | .038 | .000 |
| Step 4[a] | miR16 | .882 | .202 | 19.127 | 1 | .000 | 2.417 |
| | miR211 | −.373 | .071 | 27.808 | 1 | .000 | .690 |
| | miR4487 | −.428 | .145 | 8.765 | 1 | .003 | .652 |
| | miR509.3p | .914 | .210 | 18.979 | 1 | .000 | 2.496 |
| | Constant | −9.277 | 5.345 | 3.012 | 1 | .083 | .000 |

TABLE 6-continued

Tables were compiled following Binary Logistic Regression analysis performed in SPSS for Windows. version 21.0. To represent the overall analysis performed for each cohort. only the "classification table" and the "variables in the equation" are shown.

[a]Variable(s) entered on step 1: miR16, miR211, miR4487, miR4706, miR4731, miR509.3p, miR509.5p.

Stage III vs Stage IV

Classification Table[a]

| | | | Predicted | | |
|---|---|---|---|---|---|
| | | | Cohorts | | Percentage |
| Observed | | | Stage III | Stage IV | Correct |
| Step 1 | Cohorts | Stage III | 40 | 10 | 60.0 |
| | | Stage IV | 9 | 110 | 92.4 |
| | Overall Percentage | | | | 88.8 |
| Step 2 | Cohorts | Stage I/II | 40 | 10 | 90.0 |
| | | Stage IV | 8 | 111 | 93.3 |
| | Overall Percentage | | | | 89.3 |
| Step 3 | Cohorts | Stage III | 40 | 10 | 80.0 |
| | | Stage IV | 8 | 111 | 93.3 |
| | Overall Percentage | | | | 89.3 |

[a]The cut value is .500

Variables in the Equation

| | | B | S.E. | Wald | df | Sig. | Exp(B) |
|---|---|---|---|---|---|---|---|
| Step 1[a] | miR16 | 1.007 | .269 | 14.032 | 1 | .000 | 2.737 |
| | miR211 | −.300 | .076 | 15.503 | 1 | .000 | .740 |
| | miR4487 | −.732 | .164 | 14.282 | 1 | .000 | .461 |
| | miR4706 | .020 | .112 | .032 | 1 | .858 | 1.020 |
| | miR4731 | .387 | .149 | 6.753 | 1 | .000 | 1.473 |
| | miR509.3p | .768 | .247 | 9.484 | 1 | .002 | 2.155 |
| | miR509.5p | .021 | .077 | .071 | 1 | .790 | 1.021 |
| | Constant | −13.209 | 6.285 | 4.417 | 1 | .030 | .000 |
| Step 2[a] | miR16 | 1.005 | .268 | 14.098 | 1 | .000 | 2.733 |
| | miR211 | −.299 | .075 | 15.840 | 1 | .000 | .742 |
| | miR4487 | −.728 | .192 | 14.356 | 1 | .000 | .483 |
| | miR4731 | .391 | .148 | 6.957 | 1 | .008 | 1.479 |
| | miR509.3p | .764 | .245 | 9.751 | 1 | .002 | 2.147 |
| | miR509.5p | .028 | .066 | .175 | 1 | .675 | 1.028 |
| | Constant | −12.880 | 5.997 | 4.613 | 1 | .032 | .000 |
| Step 3[a] | miR16 | 1.013 | .260 | 14.170 | 1 | .000 | 2.753 |
| | miR211 | −.294 | .073 | 15.983 | 1 | .000 | .746 |
| | miR4487 | −.710 | .185 | 14.656 | 1 | .000 | .492 |
| | miR4731 | .356 | .147 | 6.905 | 1 | .009 | 1.472 |
| | miR509.3p | .781 | .243 | 10.331 | 1 | .001 | 2.184 |
| | Constant | −12.654 | 6.017 | 4.634 | 1 | .031 | .000 |

[a]Variable(s) entered on step 1: miR16, miR211, miR4487, miR4706, miR4731, miR509.3p, miR509.5p.

Stage III (NSR) vs Stage III (REC)

Classification Table[a]

| | | | Predicted | | |
|---|---|---|---|---|---|
| | | | Cohorts | | Percentage |
| Observed | | | NSR | REC | Correct |
| Step 1 | Cohorts | NSR | 33 | 4 | 89.2 |
| | | REC | 5 | 8 | 61.5 |
| | Overall Percentage | | | | 82.0 |
| Step 2 | Cohorts | NSR | 32 | 5 | 86.5 |
| | | REC | 5 | 8 | 61.5 |
| | Overall Percentage | | | | 80.0 |
| Step 3 | Cohorts | NSR | 34 | 3 | 91.9 |
| | | REC | 5 | 8 | 61.5 |
| | Overall Percentage | | | | 84.0 |
| Step 4 | Cohorts | NSR | 33 | 4 | 89.2 |
| | | REC | 6 | 7 | 53.8 |
| | Overall Percentage | | | | 80.0 |
| Step 5 | Cohorts | NSR | 35 | 2 | 94.6 |
| | | REC | 6 | 7 | 53.8 |
| | Overall Percentage | | | | 84.0 |

TABLE 6-continued

Tables were compiled following Binary Logistic Regression analysis performed in SPSS for Windows. version 21.0. To represent the overall analysis performed for each cohort. only the "classification table" and the "variables in the equation" are shown.

Variables in the Equation

| | | B | S.E. | Wald | df | Sig. | Exp(B) |
|---|---|---|---|---|---|---|---|
| Step 1[a] | miR16 | .941 | .480 | 3.842 | 1 | .050 | 2.563 |
| | miR211 | −.161 | .099 | 2.635 | 1 | .105 | .852 |
| | miR4487 | −.188 | .103 | 1.327 | 1 | .249 | .829 |
| | miR4706 | .027 | .155 | .031 | 1 | .861 | 1.027 |
| | miR4731 | −.410 | .238 | 2.976 | 1 | .084 | .664 |
| | miR509.3p | .266 | .438 | .371 | 1 | .542 | 1.304 |
| | miR509.5p | .293 | .121 | 5.872 | 1 | .015 | 1.340 |
| | Constant | −7.428 | 9.761 | .579 | 1 | .447 | .001 |
| Step 2[a] | miR16 | .903 | .423 | 4.647 | 1 | .033 | 2.467 |
| | miR211 | −.161 | .099 | 2.650 | 1 | .104 | .851 |
| | miR4487 | −.186 | .163 | 1.294 | 1 | .255 | .830 |
| | miR4731 | −.389 | .203 | 3.684 | 1 | .055 | .678 |
| | miR509.3p | .283 | .428 | .438 | 1 | .508 | 1.327 |
| | miR509.5p | .298 | .118 | 6.370 | 1 | .012 | 1.347 |
| | Constant | −7.190 | 9.731 | .646 | 1 | .460 | .001 |
| Step 3[a] | miR16 | .898 | .416 | 4.661 | 1 | .031 | 2.454 |
| | miR211 | −.152 | .097 | 2.448 | 1 | .118 | .859 |
| | miR4487 | −.108 | .159 | 1.107 | 1 | .293 | .846 |
| | miR4731 | −.354 | .190 | 3.479 | 1 | .062 | .702 |
| | miR509.5p | .297 | .116 | 6.524 | 1 | .011 | 1.346 |
| | Constant | −2.508 | 6.746 | .155 | 1 | .693 | .009 |
| Step 4[a] | miR16 | .880 | .417 | 4.457 | 1 | .035 | 2.410 |
| | miR211 | −.131 | .094 | 1.933 | 1 | .164 | .877 |
| | miR4731 | −.415 | .186 | 4.955 | 1 | .026 | .001 |
| | miR509.5p | .250 | .106 | 5.533 | 1 | .019 | 1.285 |
| | Constant | −1.610 | 6.620 | .485 | 1 | .486 | .010 |
| Step 5[a] | miR16 | .795 | .390 | 4.143 | 1 | .042 | 2.214 |
| | miR4731 | −.409 | .182 | 5.067 | 1 | .024 | .664 |
| | miR509.5p | .272 | .104 | 6.797 | 1 | .009 | 1.313 |
| | Constant | −9.285 | 5.915 | 1.962 | 1 | .161 | .000 |

[a]Variable(s) entered on step 1: miR16, miR211, miR4487, miR4706, miR4731, miR509.3p, miR509.5p.

Surival of Stage IV (<2 yr) vs Stage IV (>2 yr)

Classification Table[a]

| Observed | | | Predicted: Cohorts: Short Survivor | Predicted: Cohorts: Long Survivor | Predicted: Percentage Correct |
|---|---|---|---|---|---|
| Step 1 | Cohorts | Short Survivor | 57 | 10 | 85.1 |
| | | Long Survivor | 10 | 33 | 63.5 |
| | Overall Percentage | | | | 75.6 |
| Step 2 | Cohorts | Short Survivor | 66 | 11 | 63.8 |
| | | Long Survivor | 19 | 33 | 63.5 |
| | Overall Percentage | | | | 74.8 |
| Step 3 | Cohorts | Short Survivor | 55 | 12 | 82.1 |
| | | Long Survivor | 19 | 33 | 63.5 |
| | Overall Percentage | | | | 73.9 |
| Step 4 | Cohorts | Short Survivor | 59 | 8 | 85.1 |
| | | Long Survivor | 19 | 33 | 63.5 |
| | Overall Percentage | | | | 73.3 |

[a]The cut value is .500

Variables in the Equation

| | | B | S.E. | Wald | df | Sig. | Exp(B) |
|---|---|---|---|---|---|---|---|
| Step 1[a] | miR16 | −.101 | .191 | .279 | 1 | .597 | .904 |
| | miR211 | .230 | .058 | 16.780 | 1 | .000 | 1.259 |
| | miR4487 | .071 | .134 | .282 | 1 | .598 | 1.074 |
| | miR4706 | .265 | .089 | 8.438 | 1 | .004 | 1.200 |
| | miR4731 | .097 | .083 | 1.356 | 1 | .244 | 1.102 |
| | miR509.3p | .008 | .039 | .048 | 1 | .026 | .992 |
| | miR509.5p | −.113 | .051 | 4.978 | 1 | .026 | .893 |
| | Constant | −15.131 | 7.062 | 4.690 | 1 | .032 | .000 |

TABLE 6-continued

Tables were compiled following Binary Logistic Regression analysis performed in SPSS for Windows. version 21.0. To represent the overall analysis performed for each cohort. only the "classification table" and the "variables in the equation" are shown.

| | | | | | | | |
|---|---|---|---|---|---|---|---|
| Step 2[a] | miR16 | −.089 | .183 | .239 | 1 | .625 | .915 |
| | miR211 | .226 | .053 | 18.189 | 1 | .000 | 1.254 |
| | miR4487 | .071 | .134 | .285 | 1 | .593 | 1.074 |
| | miR4706 | .256 | .088 | 8.541 | 1 | .003 | 1.292 |
| | miR4731 | .094 | .082 | 1.303 | 1 | .254 | 1.000 |
| | miR509.5p | −.115 | .050 | 5.163 | 1 | .023 | .892 |
| | Constant | −15.338 | 6.097 | 4.804 | 1 | .029 | .000 |
| Step 3[a] | miR211 | .226 | .053 | 18.095 | 1 | .000 | 1.254 |
| | miR4487 | .098 | .123 | .634 | 1 | .426 | 1.103 |
| | miR4706 | .257 | .088 | 8.601 | 1 | .003 | 1.293 |
| | miR4731 | .115 | .071 | 2.610 | 1 | .106 | 1.122 |
| | miR509.5p | −.112 | .050 | 5.015 | 1 | .025 | .894 |
| | Constant | −17.894 | 4.762 | 14.122 | 1 | .000 | .000 |
| Step 4[a] | miR211 | .210 | .052 | 17.017 | 1 | .000 | 1.244 |
| | miR4706 | .257 | .087 | 8.836 | 1 | .003 | 1.293 |
| | miR4731 | .142 | .063 | 5.026 | 1 | .025 | 1.152 |
| | miR509.5p | −.109 | .050 | 4.656 | 1 | .028 | .897 |
| | Constant | −15.991 | 4.029 | 15.766 | 1 | .000 | .000 |

[a]Variable(s) entered on step 1: miR16, miR211, miR4487, miR4706, miR4731, miR509.3p, miR509.5p.

M Stage Prediction

Classification Table[a]

| Observed | | | Predicted | | |
|---|---|---|---|---|---|
| | | | Cohorts | | Percentage |
| | | | M1a | M1c | Correct |
| Step 1 | Cohorts | M1a | 14 | 0 | 100.0 |
| | | M1c | 0 | 16 | 100.0 |
| | Overall Percentage | | | | 100.0 |

[a]The cut value is .500

Variables in the Equation

| | | B | S.E. | Wald | df | Sig. | Exp(B) |
|---|---|---|---|---|---|---|---|
| Step 1[a] | miR16 | −88.890 | 3606.263 | .001 | 1 | .990 | .000 |
| | miR211 | 11.432 | 436.925 | .001 | 1 | .979 | 92223.759 |
| | miR4487 | 195.085 | 6137.855 | .001 | 1 | .975 | 5.299E+84 |
| | miR4706 | −157.880 | 6104.067 | .001 | 1 | .975 | .000 |
| | miR4731 | −97.471 | 3096.981 | .001 | 1 | .975 | .000 |
| | miR509.3p | −37.668 | 1191.865 | .001 | 1 | .975 | .000 |
| | miR509.5p | −17.797 | 314.043 | .001 | 1 | .977 | .000 |
| | Constant | 6098.464 | 1.971E+05 | .001 | 1 | .975 | |

[a]Variable(s) entered on step 1: miR16, miR211, miR4487, miR4706, miR4731, miR509.3p, miR509.5p.

Classification Table[a]

| Observed | | | Predicted | | |
|---|---|---|---|---|---|
| | | | Cohorts | | Percentage |
| | | | M1a | M1b | Correct |
| Step 1 | Cohorts | M1a | 14 | 0 | 100.0 |
| | | M1b | 2 | 4 | 66.7 |
| | Overall Percentage | | | | 90.0 |
| Step 2 | Cohorts | M1a | 14 | 0 | 100.0 |
| | | M1b | 2 | 4 | 66.7 |
| | Overall Percentage | | | | 90.0 |
| Step 3 | Cohorts | M1a | 13 | 1 | 92.9 |
| | | M1b | 1 | 5 | 83.3 |
| | Overall Percentage | | | | 90.0 |

[a]The cut value is .500

Variables in the Equation

| | | B | S.E. | Wald | df | Sig. | Exp(B) |
|---|---|---|---|---|---|---|---|
| Step 1[a] | miR16 | −.721 | 1.078 | .448 | 1 | .503 | .486 |
| | miR211 | .145 | .220 | .435 | 1 | .510 | 1.156 |
| | miR4487 | 1.157 | .854 | 1.835 | 1 | .176 | 3.182 |
| | miR4706 | −.790 | .627 | 2.249 | 1 | .134 | .454 |
| | miR4731 | −.490 | .354 | 1.918 | 1 | .166 | .613 |

TABLE 6-continued

Tables were compiled following Binary Logistic Regression analysis performed in SPSS for Windows. version 21.0. To represent the overall analysis performed for each cohort. only the “classification table” and the “variables in the equation” are shown.

| | | | | | | | |
|---|---|---|---|---|---|---|---|
| | miR509.3p | −.270 | .215 | 1.576 | 1 | .209 | .764 |
| | miR509.5p | −.010 | .213 | .002 | 1 | .962 | .960 |
| | Constant | 25.245 | 29.936 | .711 | 1 | .399 | [illegible] |
| Step 2[a] | miR16 | −.693 | .889 | .609 | 1 | .435 | .500 |
| | miR211 | .145 | .219 | .438 | 1 | .508 | 1.158 |
| | miR4487 | 1.165 | .847 | 1.892 | 1 | .169 | 3.205 |
| | miR4706 | −.601 | .481 | 2.770 | 1 | .096 | .449 |
| | miR4731 | −.487 | .350 | 1.941 | 1 | .164 | .614 |
| | miR509.3p | −.267 | .205 | 1.697 | 1 | .193 | .756 |
| | Constant | 24.617 | 26.819 | .843 | 1 | .359 | [illegible] |
| Step 3[a] | miR16 | −.935 | .678 | 1.133 | 1 | .287 | .393 |
| | miR4487 | .910 | .694 | 1.769 | 1 | .183 | 2.485 |
| | miR4706 | −.726 | .425 | 2.909 | 1 | .088 | .484 |
| | miR4731 | −.607 | .344 | 2.174 | 1 | .140 | .602 |
| | miR509.3p | −.221 | .155 | 2.048 | 1 | .152 | .801 |
| | Constant | 34.560 | 26.076 | 1.899 | 1 | .108 | [illegible] |

[a]Variable(s) entered on step 1: miR16, miR211, miR4487 miR4706, miR4731, miR509.3p, miR509.5p.

Classification Table[a]

| Observed | | | Predicted | | |
|---|---|---|---|---|---|
| | | | Cohorts | | Percentage |
| | | | M1b | M1c | Correct |
| Step 1 | Cohorts | M1b | 4 | 2 | 66.7 |
| | | M1c | 1 | 15 | 93.8 |
| | Overall Percentage | | | | 86.4 |
| Step 2 | Cohorts | M1b | 4 | 2 | 66.7 |
| | | M1c | 1 | 15 | 93.8 |
| | Overall Percentage | | | | 86.4 |
| Step 3 | Cohorts | M1b | 4 | 2 | 66.7 |
| | | M1c | 1 | 15 | 93.8 |
| | Overall Percentage | | | | 86.4 |
| Step 4 | Cohorts | M1b | 2 | 4 | 33.3 |
| | | M1c | 1 | 15 | 93.8 |
| | Overall Percentage | | | | 77.3 |
| Step 5 | Cohorts | M1b | 2 | 4 | 33.3 |
| | | M1c | 2 | 14 | 87.5 |
| | Overall Percentage | | | | 72.7 |
| Step 6 | Cohorts | M1b | 2 | 4 | 33.3 |
| | | M1c | 1 | 15 | 93.8 |
| | Overall Percentage | | | | 77.3 |
| Step 7 | Cohorts | M1b | 1 | 5 | 16.7 |
| | | M1c | 0 | 16 | 100.0 |
| | Overall Percentage | | | | 77.3 |
| Step 8 | Cohorts | M1b | 0 | 5 | 0.0 |
| | | M1c | 0 | 16 | 100.0 |
| | Overall Percentage | | | | 72.7 |

[a]The cut value is .500

Variables in the Equation

| | | B | S.E. | Wald | df | Sig. | Exp(B) |
|---|---|---|---|---|---|---|---|
| Step 1[a] | miR16 | 1.034 | 1.239 | .697 | 1 | .404 | 2.813 |
| | miR211 | −.191 | .133 | 2.055 | 1 | .152 | .826 |
| | miR4487 | .398 | .419 | .854 | 1 | .355 | 1.473 |
| | miR4706 | .039 | .220 | .031 | 1 | .851 | 1.039 |
| | miR4731 | −.377 | .291 | 1.675 | 1 | .196 | .686 |
| | miR509.3p | −.103 | .122 | .707 | 1 | .401 | .903 |
| | miR509.5p | .008 | .140 | .003 | 1 | .953 | 1.008 |
| | Constant | −2.212 | 16.670 | .018 | 1 | .894 | .109 |
| Step 2[a] | miR16 | 1.014 | 1.189 | .727 | 1 | .394 | 2.757 |
| | miR211 | −.188 | .121 | 2.393 | 1 | .122 | .829 |
| | miR4487 | .390 | .419 | .865 | 1 | .352 | 1.477 |
| | miR4706 | .043 | .206 | .044 | 1 | .834 | 1.044 |
| | miR4731 | −.376 | .292 | 1.650 | 1 | .108 | .886 |
| | miR509.3p | −.102 | .122 | .702 | 1 | .402 | .903 |
| | Constant | −2.079 | 16.453 | .015 | 1 | .899 | .125 |
| Step 3[a] | miR16 | .911 | 1.062 | .735 | 1 | .391 | 2.487 |
| | miR211 | −.181 | .115 | 2.456 | 1 | .117 | .835 |
| | miR4487 | .415 | .402 | 1.064 | 1 | .302 | 1.514 |
| | miR4731 | −.392 | .281 | 1.948 | 1 | .163 | .676 |

TABLE 6-continued

Tables were compiled following Binary Logistic Regression analysis performed in SPSS for Windows. version 21.0. To represent the overall analysis performed for each cohort. only the "classification table" and the "variables in the equation" are shown.

| | | | | | | | |
|---|---|---|---|---|---|---|---|
| | miR509.3p | −.098 | .120 | .669 | 1 | .413 | .907 |
| | Constant | .037 | 13.133 | .000 | 1 | .998 | 1.038 |
| Step 4[a] | miR16 | .602 | .809 | .553 | 1 | .457 | 1.825 |
| | miR211 | −.202 | .115 | 3.055 | 1 | .080 | .817 |
| | miR4487 | .349 | .360 | .943 | 1 | .332 | 1.418 |
| | miR4731 | −.318 | .232 | 1.883 | 1 | .170 | .727 |
| | Constant | .193 | 12.401 | .000 | 1 | .988 | 1.213 |
| Step 5[a] | miR211 | −.160 | .094 | 2.905 | 1 | .088 | .852 |
| | miR4487 | .255 | .332 | .591 | 1 | .442 | 1.290 |
| | miR4731 | −.314 | .215 | 2.127 | 1 | .145 | .731 |
| | Constant | 8.004 | 8.755 | .826 | 1 | .361 | 2991.756 |
| Step 6[a] | miR211 | −.149 | .091 | 2.707 | 1 | .100 | .881 |
| | miR4731 | −.233 | .188 | 1.532 | 1 | .216 | .792 |
| | Constant | 12.449 | 7.167 | 3.017 | 1 | .082 | [illegible] |
| Step 7[a] | miR211 | −.128 | .089 | 2.087 | 1 | .149 | .880 |
| | Constant | 4.287 | 2.419 | 3.140 | 1 | .076 | 72.747 |
| Step 8[a] | Constant | .981 | .479 | 4.198 | 1 | .040 | 2.667 |

[a]Variable(s) entered on step 1: miR16, miR211, miR4487 miR4706, miR4731, miR509.3p, miR509.5p.

Example 2

Materials and Methods

Cell Culture and Total RNA extraction. All melanoma (cutaneous and uveal) cell lines (Table 8) were established and have been previously described[63,64]. All other solid cancer cell lines (Table 8) were kind donations from investigators at QIMR Berghofer. Most of the solid cancer cell lines are available from the cell line repositories ATCC or CellBank Australia.

All cell lines were cultured in RPMI (#31800-089. Life Technologies, Foster City, CA, USA) supplemented with 10% FBS (Life Technologies, Foster City, CA, USA) with HEPES. 100 U/ml penicillin and 100 μg/ml streptomycin (Life Technologies, Foster City, CA, USA) at 37° C. (5% CO2) and were periodically authenticated via short tandem repeat profiling according to the manufacturer's instructions (AmpFISTR Profiler Plus ID kit; Life Technologies. Poster City, CA, USA). Primary human melanoblasts (QFI160 MB) and melanocytes (MELA) were established from human neonatal foreskin and cultured as described[65, 66]. Cells were harvested from the plate and column-purified using the miRNeasy Kit (QIAGEN, Hilden, Germany) according to the manufacturer's instructions.

Serum/Plasma collection and Total RNA extraction. Ethical approval was granted by the QIMR Berghofer's Human Research Ethics Committee (HREC) approval number P1237. Serum and Plasma were processed using standard methodologies and total RNA was extracted using the Plasma/Serum Circulating RNA Purification Kit (#30000; Norgen Biotek, Ontario, Canada) according to manufacturer's instructions.

microRNA microarray profiling and data analysis. 5 μg of total RNA was shipped to LC Sciences (Houston, USA) for miRNA profiling using a custom array platform (μParaflo® technology) containing 1898 miRNAs (miRBase V18)(67). All QC, labelling (Cy-3), hybridization, scanning, signal background subtraction and global normalisation (LOWES) were performed by LC Sciences as per technical note: (www.lesciences.com/documents/application-notes/Tech-Bul l-MicroRNA-Microarray-Data-Analysis.pdf).

Advanced data analyses were performed in Genespring GX12.5 (Agilent Technologies, Santa Clara, USA) using the LOWES normalised signal intensity values. All values<30 were considered 'background expression' (personal communication with LC Sciences) and changed to 0.01 prior to $\log_2$ transformation. So as to identify 'melanoma-specific' miRNAs that were potentially more relevant to melanoma, samples were classified as either 'melanoma' or 'other ca' (melanocytes, melanoblasts, nevocyte, and serum derived samples were excluded from these categories). To identify differentially expressed miRNAs, a Mann-Whitney U-test (unpaired) was applied to a 'volcano-plot' analysis with thresholds set at $p<0.05$ and ≥2 fold. The gene list derived from these analyses was then applied to all samples in an unsupervised manner using hierarchical clustering (Euclidean similarity with average linkage).

miScript quantitative RT-PCR validation. A selection of miRNAs was validated using quantitative real-time-PCR to check the integrity of the microarray data. Briefly, all samples included on the microarray along with an extended cohort of melanoma cell lines (as described in ref 54) were reverse transcribed using the miScript II RT Kit (QIAGEN, Hilden, Germany) according to the manufacturer's instructions. Real-time PCR was subsequently performed with a miScript SYBR Green PCR Kit (QIAGEN, Hilden, Germany) using the 7900HT Fast Real Time PCR System (Life Technologies, Foster City, CA, LISA). Data were analysed in Microsoft Excel using the ΔCT method compared to RNU6 which was assessed in every sample.

Results

'Melanoma-specific' miRNA discovery profiling in melanoma. This comprehensive analysis of a large panel of melanoma cell lines identified distinct 'tissue-specific' expression as compared to other solid malignancies. We used miRNA microarrays (LC Sciences, Houston. USA. miRBaseV18; 1898 miRNAs) to comprehensively study the miRNA profile of cutaneous melanoma (n=55), uveal melanoma (n=7), and RNA derived from melanoma patient scrum/plasma (n=3) in relation to 'other' solid malignancies (n=34). Normal pigment (melanocytes and melanoblasts) and pre-malignant (nevocyte) cells were also included as controls ('Discovery cohort'). In this 'Discovery' set, a total of 233/1898 differentially expressed (≥2 fold, $p<0.05$; See Materials and Methods) miRNAs were identified which may fit this criteria when 'melanomas' were compared to 'other' cancers (FIG. 8 and Table 7). We identified a significant number of miRNAs (FIGS. 16A-16DD) with known and novel relationship to melanoma. Table 8 summarizes the top up and down regulated miRNAs by at least 10 fold, most of which have a known association either with melanoma or tumorigenesis.

Figure 9A:
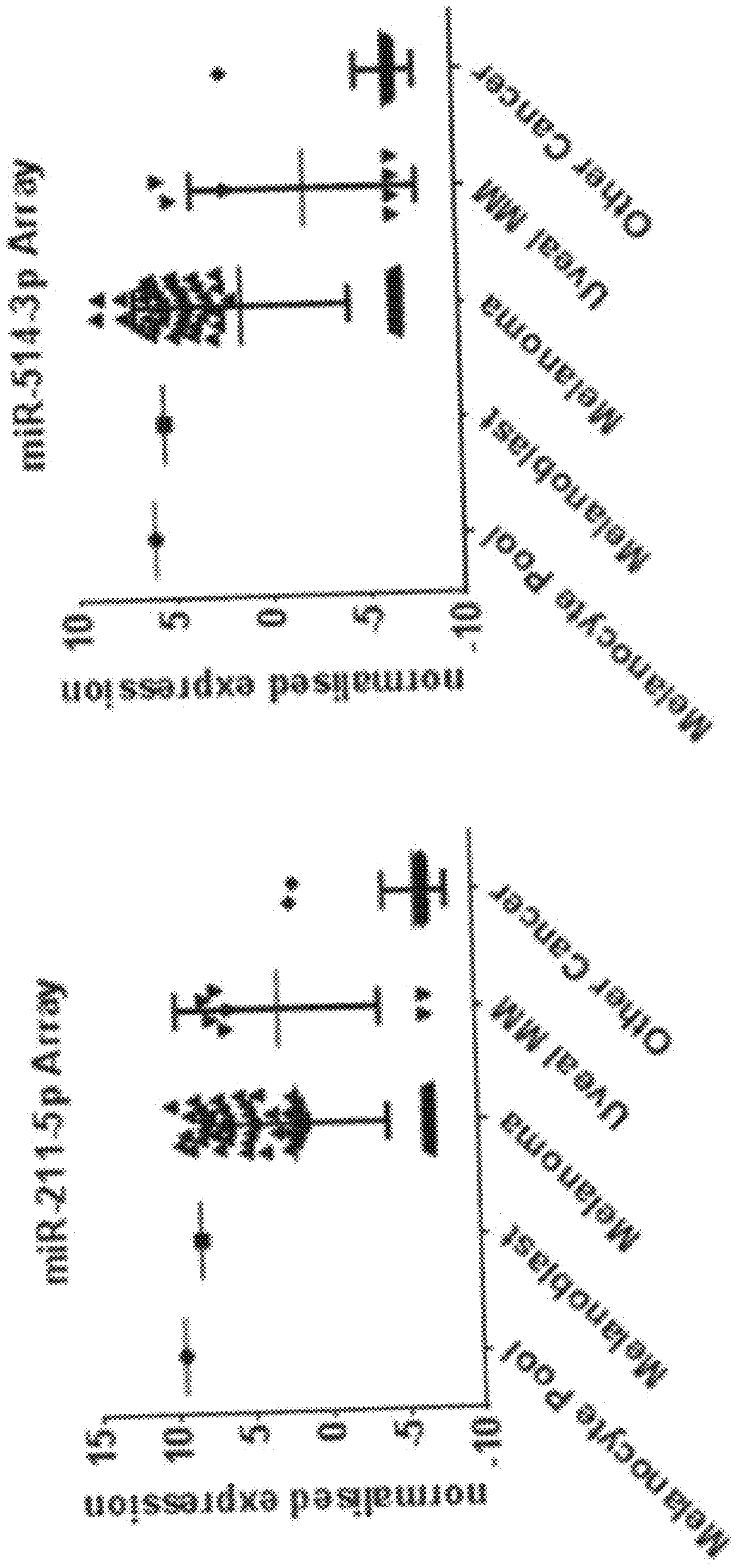
FIGS. 9A-9C. The top 3 upregulated miRNAs were validated using qRT-PCR with all samples present on the microarray along with an extended cohort of melanoma cell lines (Table 10). For comparative purposes the array data was also plotted to highlight the high correlation between the array and qRT-PCR FIG. 10. The nucleic acid sequence and observed sequence variation of miRNA-4487.
Figure 9B:
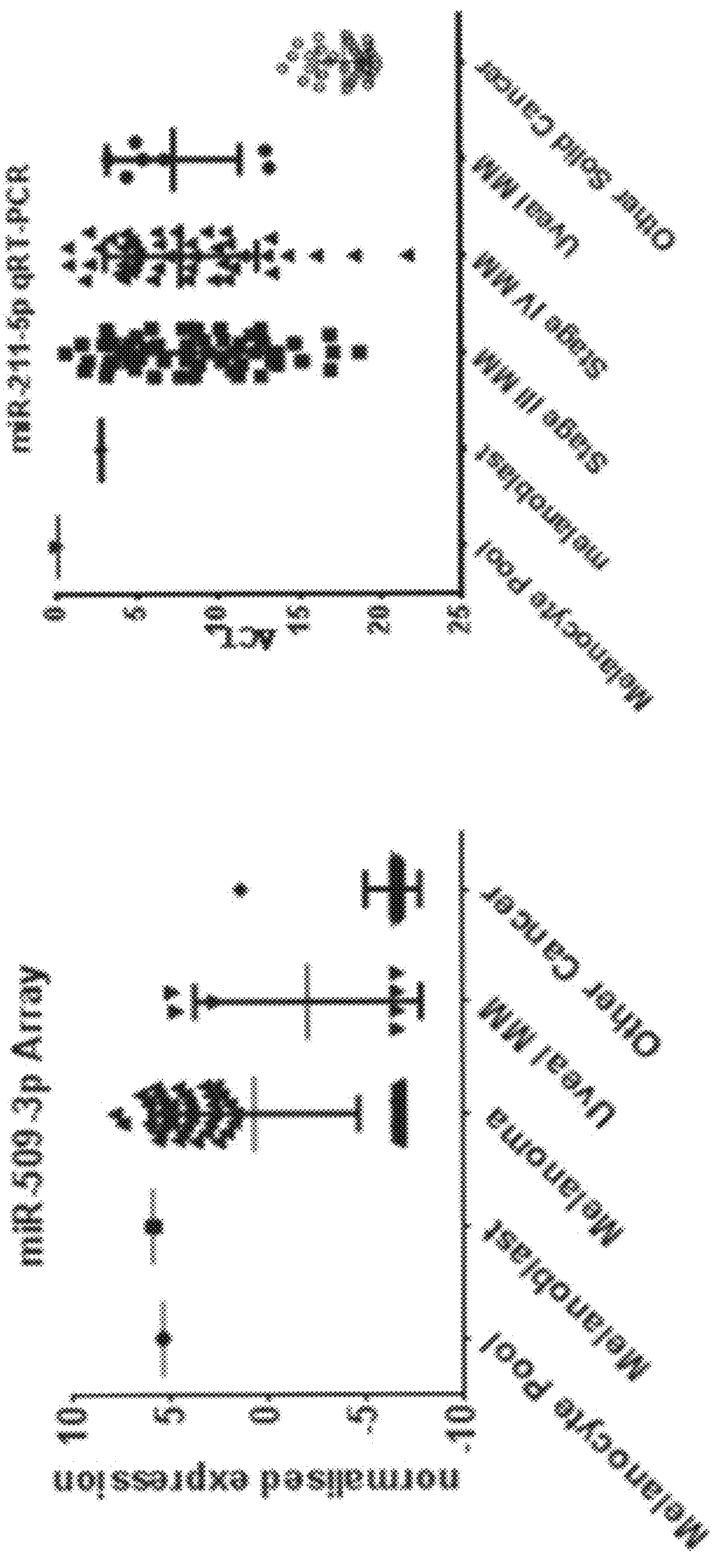
Figure 9C:
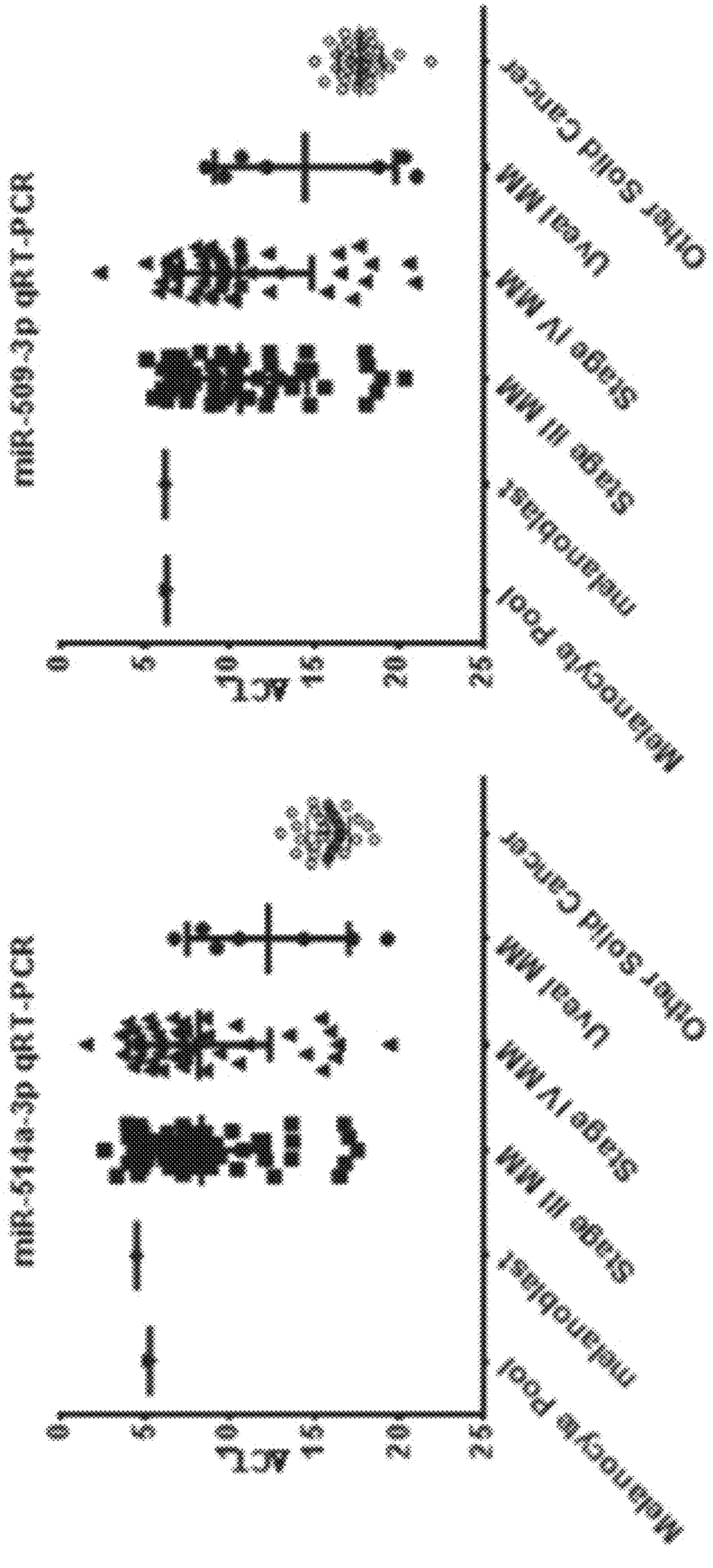
Figure 16H:
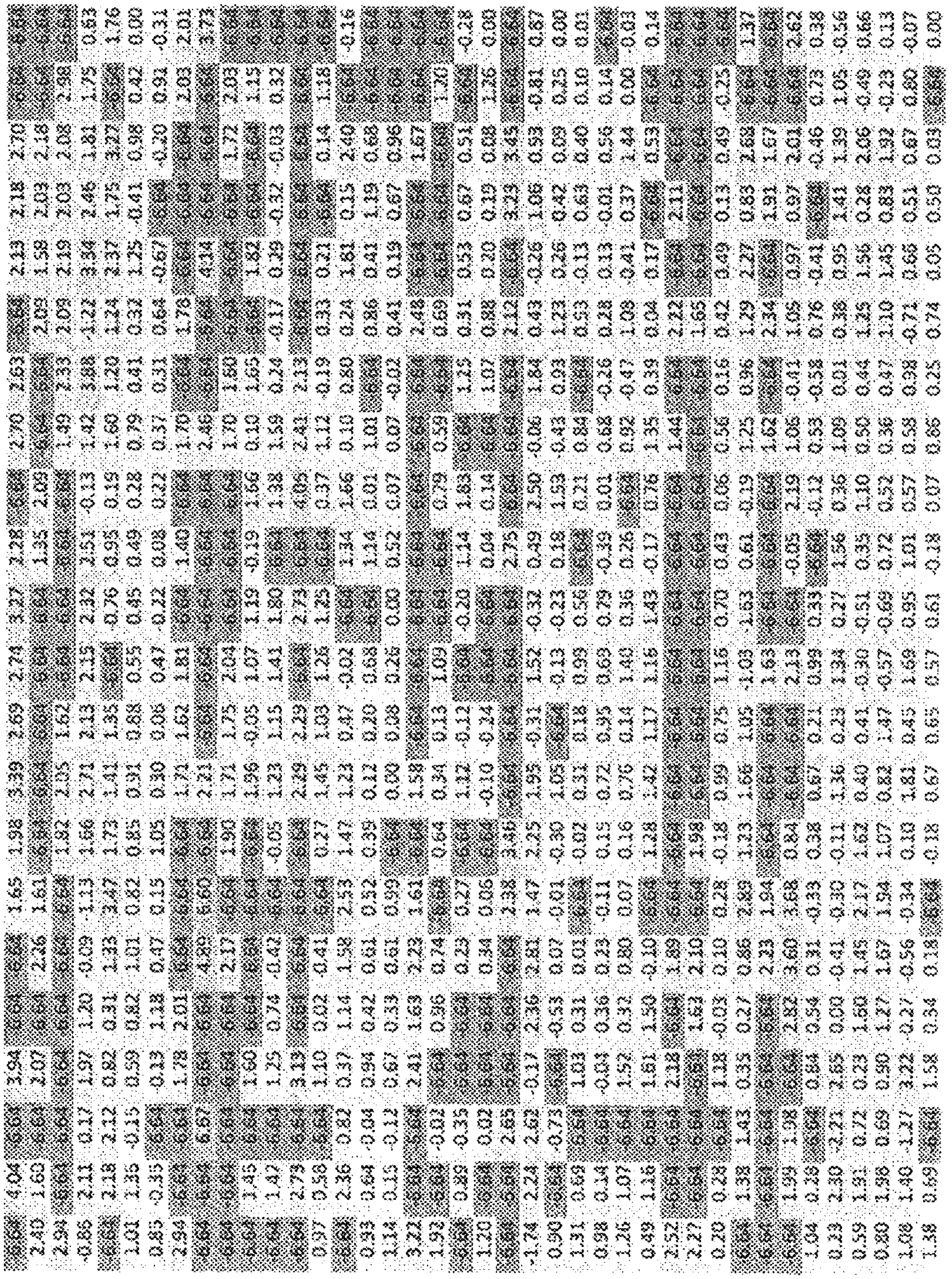
FIGS. 16A-16DD. The miRNA expression in melanoma and other cancers.
Figure 16K:
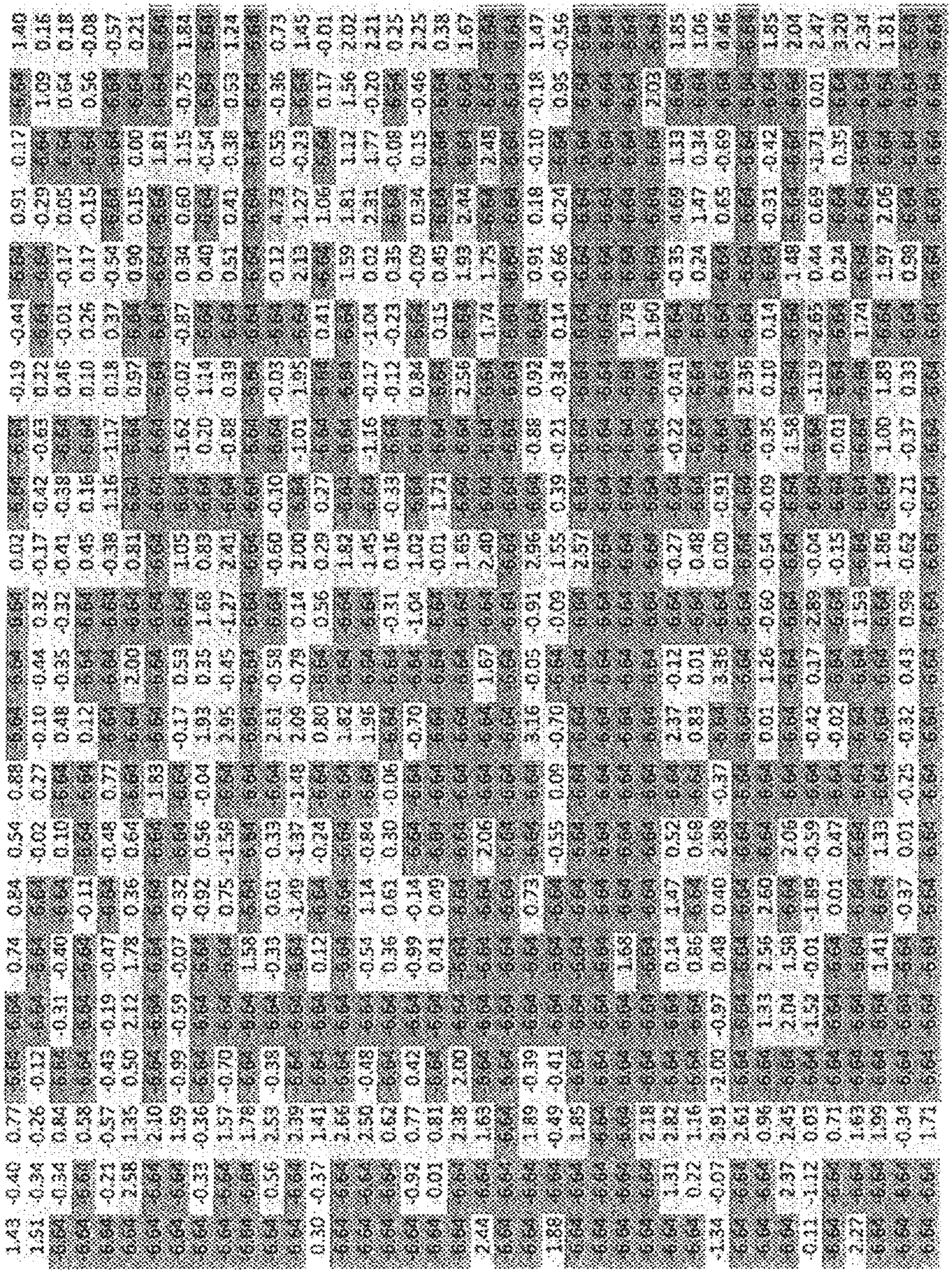
Figure 16P:
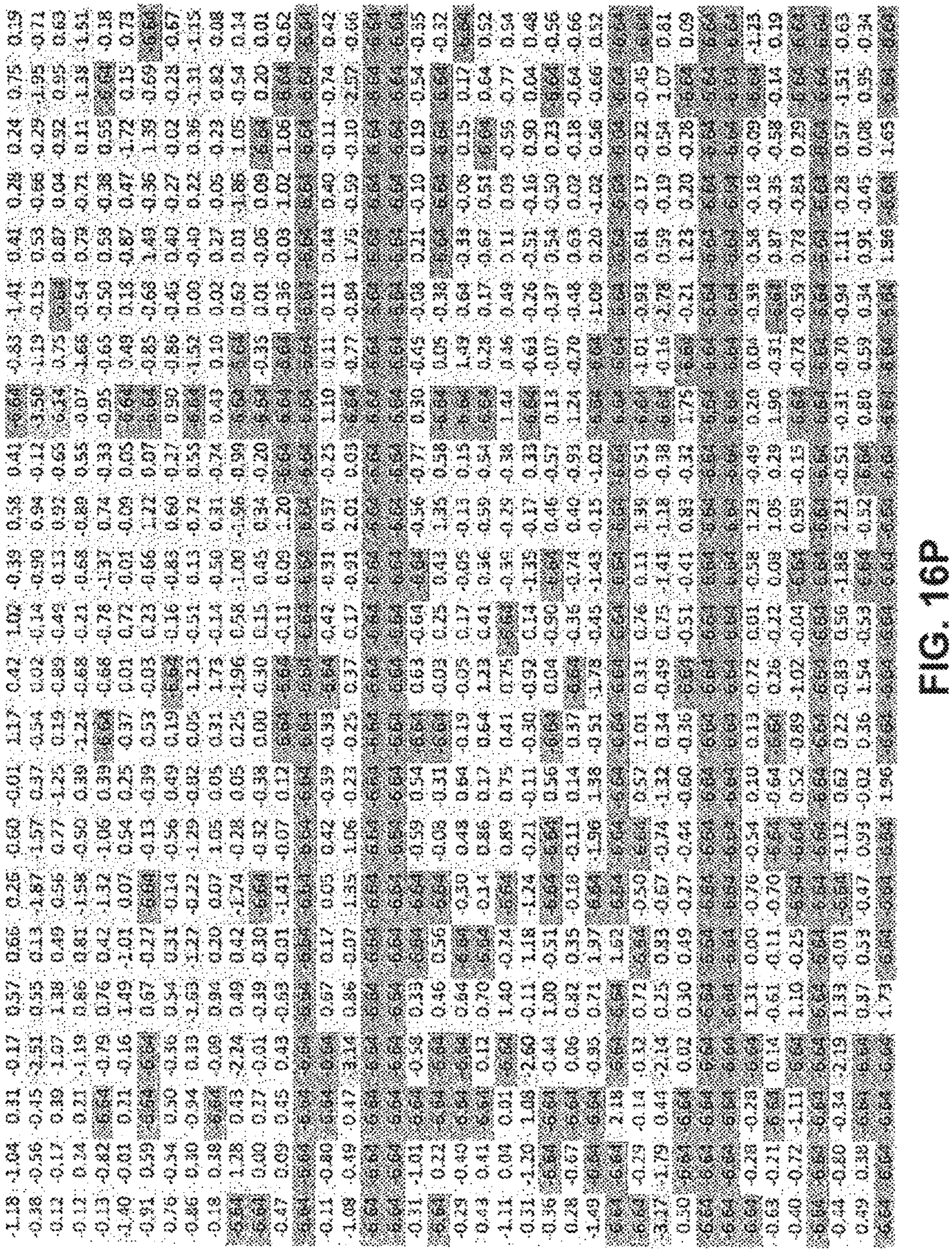
Figure 16Q:
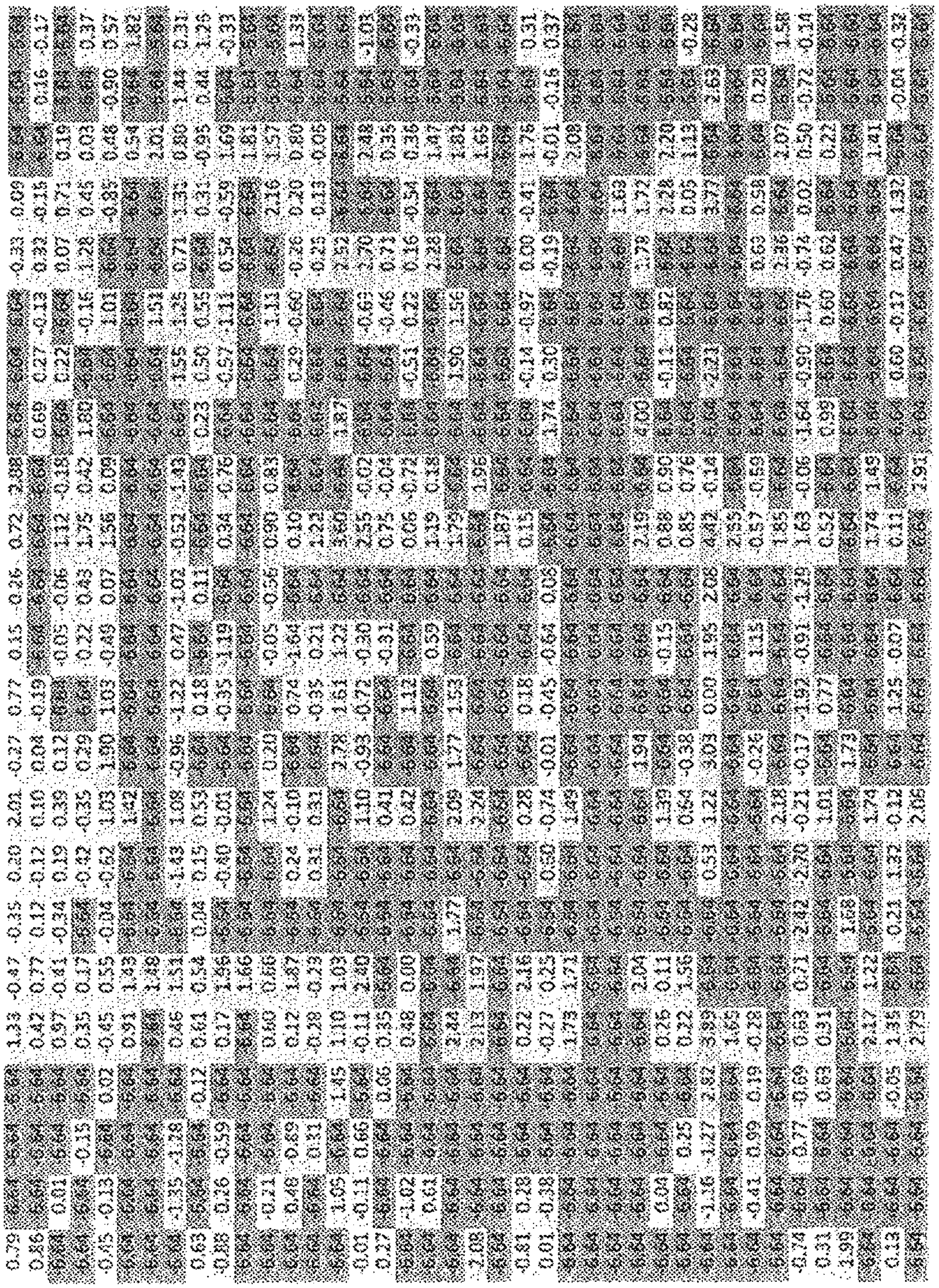
Figure 16R:
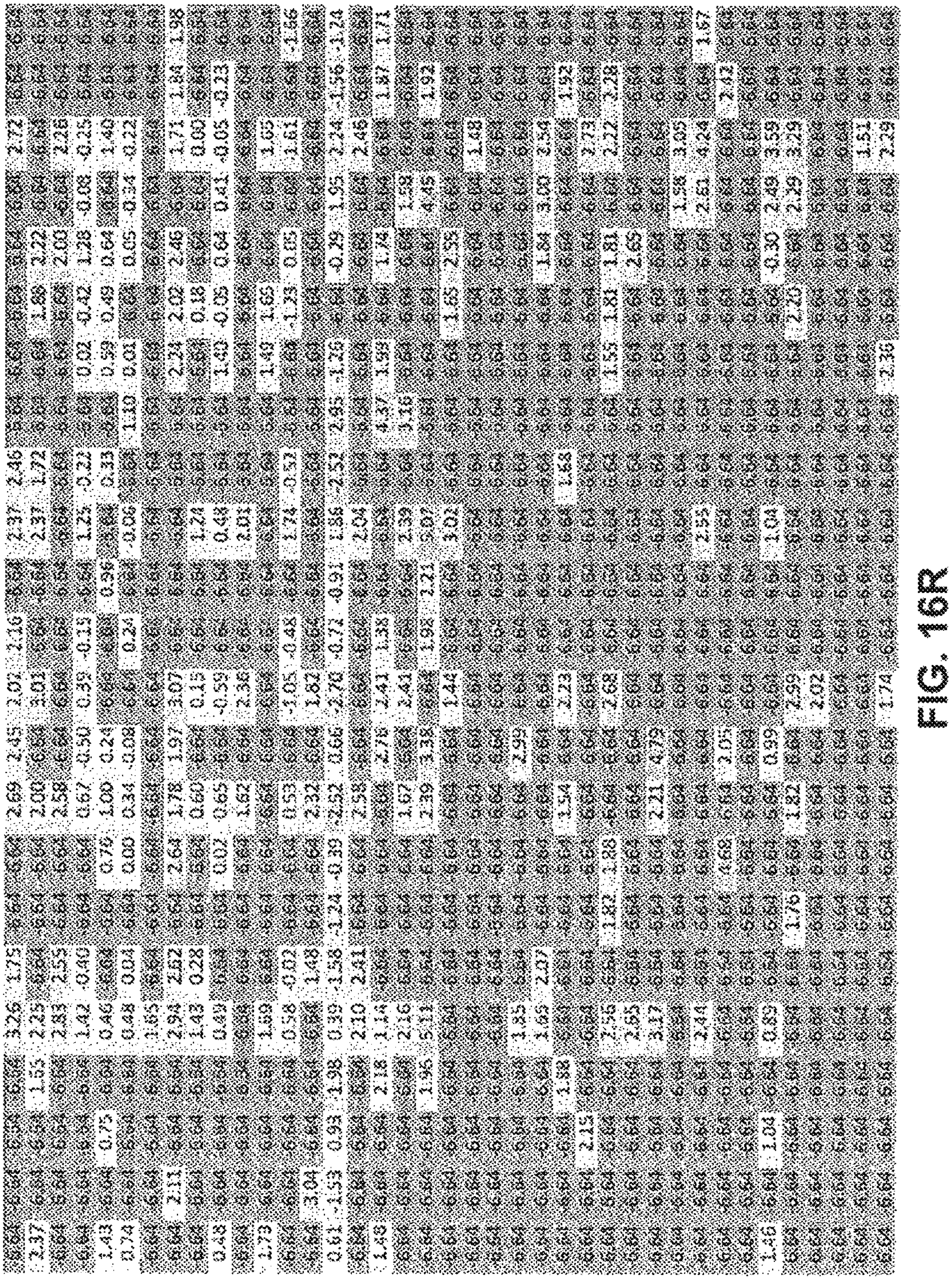
Figure 16T:
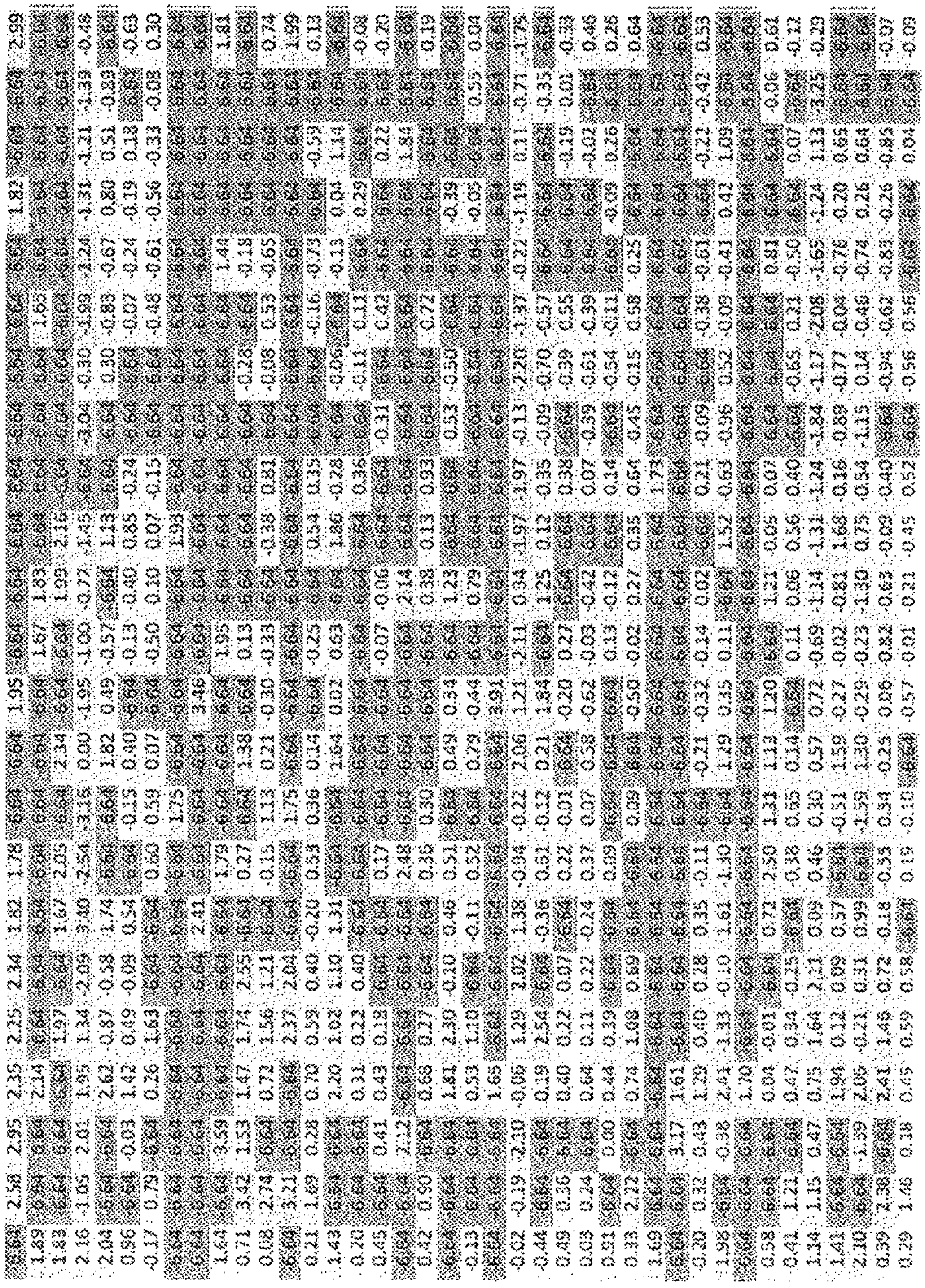
Figure 16W:
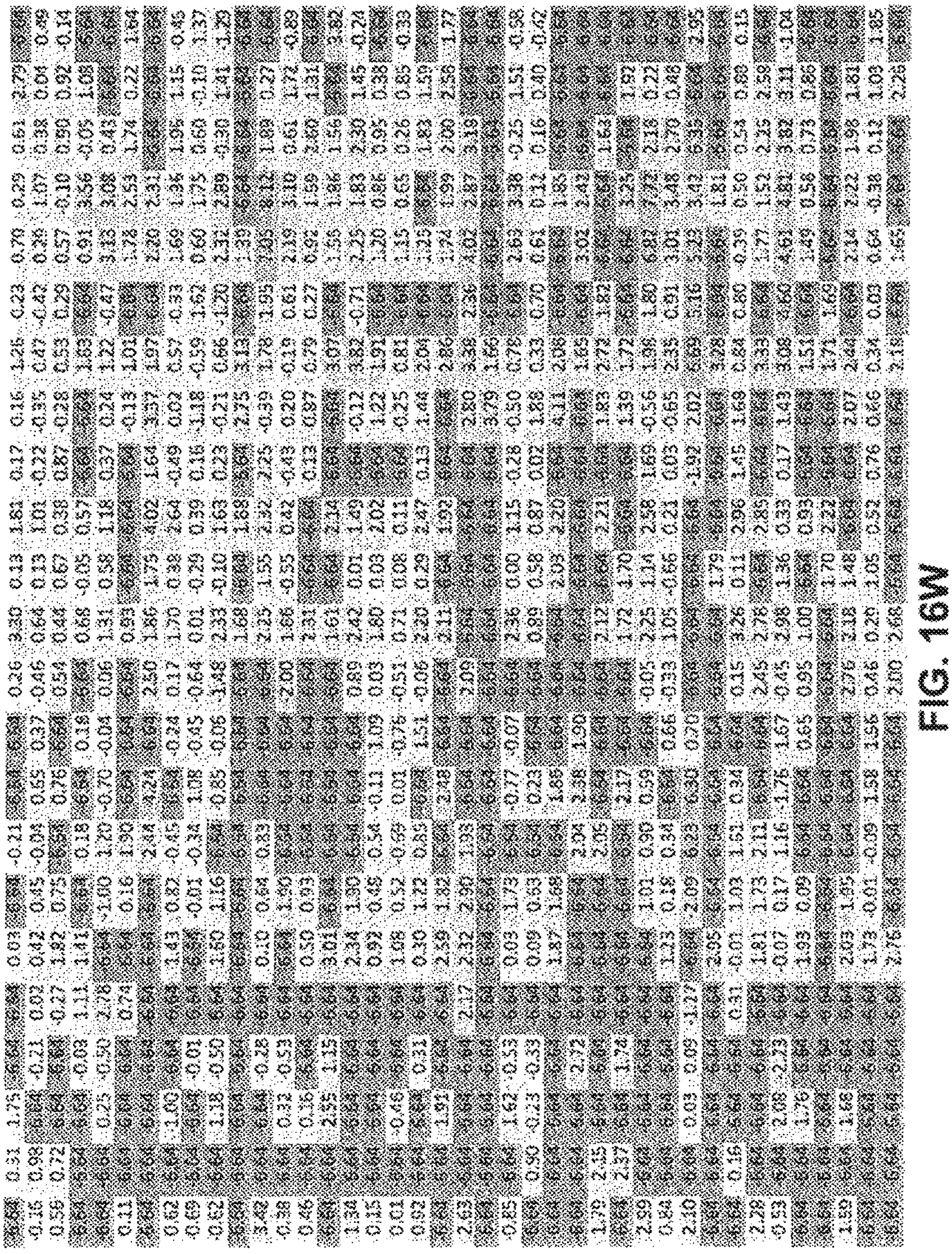
Figure 16X:
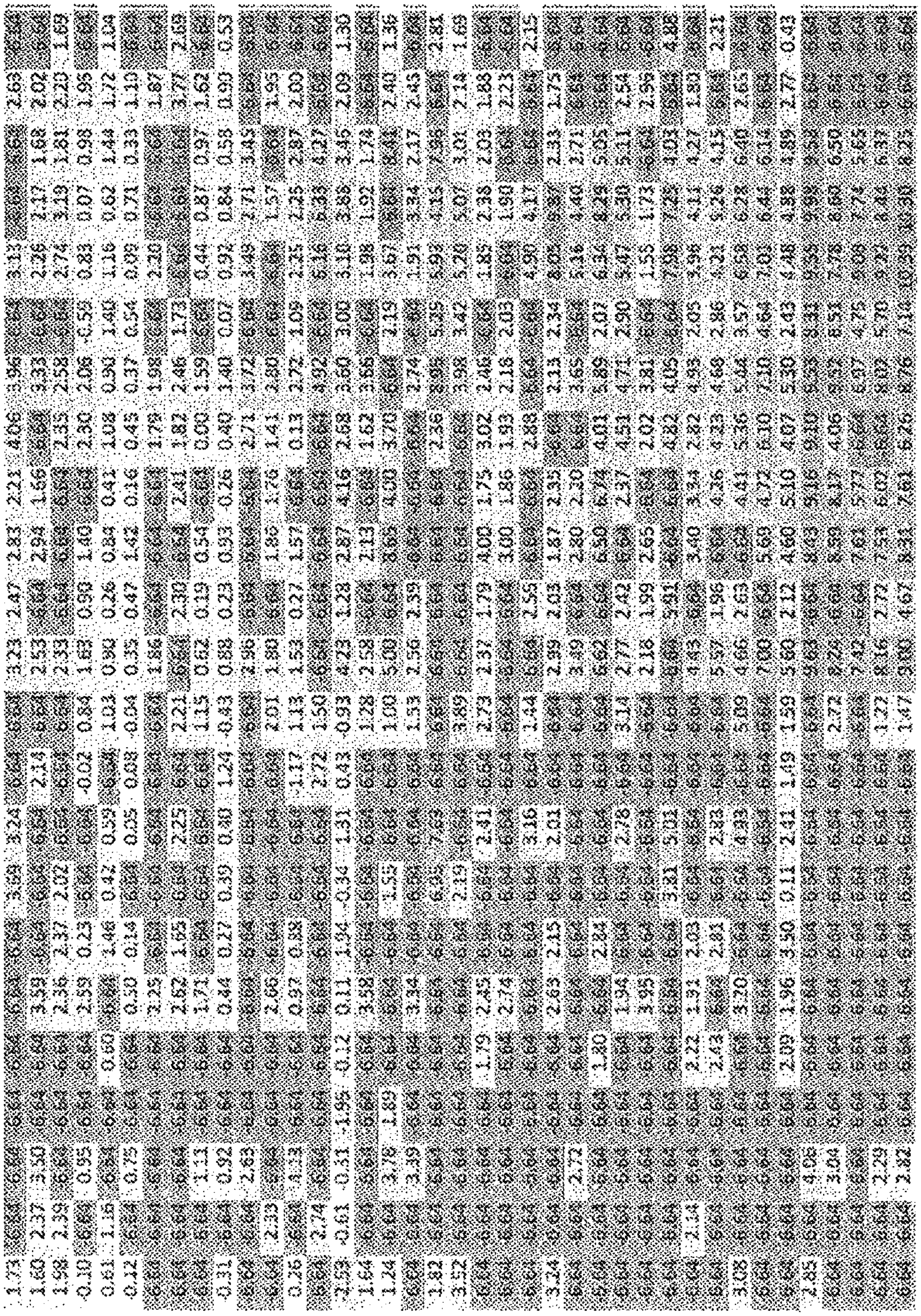
Figure 16Y:
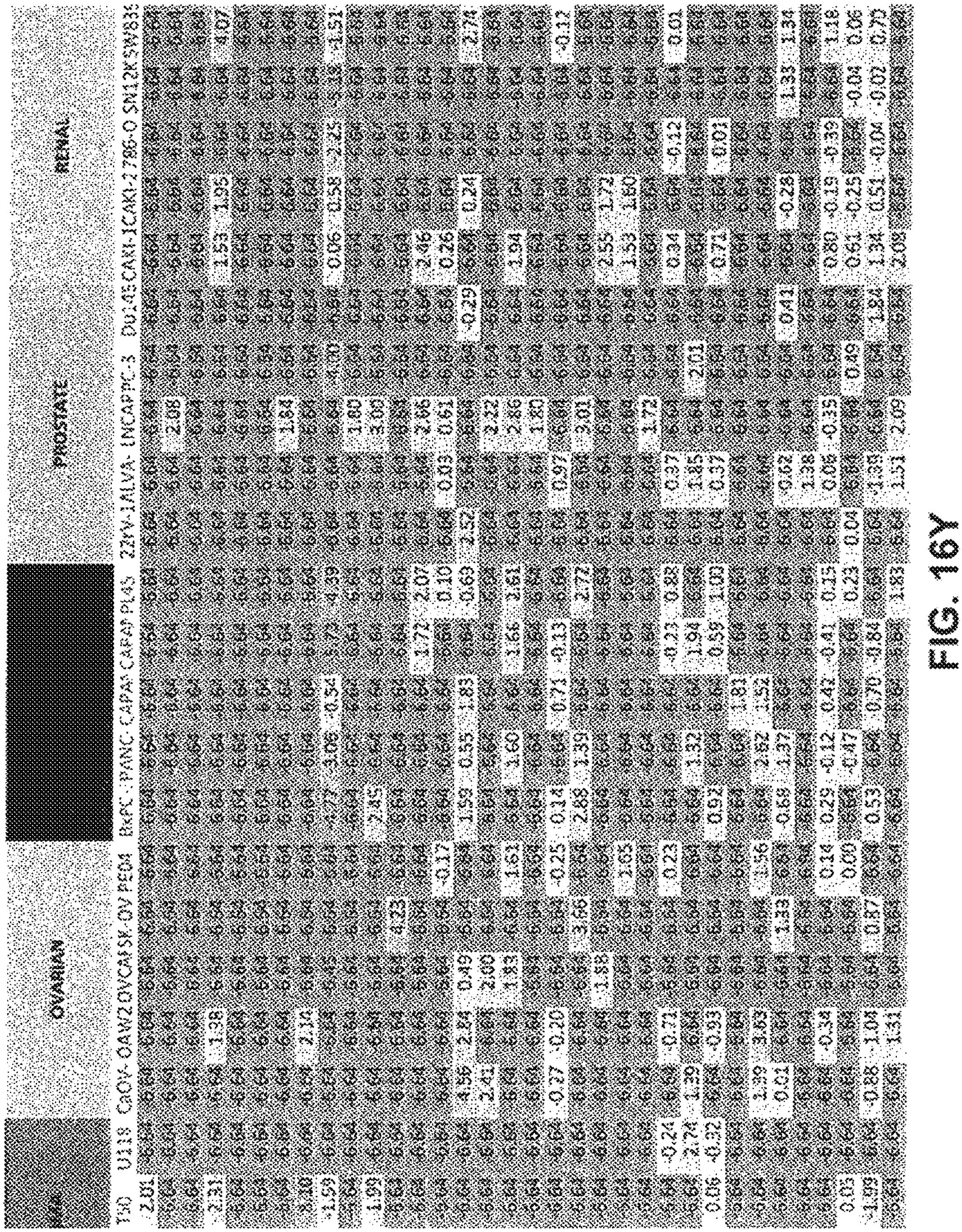
Figure 16Z:
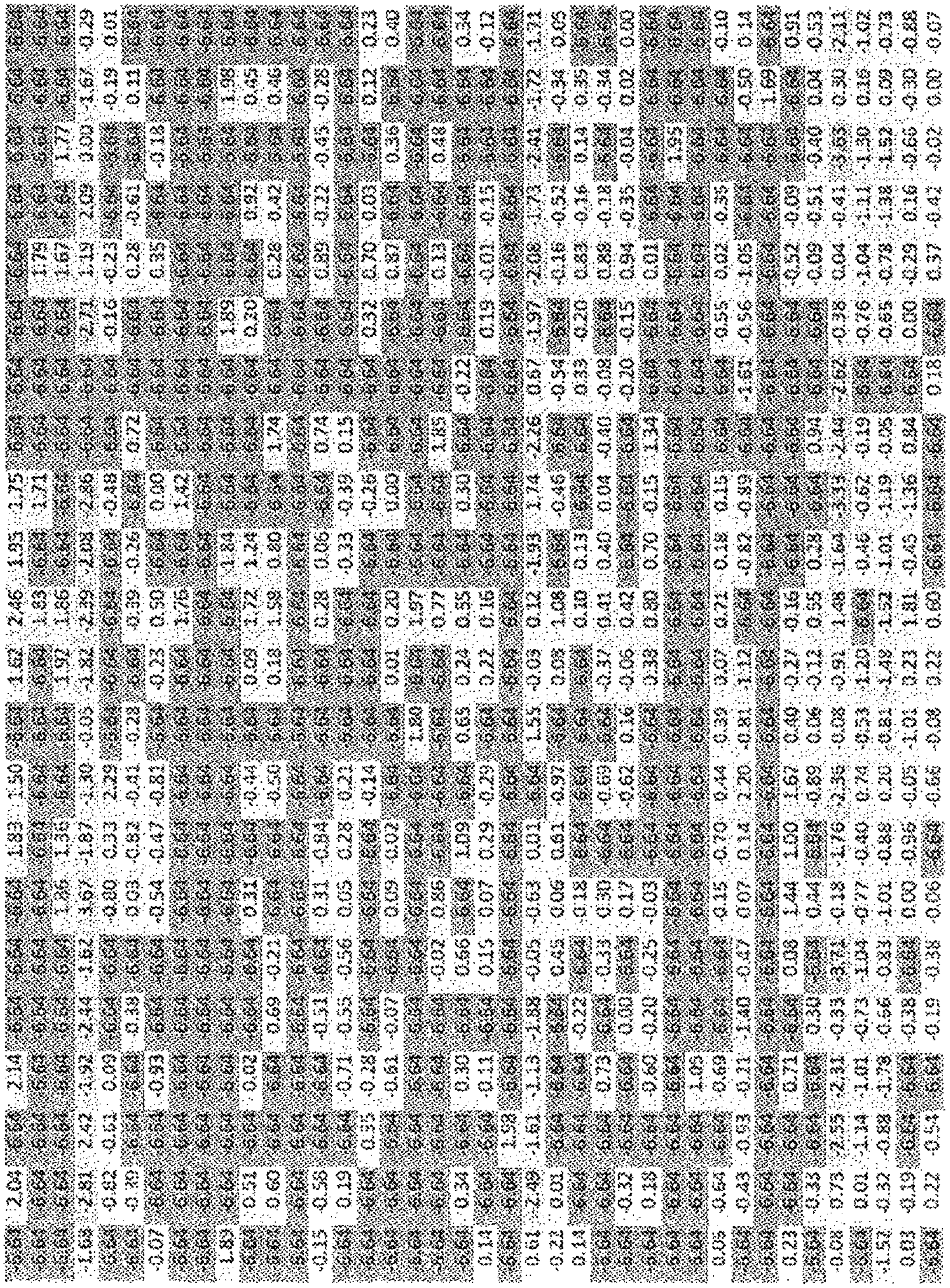
Figure 16:
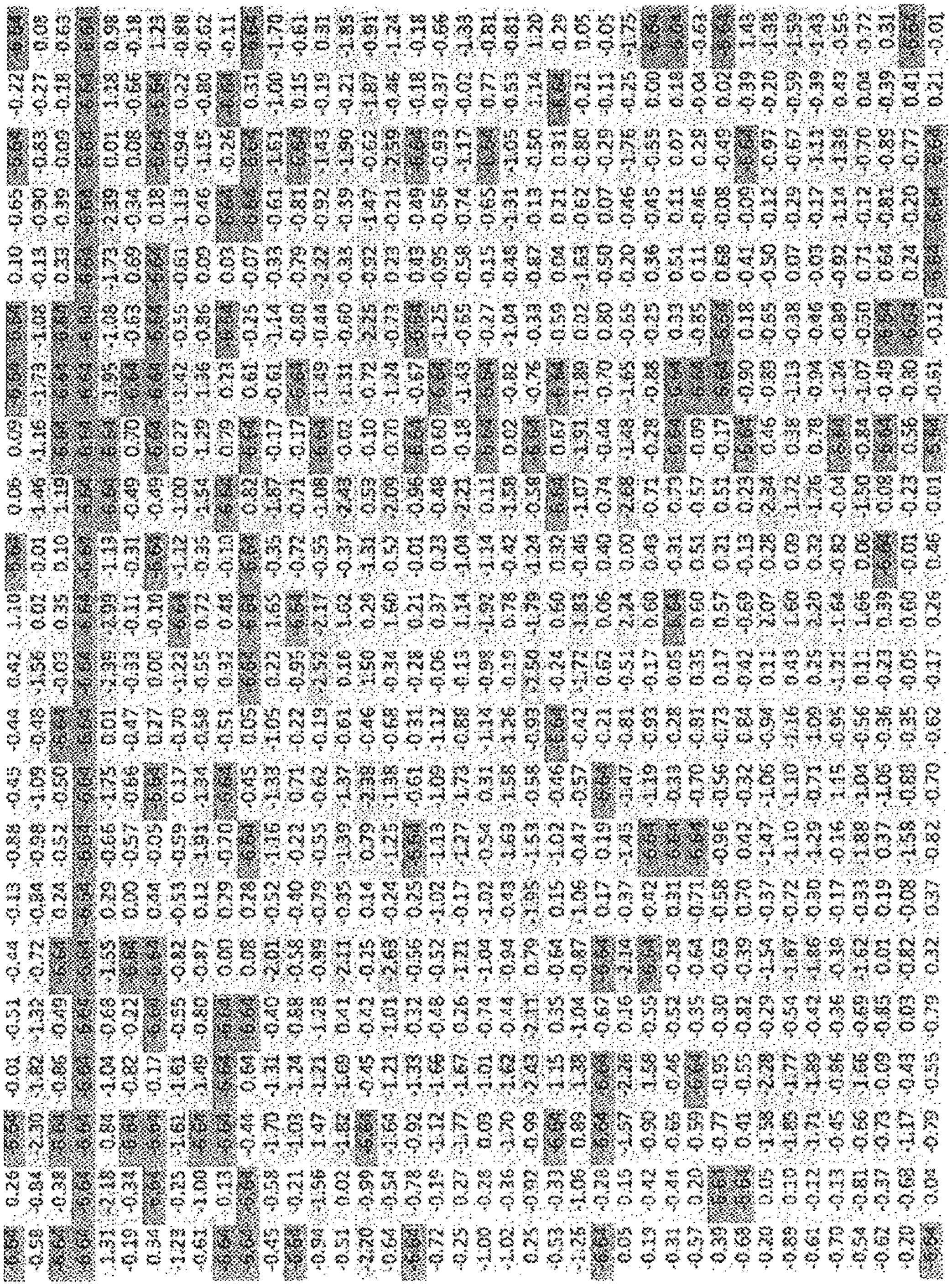
Figure 16C:
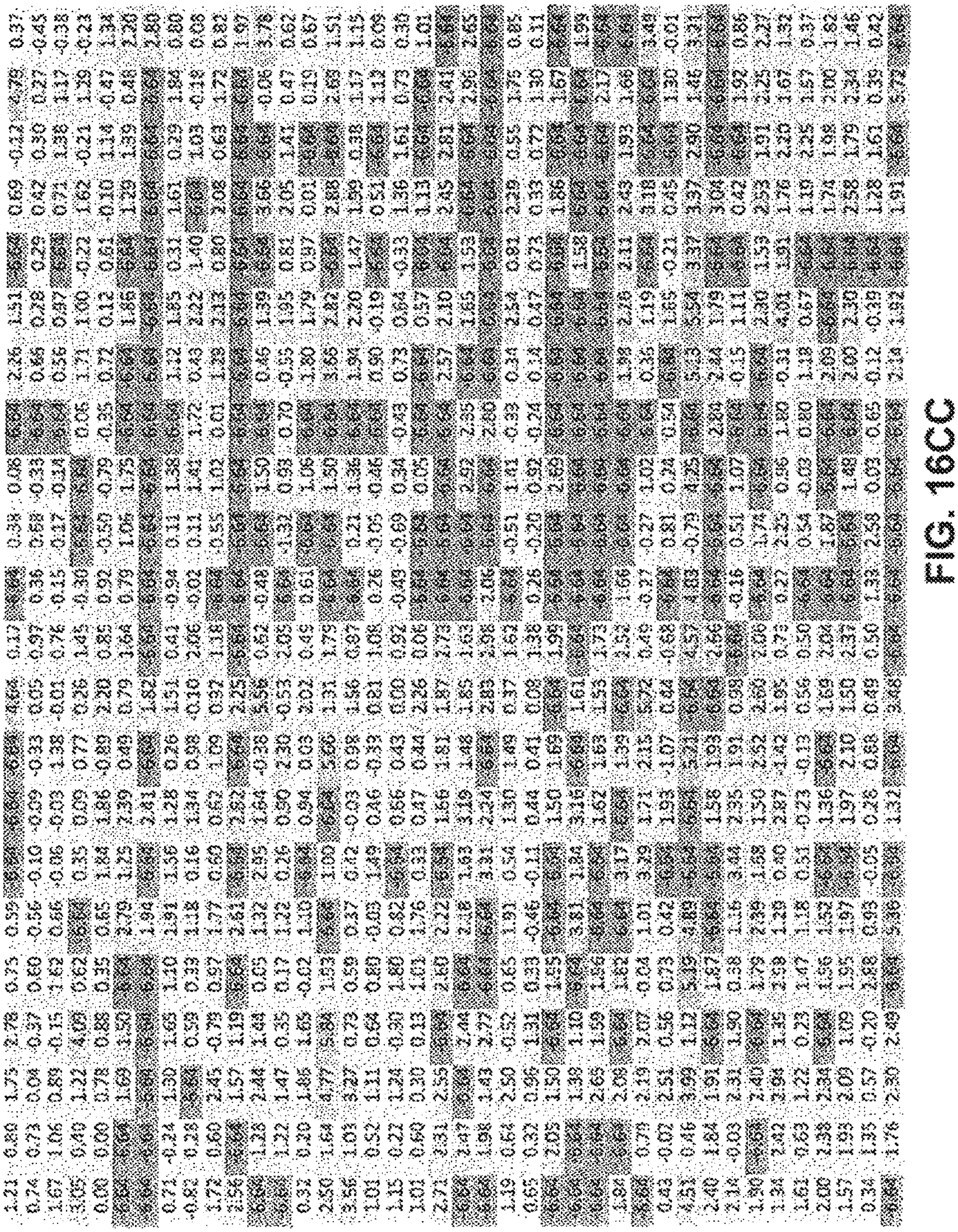
Figure 16D:
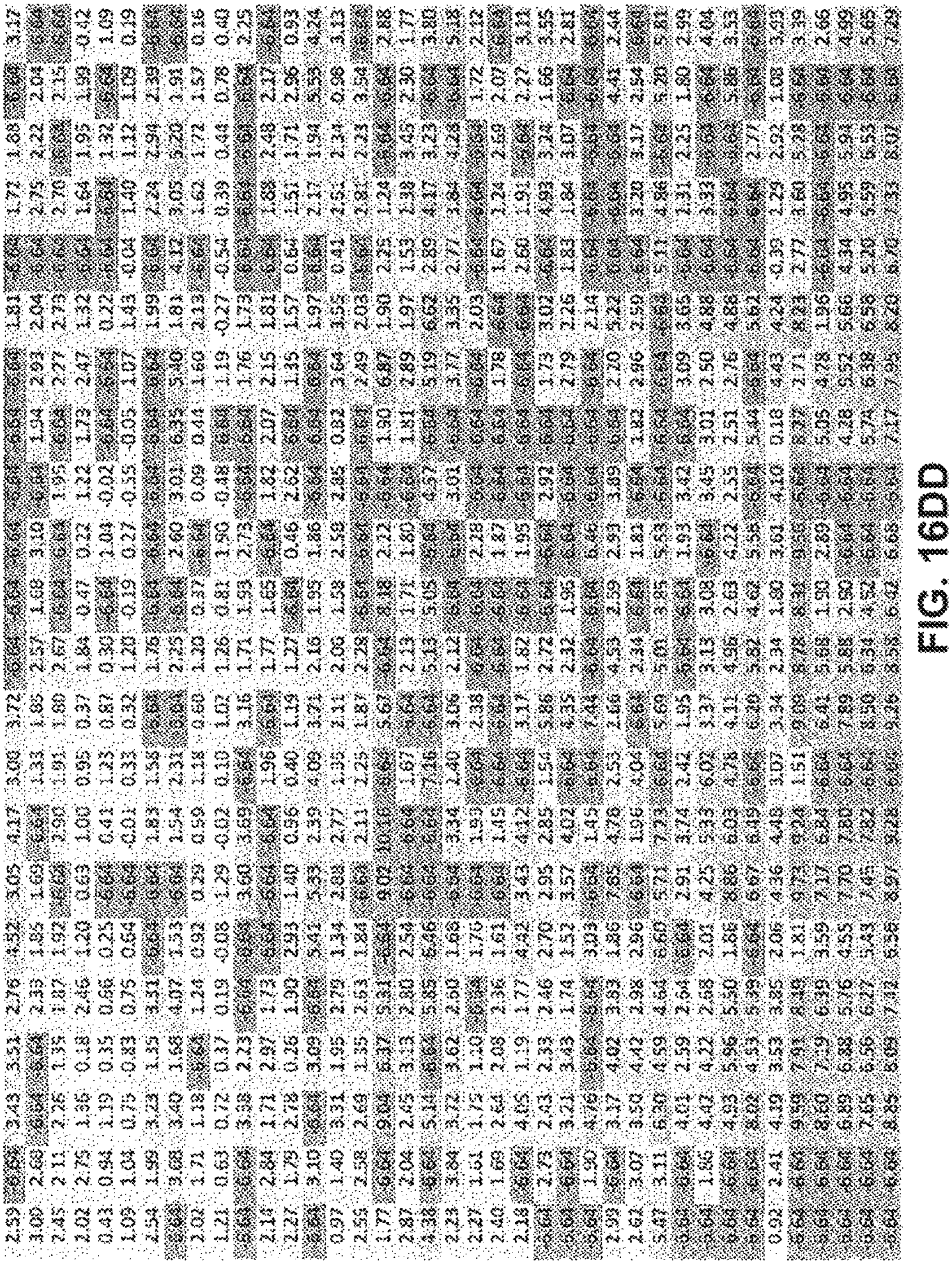

'Lineage-specific' miRNA validation. Notably the top two miRNAs up-regulated in melanoma were hsa-miR-211-5p (miR-211) and hsa-miR-514a-3p (miR-514a) with profound average fold changes of 276 and 204 respectively compared to other solid malignancies (FIGS. 16A-16DD). To test the robustness of the array data, quantitative real-time PCR validation was performed with these miRNAs along with a selection of other miRNAs from the array (FIG. 9 and Table 9).

Discussion

MicroRNAs have been proven to be powerful regulators of protein coding gene expression in almost all facets of cell biology. In cancer, their dysregulation can be far reaching, spanning a multitude of different signalling pathways due to the number of genes being directly and indirectly regulated and as such, they have been intensively studied for over a decade. In melanoma, the comprehensive analysis of miRNA has been limited, with most studies performed using only a few hundred miRNAs[28]. Newly characterised miRNAs have seen the expansion of miRBASE (curated miRNA database), largely due to the advent of deep sequencing technologies. As most of the newly identified miRNAs have no known association with melanoma, here we sort to survey a large panel of melanoma cell lines in relation to other solid malignancies to strengthen prior studies into melanoma-specific miRNAs and to identify those that were previously unknown to be involved in melanomagenesis. Identification of a panel in a comprehensive manner such as this has the ability to open new avenues for research in this burgeoning field, which may provide a greater understanding of this complex disease. In our comprehensive analysis of 1898 miRNAs (miRBaseV18), we have successfully identified a large number of miRNAs (n=233) that were found to be statistically significant (P<0.05, ≥2 fold) when melanoma (n=55) was compared with other solid cancer (n=34). Indeed, many of the identified miRNAs have a known association with melanoma however most have no known association. The main premise of the study was to identify a panel of melanoma-specific miRNAs (or more predominantly expressed) and these are more readily observed in the up-regulated collection of miRNAs. However it is worth noting that many of the down-regulated miRNAs have been previously associated with melanoma. Our dataset confirms and strengthens the associated loss of the miR-200 family (including miR-141)[47,48] along with the frequently silenced miRNA, miR-205[49-53].

TABLE 7

Differentially expressed miRNAs in melanoma

| GeneName | p (Corr) | p | FC (abs) | Regulation |
|---|---|---|---|---|
| hsa-miR-200c-3p | 1.29E−06 | 2.24E−08 | 250.7467 | down |
| hsa-miR-204-5p | 5.50E−06 | 1.39E−07 | 93.67072 | up |
| hsa-miR-145-5p | 1.31E−04 | 6.27E−06 | 54.31673 | up |
| hsa-miR-211-5p | 3.43E−07 | 3.97E−09 | 276.8409 | up |
| hsa-miR-363-3p | 0.001081 | 8.32E−05 | 17.00228 | up |
| hsa-miR-510 | 0.001869 | 1.69E−04 | 11.33646 | up |
| hsa-miR-514a-5p | 0.004085 | 4.44E−04 | 8.814804 | up |

TABLE 7-continued

Differentially expressed miRNAs in melanoma

| GeneName | p (Corr) | p | FC (abs) | Regulation |
|---|---|---|---|---|
| hsa-miR-509-3-5p | 3.46E−06 | 7.48E−08 | 55.9232 | up |
| hsa-miR-509-3p | 5.15E−07 | 6.24E−09 | 139.3508 | up |
| hsa-miR-514a-3p | 2.96E−07 | 3.12E−09 | 204.0894 | up |
| hsa-miR-506-3p | 1.47E−04 | 7.38E−06 | 27.69136 | up |
| hsa-miR-509-5p | 2.29E−06 | 4.59E−08 | 65.2407 | up |
| hsa-miR-513c-5p | 1.56E−04 | 7.97E−06 | 26.93033 | up |
| hsa-miR-508-3p | 7.57E−05 | 3.03E−06 | 31.90864 | up |
| hsa-miR-513b | 1.08E−05 | 3.13E−07 | 61.25974 | up |
| hsa-miR-205-5p | 0.001084 | 8.52E−05 | 19.47374 | down |
| hsa-miR-200a-5p | 4.47E−06 | 1.06E−07 | 31.4116 | down |
| hsa-miR-200c-5p | 2.14E−04 | 1.17E−05 | 13.61658 | down |
| hsa-miR-141-3p | 1.08E−08 | 5.70E−11 | 206.6276 | down |
| hsa-miR-203 | 2.10E−08 | 1.44E−10 | 273.6629 | down |
| hsa-miR-200b-3p | 3.83E−10 | 1.01E−12 | 1717.021 | down |
| hsa-miR-200a-3p | 6.01E−10 | 1.90E−12 | 680.575 | down |
| hsa-miR-429 | 3.83E−10 | 9.84E−13 | 515.7665 | down |
| hsa-miR-183-5p | 3.29E−11 | 1.73E−14 | 220.7499 | down |
| hsa-miR-96-5p | 1.73E−08 | 1.10E−10 | 120.4834 | down |
| hsa-miR-299-3p | 0.001145 | 9.29E−05 | 10.29763 | down |
| hsa-miR-183-3p | 4.11E−09 | 1.73E−11 | 101.0339 | down |
| hsa-miR-375 | 1.84E−05 | 6.29E−07 | 34.56165 | down |
| hsa-miR-335-3p | 9.59E−07 | 1.36E−08 | 40.52689 | down |
| hsa-miR-335-5p | 2.00E−07 | 1.89E−09 | 138.4271 | down |
| hsa-miR-27b-5p | 0.002927 | 2.98E−04 | 9.261446 | down |
| hsa-miR-4520a-3p | 0.022563 | 0.003721 | 6.89 | down |
| hsa-miR-224-5p | 1.05E−06 | 1.66E−08 | 93.71726 | down |
| hsa-miR-452-5p | 3.02E−06 | 6.36E−08 | 28.70594 | down |
| hsa-miR-2115-3p | 1.64E−04 | 8.45E−06 | 13.62161 | down |
| hsa-miR-610 | 0.006736 | 8.06E−04 | 6.325314 | down |
| hsa-miR-4474-5p | 0.004085 | 4.46E−04 | 7.169808 | down |
| hsa-miR-4768-3p | 3.71E−04 | 2.23E−05 | 11.11902 | down |
| hsa-miR-3120-3p | 9.80E−07 | 1.50E−08 | 25.58355 | down |
| hsa-miR-3131 | 0.002805 | 2.81E−04 | 8.680573 | down |
| hsa-miR-3064-5p | 0.03839 | 0.006966 | 4.001939 | down |
| hsa-miR-3146 | 0.001636 | 1.43E−04 | 9.022174 | down |
| hsa-miR-29b-2-5p | 4.74E−06 | 1.17E−07 | 24.81251 | down |
| hsa-miR-23b-5p | 0.010427 | 0.001494 | 5.084345 | down |
| hsa-miR-29c-5p | 0.018817 | 0.002954 | 4.759145 | down |
| hsa-miR-181c-3p | 0.003249 | 3.41E−04 | 6.808747 | down |
| hsa-miR-934 | 0.004177 | 4.58E−04 | 5.713632 | down |
| hsa-miR-224-3p | 8.00E−04 | 5.69E−05 | 6.372761 | down |
| hsa-miR-3664-3p | 0.046873 | 0.008718 | 2.658377 | down |
| hsa-miR-182-3p | 0.004453 | 4.97E−04 | 3.530612 | down |
| hsa-miR-26b-3p | 0.007891 | 9.94E−04 | 3.759939 | down |
| hsa-miR-1224-3p | 0.02713 | 0.004603 | 3.188798 | down |
| hsa-miR-4639-3p | 0.046873 | 0.008718 | 2.577534 | down |
| hsa-miR-136-3p | 0.009735 | 0.001349 | 3.622702 | down |
| hsa-miR-889 | 0.022175 | 0.003622 | 2.626288 | down |
| hsa-miR-146a-3p | 0.006231 | 7.35E−04 | 8.144401 | up |
| hsa-miR-551b-3p | 0.002793 | 2.75E−04 | 13.10246 | up |
| hsa-miR-4436b-5p | 0.029436 | 0.005087 | 5.61163 | up |
| hsa-miR-4655-3p | 0.007966 | 0.001032 | 9.83113 | up |
| hsa-miR-3909 | 0.001779 | 1.60E−04 | 9.591683 | up |
| hsa-miR-4469 | 0.026951 | 0.004558 | 4.714384 | up |
| hsa-miR-199b-5p | 0.010553 | 0.001518 | 6.022791 | up |
| hsa-miR-20b-3p | 0.030173 | 0.005262 | 4.286351 | up |
| hsa-miR-3189-5p | 0.010122 | 0.001419 | 6.377651 | up |
| hsa-miR-3944-3p | 0.010203 | 0.001441 | 6.720376 | up |
| hsa-miR-3972 | 0.002615 | 2.54E−04 | 7.432085 | up |
| hsa-miR-4654 | 0.047201 | 0.008845 | 2.915873 | up |
| hsa-miR-3677-5p | 0.046873 | 0.008704 | 3.970655 | up |
| hsa-miR-4785 | 0.033194 | 0.005929 | 3.763893 | up |
| hsa-miR-4665-5p | 0.047031 | 0.008772 | 4.908286 | up |
| hsa-miR-646 | 0.028359 | 0.004856 | 3.96194 | up |
| hsa-miR-4722-3p | 0.006789 | 8.18E−04 | 7.179308 | up |
| hsa-miR-4731-5p | 1.47E−04 | 7.29E−06 | 24.1787 | up |
| hsa-miR-31-3p | 0.001084 | 8.62E−05 | 22.97718 | down |
| hsa-miR-31-5p | 0.003738 | 4.00E−04 | 7.086216 | down |
| hsa-miR-5701 | 0.008838 | 0.001197 | 10.01555 | up |
| hsa-miR-4781-5p | 0.014003 | 0.002132 | 5.305426 | up |
| hsa-miR-548q | 0.004951 | 5.61E−04 | 5.547026 | up |
| hsa-miR-4708-3p | 0.001086 | 8.76E−05 | 12.24264 | up |
| hsa-miR-654-5p | 0.009938 | 0.001386 | 7.699157 | up |
| hsa-miR-658 | 0.010971 | 0.001607 | 6.930552 | up |
| hsa-miR-4719 | 0.007075 | 8.69E−04 | 11.2437 | down |

TABLE 7-continued

Differentially expressed miRNAs in melanoma

| GeneName | p (Corr) | p | FC (abs) | Regu-lation |
|---|---|---|---|---|
| hsa-miR-4539 | 0.021122 | 0.003405 | 6.615453 | up |
| hsa-miR-4321 | 0.008674 | 0.00117 | 8.399978 | up |
| hsa-miR-92a-1-5p | 0.032566 | 0.005782 | 5.652854 | down |
| hsa-let-7a-3p | 0.031593 | 0.005576 | 4.507036 | down |
| hsa-miR-16-1-3p | 0.010709 | 0.001557 | 7.805436 | down |
| hsa-miR-3127-5p | 0.021434 | 0.003479 | 4.025753 | down |
| hsa-miR-149-5p | 1.47E−04 | 7.24E−06 | 7.747861 | down |
| hsa-miR-103b | 0.013613 | 0.002044 | 5.532397 | down |
| hsa-miR-1306-3p | 4.41E−04 | 2.74E−05 | 5.499783 | down |
| hsa-miR-4277 | 0.019562 | 0.003082 | 4.243334 | down |
| hsa-miR-7-1-3p | 0.013779 | 0.002091 | 7.00258 | down |
| hsa-miR-192-5p | 0.008451 | 0.001122 | 5.301906 | down |
| hsa-miR-194-5p | 0.010414 | 0.001487 | 6.899473 | down |
| hsa-miR-625-3p | 6.00E−04 | 3.98E−05 | 5.362473 | down |
| hsa-miR-1244 | 1.30E−05 | 4.04E−07 | 13.87607 | down |
| hsa-miR-3609 | 0.00615 | 7.19E−04 | 5.480611 | down |
| hsa-miR-374a-5p | 0.005488 | 6.33E−04 | 5.316285 | down |
| hsa-miR-374b-5p | 7.74E−04 | 5.45E−05 | 4.971394 | down |
| hsa-miR-374c-5p | 0.002805 | 2.80E−04 | 6.082301 | down |
| hsa-miR-4644 | 7.74E−04 | 5.47E−05 | 5.508903 | down |
| hsa-miR-3148 | 2.36E−04 | 1.33E−05 | 3.753175 | down |
| hsa-miR-670 | 1.31E−04 | 6.20E−06 | 2.954435 | down |
| hsa-miR-3125 | 1.56E−05 | 5.17E−07 | 10.45982 | down |
| hsa-miR-3682-3p | 8.17E−05 | 3.31E−06 | 13.37263 | down |
| hsa-miR-617 | 1.49E−05 | 4.87E−07 | 10.12681 | down |
| hsa-miR-196b-3p | 0.035312 | 0.006363 | 2.420995 | down |
| hsa-miR-631 | 0.047798 | 0.008991 | 2.766758 | down |
| hsa-miR-4712-3p | 0.008318 | 0.001099 | 4.874474 | down |
| hsa-miR-1183 | 4.14E−06 | 9.60E−08 | 13.50259 | down |
| hsa-miR-1305 | 1.48E−05 | 4.76E−07 | 8.817349 | down |
| hsa-miR-3616-3p | 0.01974 | 0.00312 | 3.940568 | down |
| hsa-miR-4750 | 0.007443 | 9.29E−04 | 4.045383 | down |
| hsa-miR-622 | 5.67E−06 | 1.46E−07 | 6.138279 | down |
| hsa-miR-1914-5p | 0.0043 | 4.75E−04 | 4.031873 | up |
| hsa-miR-557 | 0.002559 | 2.45E−04 | 3.978653 | up |
| hsa-miR-3937 | 7.27E−05 | 2.87E−06 | 8.556762 | up |
| hsa-miR-612 | 0.018014 | 0.002819 | 2.968695 | up |
| hsa-miR-498 | 0.01123 | 0.001651 | 5.406655 | up |
| hsa-miR-596 | 3.88E−04 | 2.39E−05 | 4.02502 | up |
| hsa-miR-637 | 5.32E−04 | 3.42E−05 | 3.097873 | up |
| hsa-miR-1914-3p | 5.84E−04 | 3.84E−05 | 3.166935 | up |
| hsa-miR-4783-5p | 6.75E−04 | 4.59E−05 | 2.468174 | up |
| hsa-miR-593-5p | 4.55E−05 | 1.70E−06 | 7.19713 | up |
| hsa-miR-138-5p | 0.001269 | 1.06E−04 | 7.184394 | up |
| hsa-miR-146a-5p | 3.50E−10 | 5.54E−13 | 36.32244 | up |
| hsa-miR-4468 | 0.007443 | 9.29E−04 | 3.498524 | down |
| hsa-miR-4435 | 0.001689 | 1.49E−04 | 3.713703 | down |
| hsa-miR-4675 | 0.011764 | 0.001742 | 3.270106 | down |
| hsa-miR-4303 | 7.50E−04 | 5.18E−05 | 4.217161 | down |
| hsa-miR-200b-5p | 9.31E−04 | 6.99E−05 | 4.466938 | down |
| hsa-miR-505-3p | 0.030783 | 0.005417 | 2.509697 | down |
| hsa-miR-4689 | 0.002805 | 2.80E−04 | 2.843713 | down |
| hsa-miR-182-5p | 1.59E−10 | 1.67E−13 | 16.29153 | down |
| hsa-miR-3126-3p | 0.005012 | 5.70E−04 | 2.052046 | down |
| hsa-miR-134 | 0.010971 | 0.001605 | 2.169331 | down |
| hsa-miR-135b-3p | 0.021434 | 0.00349 | 2.782404 | down |
| hsa-miR-15b-3p | 3.97E−05 | 1.40E−06 | 4.796393 | down |
| hsa-miR-16-2-3p | 0.005456 | 6.27E−04 | 3.170327 | down |
| hsa-miR-7-5p | 5.58E−08 | 4.12E−10 | 8.046594 | down |
| hsa-miR-98 | 9.47E−04 | 7.18E−05 | 2.361425 | down |
| hsa-miR-23c | 4.38E−05 | 1.61E−06 | 3.371118 | down |
| hsa-miR-454-3p | 0.002884 | 2.92E−04 | 2.117273 | down |
| hsa-miR-331-3p | 9.31E−04 | 6.97E−05 | 2.204815 | down |
| hsa-miR-5011-5p | 2.97E−04 | 1.72E−05 | 2.12799 | down |
| hsa-miR-26b-5p | 2.04E−06 | 3.86E−08 | 2.913235 | down |
| hsa-miR-27b-3p | 0.001741 | 1.55E−04 | 2.012356 | down |
| hsa-miR-4753-5p | 0.004079 | 4.41E−04 | 2.579822 | down |
| hsa-miR-3667-5p | 2.33E−04 | 1.30E−05 | 3.667121 | down |
| hsa-miR-601 | 1.18E−05 | 3.53E−07 | 3.796099 | down |
| hsa-miR-595 | 0.001086 | 8.75E−05 | 2.123006 | down |
| hsa-miR-3149 | 1.18E−04 | 5.33E−06 | 2.016392 | down |
| hsa-miR-568 | 6.07E−04 | 4.06E−05 | 2.588553 | down |
| hsa-miR-4700-5p | 1.30E−04 | 5.95E−06 | 3.067645 | down |
| hsa-miR-4701-3p | 9.92E−05 | 4.18E−06 | 2.177509 | down |
| hsa-miR-1273f | 0.0043 | 4.76E−04 | 2.661917 | down |

TABLE 7-continued

Differentially expressed miRNAs in melanoma

| GeneName | p (Corr) | p | FC (abs) | Regu-lation |
|---|---|---|---|---|
| hsa-miR-3156-5p | 0.029612 | 0.005149 | 2.818424 | down |
| hsa-miR-4489 | 0.008561 | 0.001149 | 2.226271 | down |
| hsa-miR-1538 | 0.022286 | 0.003652 | 2.002481 | up |
| hsa-miR-602 | 4.35E−05 | 1.56E−06 | 3.929173 | up |
| hsa-miR-152 | 0.001604 | 1.39E−04 | 2.903808 | up |
| hsa-miR-361-3p | 0.004367 | 4.85E−04 | 2.0819 | up |
| hsa-miR-660-5p | 4.69E−04 | 2.94E−05 | 3.816789 | up |
| hsa-miR-532-3p | 8.07E−04 | 5.87E−05 | 2.41832 | up |
| hsa-miR-532-5p | 0.001258 | 1.04E−04 | 2.049957 | up |
| hsa-miR-500a-5p | 1.92E−04 | 1.01E−05 | 2.592344 | up |
| hsa-miR-502-3p | 2.08E−06 | 4.05E−08 | 2.867455 | up |
| hsa-miR-500a-3p | 2.81E−06 | 5.78E−08 | 3.288926 | up |
| hsa-miR-500b | 4.14E−06 | 9.15E−08 | 3.306766 | up |
| hsa-miR-146b-5p | 9.66E−07 | 1.42E−08 | 6.577508 | up |
| hsa-miR-4758-3p | 0.007443 | 9.27E−04 | 2.140459 | up |
| hsa-miR-572 | 0.007836 | 9.83E−04 | 2.122475 | up |
| hsa-miR-4707-3p | 2.78E−04 | 1.58E−05 | 2.890006 | up |
| hsa-miR-4467 | 1.45E−05 | 4.59E−07 | 3.269783 | up |
| hsa-miR-211-3p | 0.01656 | 0.002572 | 2.137208 | up |
| hsa-miR-514b-5p | 4.14E−06 | 9.46E−08 | 2.451853 | up |
| hsa-miR-584-5p | 2.00E−06 | 3.68E−08 | 4.172919 | up |
| hsa-miR-140-3p | 2.94E−04 | 1.69E−05 | 2.380397 | up |
| hsa-miR-185-5p | 1.18E−05 | 3.55E−07 | 2.566472 | up |
| hsa-miR-4306 | 9.11E−06 | 2.59E−07 | 2.30042 | up |
| hsa-miR-33b-3p | 0.001779 | 1.60E−04 | 2.029654 | up |
| hsa-miR-718 | 0.001673 | 1.47E−04 | 2.019544 | up |
| hsa-miR-513a-5p | 1.57E−05 | 5.28E−07 | 2.5497 | up |
| hsa-miR-3180 | 1.03E−04 | 4.44E−06 | 2.207144 | up |
| hsa-miR-4634 | 7.24E−08 | 5.72E−10 | 2.783406 | up |
| hsa-miR-187-5p | 4.38E−05 | 1.62E−06 | 2.040338 | up |
| hsa-miR-3195 | 8.82E−10 | 3.25E−12 | 3.056716 | up |
| hsa-miR-4532 | 1.08E−08 | 5.66E−11 | 2.402943 | up |
| hsa-miR-4497 | 3.24E−07 | 3.58E−09 | 2.42442 | up |
| hsa-miR-3196 | 1.22E−08 | 7.09E−11 | 2.634303 | up |
| hsa-miR-4488 | 2.77E−07 | 2.77E−09 | 2.560814 | up |
| hsa-miR-3940-5p | 7.03E−06 | 1.89E−07 | 2.071707 | up |
| hsa-miR-4466 | 4.49E−06 | 1.09E−07 | 2.079208 | up |
| hsa-miR-4707-5p | 7.75E−06 | 2.16E−07 | 2.062567 | up |
| hsa-miR-3178 | 1.96E−06 | 3.51E−08 | 3.343691 | up |
| hsa-miR-1469 | 1.21E−05 | 3.71E−07 | 2.23717 | up |
| hsa-miR-663a | 1.75E−07 | 1.49E−09 | 2.543887 | up |
| hsa-miR-4440 | 0.013465 | 0.002015 | 2.267684 | up |
| hsa-miR-4487 | 0.007933 | 0.001024 | 2.725489 | up |
| hsa-miR-3907 | 7.04E−06 | 1.93E−07 | 6.43762 | up |
| hsa-miR-501-3p | 6.88E−07 | 9.19E−09 | 6.462504 | up |
| hsa-miR-5587-5p | 3.80E−04 | 2.30E−05 | 5.271441 | up |
| hsa-miR-4706 | 0.029612 | 0.005149 | 2.311177 | up |
| hsa-miR-5008-5p | 0.011546 | 0.001703 | 3.408319 | up |
| hsa-miR-628-3p | 0.02025 | 0.003233 | 4.679494 | up |
| hsa-miR-3184-5p | 0.001423 | 1.23E−04 | 8.294511 | up |
| hsa-miR-3194-3p | 0.002812 | 2.83E−04 | 4.127772 | up |
| hsa-miR-3619-3p | 0.008931 | 0.001214 | 4.414144 | up |
| hsa-miR-508-5p | 6.88E−07 | 9.42E−09 | 21.59629 | up |
| hsa-miR-218-2-3p | 7.74E−04 | 5.43E−05 | 7.18456 | up |
| hsa-miR-4323 | 9.31E−04 | 7.02E−05 | 4.921013 | up |
| hsa-miR-636 | 0.032688 | 0.005821 | 2.65164 | up |
| hsa-miR-3944-5p | 0.001908 | 1.74E−04 | 4.912326 | up |
| hsa-miR-4665-3p | 5.11E−04 | 3.26E−05 | 4.010174 | up |
| hsa-miR-181a-3p | 0.022309 | 0.003667 | 3.537355 | up |
| hsa-miR-30b-3p | 0.047798 | 0.009016 | 2.869683 | up |
| hsa-miR-362-3p | 2.02E−04 | 1.08E−05 | 6.514883 | up |
| hsa-miR-501-5p | 0.002222 | 2.07E−04 | 5.113965 | up |
| hsa-miR-140-5p | 0.002789 | 2.73E−04 | 7.660998 | up |
| hsa-miR-584-3p | 9.67E−05 | 4.02E−06 | 10.36175 | up |
| hsa-miR-10a-3p | 0.001258 | 1.04E−04 | 15.86066 | down |
| hsa-miR-196b-5p | 1.03E−04 | 4.44E−06 | 23.30624 | down |
| hsa-miR-654-3p | 0.040924 | 0.007482 | 5.409095 | down |
| hsa-miR-3713 | 0.006907 | 8.44E−04 | 9.587804 | down |
| hsa-miR-3170 | 5.75E−04 | 3.75E−05 | 8.304263 | down |
| hsa-miR-4672 | 1.31E−04 | 6.27E−06 | 22.65654 | down |
| hsa-miR-215 | 3.54E−04 | 2.11E−05 | 30.10806 | down |
| hsa-miR-206 | 3.85E−04 | 2.35E−05 | 18.04436 | down |
| hsa-miR-539-5p | 1.20E−06 | 2.03E−08 | 43.96934 | down |

TABLE 7-continued

Differentially expressed miRNAs in melanoma

| GeneName | p (Corr) | p | FC (abs) | Regulation |
|---|---|---|---|---|
| hsa-miR-4311 | 0.010702 | 0.001551 | 5.535323 | down |
| hsa-miR-2278 | 0.001325 | 1.12E−04 | 8.703324 | down |
| hsa-miR-297 | 0.010271 | 0.001461 | 9.661793 | down |

TABLE 8

The top up and down regulated miRNAs by at least 10 fold in melanoma

| GeneName | p (Corr) | p | FC (abs) | Regulation |
|---|---|---|---|---|
| hsa-miR-211-5p | 3.43E−07 | 3.97E−09 | 276.84088 | up |
| hsa-miR-514a-3p | 2.96E−07 | 3.12E−09 | 204.08942 | up |
| hsa-miR-509-3p | 5.15E−07 | 6.24E−09 | 139.35081 | up |
| hsa-miR-204-5p | 5.50E−06 | 1.39E−07 | 93.670715 | up |
| hsa-miR-509-5p | 2.29E−06 | 4.59E−08 | 65.2407 | up |
| hsa-miR-513b | 1.08E−05 | 3.13E−07 | 61.259735 | up |
| hsa-miR-509-3-5p | 3.46E−06 | 7.48E−08 | 55.923203 | up |
| hsa-miR-145-5p | 1.31E−04 | 6.27E−06 | 54.31673 | up |
| hsa-miR-146a-5p | 3.50E−10 | 5.54E−13 | 36.32244 | up |
| hsa-miR-508-3p | 7.57E−05 | 3.03E−06 | 31.908644 | up |
| hsa-miR-506-3p | 1.47E−04 | 7.38E−06 | 27.691364 | up |
| hsa-miR-513c-5p | 1.56E−04 | 7.97E−06 | 26.930325 | up |
| hsa-miR-4731-5p | 1.47E−04 | 7.29E−06 | 24.178703 | up |
| hsa-miR-508-5p | 6.88E−07 | 9.42E−09 | 21.59629 | up |
| hsa-miR-363-3p | 0.001080965 | 8.32E−05 | 17.002277 | up |
| hsa-miR-551b-3p | 0.002793076 | 2.75E−04 | 13.102462 | up |
| hsa-miR-4708-3p | 0.001086084 | 8.76E−05 | 12.242638 | up |
| hsa-miR-510 | 0.001869193 | 1.69E−04 | 11.336461 | up |
| hsa-miR-584-3p | 9.67E−05 | 4.02E−06 | 10.361748 | up |
| hsa-miR-5701 | 0.008838477 | 0.00119678 | 10.0155525 | up |
| hsa-miR-617 | 1.49E−05 | 4.87E−07 | 10.126807 | down |
| hsa-miR-299-3p | 0.001144688 | 9.29E−05 | 10.297629 | down |
| hsa-miR-3125 | 1.56E−05 | 5.17E−07 | 10.459817 | down |
| hsa-miR-4768-3p | 3.71E−04 | 2.23E−05 | 11.119021 | down |
| hsa-miR-4719 | 0.00707513 | 8.69E−04 | 11.243696 | down |
| hsa-miR-3682-3p | 8.17E−05 | 3.31E−06 | 13.372626 | down |
| hsa-miR-1183 | 4.14E−06 | 9.60E−08 | 13.502589 | down |
| hsa-miR-200c-5p | 2.14E−04 | 1.17E−05 | 13.616578 | down |
| hsa-miR-2115-3p | 1.64E−04 | 8.45E−06 | 13.621608 | down |
| hsa-miR-1244 | 1.30E−05 | 4.04E−07 | 13.876072 | down |
| hsa-miR-10a-3p | 0.001257804 | 1.04E−04 | 15.860663 | down |
| hsa-miR-182-5p | 1.59E−10 | 1.67E−13 | 16.291529 | down |
| hsa-miR-206 | 3.85E−04 | 2.35E−05 | 18.044355 | down |
| hsa-miR-205-5p | 0.001083732 | 8.52E−05 | 19.473736 | down |
| hsa-miR-182-5p | 1.59E−10 | 1.67E−13 | 16.291529 | down |
| hsa-miR-206 | 3.85E−04 | 2.35E−05 | 18.044355 | down |
| hsa-miR-205-5p | 0.001083732 | 8.52E−05 | 19.473736 | down |
| hsa-miR-4672 | 1.31E−04 | 6.27E−06 | 22.656536 | down |
| hsa-miR-31-3p | 0.001083732 | 8.62E−05 | 22.977182 | down |
| hsa-miR-196b-5p | 1.03E−04 | 4.44E−06 | 23.306242 | down |
| hsa-miR-29b-2-5p | 4.74E−06 | 1.17E−07 | 24.812508 | down |
| hsa-miR-3120-3p | 9.80E−07 | 1.50E−08 | 25.58355 | down |
| hsa-miR-452-5p | 3.02E−06 | 6.36E−08 | 28.705942 | down |
| hsa-miR-215 | 3.54E−04 | 2.11E−05 | 30.10806 | down |
| hsa-miR-200a-5p | 4.47E−06 | 1.06E−07 | 31.411602 | down |
| hsa-miR-375 | 1.84E−05 | 6.29E−07 | 34.56165 | down |
| hsa-miR-335-3p | 9.59E−07 | 1.36E−08 | 40.526886 | down |
| hsa-miR-539-5p | 1.20E−06 | 2.03E−08 | 43.96934 | down |

TABLE 8-continued

The top up and down regulated miRNAs by at least 10 fold in melanoma

| GeneName | p (Corr) | p | FC (abs) | Regulation |
|---|---|---|---|---|
| hsa-miR-224-5p | 1.05E−06 | 1.66E−08 | 93.71726 | down |
| hsa-miR-183-3p | 4.11E−09 | 1.73E−11 | 101.033875 | down |
| hsa-miR-96-5p | 1.73E−08 | 1.10E−10 | 120.48337 | down |
| hsa-miR-335-5p | 2.00E−07 | 1.89E−09 | 138.42706 | down |
| hsa-miR-141-3p | 1.08E−08 | 5.70E−11 | 206.62756 | down |
| hsa-miR-183-5p | 3.29E−11 | 1.73E−14 | 220.74986 | down |
| hsa-miR-200c-3p | 1.29E−06 | 2.24E−08 | 250.74672 | down |
| hsa-miR-203 | 2.10E−08 | 1.44E−10 | 273.66293 | down |
| hsa-miR-429 | 3.83E−10 | 9.84E−13 | 515.76654 | down |
| hsa-miR-200a-3p | 6.01E−10 | 1.90E−12 | 680.57495 | down |
| hsa-miR-200b-3p | 3.83E−10 | 1.01E−12 | 1717.0214 | down |

TABLE 9

Cell lines in which quantitative real-time PCR validation was performed

| Sample ID | Type | Cohort | qRT PCR validation |
|---|---|---|---|
| QF1160MB | Melanoblast | Discovery | Yes |
| MELA | Melanocyte | Discovery | Yes |
| MM653 | Nevus | Discovery | Yes |
| 22rV-1 | Other | Discovery | Yes |
| 786-O | Other | Discovery | Yes |
| ALVA-1 | Other | Discovery | Yes |
| BT474 | Other | Discovery | Yes |
| BxPC-3 | Other | Discovery | Yes |
| CAKI-1 | Other | Discovery | Yes |
| CAKI-2 | Other | Discovery | Yes |
| CaOV-3 | Other | Discovery | Yes |
| CAPAN-1 | Other | Discovery | Yes |
| CAPAN-2 | Other | Discovery | Yes |
| Co115 | Other | Discovery | Yes |
| Du145 | Other | Discovery | Yes |
| HT29 | Other | Discovery | Yes |
| LIM1899 | Other | Discovery | Yes |
| LIM2405 | Other | Discovery | Yes |
| LN-18 | Other | Discovery | Yes |
| LNCAP | Other | Discovery | Yes |
| MCF-7 | Other | Discovery | Yes |
| MDAMB231 | Other | Discovery | Yes |
| OAW28 | Other | Discovery | Yes |
| OVCAR-3 | Other | Discovery | Yes |
| PANC-1 | Other | Discovery | Yes |
| PC-3 | Other | Discovery | Yes |
| PE04 | Other | Discovery | Yes |
| PL45 | Other | Discovery | Yes |
| SKBR3 | Other | Discovery | Yes |
| SK-OV-3 | Other | Discovery | Yes |
| SN12K-1 | Other | Discovery | Yes |
| SW48 | Other | Discovery | Yes |
| SW839 | Other | Discovery | Yes |
| T46 | Other | Discovery | Yes |
| T47D | Other | Discovery | Yes |
| T50 | Other | Discovery | Yes |
| U118 | Other | Discovery | Yes |
| MM200 | STAGE I/II | Validation | Yes |
| MM229 | STAGE I/II | Validation | Yes |
| MM329 | STAGE I/II | Validation | Yes |
| MM540 | STAGE I/II | Validation | Yes |
| C001 | STAGE_III_MM | Discovery | Yes |
| C002 | STAGE_III_MM | Discovery | Yes |
| C003 | STAGE_III_MM | Discovery | Yes |
| C004 | STAGE_III_MM | Discovery | Yes |
| C006 | STAGE_III_MM | Discovery | Yes |
| C008 | STAGE_III_MM | Discovery | Yes |
| C011 | STAGE_III_MM | Discovery | Yes |
| C012 | STAGE_III_MM | Discovery | Yes |
| C013 | STAGE_III_MM | Discovery | Yes |

TABLE 9-continued

Cell lines in which quantitative real-time PCR validation was performed

| Sample ID | Type | Cohort | qRT PCR validation |
|---|---|---|---|
| C016 | STAGE_III_MM | Discovery | Yes |
| C017 | STAGE_III_MM | Discovery | Yes |
| C021 | STAGE_III_MM | Discovery | Yes |
| C022 | STAGE_III_MM | Discovery | Yes |
| C025 | STAGE_III_MM | Discovery | Yes |
| C027 | STAGE_III_MM | Discovery | Yes |
| C028 | STAGE_III_MM | Discovery | Yes |
| C037 | STAGE_III_MM | Discovery | Yes |
| C038 | STAGE_III_MM | Discovery | Yes |
| C042 | STAGE_III_MM | Discovery | Yes |
| C043 | STAGE_III_MM | Discovery | Yes |
| C044 | STAGE_III_MM | Discovery | Yes |
| C045 | STAGE_III_MM | Discovery | Yes |
| C050 | STAGE_III_MM | Discovery | Yes |
| C052 | STAGE_III_MM | Discovery | Yes |
| C054 | STAGE_III_MM | Discovery | Yes |
| C057 | STAGE_III_MM | Discovery | Yes |
| C058 | STAGE_III_MM | Discovery | Yes |
| C060 | STAGE_III_MM | Discovery | Yes |
| C062 | STAGE_III_MM | Discovery | Yes |
| C065 | STAGE_III_MM | Discovery | Yes |
| C067 | STAGE_III_MM | Discovery | Yes |
| C071 | STAGE_III_MM | Discovery | Yes |
| C074 | STAGE_III_MM | Discovery | Yes |
| C076 | STAGE_III_MM | Discovery | Yes |
| C077 | STAGE_III_MM | Discovery | Yes |
| C078 | STAGE_III_MM | Discovery | Yes |
| C079 | STAGE_III_MM | Discovery | Yes |
| C080 | STAGE_III_MM | Discovery | Yes |
| C081 | STAGE_III_MM | Discovery | Yes |
| C083 | STAGE_III_MM | Discovery | Yes |
| C084 | STAGE_III_MM | Discovery | Yes |
| C086 | STAGE_III_MM | Discovery | Yes |
| C088 | STAGE_III_MM | Discovery | Yes |
| C089 | STAGE_III_MM | Discovery | Yes |
| C091 | STAGE_III_MM | Discovery | Yes |
| C092 | STAGE_III_MM | Discovery | Yes |
| C094 | STAGE_III_MM | Discovery | Yes |
| C096 | STAGE_III_MM | Discovery | Yes |
| C097 | STAGE_III_MM | Discovery | Yes |
| C100 | STAGE_III_MM | Discovery | Yes |
| C106 | STAGE_III_MM | Discovery | Yes |
| C108 | STAGE_III_MM | Discovery | Yes |
| A02 | STAGE_IV_MM | Discovery | Yes |
| A04 | STAGE_IV_MM | Discovery | Yes |
| A06 | STAGE_IV_MM | Validation | Yes |
| A13 | STAGE_IV_MM | Validation | Yes |
| A15 | STAGE_IV_MM | Validation | Yes |
| AF6 | STAGE_IV_MM | Validation | Yes |
| C-32 | STAGE_IV_MM | Validation | Yes |
| CJM | STAGE_IV_MM | Validation | Yes |
| D01 | STAGE_IV_MM | Validation | Yes |
| D04 | STAGE_IV_MM | Validation | Yes |
| D05 | STAGE_IV_MM | Validation | Yes |
| D08 | STAGE_IV_MM | Validation | Yes |
| D10 | STAGE_IV_MM | Validation | Yes |
| D11 | STAGE_IV_MM | Validation | Yes |
| D14 | STAGE_IV_MM | Validation | Yes |
| D17 | STAGE_IV_MM | Validation | Yes |
| D20 | STAGE_IV_MM | Validation | Yes |
| D22 | STAGE_IV_MM | Validation | Yes |
| D24 | STAGE_IV_MM | Validation | Yes |
| D25 | STAGE_IV_MM | Validation | Yes |
| D28 | STAGE_IV_MM | Validation | Yes |
| D29 | STAGE_IV_MM | Validation | Yes |
| D32 | STAGE_IV_MM | Validation | Yes |
| D35 | STAGE_IV_MM | Validation | Yes |
| D36 | STAGE_IV_MM | Validation | Yes |
| D40 | STAGE_IV_MM | Validation | Yes |
| D41 | STAGE_IV_MM | Validation | Yes |
| D59 | STAGE_IV_MM | Discovery | Yes |
| HT144 | STAGE_IV_MM | Validation | Yes |
| MM127 | STAGE_IV_MM | Validation | Yes |
| MM253 | STAGE_IV_MM | Validation | Yes |
| MM370 | STAGE_IV_MM | Validation | Yes |
| MM386 | STAGE_IV_MM | Validation | Yes |
| MM415 | STAGE_IV_MM | Validation | Yes |
| MM426 | STAGE_IV_MM | Validation | Yes |
| MM466 | STAGE_IV_MM | Validation | Yes |
| MM473 | STAGE_IV_MM | Validation | Yes |
| MM485 | STAGE_IV_MM | Validation | Yes |
| MM537 | STAGE_IV_MM | Validation | Yes |
| MM548 | STAGE_IV_MM | Validation | Yes |
| MM649 | STAGE_IV_MM | Validation | Yes |
| MM96L | STAGE_IV_MM | Validation | Yes |
| SKMEL28 | STAGE_IV_MM | Validation | Yes |
| SKMEL5 | STAGE_IV_MM | Validation | Yes |
| 92_1 | Uveal MM | Discovery | Yes |
| MEL202 | Uveal MM | Discovery | Yes |
| MEL270 | Uveal MM | Discovery | Yes |
| MEL285 | Uveal MM | Discovery | Yes |
| MEL290 | Uveal MM | Discovery | Yes |
| OCM8 | Uveal MM | Discovery | Yes |
| OMM1 | Uveal MM | Discovery | Yes |

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

REFERENCES

1. Balch C M, Gershenwald J E, Soong S J, et al. Final version of 2009 AJCC melanoma staging and classification. J Clin Oncol 2009; 27(36): 6199-206.
2. AIHW. Australian Cancer Incidence and Mortality (ACIM) books: Melanoma of the skin: Canberra: AIHW; 2014.
3. SEER. SEER Cancer Statistics Review, 1975-2011, National Cancer Institute. Bethesda, M D: National Cancer Institute. 2014.
4. Brochez L, Nacyaert J M. Serological markers for melanoma. Br J Dermatol 2000; 143(2): 256-68.
5. Finck S J, Giuliano A E, Morton D L. LDH and melanoma. Cancer 1983; 51(5): 840-3.
6. Karakousis C P, Batch C M. Urist M M, Ross M M, Smith T J, Bartolucci A A. Local recurrence in malignant melanoma: long-term results of the multiinstitutional randomized surgical trial. Ann Surg Oncol 1996; 3(5): 446-52.
7. Sirott M N, Bajorin D F. Wong G Y, et al. Prognostic factors in patients with metastatic malignant melanoma. A multivariate analysis. Cancer 1993; 72(10): 3091-8.
8. Weide B, Elsasser M, Benner P, et al. Serum markers lactate dehydrogenase and S100B predict independently disease outcome in melanoma patients with distant metastasis. Br J Cancer 2012; 107(3): 422-8.
9. Deichmann M, Benner A, Bock M, et al. S100-Beta. melanoma-inhibiting activity, and lactate dehydrogenase discriminate progressive from nonprogressive American Joint Committee on Cancer stage IV melanoma. J Clin Oncol 1999; 17(6): 1891-6.

10. Guo H B, Stoffel-Wagner B, Bierwirth T, Mezger J, Klingmuller D. Clinical significance of serum S100 in metastatic malignant melanoma. Eur J Cancer 1995; 31A(6): 924-8.
11. Smit L H, Korse C M, Hart A A. et al. Normal values of serum S-100B predict prolonged survival for stage IV melanoma patients. Eur J Cancer 2005; 41(3): 386-92.
12. Kruijff S, Bastiaannet E, Kobold A C, van Ginkel R J, Suurmeijer A J, Hoekstra H J. S-100B concentrations predict disease-free survival in stage III melanoma patients. Ann Surg Oncol 2009; 16(12): 3455-62.
13. Allegra A, Alonci A, Campo S, et al. Circulating microRNAs: new biomarkers in diagnosis, prognosis and treatment of cancer (review). Int J Oncol 2012; 41(6): 1897-912.
14. De Guire V, Robitaille R, Tetreault N, et al. Circulating miRNAs as sensitive and specific biomarkers for the diagnosis and monitoring of human diseases: promises and challenges. Clinical biochemistry 2013; 46(10-11): 846-60.
15. Grasedieck S, Sorrentino A, Langer C, et al. Circulating microRNAs in hematological diseases: principles, challenges, and perspectives. Blood 2013; 121(25): 4977-84.
16. Mitchell P S, Parkin R K, Kroh E M, et al. Circulating microRNAs as stable blood-based markers for cancer detection. Proc Natl Acad Sci USA 2008: 105(30): 10513-8.
17. Kanemaru H, Fukushima S, Yamashita J, et al. The circulating microRNA-221 level in patients with malignant melanoma as a new tumor marker. J Dermatol Sci 2011; 61(3): 187-93.
18. Friedman E B, Shang S. de Micra E V; et al. Serum microRNAs as biomarkers for recurrence in melanoma. J Transl Med 2012; 10: 155.
19. Griffiths-Jones S. The microRNA Registry. Nucleic Acids Res 2004; 32 (Database issue): D109-11.
20. Stark M S, Boyle G M, Bonazzi V F, et al. miR-514a regulation of the tumour-suppressor gene NF1 confers resistance to PLX4032 targeted therapy of melanoma. In preparation 2014.
21. Sturm R A, Fox C, McClenahan P, et al. Phenotypic characterization of nevus and tumor patterns in MITF E318K mutation carrier melanoma patients. J Invest Dermatol 2014; 134(1): 141-9.
22. Kroh E M, Parkin R K, Mitchell P S, Tewari M. Analysis of circulating microRNA biomarkers in plasma and serum using quantitative reverse transcription-PCR (qRT-PCR). Methods 2010; 50(4): 298-301.
23. Wians F H J. Clinical Laboratory Tests: Which, Why, and What Do The Results Mean? Lab Medicine 2009; 40(2): 105-13.
24. Weide B, Richter S, Buttner P, et al. Serum S100B, lactate dehydrogenase and brain metastasis are prognostic factors in patients with distant melanoma metastasis and systemic therapy. PLoS One 2013; 8(11): e81624.
25. Morton D L, Thompson J F, Cochran A J, et al. Final trial report of sentinel-node biopsy versus nodal observation in melanoma. N Engl J Med 2014; 370(7): 599-609.
26. Hanahan D, Weinberg R A. Hallmarks of cancer: the next generation. Cell. 2011: 144: 646-74.
27. Alexandrov L B. Nik-Zainal S, Wedge D C, Aparicio S A, Behjati S, Biankin A V, et at. Signatures of mutational processes in human cancer. Nature. 2013; 500:415-21.
28. Bonazzi V F, Stark M S, Hayward N K. MicroRNA regulation of melanoma progression. Melanoma Res. 2012; 22:101-13.
29. Gaur A, Jewell D A, Liang Y, Ridzon D, Moore J H, Chen C, et al. Characterization of microRNA expression levels and their biological correlates in human cancer cell lines. Cancer Res. 2007; 67:2456-68.
30. Ferracin M, Pedriali M, Veronese A, Zagatti B. Gafa R, Magri E, et al. MicroRNA profiling for the identification of cancers with unknown primary tissue-of-origin. J Pathol. 2011.
31. Poliseno L, Haimovic A, Segura M F, Hanniford D, Christos P J, Darvishian F, et al. Histology-specific microRNA alterations in melanoma. J Invest Dermatol. 2012; 132:1860-8.
32. Stark M S, Tyagi S, Nancarrow D J, Boyle G M, Cook A L. Whiteman D C, et al. Characterization of the Melanoma miRNAome by Deep Sequencing. PLoS One. 2010; 5:e9685.
33. Kozubek J, Ma Z, Fleming E, Duggan T, Wu R, Shin D G, et al. In-depth characterization of microRNA transcriptome in melanoma. PLoS One. 2013; 8:e72699.
34. Streicher K L. Zhu W, Lehmann K P, Georgantas R W, Morehouse C A, Brohawn P, et al. A novel oncogenic role for the miRNA-506-514 cluster in initiating melanocyte transformation and promoting melanoma growth. Oncogene. 2012; 31:1558-70.
35. Wani S. Cloonan N. Profiling direct mRNA-microRNA interactions using synthetic biotinylated microRNA-duplexes. bioRxiv. 2014.
36. Martin H C. Wani S, Steptoe A L, Krishnan K. Nones K. Nourbakhsh E, et al. Imperfect centered miRNA binding sites are common and can mediate repression of target mRNAs. Genome Biol. 2014:15:R51.
37. Maertens O, Johnson B. Hollstein P. Fredrick D T, Cooper Z A, Messiaen L, et al. Elucidating distinct roles for NF1 in melanomagenesis. Cancer Discov. 2013; 3:338-49.
38. Whittaker S R. Theurillat J P, Van Allen E, Wagle N. Hsiao J, Cowley G S, et al. A genome-scale RNA interference screen implicates NF1 loss in resistance to RAF inhibition. Cancer Discov. 2013; 3:350-62.
39. Shalem O, Sanjana N E, Hartenian E, Shi X, Scott D A. Mikkelsen T S, et al. Genome-scale CRISPR-Cas9 knockout screening in human cells. Science. 2014; 343:84-7.
40. Nissan M H, Pratilas C A, Jones A M, Ramirez R, Won H, Liu C, et al. Loss of NF1 in cutaneous melanoma is associated with RAS activation and MEK dependence. Cancer Res. 2014.
41. Levy C, Khaled M, Iliopoulos D, Janas M M, Schubert S, Pinner S, et al. Intronic miR-211 assumes the tumor suppressive function of its host gene in melanoma. Mol Cell. 2010; 40:841-9.
42. Yokoyama S, Woods S L, Boyle G M, Aoude L G, MacGregor S, Zismann V, et al. A novel recurrent mutation in MITF predisposes to familial and sporadic melanoma. Nature. 2011; 480:99-103.
43. Lito P, Rosen N, Solit D B. Tumor adaptation and resistance to RAF inhibitors. Nat Med. 2013; 19:1401-9.
44. Khan A A, *Betel* D, Miller M L, Sander C. Leslie C S, Marks D S. Transfection of small RNAs globally perturbs gene regulation by endogenous microRNAs. Nat Biotechnol. 2009; 27:549-55.
45. Hodis E, Watson I R, Kryukov G V, Arold S T, Imielinski M, Theurillat J P, et al. A landscape of driver mutations in melanoma. Cell. 2012; 150:251-63.
46. Krauthammer M, Kong Y, Ha B H; Evans P, Bacchiocchi A, McCusker J P, et al. Exome sequencing identifies recurrent somatic RACI mutations in melanoma. Nat Genet. 2012:44:1006-14.

47. van Kempen L C, van den Hurk K. Lazar V, Michiels S, Winnepenninckx V, Stas M, et al. Loss of microRNA-200a and c, and microRNA-203 expression at the invasive front of primary cutaneous melanoma is associated with increased thickness and disease progression. Virchows Arch. 2012:461:441-8.
48. Poell J B, van Haastert R J, de Gunst T, Schultz U, Gommans W M, Verheul M, et al, A functional screen identifies specific microRNAs capable of inhibiting human melanoma cell viability. PLoS One. 2012:7: e43569.
49. Dar A A, Majid S, de Semir D, Nosrati M, Bezrookove V, Kashani-Sabet M. miRNA-205 suppresses melanoma cell proliferation and induces senescence via regulation of E2F1 protein. J Biol Chem. 2011; 286:16606-14.
50. Xu Y, Brenn T, Brown F R, Doherty V, Melton D W. Differential expression of microRNAs during melanoma progression: miR-200c, miR-205 and miR-211 are down-regulated in melanoma and act as tumour suppressors. Br J Cancer. 2012; 106:553-61.
51. Liu S, Tetzlaff M T, Liu A, Liegl-Atzwanger B, Guo J, Xu X. Loss of microRNA-205 expression is associated with melanoma progression. Lab Invest. 2012; 92:1084-96.
52. Hanna J A, Hahn L, Agarwal S, Rimm D L. In situ measurement of miR-205 in malignant melanoma tissue supports its role as a tumor suppressor microRNA. Lab Invest. 2012; 92:1390-7.
53. Noguchi S, Iwasaki J, Kumazaki M, Mori T, Maruo K, Sakai H, et al. Chemically modified synthetic microRNA-205 inhibits the growth of melanoma cells in vitro and in vivo. Molecular therapy the journal of the American Society of Gene Therapy. 2013; 21:1204-11.

The invention claimed is:

1. A method of treating a melanoma in a subject including the steps of:

(a) obtaining a biological sample from the subject;

(b) measuring an expression level of one or more miRNA biomarkers in the biological sample(s), wherein the one or more miRNA biomarkers are selected from the group consisting of miRNA-4487, miRNA-4706 and miRNA-4731;

(c) comparing the expression level of the one or more miRNA biomarkers measured in (b) to a control expression level of the one or more miRNA biomarkers derived from a subject not having or in remission from melanoma;

wherein a lower expression level of the one or more miRNA biomarkers relative to the control expression level is indicative of a diagnosis of melanoma;

(d) administering to the subject a treatment to treat the melanoma in the subject based on the diagnosis determined in step (c), wherein the treatment is selected from the group consisting of an anti-PD-1 antibody, an anti-CTLA4 antibody, a MAPK pathway inhibitor, and any combination thereof.

2. The method of claim 1, further including measuring an expression level of one or more additional miRNA biomarkers selected from the group consisting of miRNA-16, miRNA-211, miRNA-509-3p and miRNA-509-5p.

3. The method of claim 1, further including the steps of measuring a further expression level of the one or more miRNA biomarkers in a further biological sample from the subject and determining whether or not the selected treatment is efficacious according to whether the further expression level of the one or more miRNA biomarkers is altered or modulated in the subject's further biological sample relative to the expression level measured in step (a).

4. The method of claim 1, wherein the biological sample is or comprises tissue, serum and/or plasma.

5. The method of claim 1, further including the step of staging the subject's melanoma once diagnosed based on the comparison in step (c), wherein a lower expression level of the one or more miRNA biomarkers relative to the control expression level is indicative of a later stage of melanoma in the subject.

6. A method of treating a melanoma in a subject including the steps of:

(a) obtaining a biological sample from the subject (b) measuring an expression level of one or more miRNA biomarkers in the biological sample, wherein the one or more miRNA biomarkers are selected from the group consisting of miRNA-4487, miRNA-4706 and miRNA-4731;

(c) comparing the expression level of the one or more miRNA biomarkers measured in (b) to a control expression level of the one or more miRNA biomarkers derived from a subject not having or in remission from melanoma, wherein a lower expression level of the one or more miRNA biomarkers relative to the control expression level is indicative of a higher stage of melanoma in the subject;

(d) selecting and administering a treatment for the subject's melanoma based on the comparison in step (c), wherein the treatment is selected from the group consisting of an anti-PD-1 antibody, an anti-CTLA4 antibody, a MAPK pathway inhibitor, and any combination thereof.

7. A method of treating a melanoma in a subject including the steps of:

(a) obtaining a biological sample from the subject;

(b) measuring an expression level of one or more miRNA biomarkers in the biological sample, wherein the one or more miRNA biomarkers are selected from the group consisting of miRNA-4487, miRNA-4706 and miRNA-4731;

(c) comparing the expression level of the one or more miRNA biomarkers measured in (b) to a control expression level of the one or more miRNA biomarkers derived from a subject not having or in remission from melanoma;

(d) selecting and administering a treatment for the subject's melanoma based on the comparison in step (c), wherein the treatment is selected from the group consisting of an anti-PD-1 antibody, an anti-CTLA4 antibody, a MAPK pathway inhibitor, and any combination thereof;

and (e) measuring a further expression level of the one or more miRNA biomarkers in a further biological sample from the subject and determining whether or not the selected treatment is efficacious according to whether the further expression level of the one or more miRNA biomarkers is altered or modulated in the subject's further biological sample relative to the expression level measured in step (b).

8. The method of claim 7, wherein a decrease in expression of the one or more miRNA biomarkers relative to the control expression level indicates that the treatment is efficacious.

* * * * *